(12) United States Patent
Short et al.

(10) Patent No.: US 9,453,211 B2
(45) Date of Patent: *Sep. 27, 2016

(54) DEHALOGENASES, NUCLEIC ACIDS ENCODING THEM AND METHODS FOR MAKING AND USING THEM

(75) Inventors: Jay M. Short, Del Mar, CA (US); Toby Richardson, San Diego, CA (US); Dan E. Robertson, San Diego, CA (US); Kevin A. Gray, San Diego, CA (US)

(73) Assignee: BASF Enzymes LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/442,514

(22) Filed: Apr. 9, 2012

(65) Prior Publication Data

US 2013/0115675 A1 May 9, 2013

Related U.S. Application Data

(62) Division of application No. 12/683,906, filed on Jan. 7, 2010, now Pat. No. 8,153,411, which is a division of application No. 11/418,828, filed on May 5, 2006, now Pat. No. 7,671,189, which is a division of application No. 10/000,997, filed on Nov. 30, 2001, now Pat. No. 7,078,504.

(60) Provisional application No. 60/250,897, filed on Dec. 1, 2000.

(51) Int. Cl.
*C12N 9/14* (2006.01)
*G06F 19/22* (2011.01)

(52) U.S. Cl.
CPC .................. *C12N 9/14* (2013.01); *G06F 19/22* (2013.01); *Y10S 422/90* (2013.01)

(58) Field of Classification Search
None
See application file for complete search history.

(56) References Cited

U.S. PATENT DOCUMENTS

| 5,108,892 A | 4/1992 | Burke et al. |
| 5,723,125 A * | 3/1998 | Chang et al. ............... 424/134.1 |
| 6,037,465 A * | 3/2000 | Hillebrand et al. ........ 536/25.42 |
| 6,632,937 B1 | 10/2003 | Swanson et al. |

FOREIGN PATENT DOCUMENTS

| JP | 2005-501515 | 1/2005 |
| WO | WO 9836080 A1 * | 8/1998 |
| WO | 00/18909 | 4/2000 |
| WO | 00/58517 | 10/2000 |
| WO | 00/71728 | 11/2000 |
| WO | 02/22810 | 3/2002 |
| WO | 02/68583 | 9/2002 |
| WO | 98/36080 | 8/2008 |

OTHER PUBLICATIONS

GenBank GI:3860530 [online] Nov. 11, 1998 [retrieved on Jul. 7, 2013] retrieved from http://www.ncbi.nlm.nih.gov/nuccore/3860530?sat=8&satkey=270707.*
BIO 101 Protocol [retrieved on Jan. 17, 2014] from: http://labs.mmg.pitt.edu/gjoerup/rapid%20pure%20miniprep.pdf.*
GenBank GI:3114654 [online] Mar. 8, 1999 [retrieved on Apr. 3, 2015] retrieved from http://www.ncbi.nlm.nih.gov/nuccore/3114654?sat=24&satkey=4877678.*
Affholter et al., Rhodococcus haloalkane dehalogenase gene in vector pEXPROK; Dec. 7, 1998 (first entry); Database GenBank (Geneseq); Accession No. AAV47592.
Damborsky et al., Protein Engineering (1998) 11:901-907.
Holloway et al., Biotechnology and Bioengineering (1998) 59:520-523.
International Search Report mailed on Jul. 27, 2004, for PCT patent application No. PCT/US01/45337 filed on Nov. 30, 2001.
Keuning et al., Journal of Bacteriology (1985) 163(2):635-639.
Krooshof et al., Biochemistry (1997) 36(31):9571-9580.
Kulakova et al., Microbiology (1997) 143 (Part 1):109-115.
Matthews et al., Anal. Biochem. (1988) 169:1-25.
Newman et al., Biochemistry (1999) 38:16105-16114.
Office Action for Australian Application No. 2001297671, date mailed on Feb. 1, 2005, 5 pages.
Poelarends et al., Journal of Bacteriology (1999) 181(7):2050-2058.
Poelarends et al., Journal of Bacteriology (2000) 182(8):2191-2199.
Rozeboom et al., Journal of Molecular Biology (1988) 200(3):611-612.
Schanstra et al., Journal of Biological Chemistry (1996) 271(25):14747-14763.
Supplementary Partial European Search Report for Application No. EP 01 27 3846, mailed on Jul. 20, 2005, 5 pages.
Supplementary Partial European Search Report for Application No. EP 01 27 3846, mailed on Sep. 23, 2005, 8 pages.
Verschueren et al., Nature (1993) 363(6431):693-698.
USPTO—Mar. 25, 2011—Office Action—U.S. Appl. No. 12/683,906.
SIPO—Aug. 16, 2011—Fourth Office Action—01822258.7.
AUIP—Sep. 20, 2011—First Examination Report—AU2011201053.
JPO—Jun. 14, 2012—Office Action—JP2010-133318.
AUIP—Oct. 16, 2012—Second Examination Report—AU2011201053.
SIPO—Mar. 27, 2013—First Office Action—CN 201210153641.1.
SIPO—Sep. 25, 2013—Third Office Action—CN 201210153641.1.
SIPO—May 18, 2015—Fourth Office Action—CN 201210153641.1.

* cited by examiner

*Primary Examiner* — Samuel Woolwine
(74) *Attorney, Agent, or Firm* — Richa Dhindsa; BASF Enzymes LLC

(57) ABSTRACT

The invention relates to haloalkane dehalogenases and to polynucleotides encoding the haloalkane dehalogenases. In addition methods of designing new dehalogenases and method of use thereof are also provided. The dehalogenases have increased activity and stability at increased pH and temperature.

20 Claims, 26 Drawing Sheets

(A=SEQ ID NO: 4; B=SEQ ID NO:2; rhod2=SEQ ID NO:40; C=SEQ ID NO:6; myco4=SEQ ID NO:42)

Summary of the catalytic and thermal amino acid upmutants:

```
                    1 *                                                    50
        A      MGDSHHHHHH GMSEIGTGFP FDPHYVEVLG ERMHYVDVGP RDGTPVLFLH
        B      MGGSHHHHHH GMSEIGTGFP FDPHYVEVLG ERMHYVDVGP RDGTPVLFLH
     rhod2     ---------- -MSEIGTGFP FDPHYVEVLG ERMHYVDVGP RDGTPVLFLH
        C      MGDSHHHHHH GMSEIGTGFP FDPHYVEVLG ERMHYVDVGP RDGTPVLFLH
     myco4     ---------- -MSEIGTGFP FDPHYVEVLG ERMHYVDVGP RDGTPVLFLH
  Consensus    ---------- -MSEIGTGFP FDPHYVEVLG ERMHYVDVGP RDGTPVLFLH 51                                        *  *       100
        A      GNPTSSYLWR NIIPHVAPSH RCIAPDLIGM GKSDKPDLDY FFDDHVRYLD
        B      GNPTSSYLWR NIIPHVAPSH RCIAPDLIGM GKSDKPDLDY FFDDHVRYLD
     rhod2     GNPTSSYLWR NIIPHVAPSH RCIAPDLIGM GKSDKPDLDY FFDDHVRYLD
        C      GNPTSSYLWR NIIPHVAPSH RCIAPDLIGM GKSDKPDLGY SFDDHVRYLD
     myco4     GNPTSSYLWR NIIPHVAPSH RCIAPDLIGM GKSDKPDLDY FFDDHVRYLD
  Consensus    GNPTSSYLWR NIIPHVAPSH RCIAPDLIGM GKSDKPDL-Y -FDDHVRYLD 101                                                   150
        A      AFIEALGLEE VVLVIHDWGS ALGFHWAKRN PERVKGIACM EFIRPIPTWD
        B      AFIEALGLEE VVLVIHDWGS ALGFHWAKRN PERVKGIACM EFIRPIPTWD
     rhod2     AFIEALGLEE VVLVIHDWGS ALGFHWAKRN PERVKGIACM EFIRPIPTWD
        C      AFIEALGLEE VVLVIHDWGS ALGFHWAKRN PERVKGIACM EFIRPIPTWD
     myco4     AFIEALGLEE VVLVIHDWGS ALGFHWAKRN PERVKGIACM EFIRPIPTWD
  Consensus    AFIEALGLEE VVLVIHDWGS ALGFHWAKRN PERVKGIACM EFIRPIPTWD 151    *                          *    *              200
        A      EWPEFARETF QAFRTADVGR ELIIDQNAFI EGVLPKFVVR PLTEVEMDHY
        B      EWPEFARETF QAFRTADVGR ELIIDQNAFI EGVLPKCVVR PLTEVEMDHY
     rhod2     EWPEFARETF QAFRTADVGR ELIIDQNAFI EGALPKCVVR PLTEVEMDHY
        C      EWPEFARELP QAFRTADVGR ELIIDQNAFI EVVLPKFVVR PLTEVEMDHY
     myco4     EWPEFARETF QAFRTADVGR ELIIDQNAFI EGALPKFVVR PLTEVEMDHY
  Consensus    EWPEFARE-F QAFRTADVGR ELIIDQNAFI E--LPK-VVR PLTEVEMDHY 201              *                       *           250
        A      REPFLKPVDR EPLWRFPNEI PIAGEPANIV ALVEAYMNWL HQSPVPKLLF
        B      REPFLKPVDR EPLWRFPNEI PIAGEPANIV ALVEAYMNWL HQSPVPKLLF
     rhod2     REPFLKPVDR EPLWRFPNEL PIAGEPANIV ALVEAYMNWL HQSPVPKLLF
        C      REPFLKPVDR EPLWRFPNEL PIAGEPANIV ALVEAYMTWL HQSPVPKLLF
     myco4     REPFLKPVDR EPLWRFPNEL PIAGEPANIV ALVEAYMNWL HQSPVPKLLF
  Consensus    REPFLKPVDR EPLWRFPNE- PIAGEPANIV ALVEAYM-WL HQSPVPKLLF 251*                                                  300
        A      WGTPGVLIPP AEAARLAESL PNCKTVDIGP GLHYLQEDNP DLIGSEIARW
        B      WGTPGVLIPP AEAARLAESL PNCKTVDIGP GLHYLQEDNP DLIGSEIARW
     rhod2     WGTPGVLIPP AEAARLAESL PNCKTVDIGP GLHYLQEDNP DLIGSEIARW
        C      YGTPGVLIPP AEAARLAESL PNCKTVDIGP GLHYLQEDNP DLIGSEIARW
     myco4     WGTPGVLISP AEAARLAESL PNCKTVDIGP GLHFLQEDNP DLIGSEIARW
  Consensus    -GTPGVLI-P AEAARLAESL PNCKTVDIGP GLH-LQEDNP DLIGSEIARW 301 *           319
        A      LPGLASGLGD YKDDDDK*-
        B      LPGLASGLGD YKDDDDK*-
     rhod2     LPAL------ ---------
        C      LAGLASGLGD YKDDDDK*-
     myco4     LPALIVGKSI EFDGGWAT*
  Consensus    L--L------ ---------
```

(SEQ ID NOS:9 and 10)

```
1
ATG AAC GCA ACG GAA CAC GAC AAG CGC TAC ATC GAG GTG CTG GGT AAG CGA
Met Asn Ala Thr Glu His Asp Lys Arg Tyr Ile Glu Val Leu Gly Lys Arg

ATG GCC TAT GTC GAG ATG GGC GAG GGT GAT CCC ATC ATT TTC CAA CAC GGC
Met Ala Tyr Val Glu Met Gly Glu Gly Asp Pro Ile Ile Phe Gln His Gly

AAT CCG ACC TCA TCG TAC CTG TGG CGC AAC ATC ATG CCC CAT GTG CAA CAG
Asn Pro Thr Ser Ser Tyr Leu Trp Arg Asn Ile Met Pro His Val Gln Gln

CTC GGT CGC TGC ATA GCG CTC GAC CTG ATC GGC ATG GGC GAT TCA GAA AAA
Leu Gly Arg Cys Ile Ala Leu Asp Leu Ile Gly Met Gly Asp Ser Glu Lys

CTC GAG GAC TCC GGA CCC GAG CGC TAC ACG TTC GTC GAG CAC AGC CGG TAT
Leu Glu Asp Ser Gly Pro Glu Arg Tyr Thr Phe Val Glu His Ser Arg Tyr

TTT GAT GCC GCG CTC GAA GCC CTG GGT GTG ACG AGC AAC GTG ACG CTG GTG
Phe Asp Ala Ala Leu Glu Ala Leu Gly Val Thr Ser Asn Val Thr Leu Val

ATC CAC GAT TGG GGT TCA GCG CTG GGC TTC CAC TGG GCT AAC CGC TAT CGT
Ile His Asp Trp Gly Ser Ala Leu Gly Phe His Trp Ala Asn Arg Tyr Arg

GAT GAC GTA AAA GGT ATC TGC TAC ATG GAA GCC ATC GTG TCG CCG CTG ACC
Asp Asp Val Lys Gly Ile Cys Tyr Met Glu Ala Ile Val Ser Pro Leu Thr

TGG GAT ACG TTT CCG GAA GGT GCG CGT GGT GTT TTC CAG GGG TTT CGT TCA
Trp Asp Thr Phe Pro Glu Gly Ala Arg Gly Val Phe Gln Gly Phe Arg Ser

CCG GCT GGC GAA GCA ATG GTG CTT GAG AAC AAT GTG TTC GTC GAA AAC GTA
Pro Ala Gly Glu Ala Met Val Leu Glu Asn Asn Val Phe Val Glu Asn Val

CTT CCC GGG TCG ATA CTC AGA GAC CTC AGC GAG GAA GAA ATG AAC GTC TAC
Leu Pro Gly Ser Ile Leu Arg Asp Leu Ser Glu Glu Glu Met Asn Val Tyr

CGG CGC CCT TTC ACG GAG CCT GGC GAA GGT CGG CGT CCG ACG CTC ACC TGG
Arg Arg Pro Phe Thr Glu Pro Gly Glu Gly Arg Arg Pro Thr Leu Thr Trp

CCA CGG CAG ATT CCG ATC GAT GGC GAA CCT GCA GAC GTC GTC GCC CTG GTA
Pro Arg Gln Ile Pro Ile Asp Gly Glu Pro Ala Asp Val Val Ala Leu Val

GCC GAG TAC GCC GCC TGG TTG CAG AGT GCG GAA GTA CCG AAG TTG TTT GTG
Ala Glu Tyr Ala Ala Trp Leu Gln Ser Ala Glu Val Pro Lys Leu Phe Val

AAT GCT GAA CCA GGG GCG TTG CTC ACG GGA CCG CAG CGC GAG TTC TGC CGG
Asn Ala Glu Pro Gly Ala Leu Leu Thr Gly Pro Gln Arg Glu Phe Cys Arg

AGT TGG ACC AAT CAG AGC GAG GTC ACC GTG TCA GGT AGC CAC TTC ATC CAG
Ser Trp Thr Asn Gln Ser Glu Val Thr Val Ser Gly Ser His Phe Ile Gln

GAA GAT TCA CCG GAT GAG ATC GGT GAA GCA TTG AAA GTG TGG ATG ACT GGA
Glu Asp Ser Pro Asp Glu Ile Gly Glu Ala Leu Lys Val Trp Met Thr Gly

870
TAG
End
```

FIGURE 6B

124DL4
(SEQ ID NOS:11 and 12)

```
1
ATG CAG GTG GGG ATC GCC GCT ACG CTC GCC GAA ATG GAC AAG AAA CGT GTC
Met Gln Val Gly Ile Ala Ala Thr Leu Ala Glu Met Asp Lys Lys Arg Val

CGT GTG TAC AAC GCG GAG ATG GCC TAT GTC GAC ACG GGC CAG GGT GAT TCC
Arg Val Tyr Asn Ala Glu Met Ala Tyr Val Asp Thr Gly Gln Gly Asp Ser

GTT CTG TTT CTT CAC GGC AAC CCG ACG TCG TCG TAT CTG TGG AGG GGC GTA
Val Leu Phe Leu His Gly Asn Pro Thr Ser Ser Tyr Leu Trp Arg Gly Val

ATG CCT TTT GTG ACG GAC GTC GCC CGA TGT GTG GCT CCG GAC CTG ATC GGT
Met Pro Phe Val Thr Asp Val Ala Arg Cys Val Ala Pro Asp Leu Ile Gly

ATG GGC GAT TCC GAC AAG CTC GAG TCG TCG ATG TAC CGC TTC GAG GAT CAC
Met Gly Asp Ser Asp Lys Leu Glu Ser Ser Met Tyr Arg Phe Glu Asp His

CGG CGG TAC CTG GAT GGT TTC CTC GAT GCG GTG GAC ATC GGA GAC GAT GTG
Arg Arg Tyr Leu Asp Gly Phe Leu Asp Ala Val Asp Ile Gly Asp Asp Val

ACG GTT GTG GTG CAC GAC TGG GGC TCT GCA CTC GGC TTC GAC TGG GCG AAC
Thr Val Val Val His Asp Trp Gly Ser Ala Leu Gly Phe Asp Trp Ala Asn

CGG CAC CGC GAC CGG GTC AAA GGA ATC GCA TAC ATG GAA GCG ATC GTT CGT
Arg His Arg Asp Arg Val Lys Gly Ile Ala Tyr Met Glu Ala Ile Val Arg

CCA TTG AGC TGG GAG GAG TGG CCG GAC GCA TCT CGC CGC CTG TTC GAG GCA
Pro Leu Ser Trp Glu Glu Trp Pro Asp Ala Ser Arg Arg Leu Phe Glu Ala

ATG CGC TCA GAC GCG GGG GAG GAG ATC GTT CTC GAA AAG AAT GTC TTC GTC
Met Arg Ser Asp Ala Gly Glu Glu Ile Val Leu Glu Lys Asn Val Phe Val

GAG CGG ATT CTG CTC GGC TCG GTC CTT TGT GAT CTG ACC GAG GAG GAA ATG
Glu Arg Ile Leu Leu Gly Ser Val Leu Cys Asp Leu Thr Glu Glu Glu Met

GCG GAG TAC CGG CGC CCG TAC CTC GAG CCG GGT GAG TCA CGG CGC CCG ATG
Ala Glu Tyr Arg Arg Pro Tyr Leu Glu Pro Gly Glu Ser Arg Arg Pro Met

CTG ACA TGG CCA CGC GAG ATC CCG ATC GAC GGC CAC CCC GCC GAC GTT GCG
Leu Thr Trp Pro Arg Glu Ile Pro Ile Asp Gly His Pro Ala Asp Val Ala

AAG ATC GTC GCG GAG TAC TCG TCG TGG CTC TCC GGG TCG GAG GTG CCG AAG
Lys Ile Val Ala Glu Tyr Ser Ser Trp Leu Ser Gly Ser Glu Val Pro Lys

CTC TTC GTC GAT GCC GAC CCG GGC GCC ATC CTG ACA GGT CCG AAG CGA GAC
Leu Phe Val Asp Ala Asp Pro Gly Ala Ile Leu Thr Gly Pro Lys Arg Asp

TTC TGC AGG GCG TGG CCG AAC CAG GTC GAG ACG ACC GTG GCA GGA ATC CAC
Phe Cys Arg Ala Trp Pro Asn Gln Val Glu Thr Thr Val Ala Gly Ile His

TTC ATA CAG GAG GAT TCC TCC GCC GAG ATC GGA GCC GCG ATC AGG ACC TGG
Phe Ile Gln Glu Asp Ser Ser Ala Glu Ile Gly Ala Ala Ile Arg Thr Trp

882
TAC CTG GGA CTC TGA
Tyr Leu Gly Leu End
```

FIGURE 6C
124DL5
(SEQ ID NOS:13 and 14)

1
ATG GAG AAA CAC CGC GTA GAA GTT CTC GGT TCG GAG ATG GCC TAC ATC GAC
Met Glu Lys His Arg Val Glu Val Leu Gly Ser Glu Met Ala Tyr Ile Asp

GTG GGA GAG GGC GAC CCG ATC GTG TTC CTC CAC GGA AAT CCC ACG TCG TCG
Val Gly Glu Gly Asp Pro Ile Val Phe Leu His Gly Asn Pro Thr Ser Ser

TAC CTG TGG CGG AAC GTG ATT CCC CAC GTT GCC GGC TTG GGA CGC TGC ATC
Tyr Leu Trp Arg Asn Val Ile Pro His Val Ala Gly Leu Gly Arg Cys Ile

GCC CCG GAT CTG ATC GGC ATG GGA GAC TCG GAT AAG GTC CAT GGT CTC GAG
Ala Pro Asp Leu Ile Gly Met Gly Asp Ser Asp Lys Val His Gly Leu Glu

TAC CGC TTC GTT GAT CAC CGC CGG TAC CTC GAC GCC TTC CTT GAA GCG GTC
Tyr Arg Phe Val Asp His Arg Arg Tyr Leu Asp Ala Phe Leu Glu Ala Val

GGC GTT GAG GAT GCT GTG ACA TTC ATC GTA CAC GAC TGG GGC TCG GCT CTC
Gly Val Glu Asp Ala Val Thr Phe Ile Val His Asp Trp Gly Ser Ala Leu

GGA TTC GAC TGG GCG AAC CGT CAC CGT GAA GCG GTC GAA GGC ATC GCA TAC
Gly Phe Asp Trp Ala Asn Arg His Arg Glu Ala Val Glu Gly Ile Ala Tyr

ATG GAG GCG ATC GTG CAC CCG GTT GCT TGG AAC GAC TGG CCG GAG CTC TCT
Met Glu Ala Ile Val His Pro Val Ala Trp Asn Asp Trp Pro Glu Leu Ser

CGA CCG ATA TTT CAG GCG ATG AGG TCC TCG TCC GGT GAG AAG ATC GTG CTT
Arg Pro Ile Phe Gln Ala Met Arg Ser Ser Ser Gly Glu Lys Ile Val Leu

GAG AAG AAC GTG TTC GTG GAG CGA ATC CTG CCC GCT TCC GTG ATG CGC GAT
Glu Lys Asn Val Phe Val Glu Arg Ile Leu Pro Ala Ser Val Met Arg Asp

CTG AGC GAC GAC GAG ATG GAT GAG TAC CGT CGA CCG TTC CAG AAC CCG GGA
Leu Ser Asp Asp Glu Met Asp Glu Tyr Arg Arg Pro Phe Gln Asn Pro Gly

GAG GAT CGA AGA CCC ACG CTG ACG TGG CCA CGG GAG ATC CCG ATC GAT GGA
Glu Asp Arg Arg Pro Thr Leu Thr Trp Pro Arg Glu Ile Pro Ile Asp Gly

GAA CCG GGG GAC GTC GCC GCC ATC GTC GAT GAC TAC GGG CGA TGG CTC TCG
Glu Pro Gly Asp Val Ala Ala Ile Val Asp Asp Tyr Gly Arg Trp Leu Ser

GAG AGC GAT GTC CCA AAG CTC TTC ATC GAC GCG GAT CCG GGA GCG ATC CTC
Glu Ser Asp Val Pro Lys Leu Phe Ile Asp Ala Asp Pro Gly Ala Ile Leu

GTG GGT CCA GCG CGT GGG TTC TGC CGC GGC TGG CGG AAC CAG ACC GAA GTG
Val Gly Pro Ala Arg Gly Phe Cys Arg Gly Trp Arg Asn Gln Thr Glu Val

AGC GTC ACA GGA ACC CAC TTC ATC CAG GAA GAC TCT CCC GAC GAG ATC GGC
Ser Val Thr Gly Thr His Phe Ile Gln Glu Asp Ser Pro Asp Glu Ile Gly

849
GCT GCG CTG GCT CGA TGG ATC GAG AAC CGG TAA
Ala Ala Leu Ala Arg Trp Ile Glu Asn Arg End

FIGURE 6D
150DL2
(SEQ ID NOS:15 and 16)

```
1
ATG GCT AGC GCG CCT ATC GAC CCG ACC GAC CCG CAT CCG AGA AAG CGG ATC
Met Ala Ser Ala Pro Ile Asp Pro Thr Asp Pro His Pro Arg Lys Arg Ile

GCC GTG CTC GAT TCG GAG ATG AGC TAC GTC GAT ACC GGC GAG GGA GCG CCG
Ala Val Leu Asp Ser Glu Met Ser Tyr Val Asp Thr Gly Glu Gly Ala Pro

ATC GTG TTC CTT CAC GGC AAC CCG ACT TCC TCC TAT CTT TGG CGC AAC ATC
Ile Val Phe Leu His Gly Asn Pro Thr Ser Ser Tyr Leu Trp Arg Asn Ile

ATC CCC TAT CTC GCG GAT CAC GGC AGA TGC CTC GCA CCG GAT CTG GTC GGG
Ile Pro Tyr Leu Ala Asp His Gly Arg Cys Leu Ala Pro Asp Leu Val Gly

ATG GGC CGC TCC GGA AAA TCG CCG ACC CGG TCC TAT GGC TTT ACC GAT CAC
Met Gly Arg Ser Gly Lys Ser Pro Thr Arg Ser Tyr Gly Phe Thr Asp His

GCG CGC TAT TTG GAC GCA TGG TTC GAC GCC CTG GAC CTG ACC CGC GAC GTG
Ala Arg Tyr Leu Asp Ala Trp Phe Asp Ala Leu Asp Leu Thr Arg Asp Val

ACC CTG GTG ATT CAT GAC TGG GGA TCG GCG CTG GGC TTC CAC CGT GCC TTT
Thr Leu Val Ile His Asp Trp Gly Ser Ala Leu Gly Phe His Arg Ala Phe

CGC TTC CCC GAA CAG ATC AAG GCG ATC GCC TAT ATG GAG GCC ATC GTC CGG
Arg Phe Pro Glu Gln Ile Lys Ala Ile Ala Tyr Met Glu Ala Ile Val Arg

CCG CTC GTC TGG GCC GAC ATC GCC GGC GCC GAG CAG GCG TTT CGC GCG ATC
Pro Leu Val Trp Ala Asp Ile Ala Gly Ala Glu Gln Ala Phe Arg Ala Ile

CGA TCC GAG GCC GGC GAA CAC ATG ATT CTG GAC GAG AAC TTT TTC GTC GAA
Arg Ser Glu Ala Gly Glu His Met Ile Leu Asp Glu Asn Phe Phe Val Glu

GTG CTC CTT CCG GCG AGC ATC CTG CGC AGA TTG AGC GAT CTG GAG ATG GCC
Val Leu Leu Pro Ala Ser Ile Leu Arg Arg Leu Ser Asp Leu Glu Met Ala

GCC TAC CGC GCA CCG TTC CTC GAC CGG GAG TCG CGA TGG CCG ACC CTG CGC
Ala Tyr Arg Ala Pro Phe Leu Asp Arg Glu Ser Arg Trp Pro Thr Leu Arg

TGG CCG CGC GAG GTT CCG ATC GAG GGG GAG CCG GCC GAC GTG ACC GCC ATC
Trp Pro Arg Glu Val Pro Ile Glu Gly Glu Pro Ala Asp Val Thr Ala Ile

GTC GAG GCC TAC GGA CGA TGG ATG GCC GAG AAC ACG CTG CCG AAG CTG CTG
Val Glu Ala Tyr Gly Arg Trp Met Ala Glu Asn Thr Leu Pro Lys Leu Leu

GTC TTG GGT GAT CCG GGA GTG ATC GCT ACC GGC CGC ACG CGC GAC TTC TGT
Val Leu Gly Asp Pro Gly Val Ile Ala Thr Gly Arg Thr Arg Asp Phe Cys

CGA AGC TGG AAG AAT CAG CGG GAG GTC ACC GTA TCC GGC AGC CAC TTC CTT
Arg Ser Trp Lys Asn Gln Arg Glu Val Thr Val Ser Gly Ser His Phe Leu

CAG GAA GAC TCG CCG CAC GAG ATC GGC CTC GCG CTC CGG GAT TTC GTG CGG
Gln Glu Asp Ser Pro His Glu Ile Gly Leu Ala Leu Arg Asp Phe Val Arg

876
TCG GCG TAA
Ser Ala End
```

FIGURE 6E
149DL1
(SEQ ID NOS:17 and 18)

```
1
ATG CAA TTA ACG AAT GAA ACA GAA GCC AAC GCG ATC TCT GCG ACA AGT CCC
Met Gln Leu Thr Asn Glu Thr Glu Ala Asn Ala Ile Ser Ala Thr Ser Pro

TAC CCA AAA TTT CGG CGG TCG GTC TTC GGC CGC GAG ATG GCG TAC GTG GAA
Tyr Pro Lys Phe Arg Arg Ser Val Phe Gly Arg Glu Met Ala Tyr Val Glu

GTG GGA CGG GGC GAC CCC ATC GTA CTC TTG CAC GGC AAC CCC ACC TCG TCG
Val Gly Arg Gly Asp Pro Ile Val Leu Leu His Gly Asn Pro Thr Ser Ser

TAC CTC TGG CGC AAC GTG TTG CCG CAC CTG GCG CCG TTA GGC CGC TGT ATC
Tyr Leu Trp Arg Asn Val Leu Pro His Leu Ala Pro Leu Gly Arg Cys Ile

GCT CCA GAC CTG ATT GGT ATG GGA GAC TCA GAC AAA CTG CGT GAC AGT GGG
Ala Pro Asp Leu Ile Gly Met Gly Asp Ser Asp Lys Leu Arg Asp Ser Gly

CCG GGC TCA TAT CGC TTC GTC GAG CAG CGC CGT TAC CTC GAC GCC CTG CTC
Pro Gly Ser Tyr Arg Phe Val Glu Gln Arg Arg Tyr Leu Asp Ala Leu Leu

GAG GCT CTG GAC GTG CAC GAG CGA GTC ACG TTT GTC ATC CAT GAC TGG GGC
Glu Ala Leu Asp Val His Glu Arg Val Thr Phe Val Ile His Asp Trp Gly

TCG GCC CTC GGA TTT GAT TGG GCC AAC CGC CAC CGC GAA GCA ATG AGG GGT
Ser Ala Leu Gly Phe Asp Trp Ala Asn Arg His Arg Glu Ala Met Arg Gly

ATC GCG TAC ATG GAG GCG ATT GTG CGG CCG CAG GGC GGG GAC CAC TGG GAC
Ile Ala Tyr Met Glu Ala Ile Val Arg Pro Gln Gly Gly Asp His Trp Asp

AAC ATC AAC ATG CGT CCA CCC TTG CAG GCG CTG CGT TCA TGG GCC GGC GAG
Asn Ile Asn Met Arg Pro Pro Leu Gln Ala Leu Arg Ser Trp Ala Gly Glu

GTG ATG GTC CTG CAA GAC AAC TTC TTT ATC GAG AAG ATG CTG CCA GGG GGC
Val Met Val Leu Gln Asp Asn Phe Phe Ile Glu Lys Met Leu Pro Gly Gly

ATC CTG CGC GCC CTC TCC GCA GGG GAG ATG GCA GAA TAC CGG CGG CCG TTT
Ile Leu Arg Ala Leu Ser Ala Gly Glu Met Ala Glu Tyr Arg Arg Pro Phe

GCC GAG CCC GGC GAG GGG CGA CGA CCG ACG CTG ACA TGG CCC CGG GAA CTC
Ala Glu Pro Gly Glu Gly Arg Arg Pro Thr Leu Thr Trp Pro Arg Glu Leu

CCC ATA GAA GGC GAC CCC GCC GAA GTG GCT GCG ATC GTG GCC GCC TAC GCG
Pro Ile Glu Gly Asp Pro Ala Glu Val Ala Ala Ile Val Ala Ala Tyr Ala

GAC TGG TTA GCG ACA AGT GAT GTG CCC AAG CTT TTC CTG AAG GCC GAG CCC
Asp Trp Leu Ala Thr Ser Asp Val Pro Lys Leu Phe Leu Lys Ala Glu Pro

GGG GCG CTC ATC GCC GGC GGA GCG AAT CTC GAG ACC GTC CGC AAA TGG CCG
Gly Ala Leu Ile Ala Gly Gly Ala Asn Leu Glu Thr Val Arg Lys Trp Pro

GCG CAG ACC GAG GTA ACG GTC GCG GGG ATC CAT TTC ATC CAG GAA GAT TCG
Ala Gln Thr Glu Val Thr Val Ala Gly Ile His Phe Ile Gln Glu Asp Ser

918
CCG GAC GAG ATC GGC CGG GCG ATC GCC GAT TGG ATG AGG GCG TTG AGC TGA
Pro Asp Glu Ile Gly Arg Ala Ile Ala Asp Trp Met Arg Ala Leu Ser End
```

FIGURE 6F
149d19
(SEQ ID NOS:19 and 20)

```
1
ATG CTC GTT GCG CAG ACA AGG AAG CAT CCA ATG ACT GAA ACG CCG CTG ACA
Met Leu Val Ala Gln Thr Arg Lys His Pro Met Thr Glu Thr Pro Leu Thr

AAA AAC ACC GTC GAT GTG CTG GGC ACG TCG ATG GCC TAT CAC GCG CGC GGC
Lys Asn Thr Val Asp Val Leu Gly Thr Ser Met Ala Tyr His Ala Arg Gly

GAG GGT GCG CCA ATA TTG TTT CTG CAC GGC AAC CCG ACC TCG TCC TAT CTG
Glu Gly Ala Pro Ile Leu Phe Leu His Gly Asn Pro Thr Ser Ser Tyr Leu

TGG CGC GAC GTC ATT CCC GAA CTG GAG GGA CGC GGC CGG CTG ATC GCG CCG
Trp Arg Asp Val Ile Pro Glu Leu Glu Gly Arg Gly Arg Leu Ile Ala Pro

GAT CTG ATC GGG ATG GGC GAT TCC GCC AAA TTG CCA GAT CCC GGT GCG GAC
Asp Leu Ile Gly Met Gly Asp Ser Ala Lys Leu Pro Asp Pro Gly Ala Asp

ACC TAT CGC TTC ACG ACT CAT CGC AAA TAT CTC GAT GCC TTC GTC GAT GCG
Thr Tyr Arg Phe Thr Thr His Arg Lys Tyr Leu Asp Ala Phe Val Asp Ala

GTG ATC GGC CCG GCG CAA TCC ATC GTG ATG GTG GTG CAC GAC TGG GGC TCG
Val Ile Gly Pro Ala Gln Ser Ile Val Met Val Val His Asp Trp Gly Ser

GCG CTC GGT TTC GAC TGG GCC AAC CGT CAC CGC AAC CGT ATC CGT GGT ATC
Ala Leu Gly Phe Asp Trp Ala Asn Arg His Arg Asn Arg Ile Arg Gly Ile

GCC TAT ATG GAG GGG ATC GTG CGC CCG ATC GCC TCC TGG GAT GAA TGG AGC
Ala Tyr Met Glu Gly Ile Val Arg Pro Ile Ala Ser Trp Asp Glu Trp Ser

GCG TCG GCC ACG CCG ATC TTC CAG GGA TTT CGC TCC GAC AAG GGC GAG ACC
Ala Ser Ala Thr Pro Ile Phe Gln Gly Phe Arg Ser Asp Lys Gly Glu Thr

ATG ATC CTG GAG CGC AAC ATG TTC GTC GAG CGG GTG CTG CCG GGG TCG GTG
Met Ile Leu Glu Arg Asn Met Phe Val Glu Arg Val Leu Pro Gly Ser Val

TTG CGG AAA CTG ACC GAG GCC GAG ATG GCG GAA TAC CGC CGG CCC TAT CCG
Leu Arg Lys Leu Thr Glu Ala Glu Met Ala Glu Tyr Arg Arg Pro Tyr Pro

AAA GCC GAG GAC CGC TGG CCG ACG CTG ACC TGG CCG CGC CAG ATC CCG ATC
Lys Ala Glu Asp Arg Trp Pro Thr Leu Thr Trp Pro Arg Gln Ile Pro Ile

GCC GGC GAA CCC GCC GAT GTG GTG CAG ATC GCG GCG GAG TAT TCA CGA TGG
Ala Gly Glu Pro Ala Asp Val Val Gln Ile Ala Ala Glu Tyr Ser Arg Trp

ATG GCG GAG AAC GAC ATC CCA AAA CTG TTC GTC AAC GCC GAG CCC GGT GCG
Met Ala Glu Asn Asp Ile Pro Lys Leu Phe Val Asn Ala Glu Pro Gly Ala

ATC CTG ACC GGC GCG CCC CGG GAT TTC TGC CGA AGC TGG AAA AGC CAG ACC
Ile Leu Thr Gly Ala Pro Arg Asp Phe Cys Arg Ser Trp Lys Ser Gln Thr

GAA GTC ACC GTC GCG GGC TCG CAT TTC ATC CAG GAA GAC TCC GGA CCG GCG
Glu Val Thr Val Ala Gly Ser His Phe Ile Gln Glu Asp Ser Gly Pro Ala

912
ATC GGC CGG GCG GTA GCC GCC TGG ATG ACG GCG AAT GGG CTA TAG
Ile Gly Arg Ala Val Ala Ala Trp Met Thr Ala Asn Gly Leu End
```

FIGURE 6G
151d18
(SEQ ID NOS:21 and 22)

```
1
ATG GCT AGC ATG ACC CAG GTT TCC ATC TCG ACC GAG GAC GCT TCC TAC CGG
Met Ala Ser Met Thr Gln Val Ser Ile Ser Thr Glu Asp Ala Ser Tyr Arg

AAG CGG GTC CGC GTG CTC GAT ACC GAC ATG GCC TAT GTC GAC GTG GGC GAA
Lys Arg Val Arg Val Leu Asp Thr Asp Met Ala Tyr Val Asp Val Gly Glu

GGC GAT CCG ATC GTG TTC CTG CAC GGC AAC CCG ACG CCG TCG TTC CTG TGG
Gly Asp Pro Ile Val Phe Leu His Gly Asn Pro Thr Pro Ser Phe Leu Trp

CGC AAC ATC ATC CCC TAC GCC CTG CCC TTC GGC CGC TGC CTC GCG CCC GAC
Arg Asn Ile Ile Pro Tyr Ala Leu Pro Phe Gly Arg Cys Leu Ala Pro Asp

TAC GTG GGG ATG GGC AAT TCC GGG CCG GCG CCG GGC GGG TCG TAT CGA TTC
Tyr Val Gly Met Gly Asn Ser Gly Pro Ala Pro Gly Gly Ser Tyr Arg Phe

GTC GAT CAC CGG CGC TAT CTC GAC GCC TGG TTC GAG GCC ATG GGC CTG ACG
Val Asp His Arg Arg Tyr Leu Asp Ala Trp Phe Glu Ala Met Gly Leu Thr

GAG AAC GTC ATC CTC GTG GTG CAC GAC TGG GGC TCG GCG CTC GGC TTC GAC
Glu Asn Val Ile Leu Val Val His Asp Trp Gly Ser Ala Leu Gly Phe Asp

TGG GCG CGG CGT CAC CCC GAT CGG GTC AAG GCC ATC GTC TAT ATG GAA GGG
Trp Ala Arg Arg His Pro Asp Arg Val Lys Ala Ile Val Tyr Met Glu Gly

ATC GTC CGG CCG TTC CTG TCC TGG GAC GAA TGG CCG GCC GTC ACG CGC GCC
Ile Val Arg Pro Phe Leu Ser Trp Asp Glu Trp Pro Ala Val Thr Arg Ala

TTC TTC CAG GGC CAG CGC ACG GCG GCG GGC GAG GAC CTG ATT CTC CAG AAG
Phe Phe Gln Gly Gln Arg Thr Ala Ala Gly Glu Asp Leu Ile Leu Gln Lys

AAC CTG TTC ATC GAG TAT CTC CTG CCG CTG CGC GGC ATC CCC AAG GAG GCG
Asn Leu Phe Ile Glu Tyr Leu Leu Pro Leu Arg Gly Ile Pro Lys Glu Ala

ATC GAG GTC TAC CGC CGT CCC TTC CGG AAC CCC GGT GCC TCG CGC CAG CCG
Ile Glu Val Tyr Arg Arg Pro Phe Arg Asn Pro Gly Ala Ser Arg Gln Pro

ATG CTG ACC TGG ACC CGC GAA CTG CCG ATC GCC GGC GAG CCC GCC GAC GTC
Met Leu Thr Trp Thr Arg Glu Leu Pro Ile Ala Gly Glu Pro Ala Asp Val

GTG GCC ATC GTC GAG GAC TAC GCC CGC TTC CTC TCC ACC AGC CCG ATC CCC
Val Ala Ile Val Glu Asp Tyr Ala Arg Phe Leu Ser Thr Ser Pro Ile Pro

AAG CTG TTC ATC GAC GCC GAG CCC GGC GGC TTC CTG ATC GGC GCC CAG CGC
Lys Leu Phe Ile Asp Ala Glu Pro Gly Gly Phe Leu Ile Gly Ala Gln Arg

GAA TTC TGC CGC GCC TGG CCC AAC CAG ACC GAG GTG ACG GTC CCA GGC GTC
Glu Phe Cys Arg Ala Trp Pro Asn Gln Thr Glu Val Thr Val Pro Gly Val

CAT TTC GTC CAG GAG GAC AGT CCG AGG GCG ATC GGC GAG GCA GTG TCC GCC
His Phe Val Gln Glu Asp Ser Pro Arg Ala Ile Gly Glu Ala Val Ser Ala
                                                                 894
TTC GTT GTT TCG TTG CGG GGC GCG TAG
Phe Val Val Ser Leu Arg Gly Ala End
```

FIGURE 6H
757d16
(SEQ ID NOS:23 and 24)

```
1
ATG AAT GTG GCG CGA GGC GAC ACG GTC GTC ACC GCC GCG GAG CCT GAT GGC
Met Asn Val Ala Arg Gly Asp Thr Val Val Thr Ala Ala Glu Pro Asp Gly

CCG GAC CAC CTG CCT CGG CGT CGC GTG AAG GTG ATG GAT ACC GAA ATC AGC
Pro Asp His Leu Pro Arg Arg Arg Val Lys Val Met Asp Thr Glu Ile Ser

TAT GTC GAT GTC GGT GAA GGT GAG CCC GTC GTC TTT CTG CAC GGC AAT CCC
Tyr Val Asp Val Gly Glu Gly Glu Pro Val Val Phe Leu His Gly Asn Pro

ACG TGG TCC TAT CAA TGG CGC AAT ATC ATT CCT TAC ATC AGC CCC GTT CGC
Thr Trp Ser Tyr Gln Trp Arg Asn Ile Ile Pro Tyr Ile Ser Pro Val Arg

CGC TGT CTC GCG CCC GAT CTT GTC GGC ATG GGT TGG TCC GGC AAG TCG CCG
Arg Cys Leu Ala Pro Asp Leu Val Gly Met Gly Trp Ser Gly Lys Ser Pro

GGC AAA GCC TAT CGT TTC GTC GAT CAG GCC CGC TAC ATG GAT GCC TGG TTC
Gly Lys Ala Tyr Arg Phe Val Asp Gln Ala Arg Tyr Met Asp Ala Trp Phe

GAG GCG TTG CAG CTG ACC CGG AAC GTT ACG TTG GTG TTG CAC GAC TGG GGC
Glu Ala Leu Gln Leu Thr Arg Asn Val Thr Leu Val Leu His Asp Trp Gly

GCG GCC ATC GGC TTC TAT CGC GCC CGG CGC CAT CCT GAG CAG ATA AAG GCG
Ala Ala Ile Gly Phe Tyr Arg Ala Arg Arg His Pro Glu Gln Ile Lys Ala

ATT GCC TAT TAT GAA GCT GTC GCT CAC TCG CGC CGA TGG GAC GAC TTC TCT
Ile Ala Tyr Tyr Glu Ala Val Ala His Ser Arg Arg Trp Asp Asp Phe Ser

GGC GGC CGC GAC CGC CAA TTC CGC CTA TTA CGC TCG CCC GAC GGA GAA CGC
Gly Gly Arg Asp Arg Gln Phe Arg Leu Leu Arg Ser Pro Asp Gly Glu Arg

CTC GTC CTC GAC GAG AAC ATG TTC GTG GAA GTC GTC CTG CCG CGC GGC ATT
Leu Val Leu Asp Glu Asn Met Phe Val Glu Val Val Leu Pro Arg Gly Ile

TTG CGC AAG CTA ACC GAT GAC GAG ATG GAA GCC TAC CGA GCT CCT TAT CGC
Leu Arg Lys Leu Thr Asp Asp Glu Met Glu Ala Tyr Arg Ala Pro Tyr Arg

GAT CGC GAG CGG CGC CTG CCG ACC CTG ATT TGG CCG CGC GAG GTG CCG ATC
Asp Arg Glu Arg Arg Leu Pro Thr Leu Ile Trp Pro Arg Glu Val Pro Ile

GAA GGA GAG CCC GCG GAC GTC GTG GCC ATT GTC GAT GAG AAT GCG CGA TGG
Glu Gly Glu Pro Ala Asp Val Val Ala Ile Val Asp Glu Asn Ala Arg Trp

CTT GCG GCC AGC GAT CGG CTG CCG AAG CTG TTC ATC AAG GGC GAT CCC GGA
Leu Ala Ala Ser Asp Arg Leu Pro Lys Leu Phe Ile Lys Gly Asp Pro Gly

GCA ATC CAT ACC GGA CGC TTG CTC GAT CTG GTT CGC GCG TTT CCC AAT CAG
Ala Ile His Thr Gly Arg Leu Leu Asp Leu Val Arg Ala Phe Pro Asn Gln

CGC GAG GTG ACC GTC AAG GGG CTG CAC CAC CTG CAG GAC GAT TCG CCA GAC
Arg Glu Val Thr Val Lys Gly Leu His His Leu Gln Asp Asp Ser Pro Asp

915
GAA ATC GGC GCT GCG CTG CGG GCA TTC GTG CTC CGC AAA GGG ATT TGA
Glu Ile Gly Ala Ala Leu Arg Ala Phe Val Leu Arg Lys Gly Ile End
```

FIGURE 6I
664d110
(SEQ ID NOS:25 and 26)

```
1
ATG CTG GAC AGG ATT TCT GCC AAA GGC AAT CTT ACT CGT AGC TGC GTA AGC
Met Leu Asp Arg Ile Ser Ala Lys Gly Asn Leu Thr Arg Ser Cys Val Ser

GTC CTT GAC AGC GAG ATG AGT TAC GTC GCG ACT GGT CGG GGG CAC CCA ATC
Val Leu Asp Ser Glu Met Ser Tyr Val Ala Thr Gly Arg Gly His Pro Ile

GTT TTC CTG CAC GGG AAC CCG ACC TCA TCT TAT CTT TGG CGT AAC GTC ATC
Val Phe Leu His Gly Asn Pro Thr Ser Ser Tyr Leu Trp Arg Asn Val Ile

CCC CAC GTC AGC AAC CTT GGC CGG TGC CTC GCG CCG GAC CTC GTT GGT ATG
Pro His Val Ser Asn Leu Gly Arg Cys Leu Ala Pro Asp Leu Val Gly Met

GGC CAG CCG GCC GCC TCT CCA CGG GGC GCC TAT CGC TTT GTG GAC CAT TCA
Gly Gln Pro Ala Ala Ser Pro Arg Gly Ala Tyr Arg Phe Val Asp His Ser

CGT TAT CTC GAC GCA TGG TTT GAG GCC CTG GAC TTG CGT AGA AAC GTT ACC
Arg Tyr Leu Asp Ala Trp Phe Glu Ala Leu Asp Leu Arg Arg Asn Val Thr

CTG GTG GTG CAC GAT TGG GGA TCG GCG CTC GGC TTT CAT TGG GCT TCC AGG
Leu Val Val His Asp Trp Gly Ser Ala Leu Gly Phe His Trp Ala Ser Arg

CAT CCC GAG CGG GTG CGG GCC ATC GCT TAC ATG GAG TCG ATC GTT CAG CCG
His Pro Glu Arg Val Arg Ala Ile Ala Tyr Met Glu Ser Ile Val Gln Pro

CGC GAC TGG GAA GAC CTC CCC CCA AGT CGG GCG CCG ATC TTT CGC GAC CTG
Arg Asp Trp Glu Asp Leu Pro Pro Ser Arg Ala Pro Ile Phe Arg Asp Leu

CGG TCC AAT AAA GGT GAG CGC ATG ATC CTC GAC GAA AAT GCC TTC ATT GAG
Arg Ser Asn Lys Gly Glu Arg Met Ile Leu Asp Glu Asn Ala Phe Ile Glu

ATT CTC TTG CCG AAG CTC GTC ATC CGG ACT CTG ACC AGC GCT GAG ATG GAT
Ile Leu Leu Pro Lys Leu Val Ile Arg Thr Leu Thr Ser Ala Glu Met Asp

GCA TAT CGT CGT CCA TTT ATT GAA CCG AAC TCG CGC TGG CCT ACA CTT ATC
Ala Tyr Arg Arg Pro Phe Ile Glu Pro Asn Ser Arg Trp Pro Thr Leu Ile

TGG CCG CGC GAG CTA CCG ATC GGT GGC GAA CCT GCC GAC GTG GTG AAA ATT
Trp Pro Arg Glu Leu Pro Ile Gly Gly Glu Pro Ala Asp Val Val Lys Ile

GTC GAA GAT TAC GGG CAA TGG CTT CTC AAG ACC CCG TTG CCG AAG TTG TTT
Val Glu Asp Tyr Gly Gln Trp Leu Leu Lys Thr Pro Leu Pro Lys Leu Phe

ATC AAC GCC GAG CCA GGG TCG CTG TTG ATC GGA CGG GCA CGT GAA TTC TGC
Ile Asn Ala Glu Pro Gly Ser Leu Leu Ile Gly Arg Ala Arg Glu Phe Cys

CGC TCC TGG CCA AAT CAA GAG GAA GTG ACG GTT CGG GGT ATC CAT TTT ATT
Arg Ser Trp Pro Asn Gln Glu Glu Val Thr Val Arg Gly Ile His Phe Ile

CAG GAA GAC AGT CCC GAT GAG ATT GGC GCT GCG CTT ACG CGC TTC ATG AGG
Gln Glu Asp Ser Pro Asp Glu Ile Gly Ala Ala Leu Thr Arg Phe Met Arg
                                                                  900
CAA ATA AGT CCA GAT TCC GTG ATC CGA AAC TAA
Gln Ile Ser Pro Asp Ser Val Ile Arg Asn End
```

FIGURE 6J
664d17
(SEQ ID NOS:27 and 28)

```
1
ATG ATC TCT GCA GCA TTT CCG TAC CAA AAG AAG CGG CGG CAG GTC CTC GGC
Met Ile Ser Ala Ala Phe Pro Tyr Gln Lys Lys Arg Arg Gln Val Leu Gly

AGC GAG ATG GCA TAC GTC GAG GTA GGA GAG GGC GAC CCC ATC GTG TCG CTG
Ser Glu Met Ala Tyr Val Glu Val Gly Glu Gly Asp Pro Ile Val Ser Leu

CAC GGT AAT CCC ACC TCG TCC TAC CTC TGG CGC AAC ACA TTG CCC TAC CTG
His Gly Asn Pro Thr Ser Ser Tyr Leu Trp Arg Asn Thr Leu Pro Tyr Leu

CAG CCA CTA GGC CGC TGC ATC GCC CCC GAC CTG ATC GGC ATG GGC GAC TCC
Gln Pro Leu Gly Arg Cys Ile Ala Pro Asp Leu Ile Gly Met Gly Asp Ser

GCC AAG CTG CCT AAC AGT GGC CCC GGC TCG TAT CGA TTC GTC GAG CAC CGC
Ala Lys Leu Pro Asn Ser Gly Pro Gly Ser Tyr Arg Phe Val Glu His Arg

CGC TAC CTC GAC ACC CTG CTC GAG GCC TTA AAT ATG CGC GAG CGG GTC ACC
Arg Tyr Leu Asp Thr Leu Leu Glu Ala Leu Asn Met Arg Glu Arg Val Thr

TTC GTC GCC CAT GAC TGG GGC TCG GCC CTC GCC TTC GAT TGG GCC AAT CGC
Phe Val Ala His Asp Trp Gly Ser Ala Leu Ala Phe Asp Trp Ala Asn Arg

CAC CGC GAG GCA GTG AAG GGT ATC GCG CAC ATG GAG GCG ATC GTG CGG CCG
His Arg Glu Ala Val Lys Gly Ile Ala His Met Glu Ala Ile Val Arg Pro

CAG GAC TGG ACC CAC TGG GAC ACG ATG GGG GCG CGT CCA ATC TTG CAG CAG
Gln Asp Trp Thr His Trp Asp Thr Met Gly Ala Arg Pro Ile Leu Gln Gln

TTG CGT TCC GAG GCT GGC GAG AAG TTG ATG CTG CAA GAA AAC CTC TTC ATC
Leu Arg Ser Glu Ala Gly Glu Lys Leu Met Leu Gln Glu Asn Leu Phe Ile

GAG ACG TTC CTG CCT AAG GCC ATC AAG CGA ACC CTC TCC GCC GAG GAG AAG
Glu Thr Phe Leu Pro Lys Ala Ile Lys Arg Thr Leu Ser Ala Glu Glu Lys

GCG GAG TAT AGA CGG CCG TTC GCC GAG CCG GGC GAG GGG CGA CGG CCG ACG
Ala Glu Tyr Arg Arg Pro Phe Ala Glu Pro Gly Glu Gly Arg Arg Pro Thr

CTG ACG TGG GTC CGG CAG ATC CCC ATC GAC GGC GAG CCC GCC GAC GTG ACT
Leu Thr Trp Val Arg Gln Ile Pro Ile Asp Gly Glu Pro Ala Asp Val Thr

TCG ATC GTA TCC GCC TAT GGG GAG TGG CTG GCG AAA AGC AAT GTG CCC AAG
Ser Ile Val Ser Ala Tyr Gly Glu Trp Leu Ala Lys Ser Asn Val Pro Lys

CTG TTC GTG AAG GCT GAG CCG GGC GTC CTC GTT GCT GGT GGC GCG AAC CTT
Leu Phe Val Lys Ala Glu Pro Gly Val Leu Val Ala Gly Gly Ala Asn Leu

GAC GCC GTC CGC TCA TGG CCA GCA CAG ACC GAG GTG ACG GTC CCG GGA ATC
Asp Ala Val Arg Ser Trp Pro Ala Gln Thr Glu Val Thr Val Pro Gly Ile

CAT TTC ATC CAG GAA GAT TCG CCG GAC GAG ATT GGG CGG GCC ATC GCC GGC
His Phe Ile Gln Glu Asp Ser Pro Asp Glu Ile Gly Arg Ala Ile Ala Gly

888
TGG ATT AAG ACG TTG GGC TAA
Trp Ile Lys Thr Leu Gly End
```

FIGURE 6K
124d148
(SEQ ID NOS:29 and 30)

```
1
ATG ACG GAG CAG GAG ATA TCA GCG GCG TTT CCC TTC GAG TCG AAG TTC GTG
Met Thr Glu Gln Glu Ile Ser Ala Ala Phe Pro Phe Glu Ser Lys Phe Val

GAT GTG CAA GGC TCC CGC ATG CAC TAC GTG GAG GAG GGC TCG GGC GAC CCG
Asp Val Gln Gly Ser Arg Met His Tyr Val Glu Glu Gly Ser Gly Asp Pro

GTG GTG TTC CTC CAC GGC AAC CCG ACC TCG TCC TAC CTG TGG CGG AAC GTC
Val Val Phe Leu His Gly Asn Pro Thr Ser Ser Tyr Leu Trp Arg Asn Val

ATC CCT CAC GTG TCC CCG CTT GCG AGG TGC ATC GCG CCG GAC CTC ATC GGC
Ile Pro His Val Ser Pro Leu Ala Arg Cys Ile Ala Pro Asp Leu Ile Gly

ATG GGG AAG TCG GAC AAA CCG GAT ATC GAG TAC CGC TTC TTC GAC CAC GCC
Met Gly Lys Ser Asp Lys Pro Asp Ile Glu Tyr Arg Phe Phe Asp His Ala

GGG TAC GTT GAC GGG TTC ATC GAG GCA CTG GGA CTG CGG AAC ATC ACC TTC
Gly Tyr Val Asp Gly Phe Ile Glu Ala Leu Gly Leu Arg Asn Ile Thr Phe

GTC GCC TAC GAC TGG GGC TCC GCG CTG GCG TTC CAC TAC GCG CGA CGG CAC
Val Ala Tyr Asp Trp Gly Ser Ala Leu Ala Phe His Tyr Ala Arg Arg His

GAG GAT AAC GTA AAG GGG TTG GCG TTC ATG GAG GCC ATC GTG CGA CCG CTC
Glu Asp Asn Val Lys Gly Leu Ala Phe Met Glu Ala Ile Val Arg Pro Leu

ACC TGG GAC GAG TGG CCG GAG CAG GCA AGG CAG ATG TTC CAG GCG TTC CGG
Thr Trp Asp Glu Trp Pro Glu Gln Ala Arg Gln Met Phe Gln Ala Phe Arg

ACG CCG GGC GTC GGG GAG AAG ATG ATC CTG GAG GAA AAC GCC TTC GTG GAG
Thr Pro Gly Val Gly Glu Lys Met Ile Leu Glu Glu Asn Ala Phe Val Glu

CAG GTG TTG CCG GGA GCG ATC CTC CGC AAG CTG TCC GAC GAG GAG ATG GAC
Gln Val Leu Pro Gly Ala Ile Leu Arg Lys Leu Ser Asp Glu Glu Met Asp

CGC TAC CGG GAG CCG TTC CCC GAC CCC ACC AGC CGG AGG CCG ACG TGG CGC
Arg Tyr Arg Glu Pro Phe Pro Asp Pro Thr Ser Arg Arg Pro Thr Trp Arg

TGG CCC AAC GAG ATA CCT GTC GAG GGG AAG CCG CCG GAC GTG GTT GAG GCA
Trp Pro Asn Glu Ile Pro Val Glu Gly Lys Pro Pro Asp Val Val Glu Ala

GTG CAG GCC TAC GCC GAT TGG ATG GGC GAG TCG GAT GTG CCC AAG CTC CTC
Val Gln Ala Tyr Ala Asp Trp Met Gly Glu Ser Asp Val Pro Lys Leu Leu

CTG TAC GCT CAC CCA GGC GCG ATC CTC CGA GAG CCG CTG CTG GAG TGG TGC
Leu Tyr Ala His Pro Gly Ala Ile Leu Arg Glu Pro Leu Leu Glu Trp Cys

CGC AAC AAC ATG CGC AAC CTG AAG ACG GTC GAC ATC GGG CCC GGG GTG CAC
Arg Asn Asn Met Arg Asn Leu Lys Thr Val Asp Ile Gly Pro Gly Val His

TTC GTG CCG GAG GAC CGC CCC CAC GAG ATC GGG GAG GCC ATC GCG GAG TGG
Phe Val Pro Glu Asp Arg Pro His Glu Ile Gly Glu Ala Ile Ala Glu Trp

882
TAC CAG CGG CTG TAG
Tyr Gln Arg Leu End
```

FIGURE 6L
124d149
(SEQ ID NOS:31 and 32)

```
1
GTG AGC GAG ATC TCC CCG AAA GAG CCC ATG GAC AAG AAG CAC ATC CCC GTA
Met Ser Glu Ile Ser Pro Lys Glu Pro Met Asp Lys Lys His Ile Pro Val

CTC GGA AAA TCG ATG GCG TAC CGG GAC GTA GGT GAG GGA GAC CCG ATC GTC
Leu Gly Lys Ser Met Ala Tyr Arg Asp Val Gly Glu Gly Asp Pro Ile Val

TTC CTG CAC GGC AAC CCC ACC TCG TCG TAT CTC TGG CGC AAC ATC ATC CCC
Phe Leu His Gly Asn Pro Thr Ser Ser Tyr Leu Trp Arg Asn Ile Ile Pro

CAC CTC GAG CCG CAT GCA CGC TGC ATC GCG CCG GAT CTC ATC GGA ATG GGA
His Leu Glu Pro His Ala Arg Cys Ile Ala Pro Asp Leu Ile Gly Met Gly

GAT TCG GAG AAG CTC GAG CCG AGC GGA CCG GAC CGC TAT CGC TTC ATC GAA
Asp Ser Glu Lys Leu Glu Pro Ser Gly Pro Asp Arg Tyr Arg Phe Ile Glu

CAT CGC GAA TAT CTC GAT GGT TTC TTC GAG GCT CTG GCC CTG CAA CAG AAC
His Arg Glu Tyr Leu Asp Gly Phe Phe Glu Ala Leu Ala Leu Gln Gln Asn

GTC ACC CTC GTC GTC CAC GAC TGG GGC TCC GGG CTG GGC TTC GAT TGG GCC
Val Thr Leu Val Val His Asp Trp Gly Ser Gly Leu Gly Phe Asp Trp Ala

AAC CGG AAT CGG GAG CGC ATC AAG GGG ATC GCT TAT ATG GAG GCC ATC GTT
Asn Arg Asn Arg Glu Arg Ile Lys Gly Ile Ala Tyr Met Glu Ala Ile Val

CGC CCG CTC AGC TGG CAA GAC TGG CCC GAC GAC GCC CGC GCG GTC TTT CAG
Arg Pro Leu Ser Trp Gln Asp Trp Pro Asp Asp Ala Arg Ala Val Phe Gln

GGT TTT CGC TCC GAA GCA GGA GAG TCG ATG GTG ATC GAG AAG AAC GTC TTC
Gly Phe Arg Ser Glu Ala Gly Glu Ser Met Val Ile Glu Lys Asn Val Phe

GTC GAA CGG GTC CTG CCC AGC TCG GTC CTG CGG ACG CTC CGT GAC GAG GAG
Val Glu Arg Val Leu Pro Ser Ser Val Leu Arg Thr Leu Arg Asp Glu Glu

ATG GAG GTC TAT CGC AGA CCG TTT CAA GAC GCC GGA GAA TCA AGG CGC CCG
Met Glu Val Tyr Arg Arg Pro Phe Gln Asp Ala Gly Glu Ser Arg Arg Pro

ACC CTC ACC TGG CCC CGC CAG ATC CCG ATC GAG GGG GAG CCG GAG GAT GTG
Thr Leu Thr Trp Pro Arg Gln Ile Pro Ile Glu Gly Glu Pro Glu Asp Val

ACC GAG ATC GCG AGC GCG TAC AGC GCG TGG ATG GCC GAG AAC GAT CTC CCC
Thr Glu Ile Ala Ser Ala Tyr Ser Ala Trp Met Ala Glu Asn Asp Leu Pro

AAG CTC TTC GTT AAC GCC GAG CCG GGC GCG ATC CTG ATC GGT CCG CAG CGC
Lys Leu Phe Val Asn Ala Glu Pro Gly Ala Ile Leu Ile Gly Pro Gln Arg

GAG TTC TGC CGC ACG TGG AAG AAT CAA CGC GAA GTC ACG GTA AGC GGT AGC
Glu Phe Cys Arg Thr Trp Lys Asn Gln Arg Glu Val Thr Val Ser Gly Ser

CAC TTC ATC CAG GAG GAC TCT CCG CAC GAA ATC GGC GAC GCG ATT GCA GGC
His Phe Ile Gln Glu Asp Ser Pro His Glu Ile Gly Asp Ala Ile Ala Gly

885
TGG TAC GCG GAT CTC TAG
Trp Tyr Ala Asp Leu End
```

FIGURE 6M
124d147
(SEQ ID NOS:33 and 34)

```
1
ATG ACC ACC GAA ATC TCG GCA GCC GAC CCC TTC GAG CGG CAC CGG GTC ACC
Met Thr Thr Glu Ile Ser Ala Ala Asp Pro Phe Glu Arg His Arg Val Thr

GTG CTC GAC TCA GAG ATG TCG TAC ATC GAC ACC GGC CCC GGC GCC GCA GGC
Val Leu Asp Ser Glu Met Ser Tyr Ile Asp Thr Gly Pro Gly Ala Ala Gly

AGT GAG CCG ATC GTG TTT CTC CAC GGG AAC CCA ACC TCG TCC TAC CTC TGG
Ser Glu Pro Ile Val Phe Leu His Gly Asn Pro Thr Ser Ser Tyr Leu Trp

CGC AAC ATC ATT CCC CAC GTC CAG CAC CTC GGG CGC TGC CTC GCA CCG GAT
Arg Asn Ile Ile Pro His Val Gln His Leu Gly Arg Cys Leu Ala Pro Asp

CTG ATC GGG ATG GGC AAC TCG GAC CCT TCC CCT AAC GGC AGC TAC CGC TTC
Leu Ile Gly Met Gly Asn Ser Asp Pro Ser Pro Asn Gly Ser Tyr Arg Phe

GTC GAC CAC GTG AAG TAC CTC GAC GCC TGG TTG GAC GCC GTC GGC GTG ACC
Val Asp His Val Lys Tyr Leu Asp Ala Trp Leu Asp Ala Val Gly Val Thr

GAC CAG GTG ACG TTC GTG GTG CAT GAC TGG GGA TCG GCG CTC GGC TTC CAC
Asp Gln Val Thr Phe Val Val His Asp Trp Gly Ser Ala Leu Gly Phe His

TGG GCA GAC CGC CAT CGC GAC GCC ATC CGA GGC TTC GCC TAC ATG GAG GCG
Trp Ala Asp Arg His Arg Asp Ala Ile Arg Gly Phe Ala Tyr Met Glu Ala

ATC GTG CGC CCC GTC GAG TGG GAG GAC TGG CCG CCT GCG GAC GTC TTC CGA
Ile Val Arg Pro Val Glu Trp Glu Asp Trp Pro Pro Ala Asp Val Phe Arg

CGG ATG CGA TCC GAG GAG GGC GAC GAG ATG ATG CTC GAG GGC AAC TTC TTC
Arg Met Arg Ser Glu Glu Gly Asp Glu Met Met Leu Glu Gly Asn Phe Phe

GTC GAG GTG ATC CTG CCC CGC AGC GTC CTC CGC GGG CTC ACT GAC GAA GAG
Val Glu Val Ile Leu Pro Arg Ser Val Leu Arg Gly Leu Thr Asp Glu Glu

ATG GAG GTA TAC CGG CGA CCC TAC CTC GAG CGC GGC GAG TCG CGG CGT CCG
Met Glu Val Tyr Arg Arg Pro Tyr Leu Glu Arg Gly Glu Ser Arg Arg Pro

ACG CTG ACC TGG CCG CGG GAG ATC CCG CTG TCA GGC GAG CCG GCG GAT GTC
Thr Leu Thr Trp Pro Arg Glu Ile Pro Leu Ser Gly Glu Pro Ala Asp Val

GTC GAG ATC GTC AGC GCC TAC AGC AAA TGG CTG TCC GAG ACG ACC GTG CCG
Val Glu Ile Val Ser Ala Tyr Ser Lys Trp Leu Ser Glu Thr Thr Val Pro

AAG CTC CTC GTC ACT GCC GAG CCG GGT GCG ATC CTG AAC GGG CCG CAG CTG
Lys Leu Leu Val Thr Ala Glu Pro Gly Ala Ile Leu Asn Gly Pro Gln Leu

GAG TTC GCT CGC GGG TTT GCC AAC CAG ACC GAG GTC CGA GTC GCC GGC TCG
Glu Phe Ala Arg Gly Phe Ala Asn Gln Thr Glu Val Arg Val Ala Gly Ser

CAC TTC ATC CAG GAG GAC TCG CCA CAC GAG ATC GGC GCC GCC CTC GCC GAG
His Phe Ile Gln Glu Asp Ser Pro His Glu Ile Gly Ala Ala Leu Ala Glu

888
TGG TAC CCG ACG ACG ACC TGA
Trp Tyr Pro Thr Thr Thr End
```

FIGURE 6N
282d16
(SEQ ID NOS:35 and 36)

```
1
ATG TAC GAG AAA CGG TTC GTA TCT GTC CTC GGT CAC CGG ATG GCA TAC GTC
Met Tyr Glu Lys Arg Phe Val Ser Val Leu Gly His Arg Met Ala Tyr Val

GAG CAA GGA GCC GGG GAC CCG ATC GTG TTC CTA CAT GGC AAC CCC ACC TCG
Glu Gln Gly Ala Gly Asp Pro Ile Val Phe Leu His Gly Asn Pro Thr Ser

TCC TAC CTG TGG CGG AAG GTC ATC CCC GCG CTA ACG GAG CAG GGA CGA TGC
Ser Tyr Leu Trp Arg Lys Val Ile Pro Ala Leu Thr Glu Gln Gly Arg Cys

ATC GCT CCC GAC TTG ATC GGC ATG GGC GAC TCC GAG AAG CTG GCT GAC AGC
Ile Ala Pro Asp Leu Ile Gly Met Gly Asp Ser Glu Lys Leu Ala Asp Ser

GGC CCC GGT AGC TAC CGC TTC GTG GAA CAT CGG CGT TTC CTC GAT GCC TTC
Gly Pro Gly Ser Tyr Arg Phe Val Glu His Arg Arg Phe Leu Asp Ala Phe

CTC GAA AGG GTT GGG ATC AGC GAG TCG GTG GTC CTG GTG ATC CAC GAC TGG
Leu Glu Arg Val Gly Ile Ser Glu Ser Val Val Leu Val Ile His Asp Trp

GGT TCG GCC CTC GGC TTC GAC TGG GCC TAC CGC CAC CAA AAC GCC GTC AAG
Gly Ser Ala Leu Gly Phe Asp Trp Ala Tyr Arg His Gln Asn Ala Val Lys

GGG ATC GCA TAT ATG GAA GCG CTG GTC GGG CCT GTA GGT TGG AGC GAC TGG
Gly Ile Ala Tyr Met Glu Ala Leu Val Gly Pro Val Gly Trp Ser Asp Trp

CCG GAG TCG GCC CGG TCC ATC TTC CAG GCT TTC CGC TCC GAA GCC GGG GAC
Pro Glu Ser Ala Arg Ser Ile Phe Gln Ala Phe Arg Ser Glu Ala Gly Asp

AGC CTC ATC CTC GAG AAG AAC TTC TTC GTC GAG CGG GTG CTG CCC GCA TCG
Ser Leu Ile Leu Glu Lys Asn Phe Phe Val Glu Arg Val Leu Pro Ala Ser

GTG CTC GAT CCC CTG CCA GAA GAA GTG CTC GAC GAG TAT CGA CAG CCG TTT
Val Leu Asp Pro Leu Pro Glu Glu Val Leu Asp Glu Tyr Arg Gln Pro Phe

CTC GAA CCG GGC GAG TCT CGC CGA CCC ACC CTC ACC TGG CCT AGG GAG ATC
Leu Glu Pro Gly Glu Ser Arg Arg Pro Thr Leu Thr Trp Pro Arg Glu Ile

CCC ATC GAC GGT GAG CCG GCC GAC GTC CAC GAG ATC GTG TCC GCG TAC AAC
Pro Ile Asp Gly Glu Pro Ala Asp Val His Glu Ile Val Ser Ala Tyr Asn

CGC TGG ATT GGA TCC TCT CCG GTG CCC AAG CTG TAC GTC AAC GCC GAT CCC
Arg Trp Ile Gly Ser Ser Pro Val Pro Lys Leu Tyr Val Asn Ala Asp Pro

GGC TTC TTC AGC CCT GGC ATC GTC GAG GCC ACG GCC GCC TGG CCC AAC CAG
Gly Phe Phe Ser Pro Gly Ile Val Glu Ala Thr Ala Ala Trp Pro Asn Gln

GAA ACA GTC ACG GTC CGT GGC CAC CAT TTC TTG CAG GAA GAC TCT GGT GAA
Glu Thr Val Thr Val Arg Gly His His Phe Leu Gln Glu Asp Ser Gly Glu

861
GCG ATC GGT GAT GCC ATC GCC GAC TGG TAC CGG CGT GTC TCG TGA
Ala Ile Gly Asp Ala Ile Ala Asp Trp Tyr Arg Arg Val Ser End
```

FIGURE 6O
151d17
(SEQ ID NOS:37 and 38)

```
1
ATG AAT GCA ATC GCC AGT GAG CCC TAT GGG CAA CTG AGG TTC CAA GAG ATC
Met Asn Ala Ile Ala Ser Glu Pro Tyr Gly Gln Leu Arg Phe Gln Glu Ile

GCC GGC AAG CAA ATG GCG TAC ATC GAC GAG GGC GTC GGT GAT GCC ATC GTT
Ala Gly Lys Gln Met Ala Tyr Ile Asp Glu Gly Val Gly Asp Ala Ile Val

TTC CAG CAC GGC AAC CCC ACG TCG TCC TAC CTG TGG CGC AAC GTT ATG CCG
Phe Gln His Gly Asn Pro Thr Ser Ser Tyr Leu Trp Arg Asn Val Met Pro

CAC CTG GAA GGG CTG GGC CGG CTG GTG GCG TGC GAT CTG ATC GGG ATG GGG
His Leu Glu Gly Leu Gly Arg Leu Val Ala Cys Asp Leu Ile Gly Met Gly

GCG TCG GAG AAG CTC AGC CCA TCG GGC CCC GAC CGC TAT AAC TAT GCC GAG
Ala Ser Glu Lys Leu Ser Pro Ser Gly Pro Asp Arg Tyr Asn Tyr Ala Glu

CAG CGC GAC TAT CTG TTC GCG CTC TGG GAT GCG CTC GAC CTT GGC GAT CAC
Gln Arg Asp Tyr Leu Phe Ala Leu Trp Asp Ala Leu Asp Leu Gly Asp His

GTG GTG CTG GTG CTG CAT GAC TGG GGC TCA GCA TTG GGC TTC GAC TGG GCC
Val Val Leu Val Leu His Asp Trp Gly Ser Ala Leu Gly Phe Asp Trp Ala

AAC CAG CAT CGC GAC CGA GTG CAG GGC ATC GCA TTC ATG GAG GCG ATC GTC
Asn Gln His Arg Asp Arg Val Gln Gly Ile Ala Phe Met Glu Ala Ile Val

AGC CCG ATC ACA TGG GCC GAC TTC CAT CCC AGC GTG CGA GGC GTG TTC CAG
Ser Pro Ile Thr Trp Ala Asp Phe His Pro Ser Val Arg Gly Val Phe Gln

GGG TTC CGG TCG CCC GAG GGT GAG CGG ATG GTG TTG GAG CAG AAC ATC TTT
Gly Phe Arg Ser Pro Glu Gly Glu Arg Met Val Leu Glu Gln Asn Ile Phe

GTC GAA GGG GTA CTG CCC GGG GCG ATC CAG CGC CGA CTG TCT GAC GAG GAG
Val Glu Gly Val Leu Pro Gly Ala Ile Gln Arg Arg Leu Ser Asp Glu Glu

ATG GGC CAT TAC CGG CAG CCA TTC GTC GAA CCC GGC GAG GAC CGG CGA CCG
Met Gly His Tyr Arg Gln Pro Phe Val Glu Pro Gly Glu Asp Arg Arg Pro

ACC TTG TCG TGG CCA CGG AAC ATC CCC ATC GAC GGC GAG CCG GCC GAG GTC
Thr Leu Ser Trp Pro Arg Asn Ile Pro Ile Asp Gly Glu Pro Ala Glu Val

GTC GCG GTC GTC GAC GAG TAC CGT AGC TGG CTC GAG AAG AGC GAC ATT CCA
Val Ala Val Val Asp Glu Tyr Arg Ser Trp Leu Glu Lys Ser Asp Ile Pro

AAG CTG TTC GTG AAC GCC GAG CCG GGC GCG ATC GTC ACC GGC CGC ATC CGC
Lys Leu Phe Val Asn Ala Glu Pro Gly Ala Ile Val Thr Gly Arg Ile Arg

GAC TAT ATC CGG ACG TGG GCG AAC CTC AGC GAA ATC ACG GTT CCC GGA GTG
Asp Tyr Ile Arg Thr Trp Ala Asn Leu Ser Glu Ile Thr Val Pro Gly Val

CAT TTC ATC CAA GAA GAC AGC CCA GAC GGA ATC GGC TCG GCC GTG GCA CAG
His Phe Ile Gln Glu Asp Ser Pro Asp Gly Ile Gly Ser Ala Val Ala Gln
                                                                  891
TTC CTG CAG CAG CTA CGC GCC TAA
Phe Leu Gln Gln Leu Arg Ala End
```

FIGURE 6P
828DL29-1
(SEQ ID NO:43 and 44)

```
1
atg tca gaa atc ggt aca ggc ttc ccc ttc gac ccc cat tat gtg gaa
Met Ser Glu Ile Gly Thr Gly Phe Pro Phe Asp Pro His Tyr Val Glu gtc ctg ggc gag cgt atg cac tac gtc gat gtt gga ccg cgg gat ggc
Val Leu Gly Glu Arg Met His Tyr Val Asp Val Gly Pro Arg Asp Gly acg cct gtg ctg ttc ctg cac ggt aac ccg acc tcg tcc tac ctg tgg
Thr Pro Val Leu Phe Leu His Gly Asn Pro Thr Ser Ser Tyr Leu Trp cgc aac atc atc ccg cat gta gca ccg agt cat cgg tgc att gct cca
Arg Asn Ile Ile Pro His Val Ala Pro Ser His Arg Cys Ile Ala Pro gac ctg atc ggg atg gga aaa tcg gac aaa cca gac ctc ggt tat ttc
Asp Leu Ile Gly Met Gly Lys Ser Asp Lys Pro Asp Leu Gly Tyr Phe ttc gac gac cac gtc cgc tac ctc gat gcc ttc atc gaa gcc ttg ggt
Phe Asp Asp His Val Arg Tyr Leu Asp Ala Phe Ile Glu Ala Leu Gly ttg gaa gag gtc gtc ttg gtc atc cac gac tgg ggc tca gct ctc gga
Leu Glu Glu Val Val Leu Val Ile His Asp Trp Gly Ser Ala Leu Gly ttc cac tgg gcc aag cgc aat ccg gaa cgg gtc aaa ggt att gca tgt
Phe His Trp Ala Lys Arg Asn Pro Glu Arg Val Lys Gly Ile Ala Cys atg gaa ttc atc cgg tct atc ccg acg tgg gac gaa tgg ccg gaa ttc
Met Glu Phe Ile Arg Ser Ile Pro Thr Trp Asp Glu Trp Pro Glu Phe gcc cgt gag acc ttc cag gcc ttc cgg acc gcc gac gtc ggc cga gag
Ala Arg Glu Thr Phe Gln Ala Phe Arg Thr Ala Asp Val Gly Arg Glu ttg atc atc gat cag aac gct ttc atc gag cat gtg ctc ccg aaa tac
Leu Ile Ile Asp Gln Asn Ala Phe Ile Glu His Val Leu Pro Lys Tyr gtc gtc cgt ccg ctt acg gag gtc gag atg gac cac tat cgc gag ccc
Val Val Arg Pro Leu Thr Glu Val Glu Met Asp His Tyr Arg Glu Pro ttc ctc aag cct gct gac cga gag cca ctg tgg cga ttc ccc aac gag
Phe Leu Lys Pro Ala Asp Arg Glu Pro Leu Trp Arg Phe Pro Asn Glu ctc ccc atc gcc ggt gag ccc gcg aac atc gtc gcg ctc gtc gag gca
Leu Pro Ile Ala Gly Glu Pro Ala Asn Ile Val Ala Leu Val Glu Ala tac atg aac tgg ctg cac cag tca cct gtc ccg aag ttg ttg ttc tgg
Tyr Met Asn Trp Leu His Gln Ser Pro Val Pro Lys Leu Leu Phe Trp ggc aca ccc ggc cta ctg atc ccc ccg gcc gaa gcc tcg aga ctt gcc
Gly Thr Pro Gly Leu Leu Ile Pro Pro Ala Glu Ala Ser Arg Leu Ala gaa agc ctc ccc aac tgc aag aca gtg gac atc ggc ccg gga ctg cac
Glu Ser Leu Pro Asn Cys Lys Thr Val Asp Ile Gly Pro Gly Leu His ttc ctc cag gaa gac aac ccg gac ctt atc ggc agt gag atc gcg cgc
Phe Leu Gln Glu Asp Asn Pro Asp Leu Ile Gly Ser Glu Ile Ala Arg tgg ctc gcc gga ctc gcg agc ggc ctc ggc gac tac cat cat cat cat
Trp Leu Ala Gly Leu Ala Ser Gly Leu Gly Asp Tyr His His His His
       921
cat cat taa
His His END
```

FIGURE 6Q
959DL4
(SEQ ID NO:45 and 46)

```
1
atg agc gaa gaa gcg atc tcg gcc ctc gac ccg cat cca cgc aag aaa
Met Ser Glu Glu Ala Ile Ser Ala Leu Asp Pro His Pro Arg Lys Lys cag gaa ctg ctc ggc acc tcg atg tct tat gtc gat acc ggg act ggc
Gln Glu Leu Leu Gly Thr Ser Met Ser Tyr Val Asp Thr Gly Thr Gly gag ccg gtg gtg ttc ctg cac ggc aat cca acc tcc tac ttg tgg
Glu Pro Val Val Phe Leu His Gly Asn Pro Thr Ser Ser Tyr Leu Trp cgg aac gtg att cca cat gtc gcg ccg gtc gcc agg tgc atc gct ccc
Arg Asn Val Ile Pro His Val Ala Pro Val Ala Arg Cys Ile Ala Pro gac ctg atc ggg atg gga gcg tca ggg cct tcc tct agc ggc aac tac
Asp Leu Ile Gly Met Gly Ala Ser Gly Pro Ser Ser Ser Gly Asn Tyr acg ttc gcc gat cat gcg cga cat ctc gat gcg ctc ctc gac gcg att
Thr Phe Ala Asp His Ala Arg His Leu Asp Ala Leu Leu Asp Ala Ile ttg cca aag ggc cag ctc agc ttg gtg gtg cac gac tgg gga tcg gcg
Leu Pro Lys Gly Gln Leu Ser Leu Val Val His Asp Trp Gly Ser Ala ctg ggc ttc cac tgg gcc aat cgc aat cgg gat cgg gta agg gga atc
Leu Gly Phe His Trp Ala Asn Arg Asn Arg Asp Arg Val Arg Gly Ile gcc tac atg gaa gcg att gtg cga ccg gtg ctg tgg tcg gag tgg ccc
Ala Tyr Met Glu Ala Ile Val Arg Pro Val Leu Trp Ser Glu Trp Pro gaa cgt gcc cga gac att ttc aag acg ctg cga act ccg gcc ggc gaa
Glu Arg Ala Arg Asp Ile Phe Lys Thr Leu Arg Thr Pro Ala Gly Glu gag atg att ctc aaa aac aac gta ttc gtg gag cgg atc ctg ccc ggc
Glu Met Ile Leu Lys Asn Asn Val Phe Val Glu Arg Ile Leu Pro Gly agc gtc ttg cgc aaa ttg agc tcc gaa gaa atg gac aat tat cgc cgg
Ser Val Leu Arg Lys Leu Ser Ser Glu Glu Met Asp Asn Tyr Arg Arg ccc ttt cgc gac gca gga gaa tcg cgg cgg cca aca ctc acg tgg ccg
Pro Phe Arg Asp Ala Gly Glu Ser Arg Arg Pro Thr Leu Thr Trp Pro cgt cag att ccg atc gag ggt gag ccg gcc gac gtg gtg gaa atc gtg
Arg Gln Ile Pro Ile Glu Gly Glu Pro Ala Asp Val Val Glu Ile Val cag aaa tat tcc gag tgg ctg gca cag agc gcg gtg ccc aaa ctg ctc
Gln Lys Tyr Ser Glu Trp Leu Ala Gln Ser Ala Val Pro Lys Leu Leu gtg aat gcg gag ccg gga gcg att ttg ata ggc gcg cag cgc gag ttt
Val Asn Ala Glu Pro Gly Ala Ile Leu Ile Gly Ala Gln Arg Glu Phe tgc cac caa tgg ccg aat cag cgc gaa gtc acg gtc aag ggc gta cac
Cys His Gln Trp Pro Asn Gln Arg Glu Val Thr Val Lys Gly Val His ttc atc cag gaa gat tcc ccg cac gag atc ggg cga gcg atc gca gac
Phe Ile Gln Glu Asp Ser Pro His Glu Ile Gly Arg Ala Ile Ala Asp 882
tgg tac cga gga atc tga
Trp Tyr Arg Gly Ile END
```

FIGURE 6R-1
959DL2
(SEQ ID NO:47 and 48)

```
1
atg gct act act gga gaa gcg ata tct tct gca ttt ccg tac gag aag
Met Ala Thr Thr Gly Glu Ala Ile Ser Ser Ala Phe Pro Tyr Glu Lys cag cgc cgg cgg gtt ctg ggg aga gag atg gcc tat gtg gaa gtg ggg
Gln Arg Arg Arg Val Leu Gly Arg Glu Met Ala Tyr Val Glu Val Gly gcc ggc gac ccg atc gtg ctg ctg cac ggc aat ccg acc tca tcc tac
Ala Gly Asp Pro Ile Val Leu Leu His Gly Asn Pro Thr Ser Ser Tyr ctc tgg cgc aat gtc ctg ccg cat ctc caa cta cga ggc cga tgc atc
Leu Trp Arg Asn Val Leu Pro His Leu Gln Leu Arg Gly Arg Cys Ile gcg ccc gac ctg att ggc atg ggc gac tcc gat aag cta cct gac agc
Ala Pro Asp Leu Ile Gly Met Gly Asp Ser Asp Lys Leu Pro Asp Ser ggc ccg agc tcg tat cgc ttc gta gat cag cgc cgc tac ctc gat gcg
Gly Pro Ser Ser Tyr Arg Phe Val Asp Gln Arg Arg Tyr Leu Asp Ala ctg ctg gag gca ttg gac gta cgt gag cgt gtg acg ctc gtc att cat
Leu Leu Glu Ala Leu Asp Val Arg Glu Arg Val Thr Leu Val Ile His gac tgg ggc tcg gga ctt ggc ttt gac tgg gcc aac cga cac cgc gac
Asp Trp Gly Ser Gly Leu Gly Phe Asp Trp Ala Asn Arg His Arg Asp gcc gta aag ggc atc gca tac atg gag gcg atc gtg cgc ccg cag gga
Ala Val Lys Gly Ile Ala Tyr Met Glu Ala Ile Val Arg Pro Gln Gly tgg gac cac tgg gac gta atg aat atg cgt cca ttc cta gag gcg ctg
Trp Asp His Trp Asp Val Met Asn Met Arg Pro Phe Leu Glu Ala Leu cgt tcc gag gcc ggc gag aag atg gtc ctt gaa gac aac ttt ttc atc
Arg Ser Glu Ala Gly Glu Lys Met Val Leu Glu Asp Asn Phe Phe Ile gag aag att tta cca ggc gct gtt ctc cgc aag ctc acc gcg gat gaa
Glu Lys Ile Leu Pro Gly Ala Val Leu Arg Lys Leu Thr Ala Asp Glu atg gcg gag tat cgt cgg ccg ttc gct gaa ccc ggc gag gcg cga cga
Met Ala Glu Tyr Arg Arg Pro Phe Ala Glu Pro Gly Glu Ala Arg Arg ccg act ctg act tgg cca cgg gag att cct atc gat ggc aaa ccc gcc
Pro Thr Leu Thr Trp Pro Arg Glu Ile Pro Ile Asp Gly Lys Pro Ala gac gtg aat acg att gtg gcg gcc tat tcg gag tgg ctt gcg acg agc
Asp Val Asn Thr Ile Val Ala Ala Tyr Ser Glu Trp Leu Ala Thr Ser gat gtg ccc aag cta ttc ata aaa gcc gag ccc ggc gca ctc ctt ggc
Asp Val Pro Lys Leu Phe Ile Lys Ala Glu Pro Gly Ala Leu Leu Gly agc ggg att aac ctt gaa acc gct cgc tcc tgg cct gcg cag acg gaa
Ser Gly Ile Asn Leu Glu Thr Ala Arg Ser Trp Pro Ala Gln Thr Glu gta acc gtg gcc gga gtt cat ttt gtg caa gag gat tcg cca gat gag
Val Thr Val Ala Gly Val His Phe Val Gln Glu Asp Ser Pro Asp Glu att ggg cgc tcg gat tct ggc gac cct tgg ccc gct ggc gga cga aat
Ile Gly Arg Ser Asp Ser Gly Asp Pro Trp Pro Ala Gly Gly Arg Asn
```

FIGURE 6R-2

```
cgc cgt cta ctc gcc ccg tct ggc gca gca tct cga tca cta cag tcc
Arg Arg Leu Leu Ala Pro Ser Gly Ala Ala Ser Arg Ser Leu Gln Ser gtt cgc gct cag ctt cgc act gcc ctg caa tac ccc cgg cct gcg gtt
Val Arg Ala Gln Leu Arg Thr Ala Leu Gln Tyr Pro Arg Pro Ala Val 1032
cct gtg ccg cga cag ctt cga tga
Pro Val Pro Arg Gln Leu Arg END
```

DEHALOGENASES, NUCLEIC ACIDS ENCODING THEM AND METHODS FOR MAKING AND USING THEM

RELATED APPLICATIONS

This application is a divisional application of U.S. application Ser. No. 12/683,906, filed Jan. 7, 2010, now U.S. Pat. No. 8,153,411; which is a divisional application of U.S. Ser. No. 11/418,828, filed May 5, 2006, now U.S. Pat. No. 7,671,189; which is a divisional application of U.S. Ser. No. 10/000,997, filed Nov. 30, 2001, now U.S. Pat. No. 7,078,504; which claims benefit of priority under 35 U.S.C. §119(e) to Provisional Patent application U.S. Ser. No. 60/250,897, filed Dec. 1, 2000. Each of the aforementioned applications is explicitly incorporated herein by reference in its entirety and for all purposes.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| D15501D3_SequenceListing.txt | Apr. 9, 2012 | 298,496 bytes |

FIELD OF THE INVENTION

This invention relates generally to enzymes, polynucleotides encoding the enzymes, the use of such polynucleotides and polypeptides, and more specifically to enzymes having haloalkane dehalogenase activity.

BACKGROUND ART

Environmental pollutants consist of a large quantity and variety of chemicals; many of these are toxic, environmental hazards that were designated in 1979 as priority pollutants by the U.S. Environmental Protection Agency. Microbial and enzymatic biodegradation is one method for the elimination of these pollutants. Accordingly, methods have been designed to treat commercial wastes and to bioremediate polluted environments via microbial and related enzymatic processes.

Unfortunately, many chemical pollutants are either resistant to microbial degradation or are toxic to potential microbial-degraders when present in high concentrations and certain combinations.

Haloalkane dehalogenase belongs to the alpha/beta hydrolase fold family in which all of the enzymes share similar topology, reaction mechanisms, and catalytic triad residues (Krooshof, et al., *Biochemistry* 36(31):9571-9580, 1997). The enzyme cleaves carbon-halogen bonds in haloalkanes and halocarboxylic acids by hydrolysis, thus converting them to their corresponding alcohols. This reaction is important for detoxification involving haloalkanes such as ethylchloride, methylchloride, and 1,2-dichloroethane, which are considered priority pollutants by the Environmental Protection Agency (Rozeboom, H., Kingma, J., Janssen, D., Dijkstra, B., Crystallization of Haloalkane Dehalogenase from *Xanthobacter autotrophicus* GJ10, *J Mol Biol,* 200 (3), 611-612 (1988)).

The haloalkane dehalogenases are produced by microorganisms that can grow entirely on chlorinated aliphatic compounds. No metal or oxygen is needed for activity: water is the sole substrate.

*Xanthobacter autotrophicus* GJ10 is a nitrogen-fixing bacteria that utilizes 1,2-dichloroethane and a few other haloalkane and halocarboxylic acids for growth (Rozeboom, et al., *J Mol Biol,* 200 3:611-612, 1988; Keuning, et al., *J Bacteriol,* 163(2):635-639, 1985). It is the most well-studied dehalogenase because it has a known catalytic reaction mechanism, activity mechanism and crystal-structure (Schanstra, et al., *J Biol Chem,* 271(25):14747-14753, 1996).

The organism produces two different dehalogenases. One dehalogenase is for halogenated alkanes and the other for halogenated carboxylic acids. Most harmful halogenated compounds are industrially produced for use as cleaning agents, pesticides, and solvents. The natural substrate of *Xanthobacter autotrophicus* is 1,2-dichloroethane. This haloalkane is often used in vinyl production.

Enzymes are highly selective catalysts. Their hallmark is the ability to catalyze reactions with exquisite stereo-, regio-, and chemo-selectivities that are unparalleled in conventional synthetic chemistry. Moreover, enzymes are remarkably versatile. They can be tailored to function in organic solvents, operate at extreme pH's and temperatures, and catalyze reactions with compounds that are structurally unrelated to their natural, physiological substrates.

Enzymes are reactive toward a wide range of natural and unnatural substrates, thus enabling the modification of virtually any organic lead compound. Moreover, unlike traditional chemical catalysts, enzymes are highly enantio- and regio-selective. The high degree of functional group specificity exhibited by enzymes enables one to keep track of each reaction in a synthetic sequence leading to a new active compound. Enzymes are also capable of catalyzing many diverse reactions unrelated to their physiological function in nature. For example, peroxidases catalyze the oxidation of phenols by hydrogen peroxide. Peroxidases can also catalyze hydroxylation reactions that are not related to the native function of the enzyme. Other examples are proteases which catalyze the breakdown of polypeptides. In organic solution some proteases can also acylate sugars, a function unrelated to the native function of these enzymes.

The present invention exploits the unique catalytic properties of enzymes. Whereas the use of biocatalysts (i.e., purified or crude enzymes, non-living or living cells) in chemical transformations normally requires the identification of a particular biocatalyst that reacts with a specific starting compound, the present invention uses selected biocatalysts and reaction conditions that are specific for functional groups that are present in many starting compounds. Each biocatalyst is specific for one functional group, or several related functional groups, and can react with many starting compounds containing this functional group.

The biocatalytic reactions produce a population of derivatives from a single starting compound. These derivatives can be subjected to another round of biocatalytic reactions to produce a second population of derivative compounds. Thousands of variations of the original compound can be produced with each iteration of biocatalytic derivitization.

Enzymes react at specific sites of a starting compound without affecting the rest of the molecule, a process which is very difficult to achieve using traditional chemical methods. This high degree of biocatalytic specificity provides the means to identify a single active compound within the library. The library is characterized by the series of biocatalytic reactions used to produce it, a so called "biosynthetic history". Screening the library for biological activities and tracing the biosynthetic history identifies the specific reaction sequence producing the active compound. The reaction sequence is repeated and the structure of the synthesized compound determined. This mode of identification, unlike other synthesis and screening approaches, does not require immobilization technologies, and compounds can be synthesized and tested free in solution using virtually any type of screening assay. It is important to note, that the high degree of specificity of enzyme reactions on functional groups allows for the "tracking" of specific enzymatic reactions that make up the biocatalytically produced library.

Many of the procedural steps are performed using robotic automation enabling the execution of many thousands of biocatalytic reactions and screening assays per day as well as ensuring a high level of accuracy and reproducibility. As a result, a library of derivative compounds can be produced in a matter of weeks which would take years to produce using current chemical methods. (For further teachings on modification of molecules, including small molecules, See PCT/US94/09174, herein incorporated by reference in its entirety).

The publications discussed herein are provided solely for their disclosure prior to the filing date of the present application. Nothing herein is to be construed as an admission that the invention is not entitled to antedate such disclosure by virtue of prior invention.

SUMMARY OF THE INVENTION

The invention provides an isolated nucleic acid having a sequence as set forth in SEQ ID NO's: 3, 5, 7, 9, 11, 13, 15, 17, 19, 21, 23, 25, 27, 29, 31, 33, 35, 37, 43, 45, 47 and variants thereof having at least 50% sequence identity to SEQ ID NO.: 3, 5, 7, 9, 11, 13, 15, 17, 19, 21, 23, 25, 27, 29, 31, 33, 35, 37, 43, 45 or 47 and encoding polypeptides having dehalogenase activity.

One aspect of the invention is an isolated nucleic acid having a sequence as set forth in SEQ ID NO's: 3, 5, 7, 9, 11, 13, 15, 17, 19, 21, 23, 25, 27, 29, 31, 33, 35, 37, 43, 45, 47 (hereinafter referred to as "Group A nucleic acid sequences"), sequences substantially identical thereto, and sequences complementary thereto.

Another aspect of the invention is an isolated nucleic acid including at least 10 consecutive bases of a sequence as set forth in Group A nucleic acid sequences, sequences substantially identical thereto, and the sequences complementary thereto.

In yet another aspect, the invention provides an isolated nucleic acid encoding a polypeptide having a sequence as set forth in SEQ ID NO's: 4, 6, 8, 10, 12, 14, 16, 18, 20, 22, 24, 26, 28, 30, 32, 34, 36, 38, 44, 46, 48 and variants thereof encoding a polypeptide having dehalogenase activity and having at least 50% sequence identity to such sequences.

Another aspect of the invention is an isolated nucleic acid encoding a polypeptide or a functional fragment thereof having a sequence as set forth in SEQ ID NO's: 4, 6, 8, 10, 12, 14, 16, 18, 20, 22, 24, 26, 28, 30, 32, 34, 36, 38, 44, 46, 48 (hereinafter referred to as "Group B amino acid sequences"), and sequences substantially identical thereto.

Another aspect of the invention is an isolated nucleic acid encoding a polypeptide having at least 10 consecutive amino acids of a sequence as set forth in Group B amino acid sequences, and sequences substantially identical thereto.

In yet another aspect, the invention provides a purified polypeptide having a sequence as set forth in Group B amino acid sequences, and sequences substantially identical thereto.

Another aspect of the invention is an isolated or purified antibody that specifically binds to a polypeptide having a sequence as set forth in Group B amino acid sequences, and sequences substantially identical thereto.

Another aspect of the invention is an isolated or purified antibody or binding fragment thereof, which specifically binds to a polypeptide having at least 10 consecutive amino acids of one of the polypeptides of Group B amino acid sequences, and sequences substantially identical thereto.

Another aspect of the invention is a method of making a polypeptide having a sequence as set forth in Group B amino acid sequences, and sequences substantially identical thereto. The method includes introducing a nucleic acid encoding the polypeptide into a host cell, wherein the nucleic acid is operably linked to a promoter, and culturing the host cell under conditions that allow expression of the nucleic acid.

Another aspect of the invention is a method of making a polypeptide having at least 10 amino acids of a sequence as set forth in Group B amino acid sequences, and sequences substantially identical thereto. The method includes introducing a nucleic acid encoding the polypeptide into a host cell, wherein the nucleic acid is operably linked to a promoter, and culturing the host cell under conditions that allow expression of the nucleic acid, thereby producing the polypeptide.

Another aspect of the invention is a method of generating a variant including obtaining a nucleic acid having a sequence as set forth in Group A nucleic acid sequences, sequences substantially identical thereto, sequences complementary to the sequences of Group A nucleic acid sequences, fragments comprising at least 30 consecutive nucleotides of the foregoing sequences, and changing one or more nucleotides in the sequence to another nucleotide, deleting one or more nucleotides in the sequence, or adding one or more nucleotides to the sequence.

Another aspect of the invention is a computer readable medium having stored thereon a sequence as set forth in Group A nucleic acid sequences, and sequences substantially identical thereto, or a polypeptide sequence as set forth in Group B amino acid sequences, and sequences substantially identical thereto.

Another aspect of the invention is a computer system including a processor and a data storage device wherein the data storage device has stored thereon a sequence as set forth in Group A nucleic acid sequences, and sequences substantially identical thereto, or a polypeptide having a sequence as set forth in Group B amino acid sequences, and sequences substantially identical thereto.

Another aspect of the invention is a method for comparing a first sequence to a reference sequence wherein the first sequence is a nucleic acid having a sequence as set forth in Group A nucleic acid sequences, and sequences substantially identical thereto, or a polypeptide code of Group B amino acid sequences, and sequences substantially identical thereto. The method includes reading the first sequence and the reference sequence through use of a computer program which compares sequences; and determining differences between the first sequence and the reference sequence with the computer program.

Another aspect of the invention is a method for identifying a feature in a sequence as set forth in Group A nucleic acid sequences, and sequences substantially identical thereto, or a polypeptide having a sequence as set forth in Group B amino acid sequences, and sequences substantially identical thereto, including reading the sequence through the use of a computer program which identifies features in sequences; and identifying features in the sequence with the computer program.

Another aspect of the invention is an assay for identifying fragments or variants of Group B amino acid sequences, and sequences substantially identical thereto, which retain the enzymatic function of the polypeptides of Group B amino acid sequences, and sequences substantially identical thereto. The assay includes contacting the polypeptide of Group B amino acid sequences, sequences substantially identical thereto, or polypeptide fragment or variant with a substrate molecule under conditions which allow the polypeptide fragment or variant to function, and detecting either a decrease in the level of substrate or an increase in the level of the specific reaction product of the reaction between the polypeptide and substrate thereby identifying a fragment or variant of such sequences.

In yet another aspect, the invention provides a method for synthesizing glycerol. The method includes contacting trichloropropane or dichloropropanol with a polypeptide having at least 70% homology to a sequence selected from the group consisting of Group B amino acid sequences and sequences substantially identical thereto, and having dehalogenase activity, under conditions to synthesize glycerol.

In yet another aspect, the invention provides a method for producing an optically active halolactic acid. The method includes contacting a dihalopropionic acid with a polypeptide having at least 70% homology to a sequence selected from the group consisting of Group B amino acid sequences and sequences substantially identical thereto, and having dehalogenase activity, under conditions to produce optically active halolactic acid.

In yet another aspect, the invention provides a method for bioremediation by contacting an environmental sample with a polypeptide having at least 70% homology to a sequence selected from the group consisting of Group B amino acid sequences and sequences substantially identical thereto, and having dehalogenase activity.

In another aspect, the invention provides a method for removing a halogenated contaminant or halogenated impurity from a sample. The method includes contacting the sample with a polypeptide having at least 70% homology to a sequence selected from the group consisting of Group B amino acid sequences and sequences substantially identical thereto, and having dehalogenase activity.

In yet another aspect, the invention provides a method for synthesizing a diol, by contacting a dihalopropane or monohalopropanol with a polypeptide having at least 70% homology to a sequence selected from the group consisting of Group B amino acid sequences and sequences substantially identical thereto, and having dehalogenase activity, under conditions to synthesize the diol.

In yet another aspect, the invention provides a method for dehalogenating a halo-substituted cyclic hydrocarbyl. The method includes contacting the halo-substituted cyclic hydrocarbyl with a polypeptide having at least 70% homology to a sequence selected from the group consisting of Group B amino acid sequences and sequences substantially identical thereto, and having dehalogenase activity, under conditions to dehalogenate the halo-substituted cyclic hydrocarbyl.

All publications, patents, patent applications cited herein are hereby expressly incorporated by reference for all purposes.

BRIEF DESCRIPTION OF THE DRAWINGS

The following drawings are illustrative of embodiments of the invention and are not meant to limit the scope of the invention as encompassed by the claims.

FIG. 5 shows an alignment of the polypeptide sequences of the invention. A=SEQ ID NO:4; B=SEQ ID NO:2; C=SEQ ID NO:6; rhod2=SEQ ID NO:40; myco4=SEQ ID NO:42; Consensus=SEQ ID NO:49.

FIGS. 6A-6R-2 shows sequences of the invention (SEQ ID NO's: 9-38 and 43-48).

Like reference symbols in the various drawings indicate like elements.

DETAILED DESCRIPTION OF THE INVENTION

The invention relates to haloalkane dehalogenase polypeptides and polynucleotides encoding them as well as methods of use of the polynucleotides and polypeptides. As used herein, the terminology "haloalkane dehalogenase" encompasses enzymes having hydrolase activity, for example, enzymes capable of catalyzing the hydrolysis of haloalkanes via an alkyl-enzyme intermediate.

The polynucleotides of the invention have been identified as encoding polypeptides having dehalogenase activity and in particular embodiments haloalkane dehalogenase activity.

Figure 7:
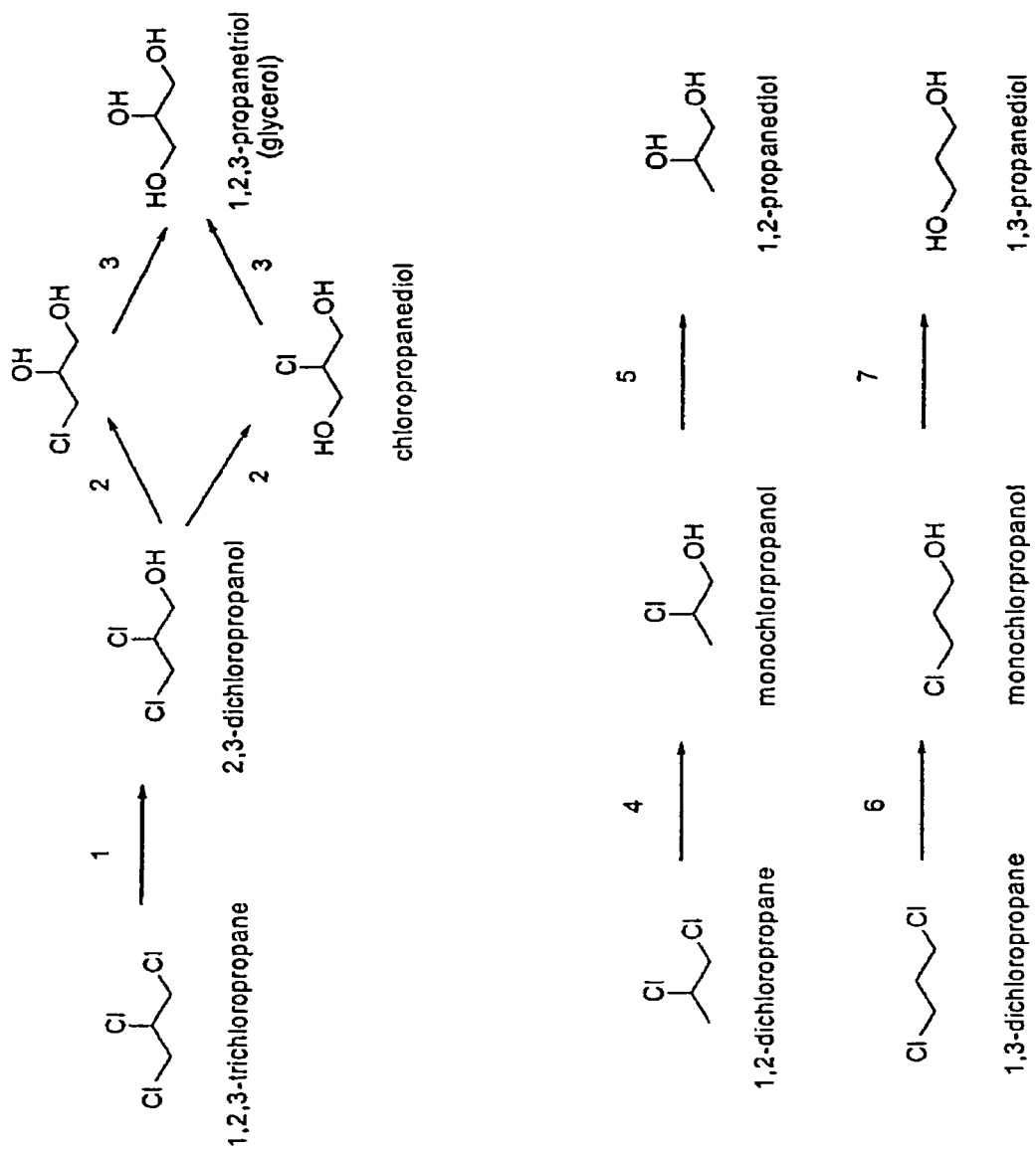
FIG. 7 shows an example of the formation of glycerol using the dehalogenases of the invention as well as the formation of 1,2-propanediol or 1,3-propanediol using the dehalogenases of the invention.
Figure 8:
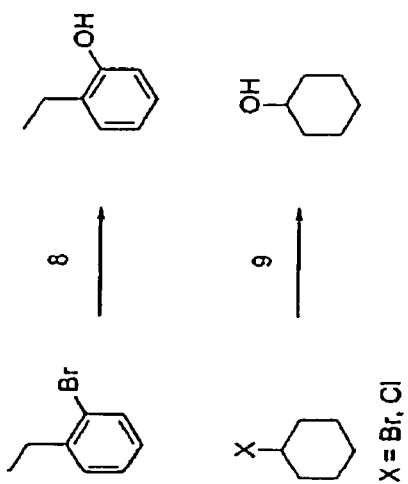
FIG. 8 shows an example of the dehalogenation of a halo-substituted cyclic hydrocarbyl using the dehalogenases of the invention.

The dehalogenases and polynucleotides encoding the dehalogenases of the invention are useful in a number of processes, methods, and compositions. For example, as discussed above, a dehalogenase can be used to remedy an environment contaminated with aliphatic organochlorine, degrade the herbicide dalapon, degrade halogenated organic acids as well as soil and water remediation, and treat by degradation halogenated organic acid in the soil and water. Furthermore, a dehalogenase of the invention can be used to remove impurities in industrial processes, in the environment, and in medicaments. For example, a dehalogenase can be used to decompose haloalkanoic acid impurities in various samples including, for example, surfactants, carboxymethyl cellulose or thioglycolic acid salts. In yet another aspect, the dehalogenases of the invention can be used in the formation of medicines, agrochemical and ferroelectric liquids by allowing oxidative dehalogenation of specific 1,2-diol or racemic halogenohydrins. For example, a dehalogenase can be used in the synthesis of optically active glycidic and lactic acids (e.g., beta halolactic acid) by treating an I, θ-dihalopropionic acid (e.g., dichloropropionic acid) with a dehalogenase. The dehalogenases of the invention can also be used in the production of active (S)-(+)-3-halo-1,2-propanediol or (R)-(−)-3 halo-1,2 propanediol from 1,3-dihalo-2-propanol. (S)-(+)-3 halo-1,2-propanediol is useful as a raw material for physiological and medical treatments and medicaments. For example, a dehalogenase of the invention can be contacted trichloropropanediol (TCP) or dichloropropanediol (DCP) under conditions and for a time sufficient to allow oxidative dehalogenation to form, for example, glycerol (e.g., DCP or TCP to glycerol) (see, for example, FIG. 7). Various diols can be produced using the methods of the invention and the enzymes of the invention. In addition, the methods and compositions of the invention can be applied to halogenated aromatic compounds. For example, the compositions of the invention can be used to dehalogenate a halo-substituted cyclic hydrocarbyl as depicted in FIG. 8. Examples of cyclic hydrocarbyl compounds include cycloalkyl, cycloalkenyl, cycloalkadienyl, cycloalkatrienyl, cycloalkynyl, cycloalkadiynyl, aromatic compounds, spiro hydrocarbons wherein two rings are joined by a single atom which is the only common member of the two rings (e.g., spiro[3,4]octanyl, and the like), bicyclic hydrocarbons wherein two rings are joined and have at least two atoms in common (e.g., bicyclo[3.2.1]octane, bicyclo[2.2.1]hept-2-ene, and the like), ring assemblies wherein two or more cyclic systems (i.e., single rings or fused systems) are directly joined to each other by single or double bonds, and the number of such ring junctions is one less than the number of cyclic systems involved (e.g., biphenylyl, biphenylylene, radicals or p-terphenyl, cyclohexylbenzyl, and the like), polycyclics, and the like.

Haloalkane Dehalogenase

Overall Structure

Haloalkane dehalogenase from *Xanthobacter autotrophicus* is composed of 310 amino acids and consists of a single polypeptide chain with a molecular weight of 36,000. The monomeric enzyme is spherical and composed of two domains. The main domain has an alpha/beta hydrolase fold structure with a mixed beta sheet of 8 strands order 12435678; strand 2 is antiparallel to the rest. The second domain is an alpha-helical cap which lies on top of the main domain. (Keuning, et al., *J Bacteriol* 163(2):635-639, 1985) As described in further detail herein, mutagenesis have done to modify the activity of the enzyme, for example, by mutating specific residues of the cap domain (Krooshof, et al., *Biochemistry* 36(31):9571-9580, 1997).

The active site of the enzyme in *Xanthobacter autotrophicus*, consisting of three catalytic residues (Asp 124, His 289, and Asp 260), is found between the two domains in an internal hydrophobic cavity. Nucleophilic Asp 124 and the general base His 289, located after beta-strands 5 and 8 respectively, are fully conserved in the alpha/beta hydrolase family, while Asp 260 is not. The active site is lined with 10 hydrophobic residues: 4 phenylalanines; 2 tryptophans; 2 leucines; 1 valine; and 1 proline. (Schanstra, et al., *J Biol Chem* 271(25):14747-14753, 1996).

During enzymatic hydrolysis of a substrate, haloalkane dehalogenase forms a covalent intermediate formed by nucleophilic substitution with Asp 124 that is hydrolyzed by a water molecule that is activated by His 289. (Verschueren, et al., *Nature* 363(6431):693-698, 1993). The role of Asp 260, which is the third member of a catalytic triad common to dehalogenase enzymes, has been studied by site-directed mutagenesis. Mutation of Asp 260 to asparagine resulted in a catalytically inactive D260N mutant, which demonstrates that the triad acid Asp 260 is essential for dehalogenase activity in the wild-type enzyme. Furthermore, Asp 260 has an important structural role, since the D260N enzyme accumulated mainly in inclusion bodies during expression, and neither substrate nor product could bind in the active-site cavity. Activity for brominated substrates was restored to D260N by replacing Asn 148 with an aspartic or glutamic acid. Both double mutants D260N+N148D and D260N+N148E had a 10-fold reduced kcat and 40-fold higher Km values for 1,2-dibromoethane compared to the wild-type enzyme. Pre-steady-state kinetic analysis of the D260N+N148E double mutant showed that the decrease in kcat was mainly caused by a 220-fold reduction of the rate of carbon-bromine bond cleavage and a 10-fold decrease in the rate of hydrolysis of the alkyl-enzyme intermediate. On the other hand, bromide was released 12-fold faster and via a different pathway than in the wild-type enzyme. Molecular modeling of the mutant showed that Glu 148 indeed could take over the interaction with His 289 and that there was a change in charge distribution in the tunnel region that connects the active site with the solvent. (Krooshof, et al., *Biochemistry* 36(31):9571-9580, 1997).

The first step in degradation of the harmful halogenated compounds utilizes haloalkane dehalogenase. The dehalogenase catalysis occurs as a two step-mechanism involving an ester intermediate. No energy is required for hydrolytic dehalogenases; therefore, it is a simple way to detoxify organic matter since the halogen, which causes the toxicity, is lost. A catalytic triad (Asp-His-Asp), along with an aspartate carboxylate (Asp 124), are the focal point of the reaction. The substrate binds to the active site cavity and the C1-alpha complex reacts with the side chain NH groups of Trp 172 and Trp 175. As a first step a halogen from the substrate is displaced by the nucleophilic aspartate, resulting in an intermediate covalent ester. His 289 then activates a water molecule which hydrolyzes the ester. As a result, an alcohol and halide are displaced from the active site. The two step mechanism involving nucleophilic Asp 124 and water hydrolysis of the ester intermediate is consistent with other alpha/beta hydrolase fold enzymes.

Haloalkane dehalogenase breaks carbon-halogen bonds in aliphatic compounds. Results show that the enzyme reaction with C—Cl bond is slower than that of other C-halide bonds, such as C—Br bonds. The ability of the leaving group is the explanation for the difference. The rate limiting step for 1,2-dichloroethane and 1,2-dibromoethane reactions is not the cleavage of the carbon-halogen bond, but rather the ion release out of the active site.

Bioremediation

The present invention provides a number of dehalogenase enzymes useful in bioremediation having improved enzymatic characteristics. The polynucleotides and polynucleotide products of the invention are useful in, for example, groundwater treatment involving transformed host cells containing a polynucleotide or polypeptide of the invention (e.g., the bacteria *Xanthobacter autotrophicus*) and the haloalkane 1,2-dichlorethane as well as removal of polychlorinated biphenyls (PCB's) from soil sediment.

The haloalkane dehalogenase of the invention are useful in carbon-halide reduction efforts. The enzymes of the invention initiate the degradation of haloalkanes. Alternatively, host cells containing a dehalogenase polynucleotide or polypeptide of the invention can feed on the haloalkanes and produce the detoxifying enzyme.

Definitions

The phrases "nucleic acid" or "nucleic acid sequence" as used herein refer to an oligonucleotide, nucleotide, polynucleotide, or to a fragment of any of these, to DNA or RNA of genomic or synthetic origin which may be single-stranded or double-stranded and may represent a sense or antisense strand, to peptide nucleic acid (PNA), or to any DNA-like or RNA-like material, natural or synthetic in origin. In one embodiment, a "nucleic acid sequence" of the invention includes, for example, a sequence encoding a polypeptide as set forth in Group B amino acid sequences and variants thereof. In another embodiment, a "nucleic acid sequence" of the invention includes, for example, a sequence as set forth in Group A nucleic acid sequences, sequences complementary thereto, fragments of the foregoing sequences and variants thereof.

A "coding sequence of" or a "nucleotide sequence encoding" a particular polypeptide or protein, is a nucleic acid sequence which is transcribed and translated into a polypeptide or protein when placed under the control of appropriate regulatory sequences.

The term "gene" means the segment of DNA involved in producing a polypeptide chain; it includes regions preceding and following the coding region (leader and trailer) as well as, where applicable, intervening sequences (introns) between individual coding segments (exons).

"Amino acid" or "amino acid sequence" as used herein refer to an oligopeptide, peptide, polypeptide, or protein sequence, or to a fragment, portion, or subunit of any of these, and to naturally occurring or synthetic molecules. In one embodiment, an "amino acid sequence" or "polypeptide sequence" of the invention includes, for example, a sequence as set forth in Group B amino acid sequences, fragments of the foregoing sequences and variants thereof. In another embodiment, an "amino acid sequence" of the invention includes, for example, a sequence encoded by a polynucleotide having a sequence as set forth in Group B nucleic acid sequences, sequences complementary thereto, fragments of the foregoing sequences and variants thereof.

The term "polypeptide" as used herein, refers to amino acids joined to each other by peptide bonds or modified peptide bonds, i.e., peptide isosteres, and may contain modified amino acids other than the 20 gene-encoded amino acids. The polypeptides may be modified by either natural processes, such as post-translational processing, or by chemical modification techniques which are well known in the art. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, PEGylation, proteolytic processing, phosphorylation, prenylation, racemization, selenoylation, sulfation, and transfer-RNA mediated addition of amino acids to protein such as arginylation. (See Creighton, T. E., *Proteins—Structure and Molecular Properties,* 2nd Ed., W.H. Freeman and Company, New York (1993); Post-translational Covalent Modification of Proteins, B. C. Johnson, Ed., Academic Press, New York, pp. 1-12 (1983)).

As used herein, the term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

As used herein, the term "purified" does not require absolute purity; rather, it is intended as a relative definition. Individual nucleic acids obtained from a library have been conventionally purified to electrophoretic homogeneity. The sequences obtained from these clones could not be obtained directly either from the library or from total human DNA. The purified nucleic acids of the invention have been purified from the remainder of the genomic DNA in the organism by at least 104-106 fold. However, the term "purified" also includes nucleic acids which have been purified from the remainder of the genomic DNA or from other sequences in a library or other environment by at least one order of magnitude, typically two or three orders, and more typically four or five orders of magnitude.

As used herein, the term "recombinant" means that the nucleic acid is adjacent to a "backbone" nucleic acid to which it is not adjacent in its natural environment. Additionally, to be "enriched" the nucleic acids will represent 5% or more of the number of nucleic acid inserts in a population of nucleic acid backbone molecules. Backbone molecules according to the invention include nucleic acids such as expression vectors, self-replicating nucleic acids, viruses, integrating nucleic acids, and other vectors or nucleic acids used to maintain or manipulate a nucleic acid insert of interest. Typically, the enriched nucleic acids represent 15% or more of the number of nucleic acid inserts in the population of recombinant backbone molecules. More typically, the enriched nucleic acids represent 50% or more of the number of nucleic acid inserts in the population of recombinant backbone molecules. In a one embodiment, the enriched nucleic acids represent 90% or more of the number of nucleic acid inserts in the population of recombinant backbone molecules.

"Recombinant" polypeptides or proteins refer to polypeptides or proteins produced by recombinant DNA techniques; i.e., produced from cells transformed by an exogenous DNA construct encoding the desired polypeptide or protein. "Synthetic" polypeptides or protein are those prepared by chemical synthesis. Solid-phase chemical peptide synthesis methods can also be used to synthesize the polypeptide or fragments of the invention. Such method have been known in the art since the early 1960's (Merrifield, R. B., *J. Am. Chem. Soc.,* 85:2149-2154, 1963) (see also Stewart, J. M. and Young, J. D., *Solid Phase Peptide Synthesis,* 2nd Ed., Pierce Chemical Co., Rockford, Ill., pp. 11-12)) and have recently been employed in commercially available laboratory peptide design and synthesis kits (Cambridge Research Biochemicals). Such commercially available laboratory kits have generally utilized the teachings of H. M. Geysen, et al., *Proc. Natl. Acad. Sci. USA,* 81:3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A automated peptide synthesizer. Such equipment provides ready access to the peptides of the invention, either by direct synthesis or by synthesis of a series of fragments that can be coupled using other known techniques.

A promoter sequence is "operably linked to" a coding sequence when RNA polymerase which initiates transcription at the promoter will transcribe the coding sequence into mRNA.

"Plasmids" are designated by a lower case "p" preceded and/or followed by capital letters and/or numbers. The starting plasmids herein are either commercially available, publicly available on an unrestricted basis, or can be constructed from available plasmids in accord with published procedures. In addition, equivalent plasmids to those described herein are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion, gel electrophoresis may be performed to isolate the desired fragment.

"Oligonucleotide" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

The phrase "substantially identical" in the context of two nucleic acids or polypeptides, refers to two or more sequences that have at least 50%, 55%, 60%, 65%, 70%, 75%, 80%, 85%, and in some aspects 90-95% nucleotide or amino acid residue identity, when compared and aligned for maximum correspondence, as measured using one of the known sequence comparison algorithms or by visual inspection. Typically, the substantial identity exists over a region of at least about 100 residues, and most commonly the sequences are substantially identical over at least about 150-200 residues. In some embodiments, the sequences are substantially identical over the entire length of the coding regions.

Additionally a "substantially identical" amino acid sequence is a sequence that differs from a reference sequence by one or more conservative or non-conservative amino acid substitutions, deletions, or insertions, particularly when such a substitution occurs at a site that is not the active site of the molecule, and provided that the polypeptide essentially retains its functional properties. A conservative amino acid substitution, for example, substitutes one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid or glutamine for asparagine). One or more amino acids can be deleted, for example, from an dehalogenase polypeptide, resulting in modification of the structure of the polypeptide, without significantly altering its biological activity. For example, amino- or carboxyl-terminal amino acids that are not required for dehalogenase biological activity can be removed. Modified polypeptide sequences of the invention can be assayed for dehalogenase biological activity by any number of methods, including contacting the modified polypeptide sequence with an dehalogenase substrate and determining whether the modified polypeptide decreases the amount of specific substrate in the assay or increases the bioproducts of the enzymatic reaction of a functional dehalogenase polypeptide with the substrate.

"Fragments" as used herein are a portion of a naturally occurring protein which can exist in at least two different conformations. Fragments can have the same or substantially the same amino acid sequence as the naturally occurring protein. "Substantially the same" means that an amino acid sequence is largely, but not entirely, the same, but retains at least one functional activity of the sequence to which it is related. In general two amino acid sequences are "substantially the same" or "substantially homologous" if they are at least about 85% identical. Fragments which have different three dimensional structures as the naturally occurring protein are also included. An example of this, is a "pro-form" molecule, such as a low activity proprotein that can be modified by cleavage to produce a mature enzyme with significantly higher activity.

"Hybridization" refers to the process by which a nucleic acid strand joins with a complementary strand through base pairing. Hybridization reactions can be sensitive and selective so that a particular sequence of interest can be identified even in samples in which it is present at low concentrations. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS, and 200 n/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "variant" refers to polynucleotides or polypeptides of the invention modified at one or more base pairs, codons, introns, exons, or amino acid residues (respectively) yet still retain the biological activity of an dehalogenase of the invention. The polynucleotides or polypeptides of the invention may also be modified by introduction of a modified base, such as inosine. Additionally, the modifications may, optionally, be repeated one or more times. Variants can be produced by any number of means including methods such as, for example, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, GSSM and any combination, permutation or iterative process thereof.

Enzymes are highly selective catalysts. Their hallmark is the ability to catalyze reactions with exquisite stereo-, regio-, and chemo-selectivities that are unparalleled in conventional synthetic chemistry. Moreover, enzymes are remarkably versatile. They can be tailored to function in organic solvents, operate at extreme pHs (for example, high pHs and low pHs) extreme temperatures (for example, high temperatures and low temperatures), extreme salinity levels (for example, high salinity and low salinity), and catalyze reactions with compounds that are structurally unrelated to their natural, physiological substrates.

Enzymes are reactive toward a wide range of natural and unnatural substrates, thus enabling the modification of virtually any organic lead compound. Moreover, unlike traditional chemical catalysts, enzymes are highly enantio- and regio-selective. The high degree of functional group specificity exhibited by enzymes enables one to keep track of each reaction in a synthetic sequence leading to a new active compound. Enzymes are also capable of catalyzing many diverse reactions unrelated to their physiological function in nature. For example, peroxidases catalyze the oxidation of phenols by hydrogen peroxide. Peroxidases can also catalyze hydroxylation reactions that are not related to the native function of the enzyme. Other examples are proteases which catalyze the breakdown of polypeptides. In organic solution some proteases can also acylate sugars, a function unrelated to the native function of these enzymes.

The present invention exploits the unique catalytic properties of enzymes. Whereas the use of biocatalysts (i.e., purified or crude enzymes, non-living or living cells) in chemical transformations normally requires the identification of a particular biocatalyst that reacts with a specific starting compound, the present invention uses selected biocatalysts and reaction conditions that are specific for functional groups that are present in many starting compounds. Each biocatalyst is specific for one functional group, or several related functional groups, and can react with many starting compounds containing this functional group.

The biocatalytic reactions produce a population of derivatives from a single starting compound. These derivatives can be subjected to another round of biocatalytic reactions to produce a second population of derivative compounds. Thousands of variations of the original compound can be produced with each iteration of biocatalytic derivitization.

Enzymes react at specific sites of a starting compound without affecting the rest of the molecule, a process which is very difficult to achieve using traditional chemical methods. This high degree of biocatalytic specificity provides the means to identify a single active compound within the library. The library is characterized by the series of biocatalytic reactions used to produce it, a so-called "biosynthetic history". Screening the library for biological activities and tracing the biosynthetic history identifies the specific reaction sequence producing the active compound. The reaction sequence is repeated and the structure of the synthesized compound determined. This mode of identification, unlike other synthesis and screening approaches, does not require immobilization technologies, and compounds can be synthesized and tested free in solution using virtually any type of screening assay. It is important to note, that the high degree of specificity of enzyme reactions on functional groups allows for the "tracking" of specific enzymatic reactions that make up the biocatalytically produced library.

Many of the procedural steps are performed using robotic automation enabling the execution of many thousands of biocatalytic reactions and screening assays per day as well as ensuring a high level of accuracy and reproducibility. As a result, a library of derivative compounds can be produced in a matter of weeks which would take years to produce using current chemical methods. (For further teachings on modification of molecules, including small molecules, see PCT/US94/09174, herein incorporated by reference in its entirety).

In one aspect, the present invention provides a non-stochastic method termed synthetic gene reassembly, that is somewhat related to stochastic shuffling, save that the nucleic acid building blocks are not shuffled or concatenated or chimerized randomly, but rather are assembled non-stochastically.

The synthetic gene reassembly method does not depend on the presence of a high level of homology between polynucleotides to be shuffled. The invention can be used to non-stochastically generate libraries (or sets) of progeny molecules comprised of over $10^{100}$ different chimeras. Conceivably, synthetic gene reassembly can even be used to generate libraries comprised of over $10^{1000}$ different progeny chimeras.

Thus, in one aspect, the invention provides a non-stochastic method of producing a set of finalized chimeric nucleic acid molecules having an overall assembly order that is chosen by design, which method is comprised of the steps of generating by design a plurality of specific nucleic acid building blocks having serviceable mutually compatible ligatable ends, and assembling these nucleic acid building blocks, such that a designed overall assembly order is achieved.

The mutually compatible ligatable ends of the nucleic acid building blocks to be assembled are considered to be "serviceable" for this type of ordered assembly if they enable the building blocks to be coupled in predetermined orders. Thus, in one aspect, the overall assembly order in which the nucleic acid building blocks can be coupled is specified by the design of the ligatable ends and, if more than one assembly step is to be used, then the overall assembly order in which the nucleic acid building blocks can be coupled is also specified by the sequential order of the assembly step(s). In a one embodiment of the invention, the annealed building pieces are treated with an enzyme, such as a ligase (e.g., T4 DNA ligase) to achieve covalent bonding of the building pieces.

In a another embodiment, the design of nucleic acid building blocks is obtained upon analysis of the sequences of a set of progenitor nucleic acid templates that serve as a basis for producing a progeny set of finalized chimeric nucleic acid molecules. These progenitor nucleic acid templates thus serve as a source of sequence information that aids in the design of the nucleic acid building blocks that are to be mutagenized, i.e., chimerized or shuffled.

In one exemplification, the invention provides for the chimerization of a family of related genes and their encoded family of related products. In a particular exemplification, the encoded products are enzymes. The dehalogenases of the present invention can be mutagenized in accordance with the methods described herein.

Thus according to one aspect of the invention, the sequences of a plurality of progenitor nucleic acid templates (e.g., polynucleotides of Group A nucleic acid sequences) are aligned in order to select one or more demarcation points, which demarcation points can be located at an area of homology. The demarcation points can be used to delineate the boundaries of nucleic acid building blocks to be generated. Thus, the demarcation points identified and selected in the progenitor molecules serve as potential chimerization points in the assembly of the progeny molecules.

Typically a serviceable demarcation point is an area of homology (comprised of at least one homologous nucleotide base) shared by at least two progenitor templates, but the demarcation point can be an area of homology that is shared by at least half of the progenitor templates, at least two thirds of the progenitor templates, at least three fourths of the progenitor templates, and preferably at almost all of the progenitor templates. Even more preferably still a serviceable demarcation point is an area of homology that is shared by all of the progenitor templates.

In a one embodiment, the gene reassembly process is performed exhaustively in order to generate an exhaustive library. In other words, all possible ordered combinations of the nucleic acid building blocks are represented in the set of finalized chimeric nucleic acid molecules. At the same time, the assembly order (i.e., the order of assembly of each building block in the 5' to 3 sequence of each finalized chimeric nucleic acid) in each combination is by design (or non-stochastic). Because of the non-stochastic nature of the method, the possibility of unwanted side products is greatly reduced.

In another embodiment, the method provides that the gene reassembly process is performed systematically, for example to generate a systematically compartmentalized library, with compartments that can be screened systematically, e.g., one by one. In other words the invention provides that, through the selective and judicious use of specific nucleic acid building blocks, coupled with the selective and judicious use of sequentially stepped assembly reactions, an experimental design can be achieved where specific sets of progeny products are made in each of several reaction vessels. This allows a systematic examination and screening procedure to be performed. Thus, it allows a potentially very large number of progeny molecules to be examined systematically in smaller groups.

Because of its ability to perform chimerizations in a manner that is highly flexible yet exhaustive and systematic as well, particularly when there is a low level of homology among the progenitor molecules, the instant invention provides for the generation of a library (or set) comprised of a large number of progeny molecules. Because of the non-stochastic nature of the instant gene reassembly invention, the progeny molecules generated preferably comprise a library of finalized chimeric nucleic acid molecules having an overall assembly order that is chosen by design. In a particularly embodiment, such a generated library is comprised of greater than $10^3$ to greater than $10^{1000}$ different progeny molecular species.

In one aspect, a set of finalized chimeric nucleic acid molecules, produced as described is comprised of a polynucleotide encoding a polypeptide. According to one embodiment, this polynucleotide is a gene, which may be a man-made gene. According to another embodiment, this polynucleotide is a gene pathway, which may be a man-made gene pathway. The invention provides that one or more man-made genes generated by the invention may be incorporated into a man-made gene pathway, such as pathway operable in a eukaryotic organism (including a plant).

In another exemplification, the synthetic nature of the step in which the building blocks are generated allows the design and introduction of nucleotides (e.g., one or more nucleotides, which may be, for example, codons or introns or regulatory sequences) that can later be optionally removed in an in vitro process (e.g., by mutagenesis) or in an in vivo process (e.g., by utilizing the gene splicing ability of a host organism). It is appreciated that in many instances the introduction of these nucleotides may also be desirable for many other reasons in addition to the potential benefit of creating a serviceable demarcation point.

Thus, according to another embodiment, the invention provides that a nucleic acid building block can be used to introduce an intron. Thus, the invention provides that functional introns may be introduced into a man-made gene of the invention. The invention also provides that functional introns may be introduced into a man-made gene pathway of the invention. Accordingly, the invention provides for the generation of a chimeric polynucleotide that is a man-made gene containing one (or more) artificially introduced intron(s).

Accordingly, the invention also provides for the generation of a chimeric polynucleotide that is a man-made gene pathway containing one (or more) artificially introduced intron(s). Preferably, the artificially introduced intron(s) are functional in one or more host cells for gene splicing much in the way that naturally-occurring introns serve functionally in gene splicing. The invention provides a process of producing man-made intron-containing polynucleotides to be introduced into host organisms for recombination and/or splicing.

A man-made gene produced using the invention can also serve as a substrate for recombination with another nucleic acid. Likewise, a man-made gene pathway produced using the invention can also serve as a substrate for recombination with another nucleic acid. In a preferred instance, the recombination is facilitated by, or occurs at, areas of homology between the man-made, intron-containing gene and a nucleic acid, which serves as a recombination partner. In a particularly preferred instance, the recombination partner may also be a nucleic acid generated by the invention, including a man-made gene or a man-made gene pathway. Recombination may be facilitated by or may occur at areas of homology that exist at the one (or more) artificially introduced intron(s) in the man-made gene.

The synthetic gene reassembly method of the invention utilizes a plurality of nucleic acid building blocks, each of which preferably has two ligatable ends. The two ligatable ends on each nucleic acid building block may be two blunt ends (i.e., each having an overhang of zero nucleotides), or preferably one blunt end and one overhang, or more preferably still two overhangs.

A useful overhang for this purpose may be a 3' overhang or a 5' overhang. Thus, a nucleic acid building block may have a 3' overhang or alternatively a 5' overhang or alternatively two 3' overhangs or alternatively two 5' overhangs. The overall order in which the nucleic acid building blocks are assembled to form a finalized chimeric nucleic acid molecule is determined by purposeful experimental design and is not random.

According to one preferred embodiment, a nucleic acid building block is generated by chemical synthesis of two single-stranded nucleic acids (also referred to as single-stranded oligos) and contacting them so as to allow them to anneal to form a double-stranded nucleic acid building block.

A double-stranded nucleic acid building block can be of variable size. The sizes of these building blocks can be small or large. Preferred sizes for building block range from 1 base pair (not including any overhangs) to 100,000 base pairs (not including any overhangs). Other preferred size ranges are also provided, which have lower limits of from 1 bp to 10,000 bp (including every integer value in between), and upper limits of from 2 bp to 100,000 bp (including every integer value in between).

Many methods exist by which a double-stranded nucleic acid building block can be generated that is serviceable for the invention; and these are known in the art and can be readily performed by the skilled artisan.

According to one embodiment, a double-stranded nucleic acid building block is generated by first generating two single stranded nucleic acids and allowing them to anneal to form a double-stranded nucleic acid building block. The two strands of a double-stranded nucleic acid building block may be complementary at every nucleotide apart from any that form an overhang; thus containing no mismatches, apart from any overhang(s). According to another embodiment, the two strands of a double-stranded nucleic acid building block are complementary at fewer than every nucleotide apart from any that form an overhang. Thus, according to this embodiment, a double-stranded nucleic acid building block can be used to introduce codon degeneracy. Preferably the codon degeneracy is introduced using the site-saturation mutagenesis described herein, using one or more N,N,G/T cassettes or alternatively using one or more N,N,N cassettes.

The in vivo recombination method of the invention can be performed blindly on a pool of unknown hybrids or alleles of a specific polynucleotide or sequence. However, it is not necessary to know the actual DNA or RNA sequence of the specific polynucleotide.

The approach of using recombination within a mixed population of genes can be useful for the generation of any useful proteins, for example, interleukin I, antibodies, tPA and growth hormone. This approach may be used to generate proteins having altered specificity or activity. The approach may also be useful for the generation of hybrid nucleic acid sequences, for example, promoter regions, introns, exons, enhancer sequences, 31 untranslated regions or 51 untranslated regions of genes. Thus this approach may be used to generate genes having increased rates of expression. This approach may also be useful in the study of repetitive DNA sequences. Finally, this approach may be useful to mutate ribozymes or aptamers.

In one aspect the invention described herein is directed to the use of repeated cycles of reductive reassortment, recombination and selection which allow for the directed molecular evolution of highly complex linear sequences, such as DNA, RNA or proteins thorough recombination.

In vivo shuffling of molecules is useful in providing variants and can be performed utilizing the natural property of cells to recombine multimers. While recombination in vivo has provided the major natural route to molecular diversity, genetic recombination remains a relatively complex process that involves 1) the recognition of homologies; 2) strand cleavage, strand invasion, and metabolic steps leading to the production of recombinant chiasma; and finally 3) the resolution of chiasma into discrete recombined molecules. The formation of the chiasma requires the recognition of homologous sequences.

In another embodiment, the invention includes a method for producing a hybrid polynucleotide from at least a first polynucleotide and a second polynucleotide. The invention can be used to produce a hybrid polynucleotide by introducing at least a first polynucleotide and a second polynucleotide which share at least one region of partial sequence homology (e.g., 3, 5, 7, 9, 11, 13, 15, 17, 19, 21, 23, 25, 27, 29, 31, 33, 35, 37, 43, 45, 47, and combinations thereof) into a suitable host cell. The regions of partial sequence homology promote processes which result in sequence reorganization producing a hybrid polynucleotide. The term "hybrid polynucleotide," as used herein, is any nucleotide sequence which results from the method of the present invention and contains sequence from at least two original polynucleotide sequences. Such hybrid polynucleotides can result from intermolecular recombination events which promote sequence integration between DNA molecules. In addition, such hybrid polynucleotides can result from intramolecular reductive reassortment processes which utilize repeated sequences to alter a nucleotide sequence within a DNA molecule.

The invention provides a means for generating hybrid polynucleotides which may encode biologically active hybrid polypeptides (e.g., hybrid haloalkane dehalogenase). In one aspect, the original polynucleotides encode biologically active polypeptides. The method of the invention produces new hybrid polypeptides by utilizing cellular processes which integrate the sequence of the original polynucleotides such that the resulting hybrid polynucleotide encodes a polypeptide demonstrating activities derived from the original biologically active polypeptides. For example, the original polynucleotides may encode a particular enzyme from different microorganisms. An enzyme encoded by a first polynucleotide from one organism or variant may, for example, function effectively under a particular environmental condition, e.g., high salinity. An enzyme encoded by a second polynucleotide from a different organism or variant may function effectively under a different environmental condition, such as extremely high temperatures. A hybrid polynucleotide containing sequences from the first and second original polynucleotides may encode an enzyme which exhibits characteristics of both enzymes encoded by the original polynucleotides. Thus, the enzyme encoded by the hybrid polynucleotide may function effectively under environmental conditions shared by each of the enzymes encoded by the first and second polynucleotides, e.g., high salinity and extreme temperatures.

Enzymes encoded by the polynucleotides of the invention include, but are not limited to, hydrolases, dehalogenases and haloalkane dehalogenases. A hybrid polypeptide resulting from the method of the invention may exhibit specialized enzyme activity not displayed in the original enzymes. For example, following recombination and/or reductive reassortment of polynucleotides encoding hydrolase activities, the resulting hybrid polypeptide encoded by a hybrid polynucleotide can be screened for specialized hydrolase activities obtained from each of the original enzymes, i.e., the type of bond on which the hydrolase acts and the temperature at which the hydrolase functions. Thus, for example, the hydrolase may be screened to ascertain those chemical functionalities which distinguish the hybrid hydrolase from the original hydrolases, such as: (a) amide (peptide bonds), i.e., proteases; (b) ester bonds, i.e., esterases and lipases; (c) acetals, i.e., glycosidases and, for example, the temperature, pH or salt concentration at which the hybrid polypeptide functions.

Sources of the original polynucleotides may be isolated from individual organisms ("isolates"), collections of organisms that have been grown in defined media ("enrichment cultures"), or, uncultivated organisms ("environmental samples"). The use of a culture-independent approach to derive polynucleotides encoding novel bioactivities from environmental samples is most preferable since it allows one to access untapped resources of biodiversity.

"Environmental libraries" are generated from environmental samples and represent the collective genomes of naturally occurring organisms archived in cloning vectors that can be propagated in suitable prokaryotic hosts. Because the cloned DNA is initially extracted directly from environmental samples, the libraries are not limited to the small fraction of prokaryotes that can be grown in pure culture. Additionally, a normalization of the environmental DNA present in these samples could allow more equal representation of the DNA from all of the species present in the original sample. This can dramatically increase the efficiency of finding interesting genes from minor constituents of the sample which may be under-represented by several orders of magnitude compared to the dominant species.

For example, gene libraries generated from one or more uncultivated microorganisms are screened for an activity of interest. Potential pathways encoding bioactive molecules of interest are first captured in prokaryotic cells in the form of gene expression libraries. Polynucleotides encoding activities of interest are isolated from such libraries and introduced into a host cell. The host cell is grown under conditions which promote recombination and/or reductive reassortment creating potentially active biomolecules with novel or enhanced activities.

The microorganisms from which the polynucleotide may be prepared include prokaryotic microorganisms, such as *Eubacteria* and *Archaebacteria*, and lower eukaryotic microorganisms such as fungi, some algae and protozoa. Polynucleotides may be isolated from environmental samples in which case the nucleic acid may be recovered without culturing of an organism or recovered from one or more cultured organisms. In one aspect, such microorganisms may be extremophiles, such as hyperthermophiles, psychrophiles, psychrotrophs, halophiles, barophiles and acidophiles. Polynucleotides encoding enzymes isolated from extremophilic microorganisms are particularly preferred. Such enzymes may function at temperatures above 100° C. in terrestrial hot springs and deep sea thermal vents, at temperatures below 0° C. in arctic waters, in the saturated salt environment of the Dead Sea, at pH values around 0 in coal deposits and geothermal sulfur-rich springs, or at pH values greater than 11 in sewage sludge. For example, several esterases and lipases cloned and expressed from extremophilic organisms show high activity throughout a wide range of temperatures and pHs.

Polynucleotides selected and isolated as hereinabove described are introduced into a suitable host cell. A suitable host cell is any cell which is capable of promoting recombination and/or reductive reassortment. The selected polynucleotides are preferably already in a vector which includes appropriate control sequences. The host cell can be a higher eukaryotic cell, such as a mammalian cell, or a lower eukaryotic cell, such as a yeast cell, or preferably, the host cell can be a prokaryotic cell, such as a bacterial cell. Introduction of the construct into the host cell can be effected by calcium phosphate transfection, DEAE-Dextran mediated transfection, or electroporation (Davis, et al., 1986).

As representative examples of appropriate hosts, there may be mentioned: bacterial cells, such as *E. coli, Streptomyces, Salmonella typhimurium*; fungal cells, such as yeast; insect cells such as *Drosophila* S2 and *Spodoptera* Sf9; animal cells such as CHO, COS or Bowes melanoma; adenoviruses; and plant cells. The selection of an appropriate host is deemed to be within the scope of those skilled in the art from the teachings herein.

With particular references to various mammalian cell culture systems that can be employed to express recombinant protein, examples of mammalian expression systems include the COS-7 lines of monkey kidney fibroblasts, described in "SV40-transformed simian cells support the replication of early SV40 mutants" (Gluzman, 1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

Host cells containing the polynucleotides of interest can be cultured in conventional nutrient media modified as appropriate for activating promoters, selecting transformants or amplifying genes. The culture conditions, such as temperature, pH and the like, are those previously used with the host cell selected for expression, and will be apparent to the ordinarily skilled artisan. The clones which are identified as having the specified enzyme activity may then be sequenced to identify the polynucleotide sequence encoding an enzyme having the enhanced activity.

In another aspect, it is envisioned the method of the present invention can be used to generate novel polynucleotides encoding biochemical pathways from one or more operons or gene clusters or portions thereof. For example, bacteria and many eukaryotes have a coordinated mechanism for regulating genes whose products are involved in related processes. The genes are clustered, in structures referred to as "gene clusters," on a single chromosome and are transcribed together under the control of a single regulatory sequence, including a single promoter which initiates transcription of the entire cluster. Thus, a gene cluster is a group of adjacent genes that are either identical or related, usually as to their function. An example of a biochemical pathway encoded by gene clusters are polyketides. Polyketides are molecules which are an extremely rich source of bioactivities, including antibiotics (such as tetracyclines and erythromycin), anti-cancer agents (daunomycin), immunosuppressants (FK506 and rapamycin), and veterinary products (monensin). Many polyketides (produced by polyketide synthases) are valuable as therapeutic agents. Polyketide synthases are multifunctional enzymes that catalyze the biosynthesis of an enormous variety of carbon chains differing in length and patterns of functionality and cyclization. Polyketide synthase genes fall into gene clusters and at least one type (designated type I) of polyketide synthases have large size genes and enzymes, complicating genetic manipulation and in vitro studies of these genes/proteins.

Gene cluster DNA can be isolated from different organisms and ligated into vectors, particularly vectors containing expression regulatory sequences which can control and regulate the production of a detectable protein or protein-related array activity from the ligated gene clusters. Use of vectors which have an exceptionally large capacity for exogenous DNA introduction are particularly appropriate for use with such gene clusters and are described by way of example herein to include the f-factor (or fertility factor) of *E. coli*. This f-factor of *E. coli* is a plasmid which affect high-frequency transfer of itself during conjugation and is ideal to achieve and stably propagate large DNA fragments, such as gene clusters from mixed microbial samples. A particularly preferred embodiment is to use cloning vectors, referred to as "fosmids" or bacterial artificial chromosome (BAC) vectors. These are derived from *E. coli* f-factor which is able to stably integrate large segments of genomic DNA. When integrated with DNA from a mixed uncultured environmental sample, this makes it possible to achieve large genomic fragments in the form of a stable "environmental DNA library." Another type of vector for use in the present invention is a cosmid vector. Cosmid vectors were originally designed to clone and propagate large segments of genomic DNA. Cloning into cosmid vectors is described in detail in Sambrook, et al., *Molecular Cloning: A Laboratory Manual*, 2nd Ed., Cold Spring Harbor Laboratory Press (1989). Once ligated into an appropriate vector, two or more vectors containing different polyketide synthase gene clusters can be introduced into a suitable host cell. Regions of partial sequence homology shared by the gene clusters will promote processes which result in sequence reorganization resulting in a hybrid gene cluster. The novel hybrid gene cluster can then be screened for enhanced activities not found in the original gene clusters.

Therefore, in a one embodiment, the invention relates to a method for producing a biologically active hybrid polypeptide and screening such a polypeptide for enhanced activity by:

1) introducing at least a first polynucleotide in operable linkage and a second polynucleotide in operable linkage, said at least first polynucleotide and second polynucleotide sharing at least one region of partial sequence homology, into a suitable host cell;
2) growing the host cell under conditions which promote sequence reorganization resulting in a hybrid polynucleotide in operable linkage;
3) expressing a hybrid polypeptide encoded by the hybrid polynucleotide;
4) screening the hybrid polypeptide under conditions which promote identification of enhanced biological activity; and
5) isolating the a polynucleotide encoding the hybrid polypeptide.

Methods for screening for various enzyme activities are known to those of skill in the art and are discussed throughout the present specification. Such methods may be employed when isolating the polypeptides and polynucleotides of the invention.

As representative examples of expression vectors which may be used, there may be mentioned viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as *bacillus, Aspergillus* and yeast). Thus, for example, the DNA may be included in any one of a variety of expression vectors for expressing a polypeptide. Such vectors include chromosomal, nonchromosomal and synthetic DNA sequences. Large numbers of suitable vectors are known to those of skill in the art, and are commercially available. The following vectors are provided by way of example: Bacterial: pQE vectors (Qiagen), pBluescript plasmids, pNH vectors, (lambda-ZAP vectors (Stratagene)); ptrc99a, pKK223-3, pDR540, pRIT2T (Pharmacia); Eukaryotic: pXT1, pSG5 (Stratagene), pSVK3, pBPV, pMSG, pSVLSV40 (Pharmacia). However, any other plasmid or other vector may be used so long as they are replicable and viable in the host. Low copy number or high copy number vectors may be employed with the present invention.

The DNA sequence in the expression vector is operatively linked to an appropriate expression control sequence(s) (promoter) to direct RNA synthesis. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using chloramphenicol transferase (CAT) vectors or other vectors with selectable markers. In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

In vivo reassortment is focused on "inter-molecular" processes collectively referred to as "recombination" which in bacteria, is generally viewed as a "RecA-dependent" phenomenon. The invention can rely on recombination processes of a host cell to recombine and re-assort sequences, or the cells' ability to mediate reductive processes to decrease the complexity of quasi-repeated sequences in the cell by deletion. This process of "reductive reassortment" occurs by an "intra-molecular," RecA-independent process.

Therefore, in another aspect of the invention, novel polynucleotides can be generated by the process of reductive reassortment. The method involves the generation of constructs containing consecutive sequences (original encoding sequences), their insertion into an appropriate vector, and their subsequent introduction into an appropriate host cell. The reassortment of the individual molecular identities occurs by combinatorial processes between the consecutive sequences in the construct possessing regions of homology, or between quasi-repeated units. The reassortment process recombines and/or reduces the complexity and extent of the repeated sequences, and results in the production of novel molecular species. Various treatments may be applied to enhance the rate of reassortment. These could include treatment with ultra-violet light, or DNA damaging chemicals, and/or the use of host cell lines displaying enhanced levels of "genetic instability". Thus the reassortment process may involve homologous recombination or the natural property of quasi-repeated sequences to direct their own evolution.

Repeated or "quasi-repeated" sequences play a role in genetic instability. In the present invention, "quasi-repeats" are repeats that are not restricted to their original unit structure. Quasi-repeated units can be presented as an array of sequences in a construct; consecutive units of similar sequences. Once ligated, the junctions between the consecutive sequences become essentially invisible and the quasi-repetitive nature of the resulting construct is now continuous at the molecular level. The deletion process the cell performs to reduce the complexity of the resulting construct operates between the quasi-repeated sequences. The quasi-repeated units provide a practically limitless repertoire of templates upon which slippage events can occur. The constructs containing the quasi-repeats thus effectively provide sufficient molecular elasticity that deletion (and potentially insertion) events can occur virtually anywhere within the quasi-repetitive units.

When the quasi-repeated sequences are all ligated in the same orientation, for instance head to tail or vice versa, the cell cannot distinguish individual units. Consequently, the reductive process can occur throughout the sequences. In contrast, when for example, the units are presented head to head, rather than head to tail, the inversion delineates the endpoints of the adjacent unit so that deletion formation will favor the loss of discrete units. Thus, it is preferable with the present method that the sequences are in the same orientation. Random orientation of quasi-repeated sequences will result in the loss of reassortment efficiency, while consistent orientation of the sequences will offer the highest efficiency. However, while having fewer of the contiguous sequences in the same orientation decreases the efficiency, it may still provide sufficient elasticity for the effective recovery of novel molecules. Constructs can be made with the quasi-repeated sequences in the same orientation to allow higher efficiency.

Sequences can be assembled in a head to tail orientation using any of a variety of methods, including the following:
a) Primers that include a poly-A head and poly-T tail which when made single-stranded would provide orientation can be utilized. This is accomplished by having the first few bases of the primers made from RNA and hence easily removed RNAseH.
b) Primers that include unique restriction cleavage sites can be utilized. Multiple sites, a battery of unique sequences, and repeated synthesis and ligation steps would be required.
c) The inner few bases of the primer could be thiolated and an exonuclease used to produce properly tailed molecules.

The recovery of the re-assorted sequences relies on the identification of cloning vectors with a reduced repetitive index (RI). The re-assorted encoding sequences can then be recovered by amplification. The products are re-cloned and expressed. The recovery of cloning vectors with reduced RI can be affected by:
1) The use of vectors only stably maintained when the construct is reduced in complexity.
2) The physical recovery of shortened vectors by physical procedures. In this case, the cloning vector would be recovered using standard plasmid isolation procedures and size fractionated on either an agarose gel, or column with a low molecular weight cut off utilizing standard procedures.
3) The recovery of vectors containing interrupted genes which can be selected when insert size decreases.
4) The use of direct selection techniques with an expression vector and the appropriate selection.

Encoding sequences (for example, genes) from related organisms may demonstrate a high degree of homology and encode quite diverse protein products. These types of sequences are particularly useful in the present invention as quasi-repeats. However, while the examples illustrated below demonstrate the reassortment of nearly identical original encoding sequences (quasi-repeats), this process is not limited to such nearly identical repeats.

The following example demonstrates a method of the invention. Encoding nucleic acid sequences (quasi-repeats) derived from three (3) unique species are described. Each sequence encodes a protein with a distinct set of properties. Each of the sequences differs by a single or a few base pairs at a unique position in the sequence. The quasi-repeated sequences are separately or collectively amplified and ligated into random assemblies such that all possible permutations and combinations are available in the population of ligated molecules. The number of quasi-repeat units can be controlled by the assembly conditions. The average number of quasi-repeated units in a construct is defined as the repetitive index (RI).

Once formed, the constructs may, or may not be size fractionated on an agarose gel according to published protocols, inserted into a cloning vector, and transfected into an appropriate host cell. The cells are then propagated and "reductive reassortment" is effected. The rate of the reductive reassortment process may be stimulated by the introduction of DNA damage if desired. Whether the reduction in RI is mediated by deletion formation between repeated sequences by an "intra-molecular" mechanism, or mediated by recombination-like events through "inter-molecular" mechanisms is immaterial. The end result is a reassortment of the molecules into all possible combinations.

Optionally, the method comprises the additional step of screening the library members of the shuffled pool to identify individual shuffled library members having the ability to bind or otherwise interact, or catalyze a particular reaction (e.g., such as catalytic domain of an enzyme) with a predetermined macromolecule, such as for example a proteinaceous receptor, an oligosaccharide, virion, or other predetermined compound or structure.

The polypeptides that are identified from such libraries can be used for therapeutic, diagnostic, research and related purposes (e.g., catalysts, solutes for increasing osmolarity of an aqueous solution, and the like), and/or can be subjected to one or more additional cycles of shuffling and/or selection.

In another aspect, it is envisioned that prior to or during recombination or reassortment, polynucleotides generated by the method of the invention can be subjected to agents or processes which promote the introduction of mutations into the original polynucleotides. The introduction of such mutations would increase the diversity of resulting hybrid polynucleotides and polypeptides encoded therefrom. The agents or processes which promote mutagenesis can include, but are not limited to: (+)-CC-1065, or a synthetic analog such as (+)-CC-1065-(N-3-Adenine (See Sun and Hurley, (1992)); an N-acetylated or deacetylated 4'-fluoro-4-aminobiphenyl adduct capable of inhibiting DNA synthesis (See, for example, van de Poll, et al. (1992)); or an N-acetylated or deacetylated 4-aminobiphenyl adduct capable of inhibiting DNA synthesis (See also, van de Poll, et al. (1992), pp. 751-758); trivalent chromium, a trivalent chromium salt, a polycyclic aromatic hydrocarbon (PAH) DNA adduct capable of inhibiting DNA replication, such as 7-bromomethyl-benz[α]anthracene ("BMA"), tris(2,3-dibromopropyl) phosphate ("Tris-BP"), 1,2-dibromo-3-chloropropane ("DBCP"), 2-bromoacrolein (2BA), benzo[α]pyrene-7,8-dihydrodiol-9-10-epoxide ("BPDE"), a platinum(II) halogen salt, N-hydroxy-2-amino-3-methylimidazo[4,5-f]-quinoline ("N-hydroxy-IQ"), and N-hydroxy-2-amino-1-methyl-6-phenylimidazo[4,5-f]-pyridine ("N-hydroxy-PhIP"). Especially preferred means for slowing or halting PCR amplification consist of UV light (+)-CC-1065 and (+)-CC-1065-(N-3-Adenine). Particularly encompassed means are DNA adducts or polynucleotides comprising the DNA adducts from the polynucleotides or polynucleotides pool, which can be released or removed by a process including heating the solution comprising the polynucleotides prior to further processing.

In another aspect the invention is directed to a method of producing recombinant proteins having biological activity by treating a sample comprising double-stranded template polynucleotides encoding a wild-type protein under conditions according to the invention which provide for the production of hybrid or re-assorted polynucleotides.

The invention also provides for the use of proprietary codon primers (containing a degenerate N,N,N sequence) to introduce point mutations into a polynucleotide, so as to generate a set of progeny polypeptides in which a full range of single amino acid substitutions is represented at each amino acid position (gene site saturation mutagenesis (GSSM)). The oligos used are comprised contiguously of a first homologous sequence, a degenerate N,N,N sequence, and preferably but not necessarily a second homologous sequence. The downstream progeny translational products from the use of such oligos include all possible amino acid changes at each amino acid site along the polypeptide, because the degeneracy of the N,N,N sequence includes codons for all 20 amino acids.

In one aspect, one such degenerate oligo (comprised of one degenerate N,N,N cassette) is used for subjecting each original codon in a parental polynucleotide template to a full range of codon substitutions. In another aspect, at least two degenerate N,N,N cassettes are used—either in the same oligo or not, for subjecting at least two original codons in a parental polynucleotide template to a full range of codon substitutions. Thus, more than one N,N,N sequence can be contained in one oligo to introduce amino acid mutations at more than one site. This plurality of N,N,N sequences can be directly contiguous, or separated by one or more additional nucleotide sequence(s). In another aspect, oligos serviceable for introducing additions and deletions can be used either alone or in combination with the codons containing an N,N,N sequence, to introduce any combination or permutation of amino acid additions, deletions, and/or substitutions.

In a particular exemplification, it is possible to simultaneously mutagenize two or more contiguous amino acid positions using an oligo that contains contiguous N,N,N triplets, i.e., a degenerate $(N,N,N)_n$ sequence.

In another aspect, the present invention provides for the use of degenerate cassettes having less degeneracy than the N,N,N sequence. For example, it may be desirable in some instances to use (e.g., in an oligo) a degenerate triplet sequence comprised of only one N, where said N can be in the first second or third position of the triplet. Any other bases including any combinations and permutations thereof can be used in the remaining two positions of the triplet. Alternatively, it may be desirable in some instances to use (e.g., in an oligo) a degenerate N,N,N triplet sequence, N,N,G/T, or an N,N, G/C triplet sequence.

It is appreciated, however, that the use of a degenerate triplet (such as N,N,G/T or an N,N, G/C triplet sequence) as disclosed in the instant invention is advantageous for several reasons. In one aspect, this invention provides a means to systematically and fairly easily generate the substitution of the full range of possible amino acids (for a total of 20 amino acids) into each and every amino acid position in a polypeptide. Thus, for a 100 amino acid polypeptide, the invention provides a way to systematically and fairly easily generate 2000 distinct species (i.e., 20 possible amino acids per position times 100 amino acid positions). It is appreciated that there is provided, through the use of an oligo containing a degenerate N,N,G/T or an N,N, G/C triplet sequence, 32 individual sequences that code for 20 possible amino acids. Thus, in a reaction vessel in which a parental polynucleotide sequence is subjected to saturation mutagenesis using one such oligo, there are generated 32 distinct progeny polynucleotides encoding 20 distinct polypeptides. In contrast, the use of a non-degenerate oligo in site-directed mutagenesis leads to only one progeny polypeptide product per reaction vessel.

This invention also provides for the use of nondegenerate oligos, which can optionally be used in combination with degenerate primers disclosed. It is appreciated that in some situations, it is advantageous to use nondegenerate oligos to generate specific point mutations in a working polynucleotide. This provides a means to generate specific silent point mutations, point mutations leading to corresponding amino acid changes, and point mutations that cause the generation of stop codons and the corresponding expression of polypeptide fragments.

Thus, in a preferred embodiment of this invention, each saturation mutagenesis reaction vessel contains polynucleotides encoding at least 20 progeny polypeptide molecules such that all 20 amino acids are represented at the one specific amino acid position corresponding to the codon position mutagenized in the parental polynucleotide. The 32-fold degenerate progeny polypeptides generated from each saturation mutagenesis reaction vessel can be subjected to clonal amplification (e.g., cloned into a suitable E. coli host using an expression vector) and subjected to expression screening. When an individual progeny polypeptide is identified by screening to display a favorable change in property (when compared to the parental polypeptide), it can be sequenced to identify the correspondingly favorable amino acid substitution contained therein.

It is appreciated that upon mutagenizing each and every amino acid position in a parental polypeptide using saturation mutagenesis as disclosed herein, favorable amino acid changes may be identified at more than one amino acid position. One or more new progeny molecules can be generated that contain a combination of all or part of these favorable amino acid substitutions. For example, if 2 specific favorable amino acid changes are identified in each of 3 amino acid positions in a polypeptide, the permutations include 3 possibilities at each position (no change from the original amino acid, and each of two favorable changes) and 3 positions. Thus, there are 3×3×3 or 27 total possibilities, including 7 that were previously examined—6 single point mutations (i.e., 2 at each of three positions) and no change at any position.

In yet another aspect, site-saturation mutagenesis can be used together with shuffling, chimerization, recombination and other mutagenizing processes, along with screening. This invention provides for the use of any mutagenizing process(es), including saturation mutagenesis, in an iterative manner. In one exemplification, the iterative use of any mutagenizing process(es) is used in combination with screening.

Thus, in a non-limiting exemplification, this invention provides for the use of saturation mutagenesis in combination with additional mutagenization processes, such as process where two or more related polynucleotides are introduced into a suitable host cell such that a hybrid polynucleotide is generated by recombination and reductive reassortment.

In addition to performing mutagenesis along the entire sequence of a gene, the instant invention provides that mutagenesis can be use to replace each of any number of bases in a polynucleotide sequence, wherein the number of bases to be mutagenized is preferably every integer from 15 to 100,000. Thus, instead of mutagenizing every position along a molecule, one can subject every or a discrete number of bases (preferably a subset totaling from 15 to 100,000) to mutagenesis. Preferably, a separate nucleotide is used for mutagenizing each position or group of positions along a polynucleotide sequence. A group of 3 positions to be mutagenized may be a codon. The mutations are preferably introduced using a mutagenic primer, containing a heterologous cassette, also referred to as a mutagenic cassette. Preferred cassettes can have from 1 to 500 bases. Each nucleotide position in such heterologous cassettes be N, A, C, G, T, A/C, A/G, A/T, C/G, C/T, G/T, C/G/T, A/G/T, A/C/T, A/C/G, or E, where E is any base that is not A, C, G, or T (E can be referred to as a designer oligo).

In a general sense, saturation mutagenesis is comprised of mutagenizing a complete set of mutagenic cassettes (wherein each cassette is preferably about 1-500 bases in length) in defined polynucleotide sequence to be mutagenized (wherein the sequence to be mutagenized is preferably from about 15 to 100,000 bases in length). Thus, a group of mutations (ranging from 1 to 100 mutations) is introduced into each cassette to be mutagenized. A grouping of mutations to be introduced into one cassette can be different or the same from a second grouping of mutations to be introduced into a second cassette during the application of one round of saturation mutagenesis. Such groupings are exemplified by deletions, additions, groupings of particular codons, and groupings of particular nucleotide cassettes.

Defined sequences to be mutagenized include a whole gene, pathway, cDNA, an entire open reading frame (ORF), and entire promoter, enhancer, repressor/transactivator, origin of replication, intron, operator, or any polynucleotide functional group. Generally, a "defined sequences" for this purpose may be any polynucleotide that a 15 base-polynucleotide sequence, and polynucleotide sequences of lengths between 15 bases and 15,000 bases (this invention specifically names every integer in between). Considerations in choosing groupings of codons include types of amino acids encoded by a degenerate mutagenic cassette.

In a particularly preferred exemplification a grouping of mutations that can be introduced into a mutagenic cassette, this invention specifically provides for degenerate codon substitutions (using degenerate oligos) that code for 2, 3, 4, 5, 6, 7, 8, 9, 10, 11, 12, 13, 14, 15, 16, 17, 18, 19, and 20 amino acids at each position, and a library of polypeptides encoded thereby.

One aspect of the invention is an isolated nucleic acid comprising one of the sequences of Group A nucleic acid sequences, and sequences substantially identical thereto, the sequences complementary thereto, or a fragment comprising at least 10, 15, 20, 25, 30, 35, 40, 50, 75, 100, 150, 200, 300, 400, or 500 consecutive bases of one of the sequences of a Group A nucleic acid sequence (or the sequences complementary thereto). The isolated, nucleic acids may comprise DNA, including cDNA, genomic DNA, and synthetic DNA. The DNA may be double-stranded or single-stranded, and if single stranded may be the coding strand or non-coding (anti-sense) strand. Alternatively, the isolated nucleic acids may comprise RNA.

As discussed in more detail below, the isolated nucleic acids of one of the Group A nucleic acid sequences, and sequences substantially identical thereto, may be used to prepare one of the polypeptides of a Group B amino acid sequence, and sequences substantially identical thereto, or fragments comprising at least 5, 10, 15, 20, 25, 30, 35, 40, 50, 75, 100, or 150 consecutive amino acids of one of the polypeptides of Group B amino acid sequences, and sequences substantially identical thereto.

Accordingly, another aspect of the invention is an isolated nucleic acid which encodes one of the polypeptides of Group B amino acid sequences, and sequences substantially identical thereto, or fragments comprising at least 5, 10, 15, 20, 25, 30, 35, 40, 50, 75, 100, or 150 consecutive amino acids of one of the polypeptides of the Group B amino acid sequences. The coding sequences of these nucleic acids may be identical to one of the coding sequences of one of the nucleic acids of Group A nucleic acid sequences, or a fragment thereof or may be different coding sequences which encode one of the polypeptides of Group B amino acid sequences, sequences substantially identical thereto, and fragments having at least 5, 10, 15, 20, 25, 30, 35, 40, 50, 75, 100, or 150 consecutive amino acids of one of the polypeptides of Group B amino acid sequences, as a result of the redundancy or degeneracy of the genetic code. The genetic code is well known to those of skill in the art and can be obtained, for example, on page 214 of B. Lewin, *Genes VI*, Oxford University Press, 1997, the disclosure of which is incorporated herein by reference.

The isolated nucleic acid which encodes one of the polypeptides of Group B amino acid sequences, and sequences substantially identical thereto, may include, but is not limited to: only the coding sequence of one of Group A nucleic acid sequences, and sequences substantially identical thereto, and additional coding sequences, such as leader sequences or proprotein sequences and non-coding sequences, such as introns or non-coding sequences 5' and/or 3' of the coding sequence. Thus, as used herein, the term "polynucleotide encoding a polypeptide" encompasses a polynucleotide which includes only the coding sequence for the polypeptide as well as a polynucleotide which includes additional coding and/or non-coding sequence.

Alternatively, the nucleic acid sequences of Group A nucleic acid sequences, and sequences substantially identical thereto, may be mutagenized using conventional techniques, such as site directed mutagenesis, or other techniques familiar to those skilled in the art, to introduce silent changes into the polynucleotides of Group A nucleic acid sequences, and sequences substantially identical thereto. As used herein, "silent changes" include, for example, changes which do not alter the amino acid sequence encoded by the polynucleotide. Such changes may be desirable in order to increase the level of the polypeptide produced by host cells containing a vector encoding the polypeptide by introducing codons or codon pairs which occur frequently in the host organism.

The invention also relates to polynucleotides which have nucleotide changes which result in amino acid substitutions, additions, deletions, fusions and truncations in the polypeptides of Group B amino acid sequences, and sequences substantially identical thereto. Such nucleotide changes may be introduced using techniques such as site directed mutagenesis, random chemical mutagenesis, exonuclease III deletion, and other recombinant DNA techniques. Alternatively, such nucleotide changes may be naturally occurring allelic variants which are isolated by identifying nucleic acids which specifically hybridize to probes comprising at least 10, 15, 20, 25, 30, 35, 40, 50, 75, 100, 150, 200, 300, 400, or 500 consecutive bases of one of the sequences of Group A nucleic acid sequences, and sequences substantially identical thereto (or the sequences complementary thereto) under conditions of high, moderate, or low stringency as provided herein.

The isolated nucleic acids of Group A nucleic acid sequences, and sequences substantially identical thereto, the sequences complementary thereto, or a fragment comprising at least 10, 15, 20, 25, 30, 35, 40, 50, 75, 100, 150, 200, 300, 400, or 500 consecutive bases of one of the sequences of Group A nucleic acid sequences, and sequences substantially identical thereto, or the sequences complementary thereto may also be used as probes to determine whether a biological sample, such as a soil sample, contains an organism having a nucleic acid sequence of the invention or an organism from which the nucleic acid was obtained. In such procedures, a biological sample potentially harboring the organism from which the nucleic acid was isolated is obtained and nucleic acids are obtained from the sample. The nucleic acids are contacted with the probe under conditions which permit the probe to specifically hybridize to any complementary sequences from which are present therein.

Where necessary, conditions which permit the probe to specifically hybridize to complementary sequences may be determined by placing the probe in contact with complementary sequences from samples known to contain the complementary sequence as well as control sequences which do not contain the complementary sequence. Hybridization conditions, such as the salt concentration of the hybridization buffer, the formamide concentration of the hybridization buffer, or the hybridization temperature, may be varied to identify conditions which allow the probe to hybridize specifically to complementary nucleic acids.

If the sample contains the organism from which the nucleic acid was isolated, specific hybridization of the probe is then detected. Hybridization may be detected by labeling the probe with a detectable agent such as a radioactive isotope, a fluorescent dye or an enzyme capable of catalyzing the formation of a detectable product.

Many methods for using the labeled probes to detect the presence of complementary nucleic acids in a sample are familiar to those skilled in the art. These include Southern Blots, Northern Blots, colony hybridization procedures, and dot blots. Protocols for each of these procedures are provided in Ausubel, et al., *Current Protocols in Molecular Biology*, John Wiley & Sons, Inc. (1997) and Sambrook, et al., *Molecular Cloning: A Laboratory Manual*, 2nd Ed., Cold Spring Harbor Laboratory Press (1989), the entire disclosures of which are incorporated herein by reference.

Alternatively, more than one probe (at least one of which is capable of specifically hybridizing to any complementary sequences which are present in the nucleic acid sample), may be used in an amplification reaction to determine whether the sample contains an organism containing a nucleic acid sequence of the invention (e.g., an organism from which the nucleic acid was isolated). Typically, the probes comprise oligonucleotides. In one embodiment, the amplification reaction may comprise a PCR reaction. PCR protocols are described in Ausubel and Sambrook, supra. Alternatively, the amplification may comprise a ligase chain reaction, 3SR, or strand displacement reaction. (See Barany, F., "The Ligase Chain Reaction in a PCR World", *PCR Methods and Applications*, 1:5-16, 1991; Fahy, E., et al., "Self-sustained Sequence Replication (3SR): An Isothermal Transcription-based Amplification System Alternative to PCR", *PCR Methods and Applications*, 1:25-33, 1991; and Walker, G. T., et al., "Strand Displacement Amplification-an Isothermal in vitro DNA Amplification Technique", *Nucleic Acid Research* 20:1691-1696, 1992, the disclosures of which are incorporated herein by reference in their entireties). In such procedures, the nucleic acids in the sample are contacted with the probes, the amplification reaction is performed, and any resulting amplification product is detected. The amplification product may be detected by performing gel electrophoresis on the reaction products and staining the gel with an intercalator such as ethidium bromide. Alternatively, one or more of the probes may be labeled with a radioactive isotope and the presence of a radioactive amplification product may be detected by autoradiography after gel electrophoresis.

Probes derived from sequences near the ends of the sequences of Group A nucleic acid sequences, and sequences substantially identical thereto, may also be used in chromosome walking procedures to identify clones containing genomic sequences located adjacent to the sequences of Group A nucleic acid sequences, and sequences substantially identical thereto. Such methods allow the isolation of genes which encode additional proteins from the host organism.

The isolated nucleic acids of Group A nucleic acid sequences, and sequences substantially identical thereto, the sequences complementary thereto, or a fragment comprising at least 10, 15, 20, 25, 30, 35, 40, 50, 75, 100, 150, 200, 300, 400, or 500 consecutive bases of one of the sequences of Group A nucleic acid sequences, and sequences substantially identical thereto, or the sequences complementary thereto may be used as probes to identify and isolate related nucleic acids. In some embodiments, the related nucleic acids may be cDNAs or genomic DNAs from organisms other than the one from which the nucleic acid was isolated. For example, the other organisms may be related organisms. In such procedures, a nucleic acid sample is contacted with the probe under conditions which permit the probe to specifically hybridize to related sequences. Hybridization of the probe to nucleic acids from the related organism is then detected using any of the methods described above.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

Hybridization may be carried out under conditions of low stringency, moderate stringency or high stringency. As an example of nucleic acid hybridization, a polymer membrane containing immobilized denatured nucleic acids is first prehybridized for 30 minutes at 45° C. in a solution consisting of 0.9 M NaCl, 50 mM $NaH_2PO_4$, pH 7.0, 5.0 mM $Na_2EDTA$, 0.5% SDS, 10×Denhardt's, and 0.5 mg/ml polyriboadenylic acid. Approximately $2 \times 10^7$ cpm (specific activity $4-9 \times 10^8$ cpm/ug) of $^{32}P$ end-labeled oligonucleotide probe are then added to the solution. After 12-16 hours of incubation, the membrane is washed for 30 minutes at room temperature in 1×SET (150 mM NaCl, 20 mM Tris hydrochloride, pH 7.8, 1 mM $Na_2EDTA$) containing 0.5% SDS, followed by a 30 minute wash in fresh 1×SET at $T_m$-10° C. for the oligonucleotide probe. The membrane is then exposed to auto-radiographic film for detection of hybridization signals.

By varying the stringency of the hybridization conditions used to identify nucleic acids, such as cDNAs or genomic DNAs, which hybridize to the detectable probe, nucleic acids having different levels of homology to the probe can be identified and isolated. Stringency may be varied by conducting the hybridization at varying temperatures below the melting temperatures of the probes. The melting temperature, $T_m$, is the temperature (under defined ionic strength and pH) at which 50% of the target sequence hybridizes to a perfectly complementary probe. Very stringent conditions are selected to be equal to or about 5° C. lower than the $T_m$ for a particular probe. The melting temperature of the probe may be calculated using the following formulas:

For probes between 14 and 70 nucleotides in length the melting temperature ($T_m$) is calculated using the formula: $T_m=81.5+16.6(\log [Na+])+0.41(\text{fraction } G+C)-(600/N)$ where N is the length of the probe.

If the hybridization is carried out in a solution containing formamide, the melting temperature may be calculated using the equation: $T_m=81.5+16.6(\log [Na+])+0.41(\text{fraction } G+C)-(0.63\% \text{ formamide})-(600/N)$ where N is the length of the probe.

Prehybridization may be carried out in 6×SSC, 5×Denhardt's reagent, 0.5% SDS, 100 µg denatured fragmented salmon sperm DNA or 6×SSC, 5×Denhardt's reagent, 0.5% SDS, 100 µg denatured fragmented salmon sperm DNA, 50% formamide. The formulas for SSC and Denhardt's solutions are listed in Sambrook, et al., supra.

Hybridization is conducted by adding the detectable probe to the prehybridization solutions listed above. Where the probe comprises double stranded DNA, it is denatured before addition to the hybridization solution. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15-25° C. below the $T_m$. For shorter probes, such as oligonucleotide probes, the hybridization may be conducted at 5-10° C. below the $T_m$. Typically, for hybridizations in 6×SSC, the hybridization is conducted at approximately 68° C. Usually, for hybridizations in 50% formamide containing solutions, the hybridization is conducted at approximately 42° C.

All of the foregoing hybridizations would be considered to be under conditions of high stringency.

Following hybridization, the filter is washed to remove any non-specifically bound detectable probe. The stringency used to wash the filters can also be varied depending on the nature of the nucleic acids being hybridized, the length of the nucleic acids being hybridized, the degree of complementarity, the nucleotide sequence composition (e.g., GC v. AT content), and the nucleic acid type (e.g., RNA v. DNA). Examples of progressively higher stringency condition washes are as follows: 2×SSC, 0.1% SDS at room temperature for 15 minutes (low stringency); 0.1×SSC, 0.5% SDS at room temperature for 30 minutes to 1 hour (moderate stringency); 0.1×SSC, 0.5% SDS for 15 to 30 minutes at between the hybridization temperature and 68° C. (high stringency); and 0.15M NaCl for 15 minutes at 72° C. (very high stringency). A final low stringency wash can be conducted in 0.1×SSC at room temperature. The examples above are merely illustrative of one set of conditions that can be used to wash filters. One of skill in the art would know that there are numerous recipes for different stringency washes. Some other examples are given below.

Nucleic acids which have hybridized to the probe are identified by autoradiography or other conventional techniques.

The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a Na+ concentration of approximately 1M. Following hybridization, the filter may be washed with 2×SSC, 0.5% SDS at the temperature of hybridization. These conditions are considered to be "moderate" conditions above 50° C. and "low" conditions below 50° C. A specific example of "moderate" hybridization conditions is when the above hybridization is conducted at 55° C. A specific example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

For example, the preceding methods may be used to isolate nucleic acids having a sequence with at least about 97%, at least 95%, at least 90%, at least 85%, at least 80%, at least 75%, at least 70%, at least 65%, at least 60%, at least 55% or at least 50% homology to a nucleic acid sequence selected from the group consisting of one of the sequences of Group A nucleic acid sequences, and sequences substantially identical thereto, or fragments comprising at least about 10, 15, 20, 25, 30, 35, 40, 50, 75, 100, 150, 200, 300, 400, or 500 consecutive bases thereof, and the sequences complementary thereto. Homology may be measured using the alignment algorithm. For example, the homologous polynucleotides may have a coding sequence which is a naturally occurring allelic variant of one of the coding sequences described herein. Such allelic variants may have a substitution, deletion or addition of one or more nucleotides when compared to the nucleic acids of Group A nucleic acid sequences or the sequences complementary thereto.

Additionally, the above procedures may be used to isolate nucleic acids which encode polypeptides having at least about 99%, 95%, at least 90%, at least 85%, at least 80%, at least 75%, at least 70%, at least 65%, at least 60%, at least 55% or at least 50% homology to a polypeptide having the sequence of one of Group B amino acid sequences, and sequences substantially identical thereto, or fragments comprising at least 5, 10, 15, 20, 25, 30, 35, 40, 50, 75, 100, or 150 consecutive amino acids thereof as determined using a sequence alignment algorithm (e.g., such as the FASTA version 3.0t78 algorithm with the default parameters).

Another aspect of the invention is an isolated or purified polypeptide comprising the sequence of one of Group A nucleic acid sequences, and sequences substantially identical thereto, or fragments comprising at least about 5, 10, 15, 20, 25, 30, 35, 40, 50, 75, 100, or 150 consecutive amino acids thereof. As discussed above, such polypeptides may be obtained by inserting a nucleic acid encoding the polypeptide into a vector such that the coding sequence is operably linked to a sequence capable of driving the expression of the encoded polypeptide in a suitable host cell. For example, the expression vector may comprise a promoter, a ribosome binding site for translation initiation and a transcription terminator. The vector may also include appropriate sequences for amplifying expression.

Promoters suitable for expressing the polypeptide or fragment thereof in bacteria include the *E. coli* lac or trp promoters, the lacI promoter, the lacZ promoter, the T3 promoter, the T7 promoter, the gpt promoter, the lambda $P_R$ promoter, the lambda $P_L$ promoter, promoters from operons encoding glycolytic enzymes such as 3-phosphoglycerate kinase (PGK), and the acid phosphatase promoter. Fungal promoters include the ∀ factor promoter. Eukaryotic promoters include the CMV immediate early promoter, the HSV thymidine kinase promoter, heat shock promoters, the early and late SV40 promoter, LTRs from retroviruses, and the mouse metallothionein-I promoter. Other promoters known to control expression of genes in prokaryotic or eukaryotic cells or their viruses may also be used.

Mammalian expression vectors may also comprise an origin of replication, any necessary ribosome binding sites, a polyadenylation site, splice donor and acceptor sites, transcriptional termination sequences, and 5' flanking non-transcribed sequences. In some embodiments, DNA sequences derived from the SV40 splice and polyadenylation sites may be used to provide the required nontranscribed genetic elements.

Vectors for expressing the polypeptide or fragment thereof in eukaryotic cells may also contain enhancers to increase expression levels. Enhancers are cis-acting elements of DNA, usually from about 10 to about 300 bp in length that act on a promoter to increase its transcription. Examples include the SV40 enhancer on the late side of the replication origin by 100 to 270, the cytomegalovirus early promoter enhancer, the polyoma enhancer on the late side of the replication origin, and the adenovirus enhancers.

In addition, the expression vectors typically contain one or more selectable marker genes to permit selection of host cells containing the vector. Such selectable markers include genes encoding dihydrofolate reductase or genes conferring neomycin resistance for eukaryotic cell culture, genes conferring tetracycline or ampicillin resistance in *E. coli*, and the *S. cerevisiae* TRP1 gene.

After the expression libraries have been generated one can include the additional step of "biopanning" such libraries prior to screening by cell sorting. The "biopanning" procedure refers to a process for identifying clones having a specified biological activity by screening for sequence homology in a library of clones prepared by (i) selectively isolating target DNA, from DNA derived from at least one microorganism, by use of at least one probe DNA comprising at least a portion of a DNA sequence encoding an biological having the specified biological activity; and (ii) optionally transforming a host with isolated target DNA to produce a library of clones which are screened for the specified biological activity.

The probe DNA used for selectively isolating the target DNA of interest from the DNA derived from at least one microorganism can be a full-length coding region sequence or a partial coding region sequence of DNA for an enzyme of known activity. The original DNA library can be preferably probed using mixtures of probes comprising at least a portion of the DNA sequence encoding an enzyme having the specified enzyme activity. These probes or probe libraries are preferably single-stranded and the microbial DNA which is probed has preferably been converted into single-stranded form. The probes that are particularly suitable are those derived from DNA encoding enzymes having an activity similar or identical to the specified enzyme activity which is to be screened.

The probe DNA should be at least about 10 bases and preferably at least 15 bases. In one embodiment, the entire coding region may be employed as a probe. Conditions for the hybridization in which target DNA is selectively isolated by the use of at least one DNA probe will be designed to provide a hybridization stringency of at least about 50% sequence identity, more particularly a stringency providing for a sequence identity of at least about 70%.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

Hybridization techniques for probing a microbial DNA library to isolate target DNA of potential interest are well known in the art and any of those which are described in the literature are suitable for use herein, particularly those which use a solid phase-bound, directly or indirectly bound, probe DNA for ease in separation from the remainder of the DNA derived from the microorganisms.

Preferably the probe DNA is "labeled" with one partner of a specific binding pair (i.e., a ligand) and the other partner of the pair is bound to a solid matrix to provide ease of separation of target from its source. The ligand and specific binding partner can be selected from, in either orientation, the following: (1) an antigen or hapten and an antibody or specific binding fragment thereof; (2) biotin or iminobiotin and avidin or streptavidin; (3) a sugar and a lectin specific therefor; (4) an enzyme and an inhibitor therefor; (5) an apoenzyme and cofactor; (6) complementary homopolymeric oligonucleotides; and (7) a hormone and a receptor therefor. The solid phase is preferably selected from: (1) a glass or polymeric surface; (2) a packed column of polymeric beads; and (3) magnetic or paramagnetic particles.

Further, it is optional but desirable to perform an amplification of the target DNA that has been isolated. In this embodiment the target DNA is separated from the probe DNA after isolation. It is then amplified before being used to transform hosts. The double stranded DNA selected to include as at least a portion thereof a predetermined DNA sequence can be rendered single stranded, subjected to amplification and reannealed to provide amplified numbers of selected double stranded DNA. Numerous amplification methodologies are now well known in the art.

The selected DNA is then used for preparing a library for screening by transforming a suitable organism. Hosts, particularly those specifically identified herein as preferred, are transformed by artificial introduction of the vectors containing the target DNA by inoculation under conditions conducive for such transformation.

The resultant libraries of transformed clones are then screened for clones which display activity for the enzyme of interest.

Having prepared a multiplicity of clones from DNA selectively isolated from an organism, such clones are screened for a specific enzyme activity and to identify the clones having the specified enzyme characteristics.

The screening for enzyme activity may be effected on individual expression clones or may be initially effected on a mixture of expression clones to ascertain whether or not the mixture has one or more specified enzyme activities. If the mixture has a specified enzyme activity, then the individual clones may be rescreened utilizing a FACS machine for such enzyme activity or for a more specific activity. Alternatively, encapsulation techniques such as gel microdroplets, may be employed to localize multiple clones in one location to be screened on a FACS machine for positive expressing clones within the group of clones which can then be broken out into individual clones to be screened again on a FACS machine to identify positive individual clones. Thus, for example, if a clone mixture has hydrolase activity, then the individual clones may be recovered and screened utilizing a FACS machine to determine which of such clones has hydrolase activity. As used herein, "small insert library" means a gene library containing clones with random small size nucleic acid inserts of up to approximately 5000 base pairs. As used herein, "large insert library" means a gene library containing clones with random large size nucleic acid inserts of approximately 5000 up to several hundred thousand base pairs or greater.

As described with respect to one of the above aspects, the invention provides a process for enzyme activity screening of clones containing selected DNA derived from a microorganism which process includes: screening a library for specified enzyme activity, said library including a plurality of clones, said clones having been prepared by recovering from genomic DNA of a microorganism selected DNA, which DNA is selected by hybridization to at least one DNA sequence which is all or a portion of a DNA sequence encoding an enzyme having the specified activity; and transforming a host with the selected DNA to produce clones which are screened for the specified enzyme activity.

In one embodiment, a DNA library derived from a microorganism is subjected to a selection procedure to select therefrom DNA which hybridizes to one or more probe DNA sequences which is all or a portion of a DNA sequence encoding an enzyme having the specified enzyme activity by:
  (a) rendering the double-stranded genomic DNA population into a single-stranded DNA population;
  (b) contacting the single-stranded DNA population of (a) with the DNA probe bound to a ligand under conditions permissive of hybridization so as to produce a double-stranded complex of probe and members of the genomic DNA population which hybridize thereto;
  (c) contacting the double-stranded complex of (b) with a solid phase specific binding partner for said ligand so as to produce a solid phase complex;
  (d) separating the solid phase complex from the single-stranded DNA population of (b);
  (e) releasing from the probe the members of the genomic population which had bound to the solid phase bound probe;
  (f) forming double-stranded DNA from the members of the genomic population of (e);
  (g) introducing the double-stranded DNA of (f) into a suitable host to form a library containing a plurality of clones containing the selected DNA; and
  (h) screening the library for the specified enzyme activity.

In another aspect, the process includes a preselection to recover DNA including signal or secretion sequences. In this manner it is possible to select from the genomic DNA population by hybridization as hereinabove described only DNA which includes a signal or secretion sequence. The following paragraphs describe the protocol for this embodiment of the invention, the nature and function of secretion signal sequences in general and a specific exemplary application of such sequences to an assay or selection process.

One aspect further comprises, after (a) but before (b) above, the steps of:
  (ai) contacting the single-stranded DNA population of (a) with a ligand-bound oligonucleotide probe that is complementary to a secretion signal sequence unique to a given class of proteins under conditions permissive of hybridization to form a double-stranded complex;
  (aii) contacting the double-stranded complex of (ai) with a solid phase specific binding partner for said ligand so as to produce a solid phase complex;
  (aiii) separating the solid phase complex from the single-stranded DNA population of (a);
  (aiv) releasing the members of the genomic population which had bound to said solid phase bound probe; and
  (av) separating the solid phase bound probe from the members of the genomic population which had bound thereto.

The DNA which has been selected and isolated to include a signal sequence is then subjected to the selection procedure hereinabove described to select and isolate therefrom DNA which binds to one or more probe DNA sequences derived from DNA encoding an enzyme(s) having the specified enzyme activity. This procedure is described and exemplified in U.S. Ser. No. 08/692,002, filed Aug. 2, 1996, incorporated herein by reference.

In vivo biopanning may be performed utilizing a FACS-based machine. Complex gene libraries are constructed with vectors which contain elements which stabilize transcribed RNA. For example, the inclusion of sequences which result in secondary structures such as hairpins which are designed to flank the transcribed regions of the RNA would serve to enhance their stability, thus increasing their half life within the cell. The probe molecules used in the biopanning process consist of oligonucleotides labeled with reporter molecules that only fluoresce upon binding of the probe to a target molecule. These probes are introduced into the recombinant cells from the library using one of several transformation methods. The probe molecules bind to the transcribed target mRNA resulting in DNA/RNA heteroduplex molecules. Binding of the probe to a target will yield a fluorescent signal which is detected and sorted by the FACS machine during the screening process.

In some embodiments, the nucleic acid encoding one of the polypeptides of Group B amino acid sequences, and sequences substantially identical thereto, or fragments comprising at least about 5, 10, 15, 20, 25, 30, 35, 40, 50, 75, 100, or 150 consecutive amino acids thereof is assembled in appropriate phase with a leader sequence capable of directing secretion of the translated polypeptide or fragment thereof. Optionally, the nucleic acid can encode a fusion polypeptide in which one of the polypeptides of Group B amino acid sequences, and sequences substantially identical thereto, or fragments comprising at least 5, 10, 15, 20, 25, 30, 35, 40, 50, 75, 100, or 150 consecutive amino acids thereof is fused to heterologous peptides or polypeptides, such as N-terminal identification peptides which impart desired characteristics, such as increased stability or simplified purification.

The appropriate DNA sequence may be inserted into the vector by a variety of procedures. In general, the DNA sequence is ligated to the desired position in the vector following digestion of the insert and the vector with appropriate restriction endonucleases. Alternatively, blunt ends in both the insert and the vector may be ligated. A variety of cloning techniques are disclosed in Ausubel, et al., *Current Protocols in Molecular Biology*, John Wiley & Sons, Inc. 1997 and Sambrook, et al., *Molecular Cloning: A Laboratory Manual*, 2nd Ed., Cold Spring Harbor Laboratory Press (1989), the entire disclosures of which are incorporated herein by reference. Such procedures and others are deemed to be within the scope of those skilled in the art.

The vector may be, for example, in the form of a plasmid, a viral particle, or a phage. Other vectors include chromosomal, nonchromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by Sambrook, et al., *Molecular Cloning: A Laboratory Manual*, 2nd Ed., Cold Spring Harbor, N.Y., (1989), the disclosure of which is hereby incorporated by reference.

Particular bacterial vectors which may be used include the commercially available plasmids comprising genetic elements of the well known cloning vector pBR322 (ATCC 37017), pKK223-3 (Pharmacia Fine Chemicals, Uppsala, Sweden), GEM1 (Promega Biotec, Madison, Wis., USA) pQE70, pQE60, pQE-9 (Qiagen), pD10, psiX174 pBluescript II KS, pNH8A, pNH16a, pNH18A, pNH46A (Stratagene), ptrc99a, pKK223-3, pKK233-3, pDR540, pRIT5 (Pharmacia), pKK232-8 and pCM7. Particular eukaryotic vectors include pSV2CAT, pOG44, pXT1, pSG (Stratagene) pSVK3, pBPV, pMSG, and pSVL (Pharmacia). However, any other vector may be used as long as it is replicable and viable in the host cell.

The host cell may be any of the host cells familiar to those skilled in the art, including prokaryotic cells, eukaryotic cells, mammalian cells, insect cells, or plant cells. As representative examples of appropriate hosts, there may be mentioned: bacterial cells, such as *E. coli, Streptomyces, Bacillus subtilis, Salmonella typhimurium* and various species within the genera *Pseudomonas, Streptomyces*, and *Staphylococcus*, fungal cells, such as yeast, insect cells such as *Drosophila* S2 and *Spodoptera* Sf9, animal cells such as CHO, COS or Bowes melanoma, and adenoviruses. The selection of an appropriate host is within the abilities of those skilled in the art.

The vector may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., *Basic Methods in Molecular Biology*, (1986)).

Where appropriate, the engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells are typically harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts (described by Gluzman, *Cell*, 23:175, 1981), and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

Alternatively, the polypeptides of Group B amino acid sequences, and sequences substantially identical thereto, or fragments comprising at least 5, 10, 15, 20, 25, 30, 35, 40, 50, 75, 100, or 150 consecutive amino acids thereof can be synthetically produced by conventional peptide synthesizers. In other embodiments, fragments or portions of the polypeptides may be employed for producing the corresponding full-length polypeptide by peptide synthesis; therefore, the fragments may be employed as intermediates for producing the full-length polypeptides.

Cell-free translation systems can also be employed to produce one of the polypeptides of Group B amino acid sequences, and sequences substantially identical thereto, or fragments comprising at least 5, 10, 15, 20, 25, 30, 35, 40, 50, 75, 100, or 150 consecutive amino acids thereof using mRNAs transcribed from a DNA construct comprising a promoter operably linked to a nucleic acid encoding the polypeptide or fragment thereof. In some embodiments, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The invention also relates to variants of the polypeptides of Group B amino acid sequences, and sequences substantially identical thereto, or fragments comprising at least 5, 10, 15, 20, 25, 30, 35, 40, 50, 75, 100, or 150 consecutive amino acids thereof. The term "variant" includes derivatives or analogs of these polypeptides. In particular, the variants may differ in amino acid sequence from the polypeptides of Group B amino acid sequences, and sequences substantially identical thereto, by one or more substitutions, additions, deletions, fusions and truncations, which may be present in any combination.

The variants may be naturally occurring or created in vitro. In particular, such variants may be created using genetic engineering techniques such as site directed mutagenesis, random chemical mutagenesis, Exonuclease III deletion procedures, and standard cloning techniques. Alternatively, such variants, fragments, analogs, or derivatives may be created using chemical synthesis or modification procedures.

Other methods of making variants are also familiar to those skilled in the art. These include procedures in which nucleic acid sequences obtained from natural isolates are modified to generate nucleic acids which encode polypeptides having characteristics which enhance their value in industrial or laboratory applications. In such procedures, a large number of variant sequences having one or more nucleotide differences with respect to the sequence obtained from the natural isolate are generated and characterized. Typically, these nucleotide differences result in amino acid changes with respect to the polypeptides encoded by the nucleic acids from the natural isolates.

For example, variants may be created using error prone PCR. In error prone PCR, PCR is performed under conditions where the copying fidelity of the DNA polymerase is low, such that a high rate of point mutations is obtained along the entire length of the PCR product. Error prone PCR is described in Leung, D. W., et al., *Technique*, 1:11-15, 1989) and Caldwell, R. C. & Joyce, G. F., *PCR Methods Applic.*, 2:28-33, 1992, the disclosure of which is incorporated herein by reference in its entirety. Briefly, in such procedures, nucleic acids to be mutagenized are mixed with PCR primers, reaction buffer, $MgCl_2$, $MnCl_2$, Taq polymerase and an appropriate concentration of dNTPs for achieving a high rate of point mutation along the entire length of the PCR product. For example, the reaction may be performed using 20 fmoles of nucleic acid to be mutagenized, 30 pmole of each PCR primer, a reaction buffer comprising 50 mM KCl, 10 mM Tris HCl (pH 8.3) and 0.01% gelatin, 7 mM $MgCl_2$, 0.5 mM $MnCl_2$, 5 units of Taq polymerase, 0.2 mM dGTP, 0.2 mM dATP, 1 mM dCTP, and 1 mM dTTP. PCR may be performed for 30 cycles of 94° C. for 1 min, 45° C. for 1 min, and 72° C. for 1 min. However, it will be appreciated that these parameters may be varied as appropriate. The mutagenized nucleic acids are cloned into an appropriate vector and the activities of the polypeptides encoded by the mutagenized nucleic acids is evaluated.

Variants may also be created using oligonucleotide directed mutagenesis to generate site-specific mutations in any cloned DNA of interest. Oligonucleotide mutagenesis is described in Reidhaar-Olson, J. F. & Sauer, R. T., et al., *Science*, 241:53-57, 1988, the disclosure of which is incorporated herein by reference in its entirety. Briefly, in such procedures a plurality of double stranded oligonucleotides bearing one or more mutations to be introduced into the cloned DNA are synthesized and inserted into the cloned DNA to be mutagenized. Clones containing the mutagenized DNA are recovered and the activities of the polypeptides they encode are assessed.

Another method for generating variants is assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in U.S. Pat. No. 5,965,408, filed Jul. 9, 1996, entitled, "Method of DNA Reassembly by Interrupting Synthesis", the disclosure of which is incorporated herein by reference in its entirety.

Still another method of generating variants is sexual PCR mutagenesis. In sexual PCR mutagenesis, forced homologous recombination occurs between DNA molecules of different but highly related DNA sequence in vitro, as a result of random fragmentation of the DNA molecule based on sequence homology, followed by fixation of the crossover by primer extension in a PCR reaction. Sexual PCR mutagenesis is described in Stemmer, W. P., *PNAS, USA*, 91:10747-10751, 1994, the disclosure of which is incorporated herein by reference. Briefly, in such procedures a plurality of nucleic acids to be recombined are digested with DNase to generate fragments having an average size of 50-200 nucleotides. Fragments of the desired average size are purified and resuspended in a PCR mixture. PCR is conducted under conditions which facilitate recombination between the nucleic acid fragments. For example, PCR may be performed by resuspending the purified fragments at a concentration of 10-30 ng/:1 in a solution of 0.2 mM of each dNTP, 2.2 mM $MgCl_2$, 50 mM KCL, 10 mM Tris HCl, pH 9.0, and 0.1% Triton X-100. 2.5 units of Taq polymerase per 100:1 of reaction mixture is added and PCR is performed using the following regime: 94° C. for 60 seconds, 94° C. for 30 seconds, 50-55° C. for 30 seconds, 72° C. for 30 seconds (30-45 times) and 72° C. for 5 minutes. However, it will be appreciated that these parameters may be varied as appropriate. In some embodiments, oligonucleotides may be included in the PCR reactions. In other embodiments, the Klenow fragment of DNA polymerase I may be used in a first set of PCR reactions and Taq polymerase may be used in a subsequent set of PCR reactions. Recombinant sequences are isolated and the activities of the polypeptides they encode are assessed.

Variants may also be created by in vivo mutagenesis. In some embodiments, random mutations in a sequence of interest are generated by propagating the sequence of interest in a bacterial strain, such as an *E. coli* strain, which carries mutations in one or more of the DNA repair pathways. Such "mutator" strains have a higher random mutation rate than that of a wild-type parent. Propagating the DNA in one of these strains will eventually generate random mutations within the DNA. Mutator strains suitable for use for in vivo mutagenesis are described in PCT Publication No. WO 91/16427, published Oct. 31, 1991, entitled "Methods for Phenotype Creation from Multiple Gene Populations" the disclosure of which is incorporated herein by reference in its entirety.

Variants may also be generated using cassette mutagenesis. In cassette mutagenesis a small region of a double stranded DNA molecule is replaced with a synthetic oligonucleotide "cassette" that differs from the native sequence. The oligonucleotide often contains completely and/or partially randomized native sequence.

Recursive ensemble mutagenesis may also be used to generate variants. Recursive ensemble mutagenesis is an algorithm for protein engineering (protein mutagenesis)

developed to produce diverse populations of phenotypically related mutants whose members differ in amino acid sequence. This method uses a feedback mechanism to control successive rounds of combinatorial cassette mutagenesis. Recursive ensemble mutagenesis is described in Arkin, A. P. and Youvan, D. C., *PNAS, USA,* 89:7811-7815, 1992, the disclosure of which is incorporated herein by reference in its entirety.

In some embodiments, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins. Exponential ensemble mutagenesis is described in Delegrave, S. and Youvan, D. C., *Biotechnology Research,* 11:1548-1552, 1993, the disclosure of which incorporated herein by reference in its entirety. Random and site-directed mutagenesis are described in Arnold, F. H., *Current Opinion in Biotechnology,* 4:450-455, 1993, the disclosure of which is incorporated herein by reference in its entirety.

In some embodiments, the variants are created using shuffling procedures wherein portions of a plurality of nucleic acids which encode distinct polypeptides are fused together to create chimeric nucleic acid sequences which encode chimeric polypeptides as described in U.S. Pat. No. 5,965,408, filed Jul. 9, 1996, entitled, "Method of DNA Reassembly by Interrupting Synthesis", and U.S. Pat. No. 5,939,250, filed May 22, 1996, entitled, "Production of Enzymes Having Desired Activities by Mutagenesis", both of which are incorporated herein by reference.

The variants of the polypeptides of Group B amino acid sequences may be variants in which one or more of the amino acid residues of the polypeptides of the Group B amino acid sequences are substituted with a conserved or non-conserved amino acid residue (preferably a conserved amino acid residue) and such substituted amino acid residue may or may not be one encoded by the genetic code.

Conservative substitutions are those that substitute a given amino acid in a polypeptide by another amino acid of like characteristics. Typically seen as conservative substitutions are the following replacements: replacements of an aliphatic amino acid such as Alanine, Valine, Leucine and Isoleucine with another aliphatic amino acid; replacement of a Serine with a Threonine or vice versa; replacement of an acidic residue such as Aspartic acid and Glutamic acid with another acidic residue; replacement of a residue bearing an amide group, such as Asparagine and Glutamine, with another residue bearing an amide group; exchange of a basic residue such as Lysine and Arginine with another basic residue; and replacement of an aromatic residue such as Phenylalanine, Tyrosine with another aromatic residue.

Other variants are those in which one or more of the amino acid residues of the polypeptides of the Group B amino acid sequences includes a substituent group.

Still other variants are those in which the polypeptide is associated with another compound, such as a compound to increase the half-life of the polypeptide (for example, polyethylene glycol).

Additional variants are those in which additional amino acids are fused to the polypeptide, such as a leader sequence, a secretory sequence, a proprotein sequence or a sequence which facilitates purification, enrichment, or stabilization of the polypeptide.

In some embodiments, the fragments, derivatives and analogs retain the same biological function or activity as the polypeptides of Group B amino acid sequences, and sequences substantially identical thereto. In other embodiments, the fragment, derivative, or analog includes a proprotein, such that the fragment, derivative, or analog can be activated by cleavage of the proprotein portion to produce an active polypeptide.

Another aspect of the invention is polypeptides or fragments thereof which have at least about 50%, at least about 55%, at least about 60%, at least about 65%, at least about 70%, at least about 75%, at least about 80%, at least about 85%, at least about 90%, at least about 95%, or more than about 95% homology to one of the polypeptides of Group B amino acid sequences, and sequences substantially identical thereto, or a fragment comprising at least 5, 10, 15, 20, 25, 30, 35, 40, 50, 75, 100, or 150 consecutive amino acids thereof. Homology may be determined using any of the programs described above which aligns the polypeptides or fragments being compared and determines the extent of amino acid identity or similarity between them. It will be appreciated that amino acid "homology" includes conservative amino acid substitutions such as those described above.

The polypeptides or fragments having homology to one of the polypeptides of Group B amino acid sequences, and sequences substantially identical thereto, or a fragment comprising at least about 5, 10, 15, 20, 25, 30, 35, 40, 50, 75, 100, or 150 consecutive amino acids thereof may be obtained by isolating the nucleic acids encoding them using the techniques described above.

Alternatively, the homologous polypeptides or fragments may be obtained through biochemical enrichment or purification procedures. The sequence of potentially homologous polypeptides or fragments may be determined by proteolytic digestion, gel electrophoresis and/or microsequencing. The sequence of the prospective homologous polypeptide or fragment can be compared to one of the polypeptides of Group B amino acid sequences, and sequences substantially identical thereto, or a fragment comprising at least about 5, 10, 15, 20, 25, 30, 35, 40, 50, 75, 100, or 150 consecutive amino acids thereof using any of the programs described above.

Another aspect of the invention is an assay for identifying fragments or variants of Group B amino acid sequences, and sequences substantially identical thereto, which retain the enzymatic function of the polypeptides of Group B amino acid sequences, and sequences substantially identical thereto. For example the fragments or variants of said polypeptides, may be used to catalyze biochemical reactions, which indicate that the fragment or variant retains the enzymatic activity of the polypeptides in the Group B amino acid sequences.

The assay for determining if fragments of variants retain the enzymatic activity of the polypeptides of Group B amino acid sequences, and sequences substantially identical thereto includes the steps of: contacting the polypeptide fragment or variant with a substrate molecule under conditions which allow the polypeptide fragment or variant to function, and detecting either a decrease in the level of substrate or an increase in the level of the specific reaction product of the reaction between the polypeptide and substrate.

The polypeptides of Group B amino acid sequences, and sequences substantially identical thereto or fragments comprising at least 5, 10, 15, 20, 25, 30, 35, 40, 50, 75, 100, or 150 consecutive amino acids thereof may be used in a variety of applications. For example, the polypeptides or fragments thereof may be used to catalyze biochemical reactions. In accordance with one aspect of the invention, there is provided a process for utilizing the polypeptides of Group B amino acid sequences, and sequences substantially identical thereto or polynucleotides encoding such polypeptides for hydrolyzing glycosidic linkages. In such procedures, a substance containing a glycosidic linkage (e.g., a starch) is contacted with one of the polypeptides of Group B amino acid sequences, or sequences substantially identical thereto under conditions which facilitate the hydrolysis of the glycosidic linkage.

The polypeptides of Group B amino acid sequences, and sequences substantially identical thereto or fragments comprising at least 5, 10, 15, 20, 25, 30, 35, 40, 50, 75, 100, or 150 consecutive amino acids thereof, may also be used to generate antibodies which bind specifically to the polypeptides or fragments. The resulting antibodies may be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of the polypeptides of Group B amino acid sequences, and sequences substantially identical thereto, or fragments comprising at least 5, 10, 15, 20, 25, 30, 35, 40, 50, 75, 100, or 150 consecutive amino acids thereof.

In immunoaffinity procedures, the antibody is attached to a solid support, such as a bead or other column matrix. The protein preparation is placed in contact with the antibody under conditions in which the antibody specifically binds to one of the polypeptides of Group B amino acid sequences, and sequences substantially identical thereto, or fragment thereof. After a wash to remove non-specifically bound proteins, the specifically bound polypeptides are eluted.

The ability of proteins in a biological sample to bind to the antibody may be determined using any of a variety of procedures familiar to those skilled in the art. For example, binding may be determined by labeling the antibody with a detectable label such as a fluorescent agent, an enzymatic label, or a radioisotope. Alternatively, binding of the antibody to the sample may be detected using a secondary antibody having such a detectable label thereon. Particular assays include ELISA assays, sandwich assays, radioimmunoassays, and Western Blots.

Polyclonal antibodies generated against the polypeptides of Group B amino acid sequences, and sequences substantially identical thereto, or fragments comprising at least 5, 10, 15, 20, 25, 30, 35, 40, 50, 75, 100, or 150 consecutive amino acids thereof can be obtained by direct injection of the polypeptides into an animal or by administering the polypeptides to an animal, for example, a nonhuman. The antibody so obtained will then bind the polypeptide itself. In this manner, even a sequence encoding only a fragment of the polypeptide can be used to generate antibodies which may bind to the whole native polypeptide. Such antibodies can then be used to isolate the polypeptide from cells expressing that polypeptide.

For preparation of monoclonal antibodies, any technique which provides antibodies produced by continuous cell line cultures can be used. Examples include the hybridoma technique (Kohler and Milstein, *Nature,* 256:495-497, 1975, the disclosure of which is incorporated herein by reference), the trioma technique, the human B-cell hybridoma technique (Kozbor, et al., *Immunology Today,* 4:72, 1983, the disclosure of which is incorporated herein by reference), and the EBV-hybridoma technique (Cole, et al., 1985, in *Monoclonal Antibodies and Cancer Therapy*, Alan R. Liss, Inc., pp. 77-96, the disclosure of which is incorporated herein by reference).

Techniques described for the production of single chain antibodies (U.S. Pat. No. 4,946,778, the disclosure of which is incorporated herein by reference) can be adapted to produce single chain antibodies to the polypeptides of Group B amino acid sequences, and sequences substantially identical thereto, or fragments comprising at least 5, 10, 15, 20, 25, 30, 35, 40, 50, 75, 100, or 150 consecutive amino acids thereof. Alternatively, transgenic mice may be used to express humanized antibodies to these polypeptides or fragments thereof.

Antibodies generated against the polypeptides of Group B amino acid sequences, and sequences substantially identical thereto, or fragments comprising at least 5, 10, 15, 20, 25, 30, 35, 40, 50, 75, 100, or 150 consecutive amino acids thereof may be used in screening for similar polypeptides from other organisms and samples. In such techniques, polypeptides from the organism are contacted with the antibody and those polypeptides which specifically bind the antibody are detected. Any of the procedures described above may be used to detect antibody binding. One such screening assay is described in "Methods for Measuring Cellulase Activities", *Methods in Enzymology,* Vol 160, pp. 87-116, which is hereby incorporated by reference in its entirety.

As used herein the term "nucleic acid sequence as set forth in SEQ ID NOS: 3, 5, 7, 9, 11, 13, 15, 17, 19, 21, 23, 25, 27, 29, 31, 33, 35, 37, 43, 45 and 47" encompasses the nucleotide sequences of Group A nucleic acid sequences, and sequences substantially identical thereto, as well as sequences homologous to Group A nucleic acid sequences, and fragments thereof and sequences complementary to all of the preceding sequences. The fragments include portions of SEQ ID NOS: 3, 5, 7, 9, 11, 13, 15, 17, 19, 21, 23, 25, 27, 29, 31, 33, 35, 37, 43, 45 and 47 comprising at least 10, 15, 20, 25, 30, 35, 40, 50, 75, 100, 150, 200, 300, 400, or 500 consecutive nucleotides of Group A nucleic acid sequences, and sequences substantially identical thereto. Homologous sequences and fragments of Group A nucleic acid sequences, and sequences substantially identical thereto, refer to a sequence having at least 99%, 98%, 97%, 96%, 95%, 90%, 85%, 80%, 75%, 70%, 65%, 60%, 55% or 50% homology to these sequences. Homology may be determined using any of the computer programs and parameters described herein, including FASTA version 3.0t78 with the default parameters. Homologous sequences also include RNA sequences in which uridines replace the thymines in the nucleic acid sequences as set forth in the Group A nucleic acid sequences. The homologous sequences may be obtained using any of the procedures described herein or may result from the correction of a sequencing error. It will be appreciated that the nucleic acid sequences as set forth in Group A nucleic acid sequences, and sequences substantially identical thereto, can be represented in the traditional single character format (See the inside back cover of Stryer, Lubert, *Biochemistry,* 3rd Ed., W. H Freeman & Co., New York.) or in any other format which records the identity of the nucleotides in a sequence.

As used herein the term "a polypeptide sequence as set forth in SEQ ID NO's: 4, 6, 8, 10, 12, 14, 16, 18, 20, 22, 24, 26, 28, 30, 32, 34, 36, 38, 44, 46 and 48" encompasses the polypeptide sequence of Group B amino acid sequences, and sequences substantially identical thereto, which are encoded by a sequence as set forth in SEQ ID NO's: 3, 5, 7, 9, 11, 13, 15, 17, 19, 21, 23, 25, 27, 29, 31, 33, 35, 37, 43, 45 and 47, polypeptide sequences homologous to the polypeptides of Group B amino acid sequences, and sequences substantially identical thereto, or fragments of any of the preceding sequences. Homologous polypeptide sequences refer to a polypeptide sequence having at least 99%, 98%, 97%, 96%, 95%, 90%, 85%, 80%, 75%, 70%, 65%, 60%, 55% or 50% homology to one of the polypeptide sequences of the Group B amino acid sequences. Homology may be determined using any of the computer programs and parameters described herein, including FASTA version 3.0t78 with the default parameters or with any modified parameters. The homologous sequences may be obtained using any of the procedures described herein or may result from the correction of a sequencing error. The polypeptide fragments comprise at least 5, 10, 15, 20, 25, 30, 35, 40, 50, 75, 100, or 150 consecutive amino acids of the polypeptides of Group B amino acid sequences, and sequences substantially identical thereto. It will be appreciated that the polypeptide codes as set forth in Group B amino acid sequences, and sequences substantially identical thereto, can be represented in the traditional single character format or three letter format (See the inside back cover of Sayer, Lubert. *Biochemistry,* 3rd Ed., W. H. Freeman & Co., New York.) or in any other format which relates the identity of the polypeptides in a sequence.

It will be appreciated by those skilled in the art that a nucleic acid sequence as set forth in SEQ ID NO's: 3, 5, 7, 9, 11, 13, 15, 17, 19, 21, 23, 25, 27, 29, 31, 33, 35, 37, 43, 45 and 47, and a polypeptide sequence as set forth in SEQ ID NO's: 4, 6, 8, 10, 12, 14, 16, 18, 20, 22, 24, 26, 28, 30, 32, 34, 36, 38, 44, 46 and 48 can be stored, recorded, and manipulated on any medium which can be read and accessed by a computer. As used herein, the words "recorded" and "stored" refer to a process for storing information on a computer medium. A skilled artisan can readily adopt any of the presently known methods for recording information on a computer readable medium to generate manufactures comprising one or more of the nucleic acid sequences as set forth in Group A nucleic acid sequences, and sequences substantially identical thereto, one or more of the polypeptide sequences as set forth in Group B amino acid sequences, and sequences substantially identical thereto. Another aspect of the invention is a computer readable medium having recorded thereon at least 2, 5, 10, 15, or 20 nucleic acid sequences as set forth in Group A nucleic acid sequences, and sequences substantially identical thereto.

Another aspect of the invention is a computer readable medium having recorded thereon one or more of the nucleic acid sequences as set forth in Group A nucleic acid sequences, and sequences substantially identical thereto. Another aspect of the invention is a computer readable medium having recorded thereon one or more of the polypeptide sequences as set forth in Group B amino acid sequences, and sequences substantially identical thereto. Another aspect of the invention is a computer readable medium having recorded thereon at least 2, 5, 10, 15, or 20 of the sequences as set forth above.

Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of other media known to those skilled in the art.

Figure 1:
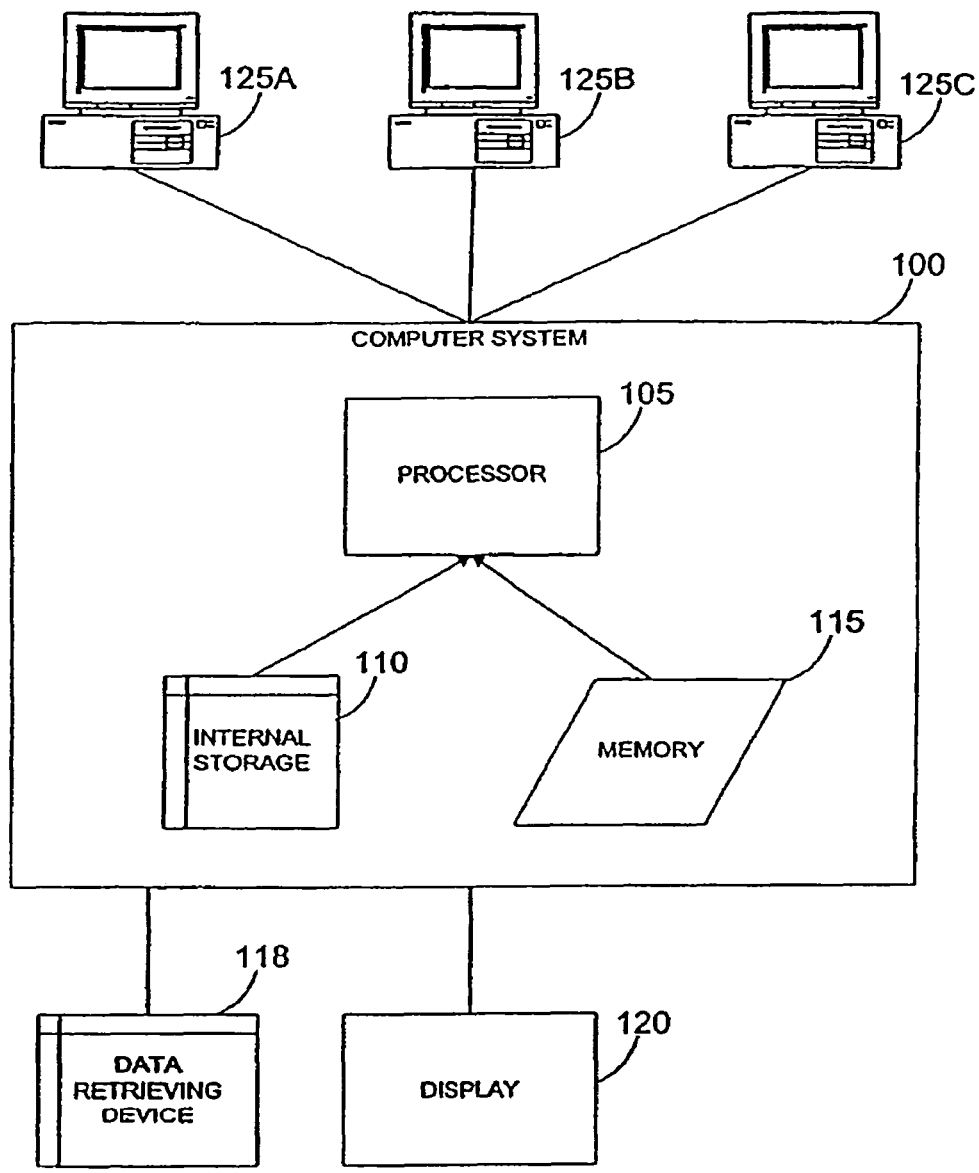
FIG. 1 is a block diagram of a computer system.

Embodiments of the invention include systems (e.g., internet based systems), particularly computer systems which store and manipulate the sequence information described herein. One example of a computer system 100 is illustrated in block diagram form in FIG. 1. As used herein, "a computer system" refers to the hardware components, software components, and data storage components used to analyze a nucleotide sequence of a nucleic acid sequence as set forth in Group A nucleic acid sequences, and sequences substantially identical thereto, or a polypeptide sequence as set forth in the Group B amino acid sequences. The computer system 100 typically includes a processor for processing, accessing and manipulating the sequence data. The processor 105 can be any well-known type of central processing unit, such as, for example, the Pentium III from Intel Corporation, or similar processor from Sun, Motorola, Compaq, AMD or International Business Machines.

Typically the computer system 100 is a general purpose system that comprises the processor 105 and one or more internal data storage components 110 for storing data, and one or more data retrieving devices for retrieving the data stored on the data storage components. A skilled artisan can readily appreciate that any one of the currently available computer systems are suitable.

In one particular embodiment, the computer system 100 includes a processor 105 connected to a bus which is connected to a main memory 115 (preferably implemented as RAM) and one or more internal data storage devices 110, such as a hard drive and/or other computer readable media having data recorded thereon. In some embodiments, the computer system 100 further includes one or more data retrieving device 118 for reading the data stored on the internal data storage devices 110.

The data retrieving device 118 may represent, for example, a floppy disk drive, a compact disk drive, a magnetic tape drive, or a modem capable of connection to a remote data storage system (e.g., via the internet), etc. In some embodiments, the internal data storage device 110 is a removable computer readable medium such as a floppy disk, a compact disk, a magnetic tape, etc., containing control logic and/or data recorded thereon. The computer system 100 may advantageously include or be programmed by appropriate software for reading the control logic and/or the data from the data storage component once inserted in the data retrieving device.

The computer system 100 includes a display 120 which is used to display output to a computer user. It should also be noted that the computer system 100 can be linked to other computer systems 125a-c in a network or wide area network to provide centralized access to the computer system 100.

Software for accessing and processing the nucleotide sequences of a nucleic acid sequence as set forth in Group A nucleic acid sequences, and sequences substantially identical thereto, or a polypeptide sequence as set forth in Group B amino acid sequences, and sequences substantially identical thereto, (such as search tools, compare tools, and modeling tools, etc.) may reside in main memory 115 during execution.

In some embodiments, the computer system 100 may further comprise a sequence comparison algorithm for comparing a nucleic acid sequence as set forth in Group A nucleic acid sequences, and sequences substantially identical thereto, or a polypeptide sequence as set forth in Group B amino acid sequences, and sequences substantially identical thereto, stored on a computer readable medium to a reference nucleotide or polypeptide sequence(s) stored on a computer readable medium. A "sequence comparison algorithm" refers to one or more programs which are implemented (locally or remotely) on the computer system 100 to compare a nucleotide sequence with other nucleotide sequences and/or compounds stored within a data storage means. For example, the sequence comparison algorithm may compare the nucleotide sequences of a nucleic acid sequence as set forth in Group A nucleic acid sequences, and sequences substantially identical thereto, or a polypeptide sequence as set forth in Group B amino acid sequences, and sequences substantially identical thereto, stored on a computer readable medium to reference sequences stored on a computer readable medium to identify homologies or structural motifs. Various sequence comparison programs identified elsewhere in this patent specification are particularly contemplated for use in this aspect of the invention. Protein and/or nucleic acid sequence homologies may be evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, *Proc. Natl. Acad. Sci. USA* 85(8):2444-2448, 1988; Altschul, et al., *J. Mol. Biol.*, 215(3):403-410, 1990; Thompson, et al., *Nucleic Acids Res.*, 22(2):4673-4680, 1994; Higgins, et al., *Methods Enzymol.*, 266:383-402, 1996; Altschul, et al., *J. Mol. Biol.*, 215(3):403-410, 1990; Altschul, et al., *Nature Genetics*, 3:266-272, 1993).

Homology or identity is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequence for comparison are well-known in the art. Optimal alignment of sequences for comparison can be conducted, e.g., by the local homology algorithm of Smith & Waterman, *Adv. Appl. Math.*, 2:482, 1981, by the homology alignment algorithm of Needleman & Wunsch, *J. Mol. Biol*, 48:443, 1970, by the search for similarity method of Pearson and Lipman, *Proc. Nat'l. Acad. Sci. USA*, 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. A number of genome databases are available, for example, a substantial portion of the human genome is available as part of the Human Genome Sequencing Project. At least twenty-one other genomes have already been sequenced, including, for example, *M. genitalium* (Fraser, et al., 1995), *M. jannaschii* (Bult, et al., 1996), *H. influenzae* (Fleischmann, et al., 1995), *E. coli* (Blattner, et al., 1997), and yeast (*S. cerevisiae*) (Mewes, et al., 1997), and *D. melanogaster* (Adams, et al., 2000). Significant progress has also been made in sequencing the genomes of model organism, such as mouse, *C. elegans*, and *Arabidopsis* sp. Several databases containing genomic information annotated with some functional information are maintained by different organization, and are accessible via the internet.

One example of a useful algorithm is BLAST and BLAST 2.0 algorithms, which are described in Altschul, et al., *Nuc. Acids Res.*, 25:3389-3402, 1977, and Altschul, et al., *J. Mol. Biol.*, 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectations (E) of 10, and the BLOSUM62 scoring matrix (see Henikoff & Henikoff, *Proc. Natl. Acad. Sci. USA*, 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Natl. Acad. Sci. USA*, 90:5873, 1993). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001.

In one embodiment, protein and nucleic acid sequence homologies are evaluated using the Basic Local Alignment Search Tool ("BLAST") In particular, five specific BLAST programs are used to perform the following task:

(1) BLASTP and BLAST3 compare an amino acid query sequence against a protein sequence database;
(2) BLASTN compares a nucleotide query sequence against a nucleotide sequence database;
(3) BLASTX compares the six-frame conceptual translation products of a query nucleotide sequence (both strands) against a protein sequence database;
(4) TBLASTN compares a query protein sequence against a nucleotide sequence database translated in all six reading frames (both strands); and
(5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet, et al., *Science*, 256:1443-1445, 1992; Henikoff and Henikoff, *Proteins*, 17:49-61, 1993). Less preferably, the PAM or PAM250 matrices may also be used (see, e.g., Schwartz and Dayhoff, eds., 1978, *Matrices for Detecting Distance Relationships Atlas of Protein Sequence and Structure*, Washington: National Biomedical Research Foundation). BLAST programs are accessible through the U.S. National Library of Medicine.

The parameters used with the above algorithms may be adapted depending on the sequence length and degree of homology studied. In some embodiments, the parameters may be the default parameters used by the algorithms in the absence of instructions from the user.

Figure 2:
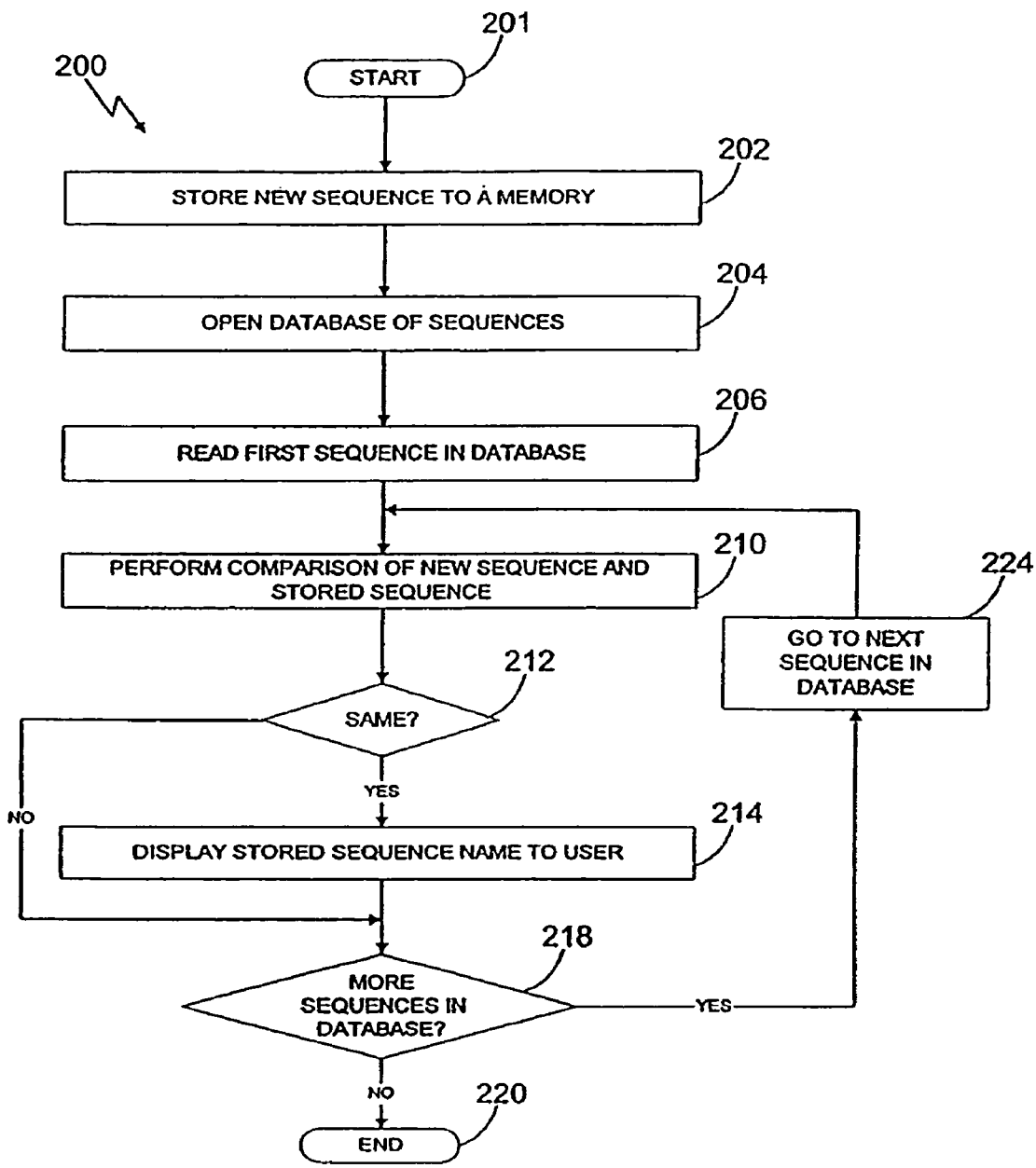
FIG. 2 is a flow diagram illustrating one embodiment of a process for comparing a new nucleotide or protein sequence with a database of sequences in order to determine the homology levels between the new sequence and the sequences in the database.

FIG. 2 is a flow diagram illustrating one embodiment of a process 200 for comparing a new nucleotide or protein sequence with a database of sequences in order to determine the homology levels between the new sequence and the sequences in the database. The database of sequences can be a private database stored within the computer system 100, or a public database such as GENBANK that is available through the Internet.

The process 200 begins at a start state 201 and then moves to a state 202 wherein the new sequence to be compared is stored to a memory in a computer system 100. As discussed above, the memory could be any type of memory, including RAM or an internal storage device.

The process 200 then moves to a state 204 wherein a database of sequences is opened for analysis and comparison. The process 200 then moves to a state 206 wherein the first sequence stored in the database is read into a memory on the computer. A comparison is then performed at a state 210 to determine if the first sequence is the same as the second sequence. It is important to note that this step is not limited to performing an exact comparison between the new sequence and the first sequence in the database. Well-known methods are known to those of skill in the art for comparing two nucleotide or protein sequences, even if they are not identical. For example, gaps can be introduced into one sequence in order to raise the homology level between the two tested sequences. The parameters that control whether gaps or other features are introduced into a sequence during comparison are normally entered by the user of the computer system.

Once a comparison of the two sequences has been performed at the state 210, a determination is made at a decision state 210 whether the two sequences are the same. Of course, the term "same" is not limited to sequences that are absolutely identical. Sequences that are within the homology parameters entered by the user will be marked as "same" in the process 200.

If a determination is made that the two sequences are the same, the process 200 moves to a state 214 wherein the name of the sequence from the database is displayed to the user. This state notifies the user that the sequence with the displayed name fulfills the homology constraints that were entered. Once the name of the stored sequence is displayed to the user, the process 200 moves to a decision state 218 wherein a determination is made whether more sequences exist in the database. If no more sequences exist in the database, then the process 200 terminates at an end state 220. However, if more sequences do exist in the database, then the process 200 moves to a state 224 wherein a pointer is moved to the next sequence in the database so that it can be compared to the new sequence. In this manner, the new sequence is aligned and compared with every sequence in the database.

It should be noted that if a determination had been made at the decision state 212 that the sequences were not homologous, then the process 200 would move immediately to the decision state 218 in order to determine if any other sequences were available in the database for comparison.

Accordingly, one aspect of the invention is a computer system comprising a processor, a data storage device having stored thereon a nucleic acid sequence as set forth in Group A nucleic acid sequences, and sequences substantially identical thereto, or a polypeptide sequence as set forth in Group B amino acid sequences, and sequences substantially identical thereto, a data storage device having retrievably stored thereon reference nucleotide sequences or polypeptide sequences to be compared to a nucleic acid sequence as set forth in Group A nucleic acid sequences, and sequences substantially identical thereto, or a polypeptide sequence as set forth in Group B amino acid sequences, and sequences substantially identical thereto, and a sequence comparer for conducting the comparison. The sequence comparer may indicate a homology level between the sequences compared or identify structural motifs in the above described nucleic acid code of Group A nucleic acid sequences, and sequences substantially identical thereto, or a polypeptide sequence as set forth in Group B amino acid sequences, and sequences substantially identical thereto, or it may identify structural motifs in sequences which are compared to these nucleic acid codes and polypeptide codes. In some embodiments, the data storage device may have stored thereon the sequences of at least 2, 5, 10, 15, 20, 25, 30 or 40 or more of the nucleic acid sequences as set forth in Group A nucleic acid sequences, and sequences substantially identical thereto, or the polypeptide sequences as set forth in Group B amino acid sequences, and sequences substantially identical thereto.

Another aspect of the invention is a method for determining the level of homology between a nucleic acid sequence as set forth in Group A nucleic acid sequences, and sequences substantially identical thereto, or a polypeptide sequence as set forth in Group B amino acid sequences, and sequences substantially identical thereto, and a reference nucleotide sequence. The method including reading the nucleic acid code or the polypeptide code and the reference nucleotide or polypeptide sequence through the use of a computer program which determines homology levels and determining homology between the nucleic acid code or polypeptide code and the reference nucleotide or polypeptide sequence with the computer program. The computer program may be any of a number of computer programs for determining homology levels, including those specifically enumerated herein, (e.g., BLAST2N with the default parameters or with any modified parameters). The method may be implemented using the computer systems described above. The method may also be performed by reading at least 2, 5, 10, 15, 20, 25, 30 or 40 or more of the above described nucleic acid sequences as set forth in the Group A nucleic acid sequences, or the polypeptide sequences as set forth in the Group B amino acid sequences through use of the computer program and determining homology between the nucleic acid codes or polypeptide codes and reference nucleotide sequences or polypeptide sequences.

Figure 3:
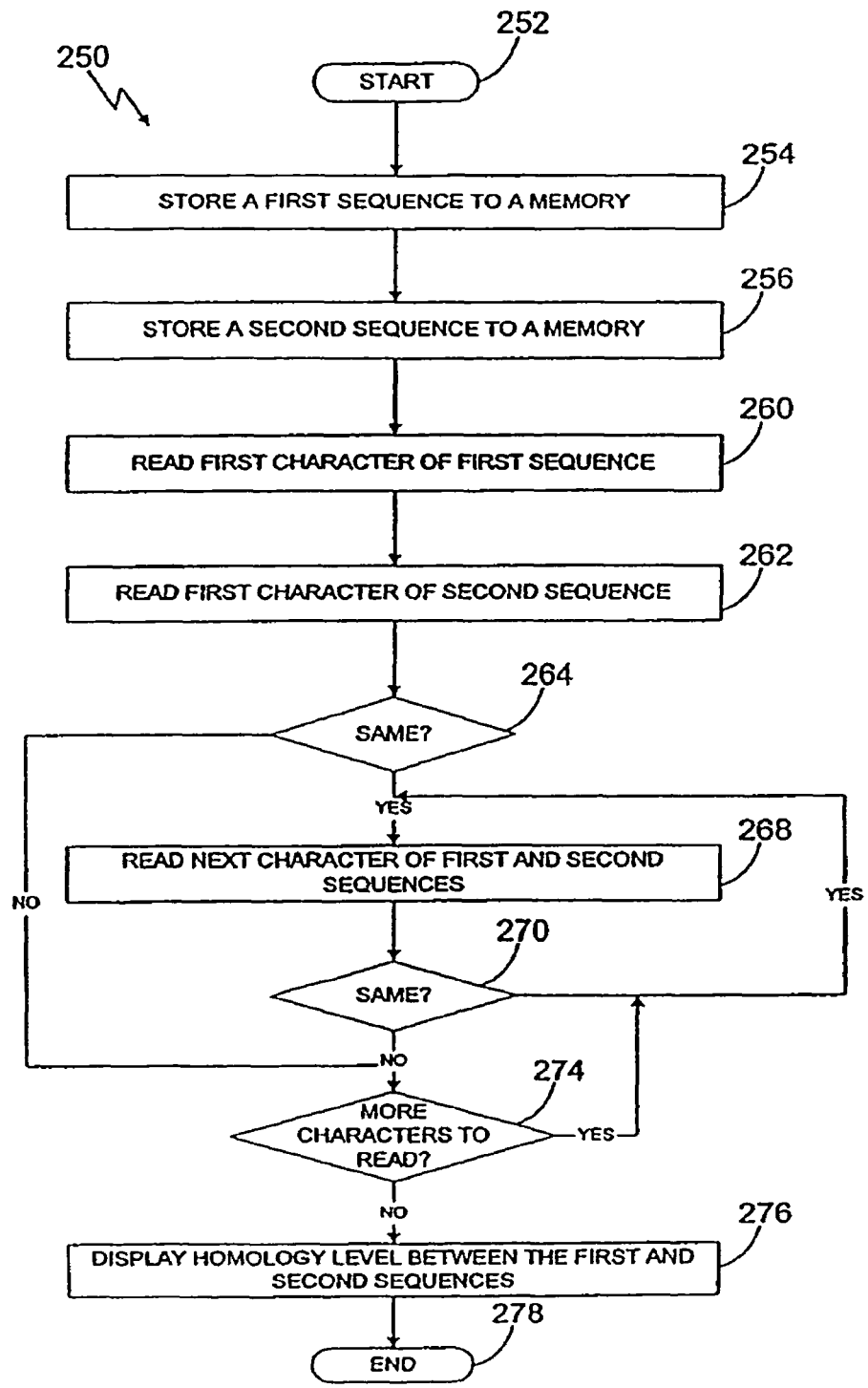
FIG. 3 is a flow diagram illustrating one embodiment of a process in a computer for determining whether two sequences are homologous.
Figure 4:
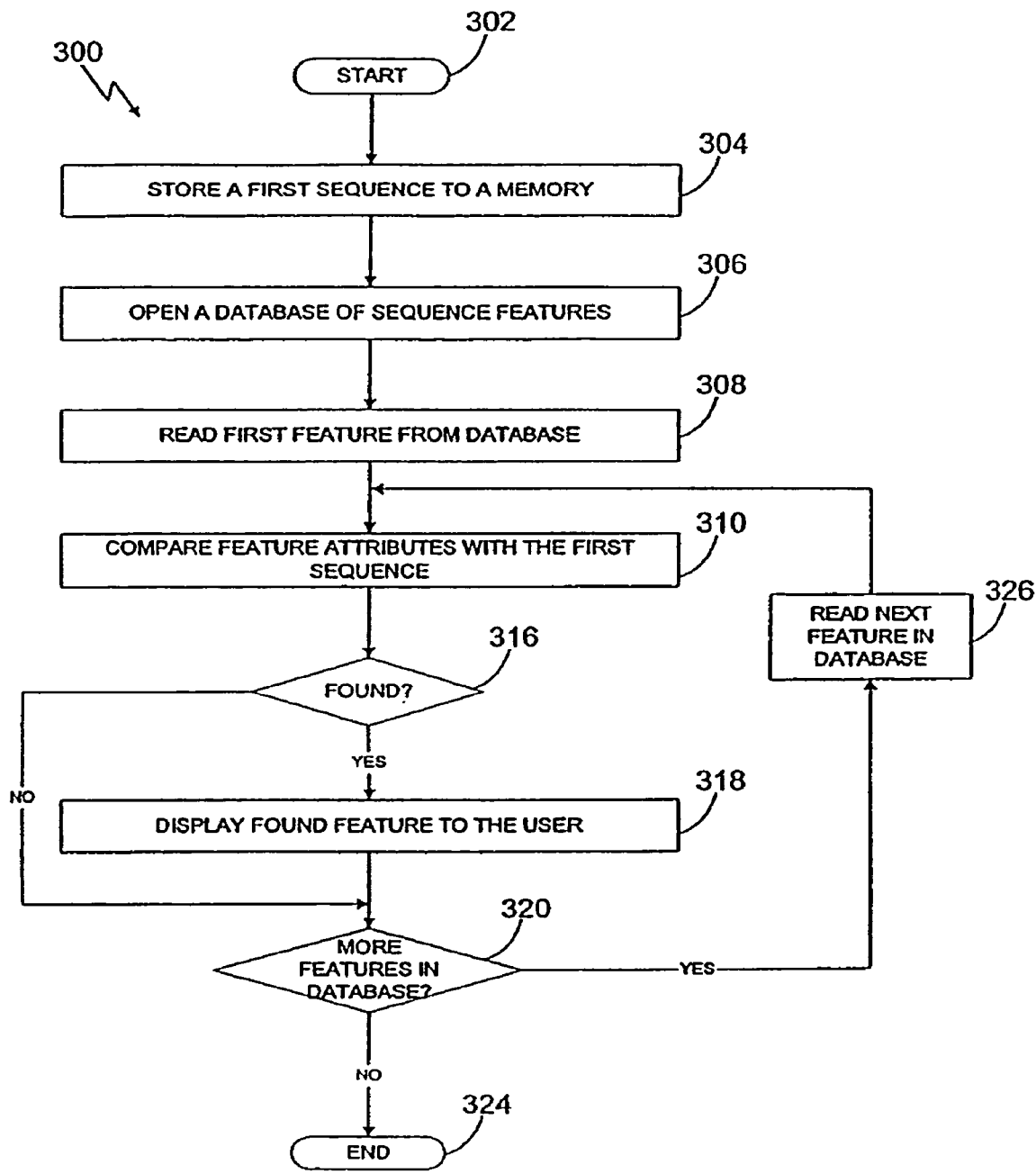
FIG. 4 is a flow diagram illustrating one embodiment of an identifier process 300 for detecting the presence of a feature in a sequence.

FIG. 3 is a flow diagram illustrating one embodiment of a process 250 in a computer for determining whether two sequences are homologous. The process 250 begins at a start state 252 and then moves to a state 254 wherein a first sequence to be compared is stored to a memory. The second sequence to be compared is then stored to a memory at a state 256. The process 250 then moves to a state 260 wherein the first character in the first sequence is read and then to a state 262 wherein the first character of the second sequence is read. It should be understood that if the sequence is a nucleotide sequence, then the character would normally be either A, T, C, G or U. If the sequence is a protein sequence, then it is preferably in the single letter amino acid code so that the first and sequence sequences can be easily compared.

A determination is then made at a decision state 264 whether the two characters are the same. If they are the same, then the process 250 moves to a state 268 wherein the next characters in the first and second sequences are read. A determination is then made whether the next characters are the same. If they are, then the process 250 continues this loop until two characters are not the same. If a determination is made that the next two characters are not the same, the process 250 moves to a decision state 274 to determine whether there are any more characters either sequence to read.

If there are not any more characters to read, then the process 250 moves to a state 276 wherein the level of homology between the first and second sequences is displayed to the user. The level of homology is determined by calculating the proportion of characters between the sequences that were the same out of the total number of sequences in the first sequence. Thus, if every character in a first 100 nucleotide sequence aligned with a every character in a second sequence, the homology level would be 100%.

Alternatively, the computer program may be a computer program which compares the nucleotide sequences of a nucleic acid sequence as set forth in the invention, to one or more reference nucleotide sequences in order to determine whether the nucleic acid code of Group A nucleic acid sequences, and sequences substantially identical thereto, differs from a reference nucleic acid sequence at one or more positions. Optionally such a program records the length and identity of inserted, deleted or substituted nucleotides with respect to the sequence of either the reference polynucleotide or a nucleic acid sequence as set forth in Group A nucleic acid sequences, and sequences substantially identical thereto. In one embodiment, the computer program may be a program which determines whether a nucleic acid sequence as set forth in Group A nucleic acid sequences, and sequences substantially identical thereto, contains a single nucleotide polymorphism (SNP) with respect to a reference nucleotide sequence.

Accordingly, another aspect of the invention is a method for determining whether a nucleic acid sequence as set forth in Group A nucleic acid sequences, and sequences substantially identical thereto, differs at one or more nucleotides from a reference nucleotide sequence comprising the steps of reading the nucleic acid code and the reference nucleotide sequence through use of a computer program which identifies differences between nucleic acid sequences and identifying differences between the nucleic acid code and the reference nucleotide sequence with the computer program. In some embodiments, the computer program is a program which identifies single nucleotide polymorphisms. The method may be implemented by the computer systems described above and the method illustrated in FIG. 3. The method may also be performed by reading at least 2, 5, 10, 15, 20, 25, 30, or 40 or more of the nucleic acid sequences as set forth in Group A nucleic acid sequences, and sequences substantially identical thereto, and the reference nucleotide sequences through the use of the computer program and identifying differences between the nucleic acid codes and the reference nucleotide sequences with the computer program.

In other embodiments the computer based system may further comprise an identifier for identifying features within a nucleic acid sequence as set forth in the Group A nucleic acid sequences or a polypeptide sequence as set forth in Group B amino acid sequences, and sequences substantially identical thereto.

An "identifier" refers to one or more programs which identifies certain features within a nucleic acid sequence as set forth in Group A nucleic acid sequences, and sequences substantially identical thereto, or a polypeptide sequence as set forth in Group B amino acid sequences, and sequences substantially identical thereto. In one embodiment, the identifier may comprise a program which identifies an open reading frame in a nucleic acid sequence as set forth in Group A nucleic acid sequences, and sequences substantially identical thereto.

FIG. 5 is a flow diagram illustrating one embodiment of an identifier process 300 for detecting the presence of a feature in a sequence. The process 300 begins at a start state 302 and then moves to a state 304 wherein a first sequence that is to be checked for features is stored to a memory 115 in the computer system 100. The process 300 then moves to a state 306 wherein a database of sequence features is opened. Such a database would include a list of each feature's attributes along with the name of the feature. For example, a feature name could be "Initiation Codon" and the attribute would be "ATG". Another example would be the feature name "TAATAA Box" and the feature attribute would be "TAATAA". An example of such a database is produced by the University of Wisconsin Genetics Computer Group. Alternatively, the features may be structural polypeptide motifs such as alpha helices, beta sheets, or functional polypeptide motifs such as enzymatic active sites, helix-turn-helix motifs or other motifs known to those skilled in the art.

Once the database of features is opened at the state 306, the process 300 moves to a state 308 wherein the first feature is read from the database. A comparison of the attribute of the first feature with the first sequence is then made at a state 310. A determination is then made at a decision state 316 whether the attribute of the feature was found in the first sequence. If the attribute was found, then the process 300 moves to a state 318 wherein the name of the found feature is displayed to the user.

The process 300 then moves to a decision state 320 wherein a determination is made whether move features exist in the database. If no more features do exist, then the process 300 terminates at an end state 324. However, if more features do exist in the database, then the process 300 reads the next sequence feature at a state 326 and loops back to the state 310 wherein the attribute of the next feature is compared against the first sequence.

It should be noted, that if the feature attribute is not found in the first sequence at the decision state 316, the process 300 moves directly to the decision state 320 in order to determine if any more features exist in the database.

Accordingly, another aspect of the invention is a method of identifying a feature within a nucleic acid sequence as set forth in Group A nucleic acid sequences, and sequences substantially identical thereto, or a polypeptide sequence as set forth in Group B amino acid sequences, and sequences substantially identical thereto, comprising reading the nucleic acid code(s) or polypeptide code(s) through the use of a computer program which identifies features therein and identifying features within the nucleic acid code(s) with the computer program. In one embodiment, computer program comprises a computer program which identifies open reading frames. The method may be performed by reading a single sequence or at least 2, 5, 10, 15, 20, 25, 30, or 40 of the nucleic acid sequences as set forth in Group A nucleic acid sequences, and sequences substantially identical thereto, or the polypeptide sequences as set forth in Group B amino acid sequences, and sequences substantially identical thereto, through the use of the computer program and identifying features within the nucleic acid codes or polypeptide codes with the computer program.

A nucleic acid sequence as set forth in Group A nucleic acid sequences, and sequences substantially identical thereto, or a polypeptide sequence as set forth in Group B amino acid sequences, and sequences substantially identical thereto, may be stored and manipulated in a variety of data processor programs in a variety of formats. For example, a nucleic acid sequence as set forth in Group A nucleic acid sequences, and sequences substantially identical thereto, or a polypeptide sequence as set forth in Group B amino acid sequences, and sequences substantially identical thereto, may be stored as text in a word processing file, such as MicrosoftWORD or WORDPERFECT or as an ASCII file in a variety of database programs familiar to those of skill in the art, such as DB2, SYBASE, or ORACLE. In addition, many computer programs and databases may be used as sequence comparison algorithms, identifiers, or sources of reference nucleotide sequences or polypeptide sequences to be compared to a nucleic acid sequence as set forth in Group A nucleic acid sequences, and sequences substantially identical thereto, or a polypeptide sequence as set forth in Group B amino acid sequences, and sequences substantially identical thereto. The following list is intended not to limit the invention but to provide guidance to programs and databases which are useful with the nucleic acid sequences as set forth in Group A nucleic acid sequences, and sequences substantially identical thereto, or the polypeptide sequences as set forth in Group B amino acid sequences, and sequences substantially identical thereto.

The programs and databases which may be used include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul, et al., *J. Mol. Biol.*, 215: 403, 1990), FASTA (Pearson and Lipman, *Proc. Natl. Acad. Sci. USA*, 85: 2444, 1988), FASTDB (Brutlag, et al., *Comp. App. Biosci.*, 6:237-245, 1990), Catalyst (Molecular Simulations Inc.), Catalyst/SHAPE (Molecular Simulations Inc.), Cerius$^2$.DB Access (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the MDL Available Chemicals Directory database, the MDL Drug Data Report data base, the Comprehensive Medicinal Chemistry database, Derwent's World Drug Index database, the BioByteMasterFile database, the Genbank database, and the Genseqn database. Many other programs and data bases would be apparent to one of skill in the art given the present disclosure.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

The present invention exploits the unique catalytic properties of enzymes. Whereas the use of biocatalysts (i.e., purified or crude enzymes, non-living or living cells) in chemical transformations normally requires the identification of a particular biocatalyst that reacts with a specific starting compound, the present invention uses selected biocatalysts and reaction conditions that are specific for functional groups that are present in many starting compounds, such as small molecules. Each biocatalyst is specific for one functional group, or several related functional groups, and can react with many starting compounds containing this functional group.

The biocatalytic reactions produce a population of derivatives from a single starting compound. These derivatives can be subjected to another round of biocatalytic reactions to produce a second population of derivative compounds. Thousands of variations of the original small molecule or compound can be produced with each iteration of biocatalytic derivitization.

Enzymes react at specific sites of a starting compound without affecting the rest of the molecule, a process which is very difficult to achieve using traditional chemical methods. This high degree of biocatalytic specificity provides the means to identify a single active compound within the library. The library is characterized by the series of biocatalytic reactions used to produce it, a so called "biosynthetic history". Screening the library for biological activities and tracing the biosynthetic history identifies the specific reaction sequence producing the active compound. The reaction sequence is repeated and the structure of the synthesized compound determined. This mode of identification, unlike other synthesis and screening approaches, does not require immobilization technologies, and compounds can be synthesized and tested free in solution using virtually any type of screening assay. It is important to note, that the high degree of specificity of enzyme reactions on functional groups allows for the "tracking" of specific enzymatic reactions that make up the biocatalytically produced library.

Many of the procedural steps are performed using robotic automation enabling the execution of many thousands of biocatalytic reactions and screening assays per day as well as ensuring a high level of accuracy and reproducibility. As a result, a library of derivative compounds can be produced in a matter of weeks which would take years to produce using current chemical methods.

In a particular embodiment, the invention provides a method for modifying small molecules, comprising contacting a polypeptide encoded by a polynucleotide described herein or enzymatically active fragments thereof with a small molecule to produce a modified small molecule. A library of modified small molecules is tested to determine if a modified small molecule is present within the library which exhibits a desired activity. A specific biocatalytic reaction which produces the modified small molecule of desired activity is identified by systematically eliminating each of the biocatalytic reactions used to produce a portion of the library, and then testing the small molecules produced in the portion of the library for the presence or absence of the modified small molecule with the desired activity. The specific biocatalytic reactions which produce the modified small molecule of desired activity is optionally repeated. The biocatalytic reactions are conducted with a group of biocatalysts that react with distinct structural moieties found within the structure of a small molecule, each biocatalyst is specific for one structural moiety or a group of related structural moieties; and each biocatalyst reacts with many different small molecules which contain the distinct structural moiety.

The invention will be further described with reference to the following examples; however, it is to be understood that the invention is not limited to such examples.

EXAMPLES

Example 1

Site-Saturation Mutagenesis

To accomplish site-saturation mutagenesis every residue (317) of a dehalogenase enzyme (SEQ ID NO:2) encoded by SEQ ID NO:1 was converted into all 20 amino acids by site directed mutagenesis using 32-fold degenerate oligonucleotide primers, as follows:
1. A culture of the dehalogenase expression construct was grown and a preparation of the plasmid was made.
2. Primers were made to randomize each codon—they have the common structure $X_{20}NN(G/T)X_{20}$, wherein $X_{20}$ represents the 20 nucleotides of the nucleic acid sequence of SEQ ID NO:1 flanking the codon to by changed.
3. A reaction mix of 25 Tl was prepared containing ~50 ng of plasmid template, 125 ng of each primer, 1× native Pfu buffer, 200 TM each dNTP and 2.5 U native Pfu DNA polymerase.
4. The reaction was cycled in a Robo96 Gradient Cycler as follows:
   Initial denaturation at 95° C. for 1 min;
   20 cycles of 95° C. for 45 sec, 53° C. for 1 min and 72° C. for 11 min; and
   Final elongation step of 72° C. for 10 min
5. The reaction mix was digested with 10 U of DpnI at 37° C. for 1 hour to digest the methylated template DNA.
6. Two Tl of the reaction mix were used to transform 50 Tl of XL1-Blue MRF' cells and the entire transformation mix was plated on a large LB-Amp-Met plate yielding 200-1000 colonies.
7. Individual colonies were toothpicked into the wells of 384-well microtiter plates containing LB-Amp-IPTG and grown overnight.
8. The clones on these plates were assayed the following day.

Example 2

Dehalogenase Thermal Stability

This invention provides that a desirable property to be generated by directed evolution is exemplified in a limiting fashion by an improved residual activity (e.g., an enzymatic activity, an immunoreactivity, an antibiotic activity, etc.) of a molecule upon subjection to altered environment, including what may be considered a harsh environment, for a specified time. Such a harsh environment may comprise any combination of the following (iteratively or not, and in any order or permutation): an elevated temperature (including a temperature that may cause denaturation of a working enzyme), a decreased temperature, an elevated salinity, a decreased salinity, an elevated pH, a decreased pH, an elevated pressure, a decreased pressure, and an change in exposure to a radiation source (including uv radiation, visible light, as well as the entire electromagnetic spectrum).

The following example shows an application of directed evolution to evolve the ability of an enzyme to regain or retain activity upon exposure to an elevated temperature.

Every residue (317) of a dehalogenase enzyme was converted into all 20 amino acids by site directed mutagenesis using 32-fold degenerate oligonucleotide primers, as described above. The screening procedure was as follows:
1. Overnight cultures in 384-well plates were centrifuged and the media removed. To each well was added 0.06 mL 1 mM Tris/$SO_4^{2-}$ pH 7.8.
2. A robot made 2 assay plates from each parent growth plate consisting of 0.02 mL cell suspension.
3. One assay plate was placed at room temperature and the other at elevated temperature (initial screen used 55° C.) for a period of time (initially 30 minutes).

4. After the prescribed time 0.08 mL room temperature substrate (TCP saturated 1 mM Tris/SO$_4^{2-}$ pH 7.8 with 1.5 mM NaN$_3$ and 0.1 mM bromothymol blue) was added to each well. TCP=trichloropropane.
5. Measurements at 620 nm were taken at various time points to generate a progress curve for each well.
6. Data were analyzed and the kinetics of the cells heated to those not heated were compared. Each plate contained 1-2 columns (24 wells) of un-mutated 20F12 controls.
7. Wells that appeared to have improved stability were regrown and tested under the same conditions.

Following this procedure clones having mutations that conferred increased thermal stability on the enzyme were sequenced to determine the exact amino acid changes at each position that were specifically responsible for the improvement. Mutants having a nucleic acid sequence as set forth in SEQ ID NO's: 5 and 7 and polypeptide sequences as set forth in SEQ ID NO's: 6 and 8, respectively, were identified. The thermal mutant at position G182V (SEQ ID NO: 6) can also be a glutamate (Q) with similar increased thermal stability. Similarly, the P302A mutation could be changed to leucine (L), serine (S), lysine (K) or arginine (R). These variants (as well as those below) are encompassed by the present invention.

Following this procedure nine single site mutations appeared to confer increased thermal stability. Sequence analysis showed that the following changes were beneficial: D89G; F91S; T159L; G182Q, G182V; I220L; N238T; W251Y; P302A, P302L, P302S, P302K; P302R/S306R. Only two sites (182 and 302) had more than one substitution. The first 5 on the list were combined (using G182Q) into a single gene.

Thermal stability was assessed by incubating the enzyme at the elevated temperature (55° C. and 80° C.) for some period of time and activity assay at 30° C. Initial rates were plotted vs. time at the higher temperature. The enzyme was in 50 mM Tris/SO$_4$ pH 7.8 for both the incubation and the assay. Product (Cl$^-$) was detected by a standard method using Fe(NO$_3$)$_3$ and HgSCN. The dehalogenase of SEQ ID NO: 2 was used as the de facto wild type. The apparent half-life (T$_{1/2}$) was calculated by fitting the data to an exponential decay function.

While the invention has been described in detail with reference to certain preferred embodiments thereof, it will be understood that modifications and variations are within the spirit and scope of that which is described and claimed.

What is claimed is:

1. A synthetic or recombinant nucleic acid operably linked to a promoter, said nucleic acid sequence comprising:
   (a) a nucleic acid sequence having at least 97% sequence identity to at least one of SEQ ID NOS: 9, 11, 13, 15, 17, 19, 21, 23, 25, 27, 29, 31, 33, 35, 37, 45, or 47; or
   (b) a nucleic acid sequence complementary to (a); or
   (c) the nucleic acid sequence of (a), wherein the nucleic acid encodes at least one polypeptide having a dehalogenase activity.

2. The nucleic acid of claim 1, wherein the nucleic acid encodes at least one polypeptide having a dehalogenase activity comprising an amino acid sequence having at least 97% sequence identity to at least one of SEQ ID NO: 10, 12, 14, 16, 18, 20, 22, 24, 26, 28, 30, 32, 34, 36, 38, 46, or 48.

3. The nucleic acid of claim 1, wherein the nucleic acid sequence has at least 98% sequence identity to at least one of SEQ ID NO: 9, 11, 13, 15, 17, 19, 21, 23, 25, 27, 29, 31, 33, 35, 37, 45, or 47.

4. The nucleic acid of claim 1, wherein the nucleic acid sequence has at least 99% sequence identity to at least one of SEQ ID NO: 9, 11, 13, 15, 17, 19, 21, 23, 25, 27, 29, 31, 33, 35, 37, 45, or 47.

5. The nucleic acid of claim 1, wherein the nucleic acid sequence comprises a sequence as set forth in at least one of SEQ ID NO: 9, 11, 13, 15, 17, 19, 21, 23, 25, 27, 29, 31, 33, 35, 37, 45, or 47.

6. The nucleic acid of claim 1, wherein the dehalogenase activity comprises catalyzing the conversion of a dihalopropionic acid to an optically active halolactic acid.

7. The nucleic acid of claim 1, wherein optionally the promoter comprises a eukaryotic promoter, a fungal promoter, a mammalian promoter, a prokaryotic promoter or a viral promoter.

8. The nucleic acid of claim 1, wherein the nucleic acid further comprises a vector.

9. The nucleic acid of claim 8, wherein the vector is a cloning vector or an expression vector.

10. The nucleic acid of claim 9, wherein the expression vector is a mammalian expression vector.

11. The nucleic acid of claim 8, wherein the vector is selected from the group consisting of a viral vector, a plasmid vector, a phage vector, a phagemid vector, a cosmid, a fosmid, a bacteriophage, an artificial chromosome, an adenovirus vector, a retroviral vector, and an adeno-associated viral vector.

12. A host cell comprising a nucleic acid as set forth in claim 1.

13. The host cell of claim 12, further comprising a vector.

14. The host cell of claim 12, wherein the host cell is a prokaryote cell, a eukaryote cell, a bacterial cell, a fungal cell, a yeast cell, a mammalian cell, a plant cell or an insect cell.

15. The nucleic acid of claim 1 wherein the nucleic acid is bound to a solid matrix or a solid phase.

16. The nucleic acid of claim 15, wherein the solid phase comprises a glass, a polymeric surface, a packed column of polymeric beads, or a magnetic or a paramagnetic particle.

17. The nucleic acid of claim 1 further comprising an antigen or hapten, an antibody, a specific binding fragment, a biotin, an iminobiotin, an avidin, a streptavidin, a sugar, a lectin, an enzyme, an apoenzyme, a cofactor, a complementary homopolymeric oligonucleotide, a hormone, a receptor.

18. A method for generating a dehalogenase-encoding nucleic acid comprising:
   (a) providing a parent nucleic acid encoding a dehalogenase comprising a sequence as set forth in claim 1; and
   (b) modifying the sequence of the parent nucleic acid by a process comprising error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, Gene Site Saturation Mutagenesis (GSSM) or any combination, permutation or iterative process thereof,
   thereby generating a dehalogenase-encoding nucleic acid.

19. A method for producing a dehalogenase comprising:
   (a) providing a nucleic acid encoding a dehalogenase comprising a sequence as set forth in claim 1; and
   (b) expressing the nucleic acid to produce a dehalogenase, wherein optionally the nucleic acid is expressed in a host cell.

20. A method for producing a halolactic acid comprising:
   (a) providing a nucleic acid encoding a dehalogenase comprising a sequence as set forth in claim 1, and a dihalopropionic acid;
   (b) expressing the nucleic acid to produce a dehalogenase; and
   (c) contacting the dihalopropionic acid with the dehalogenase under conditions to produce a halolactic acid, wherein optionally the halolactic acid is an optically active halolactic acid.

* * * * *

SEQUENCE LISTING

```
<160> NUMBER OF SEQ ID NOS: 49

<210> SEQ ID NO 1
<211> LENGTH: 954
<212> TYPE: DNA
<213> ORGANISM: Artificial Sequence
<220> FEATURE:
<223> OTHER INFORMATION: Artificially modified (mutated) dehalogenase
<221> NAME/KEY: CDS
<222> LOCATION: (1)...(951)

<400> SEQUENCE: 1 atg ggg ggt tct cat cat cat cat cat cat ggt atg tct gaa ata ggt        48
Met Gly Gly Ser His His His His His His Gly Met Ser Glu Ile Gly
1               5                   10                  15 acc ggt ttt ccc ttc gac cct cat tat gtg gaa gtc ctg ggc gag cgt        96
Thr Gly Phe Pro Phe Asp Pro His Tyr Val Glu Val Leu Gly Glu Arg
            20                  25                  30 atg cac tac gtc gat gtt gga ccg cgg gat ggc acg cct gtg ctg ttc       144
Met His Tyr Val Asp Val Gly Pro Arg Asp Gly Thr Pro Val Leu Phe
        35                  40                  45 ctg cac ggt aac ccg acc tcg tcc tac ctg tgg cgc aac atc atc ccg       192
Leu His Gly Asn Pro Thr Ser Ser Tyr Leu Trp Arg Asn Ile Ile Pro
    50                  55                  60 cat gta gca ccg agt cat cgg tgc att gct cca gac ctg atc ggg atg       240
His Val Ala Pro Ser His Arg Cys Ile Ala Pro Asp Leu Ile Gly Met
65                  70                  75                  80 gga aaa tcg gac aaa cca gac ctc gat tat ttc ttc gac gac cac gtc       288
Gly Lys Ser Asp Lys Pro Asp Leu Asp Tyr Phe Phe Asp Asp His Val
                85                  90                  95 cgc tac ctc gat gcc ttc atc gaa gcc ttg ggt ttg gaa gag gtc gtc       336
Arg Tyr Leu Asp Ala Phe Ile Glu Ala Leu Gly Leu Glu Glu Val Val
            100                 105                 110 ctg gtc atc cac gac tgg ggc tca gct ctc gga ttc cac tgg gcc aag       384
Leu Val Ile His Asp Trp Gly Ser Ala Leu Gly Phe His Trp Ala Lys
        115                 120                 125 cgc aat ccg gaa cgg gtc aaa ggt att gca tgt atg gaa ttc atc cgg       432
Arg Asn Pro Glu Arg Val Lys Gly Ile Ala Cys Met Glu Phe Ile Arg
```

```
      130                 135                 140
cct atc ccg acg tgg gac gaa tgg ccg gaa ttc gcc cgt gag acc ttc     480
Pro Ile Pro Thr Trp Asp Glu Trp Pro Glu Phe Ala Arg Glu Thr Phe
145                 150                 155                 160 cag gcc ttc cgg acc gcc gac gtc ggc cga gag ttg atc atc gat cag     528
Gln Ala Phe Arg Thr Ala Asp Val Gly Arg Glu Leu Ile Ile Asp Gln
                165                 170                 175 aac gct ttc atc gag ggt gtg ctc ccg aaa tgc gtc gtc cgt ccg ctt     576
Asn Ala Phe Ile Glu Gly Val Leu Pro Lys Cys Val Val Arg Pro Leu
            180                 185                 190 acg gag gtc gag atg gac cac tat cgc gag ccc ttc ctc aag cct gtt     624
Thr Glu Val Glu Met Asp His Tyr Arg Glu Pro Phe Leu Lys Pro Val
        195                 200                 205 gac cga gag cca ctg tgg cga ttc ccc aac gag atc ccc atc gcc ggt     672
Asp Arg Glu Pro Leu Trp Arg Phe Pro Asn Glu Ile Pro Ile Ala Gly
    210                 215                 220 gag ccc gcg aac atc gtc gcg ctc gtc gag gca tac atg aac tgg ctg     720
Glu Pro Ala Asn Ile Val Ala Leu Val Glu Ala Tyr Met Asn Trp Leu
225                 230                 235                 240 cac cag tca cct gtc ccg aag ttg ttg ttc tgg ggc aca ccc ggc gta     768
His Gln Ser Pro Val Pro Lys Leu Leu Phe Trp Gly Thr Pro Gly Val
                245                 250                 255 ctg atc ccc ccg gcc gaa gcc gcg aga ctt gcc gaa agc ctc ccc aac     816
Leu Ile Pro Pro Ala Glu Ala Ala Arg Leu Ala Glu Ser Leu Pro Asn
            260                 265                 270 tgc aag aca gtg gac atc ggc ccg gga ttg cac tac ctc cag gaa gac     864
Cys Lys Thr Val Asp Ile Gly Pro Gly Leu His Tyr Leu Gln Glu Asp
        275                 280                 285 aac ccg gac ctt atc ggc agt gag atc gcg cgc tgg ctc ccc gga ctc     912
Asn Pro Asp Leu Ile Gly Ser Glu Ile Ala Arg Trp Leu Pro Gly Leu
    290                 295                 300 gct agc ggc cta ggt gac tac aag gac gat gat gac aaa taa             954
Ala Ser Gly Leu Gly Asp Tyr Lys Asp Asp Asp Asp Lys
305                 310                 315

<210> SEQ ID NO 2
<211> LENGTH: 317
<212> TYPE: PRT
<213> ORGANISM: Artificial Sequence
<220> FEATURE:
<223> OTHER INFORMATION: Artificially modified (mutated) dehalogenase

<400> SEQUENCE: 2

Met Gly Gly Ser His His His His His His Gly Met Ser Glu Ile Gly
1               5                   10                  15

Thr Gly Phe Pro Phe Asp Pro His Tyr Val Glu Val Leu Gly Glu Arg
                20                  25                  30

Met His Tyr Val Asp Val Gly Pro Arg Asp Gly Thr Pro Val Leu Phe
            35                  40                  45

Leu His Gly Asn Pro Thr Ser Ser Tyr Leu Trp Arg Asn Ile Ile Pro
        50                  55                  60

His Val Ala Pro Ser His Arg Cys Ile Ala Pro Asp Leu Ile Gly Met
65                  70                  75                  80

Gly Lys Ser Asp Lys Pro Asp Leu Asp Tyr Phe Phe Asp Asp His Val
                85                  90                  95

Arg Tyr Leu Asp Ala Phe Ile Glu Ala Leu Gly Leu Glu Glu Val Val
            100                 105                 110

Leu Val Ile His Asp Trp Gly Ser Ala Leu Gly Phe His Trp Ala Lys
        115                 120                 125
```

```
Arg Asn Pro Glu Arg Val Lys Gly Ile Ala Cys Met Glu Phe Ile Arg
    130                 135                 140

Pro Ile Pro Thr Trp Asp Glu Trp Pro Glu Phe Ala Arg Glu Thr Phe
145                 150                 155                 160

Gln Ala Phe Arg Thr Ala Asp Val Gly Arg Glu Leu Ile Ile Asp Gln
                165                 170                 175

Asn Ala Phe Ile Glu Gly Val Leu Pro Lys Cys Val Val Arg Pro Leu
            180                 185                 190

Thr Glu Val Glu Met Asp His Tyr Arg Glu Pro Phe Leu Lys Pro Val
        195                 200                 205

Asp Arg Glu Pro Leu Trp Arg Phe Pro Asn Glu Ile Pro Ile Ala Gly
    210                 215                 220

Glu Pro Ala Asn Ile Val Ala Leu Val Glu Ala Tyr Met Asn Trp Leu
225                 230                 235                 240

His Gln Ser Pro Val Pro Lys Leu Leu Phe Trp Gly Thr Pro Gly Val
                245                 250                 255

Leu Ile Pro Pro Ala Glu Ala Ala Arg Leu Ala Glu Ser Leu Pro Asn
            260                 265                 270

Cys Lys Thr Val Asp Ile Gly Pro Gly Leu His Tyr Leu Gln Glu Asp
        275                 280                 285

Asn Pro Asp Leu Ile Gly Ser Glu Ile Ala Arg Trp Leu Pro Gly Leu
    290                 295                 300

Ala Ser Gly Leu Gly Asp Tyr Lys Asp Asp Asp Asp Lys
305                 310                 315

<210> SEQ ID NO 3
<211> LENGTH: 954
<212> TYPE: DNA
<213> ORGANISM: Artificial Sequence
<220> FEATURE:
<223> OTHER INFORMATION: Artificially modified (mutated) dehalogenase
<221> NAME/KEY: CDS
<222> LOCATION: (1)...(951)

<400> SEQUENCE: 3 atg ggg gat tct cat cat cat cat cat cat ggt atg tct gaa ata ggt        48
Met Gly Asp Ser His His His His His His Gly Met Ser Glu Ile Gly
1               5                   10                  15 acc ggt ttt ccc ttc gac cct cat tat gtg gaa gtc ctg ggc gag cgt        96
Thr Gly Phe Pro Phe Asp Pro His Tyr Val Glu Val Leu Gly Glu Arg
            20                  25                  30 atg cac tac gtc gat gtt gga ccg cgg gat ggc acg cct gtg ctg ttc       144
Met His Tyr Val Asp Val Gly Pro Arg Asp Gly Thr Pro Val Leu Phe
        35                  40                  45 ctg cac ggt aac ccg acc tcg tcc tac ctg tgg cgc aac atc atc ccg       192
Leu His Gly Asn Pro Thr Ser Ser Tyr Leu Trp Arg Asn Ile Ile Pro
    50                  55                  60 cat gta gca ccg agt cat cgg tgc att gct cca gac ctg atc ggg atg       240
His Val Ala Pro Ser His Arg Cys Ile Ala Pro Asp Leu Ile Gly Met
65                  70                  75                  80 gga aaa tcg gac aaa cca gac ctc gat tat ttc ttc gac gac cac gtc       288
Gly Lys Ser Asp Lys Pro Asp Leu Asp Tyr Phe Phe Asp Asp His Val
                85                  90                  95 cgc tac ctc gat gcc ttc atc gaa gcc ttg ggt ttg gaa gag gtc gtc       336
Arg Tyr Leu Asp Ala Phe Ile Glu Ala Leu Gly Leu Glu Glu Val Val
            100                 105                 110 ctg gtc atc cac gac tgg ggc tca gct ctc gga ttc cac tgg gcc aag       384
Leu Val Ile His Asp Trp Gly Ser Ala Leu Gly Phe His Trp Ala Lys
```

```
                115                 120                 125
cgc aat ccg gaa cgg gtc aaa ggt att gca tgt atg gaa ttc atc cgg      432
Arg Asn Pro Glu Arg Val Lys Gly Ile Ala Cys Met Glu Phe Ile Arg
    130                 135                 140 cct atc ccg acg tgg gac gaa tgg ccg gaa ttc gcc cgt gag acc ttc      480
Pro Ile Pro Thr Trp Asp Glu Trp Pro Glu Phe Ala Arg Glu Thr Phe
145                 150                 155                 160 cag gcc ttc cgg acc gcc gac gtc ggc cga gag ttg atc atc gat cag      528
Gln Ala Phe Arg Thr Ala Asp Val Gly Arg Glu Leu Ile Ile Asp Gln
                165                 170                 175 aac gct ttc atc gag ggt gtg ctc ccg aaa ttc gtc gtc cgt ccg ctt      576
Asn Ala Phe Ile Glu Gly Val Leu Pro Lys Phe Val Val Arg Pro Leu
            180                 185                 190 acg gag gtc gag atg gac cac tat cgc gag ccc ttc ctc aag cct gtt      624
Thr Glu Val Glu Met Asp His Tyr Arg Glu Pro Phe Leu Lys Pro Val
        195                 200                 205 gac cga gag cca ctg tgg cga ttc ccc aac gag atc ccc atc gcc ggt      672
Asp Arg Glu Pro Leu Trp Arg Phe Pro Asn Glu Ile Pro Ile Ala Gly
    210                 215                 220 gag ccc gcg aac atc gtc gcg ctc gtc gag gca tac atg aac tgg ctg      720
Glu Pro Ala Asn Ile Val Ala Leu Val Glu Ala Tyr Met Asn Trp Leu
225                 230                 235                 240 cac cag tca cct gtc ccg aag ttg ttg ttc tgg ggc aca ccc ggc gta      768
His Gln Ser Pro Val Pro Lys Leu Leu Phe Trp Gly Thr Pro Gly Val
                245                 250                 255 ctg atc ccc ccg gcc gaa gcc gcg aga ctt gcc gaa agc ctc ccc aac      816
Leu Ile Pro Pro Ala Glu Ala Ala Arg Leu Ala Glu Ser Leu Pro Asn
            260                 265                 270 tgc aag aca gtg gac atc ggc ccg gga ttg cac tac ctc cag gaa gac      864
Cys Lys Thr Val Asp Ile Gly Pro Gly Leu His Tyr Leu Gln Glu Asp
        275                 280                 285 aac ccg gac ctt atc ggc agt gag atc gcg cgc tgg ctc ccc gga ctc      912
Asn Pro Asp Leu Ile Gly Ser Glu Ile Ala Arg Trp Leu Pro Gly Leu
    290                 295                 300 gct agc ggc cta ggt gac tac aag gac gat gat gac aaa taa              954
Ala Ser Gly Leu Gly Asp Tyr Lys Asp Asp Asp Asp Lys
305                 310                 315

<210> SEQ ID NO 4
<211> LENGTH: 317
<212> TYPE: PRT
<213> ORGANISM: Artificial Sequence
<220> FEATURE:
<223> OTHER INFORMATION: Artificially modified (mutated) dehalogenase

<400> SEQUENCE: 4

Met Gly Asp Ser His His His His His Gly Met Ser Glu Ile Gly
1               5                   10                  15

Thr Gly Phe Pro Phe Asp Pro His Tyr Val Glu Val Leu Gly Glu Arg
                20                  25                  30

Met His Tyr Val Asp Val Gly Pro Arg Asp Gly Thr Pro Val Leu Phe
            35                  40                  45

Leu His Gly Asn Pro Thr Ser Ser Tyr Leu Trp Arg Asn Ile Ile Pro
        50                  55                  60

His Val Ala Pro Ser His Arg Cys Ile Ala Pro Asp Leu Ile Gly Met
65                  70                  75                  80

Gly Lys Ser Asp Lys Pro Asp Leu Asp Tyr Phe Phe Asp Asp His Val
                85                  90                  95

Arg Tyr Leu Asp Ala Phe Ile Glu Ala Leu Gly Leu Glu Glu Val Val
```

```
            100                 105                 110
Leu Val Ile His Asp Trp Gly Ser Ala Leu Gly Phe His Trp Ala Lys
            115                 120                 125

Arg Asn Pro Glu Arg Val Lys Gly Ile Ala Cys Met Glu Phe Ile Arg
        130                 135                 140

Pro Ile Pro Thr Trp Asp Glu Trp Pro Glu Phe Ala Arg Glu Thr Phe
145                 150                 155                 160

Gln Ala Phe Arg Thr Ala Asp Val Gly Arg Glu Leu Ile Ile Asp Gln
                165                 170                 175

Asn Ala Phe Ile Glu Gly Val Leu Pro Lys Phe Val Val Arg Pro Leu
                180                 185                 190

Thr Glu Val Glu Met Asp His Tyr Arg Glu Pro Phe Leu Lys Pro Val
            195                 200                 205

Asp Arg Glu Pro Leu Trp Arg Phe Pro Asn Glu Ile Pro Ile Ala Gly
        210                 215                 220

Glu Pro Ala Asn Ile Val Ala Leu Val Glu Ala Tyr Met Asn Trp Leu
225                 230                 235                 240

His Gln Ser Pro Val Pro Lys Leu Leu Phe Trp Gly Thr Pro Gly Val
                245                 250                 255

Leu Ile Pro Pro Ala Glu Ala Ala Arg Leu Ala Glu Ser Leu Pro Asn
                260                 265                 270

Cys Lys Thr Val Asp Ile Gly Pro Gly Leu His Tyr Leu Gln Glu Asp
            275                 280                 285

Asn Pro Asp Leu Ile Gly Ser Glu Ile Ala Arg Trp Leu Pro Gly Leu
        290                 295                 300

Ala Ser Gly Leu Gly Asp Tyr Lys Asp Asp Asp Asp Lys
305                 310                 315
```

<210> SEQ ID NO 5
<211> LENGTH: 954
<212> TYPE: DNA
<213> ORGANISM: Artificial Sequence
<220> FEATURE:
<223> OTHER INFORMATION: Artificially modified (mutated) dehalogenase
<221> NAME/KEY: CDS
<222> LOCATION: (1)...(951)

<400> SEQUENCE: 5

```
atg ggg gat tct cat cat cat cat cat cat ggt atg tct gaa ata ggt    48
Met Gly Asp Ser His His His His His His Gly Met Ser Glu Ile Gly
1               5                   10                  15 acc ggt ttt ccc ttc gac cct cat tat gtg gaa gtc ctg ggc gag cgt    96
Thr Gly Phe Pro Phe Asp Pro His Tyr Val Glu Val Leu Gly Glu Arg
            20                  25                  30 atg cac tac gtc gat gtt gga ccg cgg gat ggc acg cct gtg ctg ttc    144
Met His Tyr Val Asp Val Gly Pro Arg Asp Gly Thr Pro Val Leu Phe
        35                  40                  45 ctg cac ggt aac ccg acc tcg tcc tac ctg tgg cgc aac atc atc ccg    192
Leu His Gly Asn Pro Thr Ser Ser Tyr Leu Trp Arg Asn Ile Ile Pro
    50                  55                  60 cat gta gca ccg agt cat cgg tgc att gct cca gac ctg atc ggg atg    240
His Val Ala Pro Ser His Arg Cys Ile Ala Pro Asp Leu Ile Gly Met
65                  70                  75                  80 gga aaa tcg gac aaa cca gac ctc ggt tat tcc ttc gac gac cac gtc    288
Gly Lys Ser Asp Lys Pro Asp Leu Gly Tyr Ser Phe Asp Asp His Val
                85                  90                  95 cgc tac ctc gat gcc ttc atc gaa gcc ttg ggt ttg gaa gag gtc gtc    336
Arg Tyr Leu Asp Ala Phe Ile Glu Ala Leu Gly Leu Glu Glu Val Val
```

```
                    100                 105                      110
ctg gtc atc cac gac tgg ggc tca gct ctc gga ttc cac tgg gcc aag       384
Leu Val Ile His Asp Trp Gly Ser Ala Leu Gly Phe His Trp Ala Lys
            115                 120                 125 cgc aat ccg gaa cgg gtc aaa ggt att gca tgt atg gaa ttc atc cgg       432
Arg Asn Pro Glu Arg Val Lys Gly Ile Ala Cys Met Glu Phe Ile Arg
    130                 135                 140 cct atc ccg acg tgg gac gaa tgg ccg gaa ttc gcc cgt gag ctc ttc       480
Pro Ile Pro Thr Trp Asp Glu Trp Pro Glu Phe Ala Arg Glu Leu Phe
145                 150                 155                 160 cag gcc ttc cgg acc gcc gac gtc ggc cga gag ttg atc atc gat cag       528
Gln Ala Phe Arg Thr Ala Asp Val Gly Arg Glu Leu Ile Ile Asp Gln
                165                 170                 175 aac gct ttc atc gag cag gtg ctc ccg aaa ttc gtc gtc cgt ccg ctt       576
Asn Ala Phe Ile Glu Gln Val Leu Pro Lys Phe Val Val Arg Pro Leu
            180                 185                 190 acg gag gtc gag atg gac cac tat cgc gag ccc ttc ctc aag cct gtt       624
Thr Glu Val Glu Met Asp His Tyr Arg Glu Pro Phe Leu Lys Pro Val
        195                 200                 205 gac cga gag cca ctg tgg cga ttc ccc aac gag ctc ccc atc gcc ggt       672
Asp Arg Glu Pro Leu Trp Arg Phe Pro Asn Glu Leu Pro Ile Ala Gly
    210                 215                 220 gag ccc gcg aac atc gtc gcg ctc gtc gag gca tac atg acc tgg ctg       720
Glu Pro Ala Asn Ile Val Ala Leu Val Glu Ala Tyr Met Thr Trp Leu
225                 230                 235                 240 cac cag tca cct gtc ccg aag ttg ttg ttc tat ggc aca ccc ggc gta       768
His Gln Ser Pro Val Pro Lys Leu Leu Phe Tyr Gly Thr Pro Gly Val
                245                 250                 255 ctg atc ccc ccg gcc gaa gcc gcg aga ctt gcc gaa agc ctc ccc aac       816
Leu Ile Pro Pro Ala Glu Ala Ala Arg Leu Ala Glu Ser Leu Pro Asn
            260                 265                 270 tgc aag aca gtg gac atc ggc ccg gga ttg cac tac ctc cag gaa gac       864
Cys Lys Thr Val Asp Ile Gly Pro Gly Leu His Tyr Leu Gln Glu Asp
        275                 280                 285 aac ccg gac ctt atc ggc agt gag atc gcg cgc tgg ctc gcc gga ctc       912
Asn Pro Asp Leu Ile Gly Ser Glu Ile Ala Arg Trp Leu Ala Gly Leu
    290                 295                 300 gct agc ggc cta ggt gac tac aag gac gat gat gac aaa taa               954
Ala Ser Gly Leu Gly Asp Tyr Lys Asp Asp Asp Asp Lys
305                 310                 315

<210> SEQ ID NO 6
<211> LENGTH: 317
<212> TYPE: PRT
<213> ORGANISM: Artificial Sequence
<220> FEATURE:
<223> OTHER INFORMATION: Artificially modified (mutated) dehalogenase

<400> SEQUENCE: 6

Met Gly Asp Ser His His His His His Gly Met Ser Glu Ile Gly
1               5                   10                  15

Thr Gly Phe Pro Phe Asp Pro His Tyr Val Glu Val Leu Gly Glu Arg
            20                  25                  30

Met His Tyr Val Asp Val Gly Pro Arg Asp Gly Thr Pro Val Leu Phe
        35                  40                  45

Leu His Gly Asn Pro Thr Ser Ser Tyr Leu Trp Arg Asn Ile Ile Pro
    50                  55                  60

His Val Ala Pro Ser His Arg Cys Ile Ala Pro Asp Leu Ile Gly Met
65                  70                  75                  80
```

```
Gly Lys Ser Asp Lys Pro Asp Leu Gly Tyr Ser Phe Asp Asp His Val
             85                  90                  95

Arg Tyr Leu Asp Ala Phe Ile Glu Ala Leu Gly Leu Glu Glu Val Val
        100                 105                 110

Leu Val Ile His Asp Trp Gly Ser Ala Leu Gly Phe His Trp Ala Lys
    115                 120                 125

Arg Asn Pro Glu Arg Val Lys Gly Ile Ala Cys Met Glu Phe Ile Arg
130                 135                 140

Pro Ile Pro Thr Trp Asp Glu Trp Pro Glu Phe Ala Arg Glu Leu Phe
145                 150                 155                 160

Gln Ala Phe Arg Thr Ala Asp Val Gly Arg Glu Leu Ile Ile Asp Gln
                165                 170                 175

Asn Ala Phe Ile Glu Gln Val Leu Pro Lys Phe Val Val Arg Pro Leu
            180                 185                 190

Thr Glu Val Glu Met Asp His Tyr Arg Glu Pro Phe Leu Lys Pro Val
        195                 200                 205

Asp Arg Glu Pro Leu Trp Arg Phe Pro Asn Glu Leu Pro Ile Ala Gly
210                 215                 220

Glu Pro Ala Asn Ile Val Ala Leu Val Glu Ala Tyr Met Thr Trp Leu
225                 230                 235                 240

His Gln Ser Pro Val Pro Lys Leu Leu Phe Tyr Gly Thr Pro Gly Val
                245                 250                 255

Leu Ile Pro Pro Ala Glu Ala Ala Arg Leu Ala Glu Ser Leu Pro Asn
            260                 265                 270

Cys Lys Thr Val Asp Ile Gly Pro Gly Leu His Tyr Leu Gln Glu Asp
        275                 280                 285

Asn Pro Asp Leu Ile Gly Ser Glu Ile Ala Arg Trp Leu Ala Gly Leu
290                 295                 300

Ala Ser Gly Leu Gly Asp Tyr Lys Asp Asp Asp Asp Lys
305                 310                 315

<210> SEQ ID NO 7
<211> LENGTH: 954
<212> TYPE: DNA
<213> ORGANISM: Artificial Sequence
<220> FEATURE:
<223> OTHER INFORMATION: Artificially modified (mutated) dehalogenase
<221> NAME/KEY: CDS
<222> LOCATION: (1)...(951)

<400> SEQUENCE: 7 atg ggg gat tct cat cat cat cat cat cat ggt atg tct gaa ata ggt        48
Met Gly Asp Ser His His His His His His Gly Met Ser Glu Ile Gly
1               5                   10                  15 acc ggt ttt ccc ttc gac cct cat tat gtg gaa gtc ctg ggc gag cgt        96
Thr Gly Phe Pro Phe Asp Pro His Tyr Val Glu Val Leu Gly Glu Arg
            20                  25                  30 atg cac tac gtc gat gtt gga ccg cgg gat ggc acg cct gtg ctg ttc       144
Met His Tyr Val Asp Val Gly Pro Arg Asp Gly Thr Pro Val Leu Phe
        35                  40                  45 ctg cac ggt aac ccg acc tcg tcc tac ctg tgg cgc aac atc atc ccg       192
Leu His Gly Asn Pro Thr Ser Ser Tyr Leu Trp Arg Asn Ile Ile Pro
    50                  55                  60 cat gta gca ccg agt cat cgg tgc att gct cca gac ctg atc ggg atg       240
His Val Ala Pro Ser His Arg Cys Ile Ala Pro Asp Leu Ile Gly Met
65                  70                  75                  80 gga aaa tcg gac aaa cca gac ctc ggt tat tcc ttc gac gac cac gtc       288
Gly Lys Ser Asp Lys Pro Asp Leu Gly Tyr Ser Phe Asp Asp His Val
```

```
                    85                  90                  95
cgc tac ctc gat gcc ttc atc gaa gcc ttg ggt ttg gaa gag gtc gtc        336
Arg Tyr Leu Asp Ala Phe Ile Glu Ala Leu Gly Leu Glu Glu Val Val
            100                 105                 110 ctg gtc atc cac gac tgg ggc tca gct ctc gga ttc cac tgg gcc aag        384
Leu Val Ile His Asp Trp Gly Ser Ala Leu Gly Phe His Trp Ala Lys
            115                 120                 125 cgc aat ccg gaa cgg gtc aaa ggt att gca tgt atg gaa ttc atc cgg        432
Arg Asn Pro Glu Arg Val Lys Gly Ile Ala Cys Met Glu Phe Ile Arg
        130                 135                 140 agt atc ccg acg tgg gac gaa tgg ccg gaa ttc gcc cgt gag acc ttc        480
Ser Ile Pro Thr Trp Asp Glu Trp Pro Glu Phe Ala Arg Glu Thr Phe
145                 150                 155                 160 cag ctt ttc cgg acc gcc gac gtc ggc cga gag ttg atc atc gat cag        528
Gln Leu Phe Arg Thr Ala Asp Val Gly Arg Glu Leu Ile Ile Asp Gln
                165                 170                 175 aac gct ttc atc gag cag gtg ctc ccg aaa ttc gtc gtc cgt ccg ctt        576
Asn Ala Phe Ile Glu Gln Val Leu Pro Lys Phe Val Val Arg Pro Leu
            180                 185                 190 acg gag gtc gag atg gac cac tat cgc gag ccc ttc ctc aag cct gtt        624
Thr Glu Val Glu Met Asp His Tyr Arg Glu Pro Phe Leu Lys Pro Val
            195                 200                 205 gac cga gag cca ctg tgg cga ttc ccc aac gag ctc ccc atc gcc ggt        672
Asp Arg Glu Pro Leu Trp Arg Phe Pro Asn Glu Leu Pro Ile Ala Gly
        210                 215                 220 gag ccc gcg aac atc gtc gcg ctc gtc gag gca tac atg acc tgg ctg        720
Glu Pro Ala Asn Ile Val Ala Leu Val Glu Ala Tyr Met Thr Trp Leu
225                 230                 235                 240 cac cag tca cct gtc ccg aag ttg ttg ttc tat ggc aca ccc ggc gta        768
His Gln Ser Pro Val Pro Lys Leu Leu Phe Tyr Gly Thr Pro Gly Val
                245                 250                 255 ctg atc ccc ccg gcc gaa gcc tcg aga ctt gcc gaa agc ctc ccc aac        816
Leu Ile Pro Pro Ala Glu Ala Ser Arg Leu Ala Glu Ser Leu Pro Asn
            260                 265                 270 tgc aag aca gtg gac atc ggc ccg gga ttg cac tac ctc cag gaa gac        864
Cys Lys Thr Val Asp Ile Gly Pro Gly Leu His Tyr Leu Gln Glu Asp
            275                 280                 285 aac ccg gac ctt atc ggc agt gag atc gcg ctg tgg ctc gcc gga ctc        912
Asn Pro Asp Leu Ile Gly Ser Glu Ile Ala Leu Trp Leu Ala Gly Leu
        290                 295                 300 gct agc ggc cta ggt gac tac aag gac gat gat gac aaa taa                954
Ala Ser Gly Leu Gly Asp Tyr Lys Asp Asp Asp Asp Lys
305                 310                 315

<210> SEQ ID NO 8
<211> LENGTH: 317
<212> TYPE: PRT
<213> ORGANISM: Artificial Sequence
<220> FEATURE:
<223> OTHER INFORMATION: Artificially modified (mutated) dehalogenase

<400> SEQUENCE: 8

Met Gly Asp Ser His His His His His His Gly Met Ser Glu Ile Gly
1               5                   10                  15

Thr Gly Phe Pro Phe Asp Pro His Tyr Val Glu Val Leu Gly Glu Arg
            20                  25                  30

Met His Tyr Val Asp Val Gly Pro Arg Asp Gly Thr Pro Val Leu Phe
        35                  40                  45

Leu His Gly Asn Pro Thr Ser Ser Tyr Leu Trp Arg Asn Ile Ile Pro
    50                  55                  60
```

His Val Ala Pro Ser His Arg Cys Ile Ala Pro Asp Leu Ile Gly Met
 65                  70                  75                  80

Gly Lys Ser Asp Lys Pro Asp Leu Gly Tyr Ser Phe Asp His Val
             85                  90                  95

Arg Tyr Leu Asp Ala Phe Ile Glu Ala Leu Gly Leu Glu Val Val
        100                 105                 110

Leu Val Ile His Asp Trp Gly Ser Ala Leu Gly Phe His Trp Ala Lys
        115                 120                 125

Arg Asn Pro Glu Arg Val Lys Gly Ile Ala Cys Met Glu Phe Ile Arg
130                 135                 140

Ser Ile Pro Thr Trp Asp Glu Trp Pro Glu Phe Ala Arg Glu Thr Phe
145                 150                 155                 160

Gln Leu Phe Arg Thr Ala Asp Val Gly Arg Glu Leu Ile Ile Asp Gln
                165                 170                 175

Asn Ala Phe Ile Glu Gln Val Leu Pro Lys Phe Val Val Arg Pro Leu
            180                 185                 190

Thr Glu Val Glu Met Asp His Tyr Arg Glu Pro Phe Leu Lys Pro Val
        195                 200                 205

Asp Arg Glu Pro Leu Trp Arg Phe Pro Asn Glu Leu Pro Ile Ala Gly
210                 215                 220

Glu Pro Ala Asn Ile Val Ala Leu Val Glu Ala Tyr Met Thr Trp Leu
225                 230                 235                 240

His Gln Ser Pro Val Pro Lys Leu Leu Phe Tyr Gly Thr Pro Gly Val
                245                 250                 255

Leu Ile Pro Pro Ala Glu Ala Ser Arg Leu Ala Glu Ser Leu Pro Asn
            260                 265                 270

Cys Lys Thr Val Asp Ile Gly Pro Gly Leu His Tyr Leu Gln Glu Asp
        275                 280                 285

Asn Pro Asp Leu Ile Gly Ser Glu Ile Ala Leu Trp Leu Ala Gly Leu
    290                 295                 300

Ala Ser Gly Leu Gly Asp Tyr Lys Asp Asp Asp Lys
305                 310                 315

<210> SEQ ID NO 9
<211> LENGTH: 870
<212> TYPE: DNA
<213> ORGANISM: Artificial Sequence
<220> FEATURE:
<223> OTHER INFORMATION: Artificially modified (mutated) dehalogenase
<221> NAME/KEY: CDS
<222> LOCATION: (1)...(867)

<400> SEQUENCE: 9 atg aac gca acg gaa cac gac aag cgc tac atc gag gtg ctg ggt aag      48
Met Asn Ala Thr Glu His Asp Lys Arg Tyr Ile Glu Val Leu Gly Lys
1               5                   10                  15 cga atg gcc tat gtc gag atg ggc gag ggt gat ccc atc att ttc caa      96
Arg Met Ala Tyr Val Glu Met Gly Glu Gly Asp Pro Ile Ile Phe Gln
            20                  25                  30 cac ggc aat ccg acc tca tcg tac ctg tgg cgc aac atc atg ccc cat     144
His Gly Asn Pro Thr Ser Ser Tyr Leu Trp Arg Asn Ile Met Pro His
        35                  40                  45 gtg caa cag ctc ggt cgc tgc ata gcg ctc gac ctg atc ggc atg ggc     192
Val Gln Gln Leu Gly Arg Cys Ile Ala Leu Asp Leu Ile Gly Met Gly
    50                  55                  60 gat tca gaa aaa ctc gag gac tcc gga ccc gag cgc tac acg ttc gtc     240
Asp Ser Glu Lys Leu Glu Asp Ser Gly Pro Glu Arg Tyr Thr Phe Val

```
                65                  70                  75                  80
gag cac agc cgg tat ttt gat gcc gcg ctc gaa gcc ctg ggt gtg acg       288
Glu His Ser Arg Tyr Phe Asp Ala Ala Leu Glu Ala Leu Gly Val Thr
                85                  90                  95 agc aac gtg acg ctg gtg atc cac gat tgg ggt tca gcg ctg ggc ttc       336
Ser Asn Val Thr Leu Val Ile His Asp Trp Gly Ser Ala Leu Gly Phe
            100                 105                 110 cac tgg gct aac cgc tat cgt gat gac gta aaa ggt atc tgc tac atg       384
His Trp Ala Asn Arg Tyr Arg Asp Asp Val Lys Gly Ile Cys Tyr Met
        115                 120                 125 gaa gcc atc gtg tcg ccg ctg acc tgg gat acg ttt ccg gaa ggt gcg       432
Glu Ala Ile Val Ser Pro Leu Thr Trp Asp Thr Phe Pro Glu Gly Ala
    130                 135                 140 cgt ggt gtt ttc cag ggg ttt cgt tca ccg gct ggc gaa gca atg gtg       480
Arg Gly Val Phe Gln Gly Phe Arg Ser Pro Ala Gly Glu Ala Met Val
145                 150                 155                 160 ctt gag aac aat gtg ttc gtc gaa aac gta ctt ccc ggg tcg ata ctc       528
Leu Glu Asn Asn Val Phe Val Glu Asn Val Leu Pro Gly Ser Ile Leu
                165                 170                 175 aga gac ctc agc gag gaa gaa atg aac gtc tac cgg cgc cct ttc acg       576
Arg Asp Leu Ser Glu Glu Glu Met Asn Val Tyr Arg Arg Pro Phe Thr
            180                 185                 190 gag cct ggc gaa ggt cgg cgt ccg acg ctc acc tgg cca cgg cag att       624
Glu Pro Gly Glu Gly Arg Arg Pro Thr Leu Thr Trp Pro Arg Gln Ile
        195                 200                 205 ccg atc gat ggc gaa cct gca gac gtc gtc gcc ctg gta gcc gag tac       672
Pro Ile Asp Gly Glu Pro Ala Asp Val Val Ala Leu Val Ala Glu Tyr
    210                 215                 220 gcc gcc tgg ttg cag agt gcg gaa gta ccg aag ttg ttt gtg aat gct       720
Ala Ala Trp Leu Gln Ser Ala Glu Val Pro Lys Leu Phe Val Asn Ala
225                 230                 235                 240 gaa cca ggg gcg ttg ctc acg gga ccg cag cgc gag ttc tgc cgg agt       768
Glu Pro Gly Ala Leu Leu Thr Gly Pro Gln Arg Glu Phe Cys Arg Ser
                245                 250                 255 tgg acc aat cag agc gag gtc acc gtg tca ggt agc cac ttc atc cag       816
Trp Thr Asn Gln Ser Glu Val Thr Val Ser Gly Ser His Phe Ile Gln
            260                 265                 270 gaa gat tca ccg gat gag atc ggt gaa gca ttg aaa gtg tgg atg act       864
Glu Asp Ser Pro Asp Glu Ile Gly Glu Ala Leu Lys Val Trp Met Thr
        275                 280                 285 gga tag                                                               870
Gly

<210> SEQ ID NO 10
<211> LENGTH: 289
<212> TYPE: PRT
<213> ORGANISM: Artificial Sequence
<220> FEATURE:
<223> OTHER INFORMATION: Artificially modified (mutated) dehalogenase

<400> SEQUENCE: 10

Met Asn Ala Thr Glu His Asp Lys Arg Tyr Ile Glu Val Leu Gly Lys
1               5                   10                  15

Arg Met Ala Tyr Val Glu Met Gly Glu Gly Asp Pro Ile Ile Phe Gln
            20                  25                  30

His Gly Asn Pro Thr Ser Ser Tyr Leu Trp Arg Asn Ile Met Pro His
        35                  40                  45

Val Gln Gln Leu Gly Arg Cys Ile Ala Leu Asp Leu Ile Gly Met Gly
    50                  55                  60
```

```
Asp Ser Glu Lys Leu Glu Asp Ser Gly Pro Glu Arg Tyr Thr Phe Val
 65                  70                  75                  80

Glu His Ser Arg Tyr Phe Asp Ala Ala Leu Glu Ala Leu Gly Val Thr
                 85                  90                  95

Ser Asn Val Thr Leu Val Ile His Asp Trp Gly Ser Ala Leu Gly Phe
            100                 105                 110

His Trp Ala Asn Arg Tyr Arg Asp Asp Val Lys Gly Ile Cys Tyr Met
        115                 120                 125

Glu Ala Ile Val Ser Pro Leu Thr Trp Asp Thr Phe Pro Glu Gly Ala
130                 135                 140

Arg Gly Val Phe Gln Gly Phe Arg Ser Pro Ala Gly Glu Ala Met Val
145                 150                 155                 160

Leu Glu Asn Asn Val Phe Val Glu Asn Val Leu Pro Gly Ser Ile Leu
                165                 170                 175

Arg Asp Leu Ser Glu Glu Met Asn Val Tyr Arg Arg Pro Phe Thr
            180                 185                 190

Glu Pro Gly Glu Gly Arg Arg Pro Thr Leu Thr Trp Pro Arg Gln Ile
        195                 200                 205

Pro Ile Asp Gly Glu Pro Ala Asp Val Val Ala Leu Val Ala Glu Tyr
210                 215                 220

Ala Ala Trp Leu Gln Ser Ala Glu Val Pro Lys Leu Phe Val Asn Ala
225                 230                 235                 240

Glu Pro Gly Ala Leu Leu Thr Gly Pro Gln Arg Glu Phe Cys Arg Ser
                245                 250                 255

Trp Thr Asn Gln Ser Glu Val Thr Val Ser Gly Ser His Phe Ile Gln
            260                 265                 270

Glu Asp Ser Pro Asp Glu Ile Gly Glu Ala Leu Lys Val Trp Met Thr
        275                 280                 285

Gly

<210> SEQ ID NO 11
<211> LENGTH: 882
<212> TYPE: DNA
<213> ORGANISM: Artificial Sequence
<220> FEATURE:
<223> OTHER INFORMATION: Artificially modified (mutated) dehalogenase
<221> NAME/KEY: CDS
<222> LOCATION: (1)...(879)

<400> SEQUENCE: 11 atg cag gtg ggg atc gcc gct acg ctc gcc gaa atg gac aag aaa cgt      48
Met Gln Val Gly Ile Ala Ala Thr Leu Ala Glu Met Asp Lys Lys Arg
1               5                  10                  15 gtc cgt gtg tac aac gcg gag atg gcc tat gtc gac acg ggc cag ggt      96
Val Arg Val Tyr Asn Ala Glu Met Ala Tyr Val Asp Thr Gly Gln Gly
            20                  25                  30 gat tcc gtt ctg ttt ctt cac ggc aac ccg acg tcg tcg tat ctg tgg     144
Asp Ser Val Leu Phe Leu His Gly Asn Pro Thr Ser Ser Tyr Leu Trp
        35                  40                  45 agg ggc gta atg cct ttt gtg acg gac gtc gcc cga tgt gtg gct ccg     192
Arg Gly Val Met Pro Phe Val Thr Asp Val Ala Arg Cys Val Ala Pro
 50                  55                  60 gac ctg atc ggt atg ggc gat tcc gac aag ctc gag tcg tcg atg tac     240
Asp Leu Ile Gly Met Gly Asp Ser Asp Lys Leu Glu Ser Ser Met Tyr
65                  70                  75                  80 cgc ttc gag gat cac cgg cgg tac ctg gat ggt ttc ctc gat gcg gtg     288
Arg Phe Glu Asp His Arg Arg Tyr Leu Asp Gly Phe Leu Asp Ala Val
                85                  90                  95
```

```
gac atc gga gac gat gtg acg gtt gtg gtg cac gac tgg ggc tct gca       336
Asp Ile Gly Asp Asp Val Thr Val Val Val His Asp Trp Gly Ser Ala
             100                 105                 110 ctc ggc ttc gac tgg gcg aac cgg cac cgc gac cgg gtc aaa gga atc       384
Leu Gly Phe Asp Trp Ala Asn Arg His Arg Asp Arg Val Lys Gly Ile
         115                 120                 125 gca tac atg gaa gcg atc gtt cgt cca ttg agc tgg gag gag tgg ccg       432
Ala Tyr Met Glu Ala Ile Val Arg Pro Leu Ser Trp Glu Glu Trp Pro
     130                 135                 140 gac gca tct cgc cgc ctg ttc gag gca atg cgc tca gac gcg ggg gag       480
Asp Ala Ser Arg Arg Leu Phe Glu Ala Met Arg Ser Asp Ala Gly Glu
145                 150                 155                 160 gag atc gtt ctc gaa aag aat gtc ttc gtc gag cgg att ctg ctc ggc       528
Glu Ile Val Leu Glu Lys Asn Val Phe Val Glu Arg Ile Leu Leu Gly
                 165                 170                 175 tcg gtc ctt tgt gat ctg acc gag gag gaa atg gcg gag tac cgg cgc       576
Ser Val Leu Cys Asp Leu Thr Glu Glu Glu Met Ala Glu Tyr Arg Arg
             180                 185                 190 ccg tac ctc gag ccg ggt gag tca cgg cgc ccg atg ctg aca tgg cca       624
Pro Tyr Leu Glu Pro Gly Glu Ser Arg Arg Pro Met Leu Thr Trp Pro
         195                 200                 205 cgc gag atc ccg atc gac ggc cac ccc gcc gac gtt gcg aag atc gtc       672
Arg Glu Ile Pro Ile Asp Gly His Pro Ala Asp Val Ala Lys Ile Val
     210                 215                 220 gcg gag tac tcg tcg tgg ctc tcc ggg tcg gag gtg ccg aag ctc ttc       720
Ala Glu Tyr Ser Ser Trp Leu Ser Gly Ser Glu Val Pro Lys Leu Phe
225                 230                 235                 240 gtc gat gcc gac ccg ggc gcc atc ctg aca ggt ccg aag cga gac ttc       768
Val Asp Ala Asp Pro Gly Ala Ile Leu Thr Gly Pro Lys Arg Asp Phe
                 245                 250                 255 tgc agg gcg tgg ccg aac cag gtc gag acg acc gtg gca gga atc cac       816
Cys Arg Ala Trp Pro Asn Gln Val Glu Thr Thr Val Ala Gly Ile His
             260                 265                 270 ttc ata cag gag gat tcc tcc gcc gag atc gga gcc gcg atc agg acc       864
Phe Ile Gln Glu Asp Ser Ser Ala Glu Ile Gly Ala Ala Ile Arg Thr
         275                 280                 285 tgg tac ctg gga ctc tga                                               882
Trp Tyr Leu Gly Leu
     290

<210> SEQ ID NO 12
<211> LENGTH: 293
<212> TYPE: PRT
<213> ORGANISM: Artificial Sequence
<220> FEATURE:
<223> OTHER INFORMATION: Artificially modified (mutated) dehalogenase

<400> SEQUENCE: 12

Met Gln Val Gly Ile Ala Ala Thr Leu Ala Glu Met Asp Lys Lys Arg
1               5                   10                  15

Val Arg Val Tyr Asn Ala Glu Met Ala Tyr Val Asp Thr Gly Gln Gly
            20                  25                  30

Asp Ser Val Leu Phe Leu His Gly Asn Pro Thr Ser Ser Tyr Leu Trp
        35                  40                  45

Arg Gly Val Met Pro Phe Val Thr Asp Val Ala Arg Cys Val Ala Pro
    50                  55                  60

Asp Leu Ile Gly Met Gly Asp Ser Asp Lys Leu Glu Ser Ser Met Tyr
65                  70                  75                  80

Arg Phe Glu Asp His Arg Arg Tyr Leu Asp Gly Phe Leu Asp Ala Val
```

```
                     85                  90                  95
Asp Ile Gly Asp Asp Val Thr Val Val His Asp Trp Gly Ser Ala
                100                 105                 110
Leu Gly Phe Asp Trp Ala Asn Arg His Arg Asp Arg Val Lys Gly Ile
            115                 120                 125
Ala Tyr Met Glu Ala Ile Val Arg Pro Leu Ser Trp Glu Glu Trp Pro
        130                 135                 140
Asp Ala Ser Arg Arg Leu Phe Glu Ala Met Arg Ser Asp Ala Gly Glu
145                 150                 155                 160
Glu Ile Val Leu Glu Lys Asn Val Phe Val Glu Arg Ile Leu Leu Gly
                165                 170                 175
Ser Val Leu Cys Asp Leu Thr Glu Glu Met Ala Glu Tyr Arg Arg
                180                 185                 190
Pro Tyr Leu Glu Pro Gly Glu Ser Arg Arg Pro Met Leu Thr Trp Pro
            195                 200                 205
Arg Glu Ile Pro Ile Asp Gly His Pro Ala Asp Val Ala Lys Ile Val
        210                 215                 220
Ala Glu Tyr Ser Ser Trp Leu Ser Gly Ser Glu Val Pro Lys Leu Phe
225                 230                 235                 240
Val Asp Ala Asp Pro Gly Ala Ile Leu Thr Gly Pro Lys Arg Asp Phe
                245                 250                 255
Cys Arg Ala Trp Pro Asn Gln Val Glu Thr Thr Val Ala Gly Ile His
                260                 265                 270
Phe Ile Gln Glu Asp Ser Ser Ala Glu Ile Gly Ala Ala Ile Arg Thr
            275                 280                 285
Trp Tyr Leu Gly Leu
        290

<210> SEQ ID NO 13
<211> LENGTH: 849
<212> TYPE: DNA
<213> ORGANISM: Artificial Sequence
<220> FEATURE:
<223> OTHER INFORMATION: Artificially modified (mutated) dehalogenase
<221> NAME/KEY: CDS
<222> LOCATION: (1)...(846)

<400> SEQUENCE: 13 atg gag aaa cac cgc gta gaa gtt ctc ggt tcg gag atg gcc tac atc      48
Met Glu Lys His Arg Val Glu Val Leu Gly Ser Glu Met Ala Tyr Ile
1               5                   10                  15 gac gtg gga gag ggc gac ccg atc gtg ttc ctc cac gga aat ccc acg      96
Asp Val Gly Glu Gly Asp Pro Ile Val Phe Leu His Gly Asn Pro Thr
            20                  25                  30 tcg tcg tac ctg tgg cgg aac gtg att ccc cac gtt gcc ggc ttg gga     144
Ser Ser Tyr Leu Trp Arg Asn Val Ile Pro His Val Ala Gly Leu Gly
        35                  40                  45 cgc tgc atc gcc ccg gat ctg atc ggc atg gga gac tcg gat aag gtc     192
Arg Cys Ile Ala Pro Asp Leu Ile Gly Met Gly Asp Ser Asp Lys Val
    50                  55                  60 cat ggt ctc gag tac cgc ttc gtt gat cac cgc cgg tac ctc gac gcc     240
His Gly Leu Glu Tyr Arg Phe Val Asp His Arg Arg Tyr Leu Asp Ala
65                  70                  75                  80 ttc ctt gaa gcg gtc ggc gtt gag gat gct gtg aca ttc atc gta cac     288
Phe Leu Glu Ala Val Gly Val Glu Asp Ala Val Thr Phe Ile Val His
                85                  90                  95 gac tgg ggc tcg gct ctc gga ttc gac tgg gcg aac cgt cac cgt gaa     336
Asp Trp Gly Ser Ala Leu Gly Phe Asp Trp Ala Asn Arg His Arg Glu
```

| | | | | | | | | | | | | | | | | |
|---|---|---|---|---|---|---|---|---|---|---|---|---|---|---|---|---|
| gcg | gtc | gaa | ggc | atc | gca | tac | atg | gag | gcg | atc | gtg | cac | ccg | gtt | gct | 384 |
| Ala | Val | Glu | Gly | Ile | Ala | Tyr | Met | Glu | Ala | Ile | Val | His | Pro | Val | Ala | |
| | | 115 | | | | | 120 | | | | | 125 | | | | |
| tgg | aac | gac | tgg | ccg | gag | ctc | tct | cga | ccg | ata | ttt | cag | gcg | atg | agg | 432 |
| Trp | Asn | Asp | Trp | Pro | Glu | Leu | Ser | Arg | Pro | Ile | Phe | Gln | Ala | Met | Arg | |
| 130 | | | | | 135 | | | | | 140 | | | | | | |
| tcc | tcg | tcc | ggt | gag | aag | atc | gtg | ctt | gag | aag | aac | gtg | ttc | gtg | gag | 480 |
| Ser | Ser | Ser | Gly | Glu | Lys | Ile | Val | Leu | Glu | Lys | Asn | Val | Phe | Val | Glu | |
| 145 | | | | | 150 | | | | | 155 | | | | | 160 | |
| cga | atc | ctg | ccc | gct | tcc | gtg | atg | cgc | gat | ctg | agc | gac | gac | gag | atg | 528 |
| Arg | Ile | Leu | Pro | Ala | Ser | Val | Met | Arg | Asp | Leu | Ser | Asp | Asp | Glu | Met | |
| | | | | 165 | | | | | 170 | | | | | 175 | | |
| gat | gag | tac | cgt | cga | ccg | ttc | cag | aac | ccg | gga | gag | gat | cga | aga | ccc | 576 |
| Asp | Glu | Tyr | Arg | Arg | Pro | Phe | Gln | Asn | Pro | Gly | Glu | Asp | Arg | Arg | Pro | |
| | | | 180 | | | | | 185 | | | | | 190 | | | |
| acg | ctg | acg | tgg | cca | cgg | gag | atc | ccg | atc | gat | gga | gaa | ccg | ggg | gac | 624 |
| Thr | Leu | Thr | Trp | Pro | Arg | Glu | Ile | Pro | Ile | Asp | Gly | Glu | Pro | Gly | Asp | |
| | | 195 | | | | | 200 | | | | | 205 | | | | |
| gtc | gcc | gcc | atc | gtc | gat | gac | tac | ggg | cga | tgg | ctc | tcg | gag | agc | gat | 672 |
| Val | Ala | Ala | Ile | Val | Asp | Asp | Tyr | Gly | Arg | Trp | Leu | Ser | Glu | Ser | Asp | |
| 210 | | | | | 215 | | | | | 220 | | | | | | |
| gtc | cca | aag | ctc | ttc | atc | gac | gcg | gat | ccg | gga | gcg | atc | ctc | gtg | ggt | 720 |
| Val | Pro | Lys | Leu | Phe | Ile | Asp | Ala | Asp | Pro | Gly | Ala | Ile | Leu | Val | Gly | |
| 225 | | | | | 230 | | | | | 235 | | | | | 240 | |
| cca | gcg | cgt | ggg | ttc | tgc | cgc | ggc | tgg | cgg | aac | cag | acc | gaa | gtg | agc | 768 |
| Pro | Ala | Arg | Gly | Phe | Cys | Arg | Gly | Trp | Arg | Asn | Gln | Thr | Glu | Val | Ser | |
| | | | | 245 | | | | | 250 | | | | | 255 | | |
| gtc | aca | gga | acc | cac | ttc | atc | cag | gaa | gac | tct | ccc | gac | gag | atc | ggc | 816 |
| Val | Thr | Gly | Thr | His | Phe | Ile | Gln | Glu | Asp | Ser | Pro | Asp | Glu | Ile | Gly | |
| | | 260 | | | | | 265 | | | | | 270 | | | | |
| gct | gcg | ctg | gct | cga | tgg | atc | gag | aac | cgg | taa | | | | | | 849 |
| Ala | Ala | Leu | Ala | Arg | Trp | Ile | Glu | Asn | Arg | | | | | | | |
| | | 275 | | | | | 280 | | | | | | | | | |

<210> SEQ ID NO 14
<211> LENGTH: 282
<212> TYPE: PRT
<213> ORGANISM: Artificial Sequence
<220> FEATURE:
<223> OTHER INFORMATION: Artificially modified (mutated) dehalogenase

<400> SEQUENCE: 14

```
Met Glu Lys His Arg Val Glu Val Leu Gly Ser Glu Met Ala Tyr Ile
1               5                   10                  15

Asp Val Gly Glu Gly Asp Pro Ile Val Phe Leu His Gly Asn Pro Thr
            20                  25                  30

Ser Ser Tyr Leu Trp Arg Asn Val Ile Pro His Val Ala Gly Leu Gly
        35                  40                  45

Arg Cys Ile Ala Pro Asp Leu Ile Gly Met Gly Asp Ser Asp Lys Val
    50                  55                  60

His Gly Leu Glu Tyr Arg Phe Val Asp His Arg Arg Tyr Leu Asp Ala
65                  70                  75                  80

Phe Leu Glu Ala Val Gly Val Glu Asp Ala Val Thr Phe Ile Val His
                85                  90                  95

Asp Trp Gly Ser Ala Leu Gly Phe Asp Trp Ala Asn Arg His Arg Glu
            100                 105                 110

Ala Val Glu Gly Ile Ala Tyr Met Glu Ala Ile Val His Pro Val Ala
        115                 120                 125
```

```
Trp Asn Asp Trp Pro Glu Leu Ser Arg Pro Ile Phe Gln Ala Met Arg
    130                 135                 140

Ser Ser Ser Gly Glu Lys Ile Val Leu Glu Lys Asn Val Phe Val Glu
145                 150                 155                 160

Arg Ile Leu Pro Ala Ser Val Met Arg Asp Leu Ser Asp Asp Glu Met
                165                 170                 175

Asp Glu Tyr Arg Arg Pro Phe Gln Asn Pro Gly Glu Asp Arg Arg Pro
            180                 185                 190

Thr Leu Thr Trp Pro Arg Glu Ile Pro Ile Asp Gly Glu Pro Gly Asp
        195                 200                 205

Val Ala Ala Ile Val Asp Asp Tyr Gly Arg Trp Leu Ser Glu Ser Asp
    210                 215                 220

Val Pro Lys Leu Phe Ile Asp Ala Asp Pro Gly Ala Ile Leu Val Gly
225                 230                 235                 240

Pro Ala Arg Gly Phe Cys Arg Gly Trp Arg Asn Gln Thr Glu Val Ser
                245                 250                 255

Val Thr Gly Thr His Phe Ile Gln Glu Asp Ser Pro Asp Glu Ile Gly
            260                 265                 270

Ala Ala Leu Ala Arg Trp Ile Glu Asn Arg
        275                 280

<210> SEQ ID NO 15
<211> LENGTH: 876
<212> TYPE: DNA
<213> ORGANISM: Artificial Sequence
<220> FEATURE:
<223> OTHER INFORMATION: Artificially modified (mutated) dehalogenase
<221> NAME/KEY: CDS
<222> LOCATION: (1)...(873)

<400> SEQUENCE: 15 atg gct agc gcg cct atc gac ccg acc gac ccg cat ccg aga aag cgg      48
Met Ala Ser Ala Pro Ile Asp Pro Thr Asp Pro His Pro Arg Lys Arg
1               5                   10                  15 atc gcc gtg ctc gat tcg gag atg agc tac gtc gat acc ggc gag gga      96
Ile Ala Val Leu Asp Ser Glu Met Ser Tyr Val Asp Thr Gly Glu Gly
            20                  25                  30 gcg ccg atc gtg ttc ctt cac ggc aac ccg act tcc tcc tat ctt tgg     144
Ala Pro Ile Val Phe Leu His Gly Asn Pro Thr Ser Ser Tyr Leu Trp
        35                  40                  45 cgc aac atc atc ccc tat ctc gcg gat cac ggc aga tgc ctc gca ccg     192
Arg Asn Ile Ile Pro Tyr Leu Ala Asp His Gly Arg Cys Leu Ala Pro
    50                  55                  60 gat ctg gtc ggg atg ggc cgc tcc gga aaa tcg ccg acc cgg tcc tat     240
Asp Leu Val Gly Met Gly Arg Ser Gly Lys Ser Pro Thr Arg Ser Tyr
65                  70                  75                  80 ggc ttt acc gat cac gcg cgc tat ttg gac gca tgg ttc gac gcc ctg     288
Gly Phe Thr Asp His Ala Arg Tyr Leu Asp Ala Trp Phe Asp Ala Leu
                85                  90                  95 gac ctg acc cgc gac gtg acc ctg gtg att cat gac tgg gga tcg gcg     336
Asp Leu Thr Arg Asp Val Thr Leu Val Ile His Asp Trp Gly Ser Ala
            100                 105                 110 ctg ggc ttc cac cgt gcc ttt cgc ttc ccc gaa cag atc aag gcg atc     384
Leu Gly Phe His Arg Ala Phe Arg Phe Pro Glu Gln Ile Lys Ala Ile
        115                 120                 125 gcc tat atg gag gcc atc gtc cgg ccg ctc gtc tgg gcc gac atc gcc     432
Ala Tyr Met Glu Ala Ile Val Arg Pro Leu Val Trp Ala Asp Ile Ala
    130                 135                 140
```

```
ggc gcc gag cag gcg ttt cgc gcg atc cga tcc gag gcc ggc gaa cac          480
Gly Ala Glu Gln Ala Phe Arg Ala Ile Arg Ser Glu Ala Gly Glu His
145                 150                 155                 160 atg att ctg gac gag aac ttt ttc gtc gaa gtg ctc ctt ccg gcg agc          528
Met Ile Leu Asp Glu Asn Phe Phe Val Glu Val Leu Leu Pro Ala Ser
                165                 170                 175 atc ctg cgc aga ttg agc gat ctg gag atg gcc gcc tac cgc gca ccg          576
Ile Leu Arg Arg Leu Ser Asp Leu Glu Met Ala Ala Tyr Arg Ala Pro
            180                 185                 190 ttc ctc gac cgg gag tcg cga tgg ccg acc ctg cgc tgg ccg cgc gag          624
Phe Leu Asp Arg Glu Ser Arg Trp Pro Thr Leu Arg Trp Pro Arg Glu
        195                 200                 205 gtt ccg atc gag ggg gag ccg gcc gac gtg acc gcc atc gtc gag gcc          672
Val Pro Ile Glu Gly Glu Pro Ala Asp Val Thr Ala Ile Val Glu Ala
    210                 215                 220 tac gga cga tgg atg gcc gag aac acg ctg ccg aag ctg ctg gtc ttg          720
Tyr Gly Arg Trp Met Ala Glu Asn Thr Leu Pro Lys Leu Leu Val Leu
225                 230                 235                 240 ggt gat ccg gga gtg atc gct acc ggc cgc acg cgc gac ttc tgt cga          768
Gly Asp Pro Gly Val Ile Ala Thr Gly Arg Thr Arg Asp Phe Cys Arg
                245                 250                 255 agc tgg aag aat cag cgg gag gtc acc gta tcc ggc agc cac ttc ctt          816
Ser Trp Lys Asn Gln Arg Glu Val Thr Val Ser Gly Ser His Phe Leu
            260                 265                 270 cag gaa gac tcg ccg cac gag atc ggc ctc gcg ctc cgg gat ttc gtg          864
Gln Glu Asp Ser Pro His Glu Ile Gly Leu Ala Leu Arg Asp Phe Val
        275                 280                 285 cgg tcg gcg taa                                                          876
Arg Ser Ala
    290

<210> SEQ ID NO 16
<211> LENGTH: 291
<212> TYPE: PRT
<213> ORGANISM: Artificial Sequence
<220> FEATURE:
<223> OTHER INFORMATION: Artificially modified (mutated) dehalogenase

<400> SEQUENCE: 16

Met Ala Ser Ala Pro Ile Asp Pro Thr Asp Pro His Pro Arg Lys Arg
1               5                   10                  15

Ile Ala Val Leu Asp Ser Glu Met Ser Tyr Val Asp Thr Gly Glu Gly
                20                  25                  30

Ala Pro Ile Val Phe Leu His Gly Asn Pro Thr Ser Ser Tyr Leu Trp
            35                  40                  45

Arg Asn Ile Ile Pro Tyr Leu Ala Asp His Gly Arg Cys Leu Ala Pro
        50                  55                  60

Asp Leu Val Gly Met Gly Arg Ser Gly Lys Ser Pro Thr Arg Ser Tyr
65                  70                  75                  80

Gly Phe Thr Asp His Ala Arg Tyr Leu Asp Ala Trp Phe Asp Ala Leu
                85                  90                  95

Asp Leu Thr Arg Asp Val Thr Leu Val Ile His Asp Trp Gly Ser Ala
            100                 105                 110

Leu Gly Phe His Arg Ala Phe Arg Phe Pro Glu Gln Ile Lys Ala Ile
        115                 120                 125

Ala Tyr Met Glu Ala Ile Val Arg Pro Leu Val Trp Ala Asp Ile Ala
    130                 135                 140

Gly Ala Glu Gln Ala Phe Arg Ala Ile Arg Ser Glu Ala Gly Glu His
145                 150                 155                 160
```

```
Met Ile Leu Asp Glu Asn Phe Phe Val Glu Val Leu Pro Ala Ser
            165                 170                 175

Ile Leu Arg Arg Leu Ser Asp Leu Glu Met Ala Ala Tyr Arg Ala Pro
                180                 185                 190

Phe Leu Asp Arg Glu Ser Arg Trp Pro Thr Leu Arg Trp Pro Arg Glu
            195                 200                 205

Val Pro Ile Glu Gly Glu Pro Ala Asp Val Thr Ala Ile Val Glu Ala
    210                 215                 220

Tyr Gly Arg Trp Met Ala Glu Asn Thr Leu Pro Lys Leu Leu Val Leu
225                 230                 235                 240

Gly Asp Pro Gly Val Ile Ala Thr Gly Arg Thr Arg Asp Phe Cys Arg
                245                 250                 255

Ser Trp Lys Asn Gln Arg Glu Val Thr Val Ser Gly Ser His Phe Leu
            260                 265                 270

Gln Glu Asp Ser Pro His Glu Ile Gly Leu Ala Leu Arg Asp Phe Val
            275                 280                 285

Arg Ser Ala
    290

<210> SEQ ID NO 17
<211> LENGTH: 918
<212> TYPE: DNA
<213> ORGANISM: Artificial Sequence
<220> FEATURE:
<223> OTHER INFORMATION: Artificially modified (mutated) dehalogenase
<221> NAME/KEY: CDS
<222> LOCATION: (1)...(915)

<400> SEQUENCE: 17 atg caa tta acg aat gaa aca gaa gcc aac gcg atc tct gcg aca agt     48
Met Gln Leu Thr Asn Glu Thr Glu Ala Asn Ala Ile Ser Ala Thr Ser
1               5                   10                  15 ccc tac cca aaa ttt cgg cgg tcg gtc ttc ggc cgc gag atg gcg tac     96
Pro Tyr Pro Lys Phe Arg Arg Ser Val Phe Gly Arg Glu Met Ala Tyr
                20                  25                  30 gtg gaa gtg gga cgg ggc gac ccc atc gta ctc ttg cac ggc aac ccc    144
Val Glu Val Gly Arg Gly Asp Pro Ile Val Leu Leu His Gly Asn Pro
            35                  40                  45 acc tcg tcg tac ctc tgg cgc aac gtg ttg ccg cac ctg gcg ccg tta    192
Thr Ser Ser Tyr Leu Trp Arg Asn Val Leu Pro His Leu Ala Pro Leu
        50                  55                  60 ggc cgc tgt atc gct cca gac ctg att ggt atg gga gac tca gac aaa    240
Gly Arg Cys Ile Ala Pro Asp Leu Ile Gly Met Gly Asp Ser Asp Lys
65                  70                  75                  80 ctg cgt gac agt ggg ccg ggc tca tat cgc ttc gtc gag cag cgc cgt    288
Leu Arg Asp Ser Gly Pro Gly Ser Tyr Arg Phe Val Glu Gln Arg Arg
                85                  90                  95 tac ctc gac gcc ctg ctc gag gct ctg gac gtg cac gag cga gtc acg    336
Tyr Leu Asp Ala Leu Leu Glu Ala Leu Asp Val His Glu Arg Val Thr
            100                 105                 110 ttt gtc atc cat gac tgg ggc tcg gcc ctc gga ttt gat tgg gcc aac    384
Phe Val Ile His Asp Trp Gly Ser Ala Leu Gly Phe Asp Trp Ala Asn
        115                 120                 125 cgc cac cgc gaa gca atg agg ggt atc gcg tac atg gag gcg att gtg    432
Arg His Arg Glu Ala Met Arg Gly Ile Ala Tyr Met Glu Ala Ile Val
    130                 135                 140 cgg ccg cag ggc ggg gac cac tgg gac aac atc aac atg cgt cca ccc    480
Arg Pro Gln Gly Gly Asp His Trp Asp Asn Ile Asn Met Arg Pro Pro
145                 150                 155                 160
```

```
ttg cag gcg ctg cgt tca tgg gcc ggc gag gtg atg gtc ctg caa gac    528
Leu Gln Ala Leu Arg Ser Trp Ala Gly Glu Val Met Val Leu Gln Asp
            165                 170                 175 aac ttc ttt atc gag aag atg ctg cca ggg ggc atc ctg cgc gcc ctc    576
Asn Phe Phe Ile Glu Lys Met Leu Pro Gly Gly Ile Leu Arg Ala Leu
        180                 185                 190 tcc gca ggg gag atg gca gaa tac cgg cgg ccg ttt gcc gag ccc ggc    624
Ser Ala Gly Glu Met Ala Glu Tyr Arg Arg Pro Phe Ala Glu Pro Gly
    195                 200                 205 gag ggg cga cga ccg acg ctg aca tgg ccc cgg gaa ctc ccc ata gaa    672
Glu Gly Arg Arg Pro Thr Leu Thr Trp Pro Arg Glu Leu Pro Ile Glu
210                 215                 220 ggc gac ccc gcc gaa gtg gct gcg atc gtg gcc gcc tac gcg gac tgg    720
Gly Asp Pro Ala Glu Val Ala Ala Ile Val Ala Ala Tyr Ala Asp Trp
225                 230                 235                 240 tta gcg aca agt gat gtg ccc aag ctt ttc ctg aag gcc gag ccc ggg    768
Leu Ala Thr Ser Asp Val Pro Lys Leu Phe Leu Lys Ala Glu Pro Gly
            245                 250                 255 gcg ctc atc gcc ggc gga gcg aat ctc gag acc gtc cgc aaa tgg ccg    816
Ala Leu Ile Ala Gly Gly Ala Asn Leu Glu Thr Val Arg Lys Trp Pro
        260                 265                 270 gcg cag acc gag gta acg gtc gcg ggg atc cat ttc atc cag gaa gat    864
Ala Gln Thr Glu Val Thr Val Ala Gly Ile His Phe Ile Gln Glu Asp
    275                 280                 285 tcg ccg gac gag atc ggc cgg gcg atc gcc gat tgg atg agg gcg ttg    912
Ser Pro Asp Glu Ile Gly Arg Ala Ile Ala Asp Trp Met Arg Ala Leu
290                 295                 300 agc tga                                                             918
Ser
305

<210> SEQ ID NO 18
<211> LENGTH: 305
<212> TYPE: PRT
<213> ORGANISM: Artificial Sequence
<220> FEATURE:
<223> OTHER INFORMATION: Artificially modified (mutated) dehalogenase

<400> SEQUENCE: 18

Met Gln Leu Thr Asn Glu Thr Glu Ala Asn Ala Ile Ser Ala Thr Ser
1               5                   10                  15

Pro Tyr Pro Lys Phe Arg Arg Ser Val Phe Gly Arg Glu Met Ala Tyr
            20                  25                  30

Val Glu Val Gly Arg Gly Asp Pro Ile Val Leu Leu His Gly Asn Pro
        35                  40                  45

Thr Ser Ser Tyr Leu Trp Arg Asn Val Leu Pro His Leu Ala Pro Leu
    50                  55                  60

Gly Arg Cys Ile Ala Pro Asp Leu Ile Gly Met Gly Asp Ser Asp Lys
65                  70                  75                  80

Leu Arg Asp Ser Gly Pro Gly Ser Tyr Arg Phe Val Glu Gln Arg Arg
                85                  90                  95

Tyr Leu Asp Ala Leu Leu Glu Ala Leu Asp Val His Glu Arg Val Thr
            100                 105                 110

Phe Val Ile His Asp Trp Gly Ser Ala Leu Gly Phe Asp Trp Ala Asn
        115                 120                 125

Arg His Arg Glu Ala Met Arg Gly Ile Ala Tyr Met Glu Ala Ile Val
    130                 135                 140

Arg Pro Gln Gly Gly Asp His Trp Asp Asn Ile Asn Met Arg Pro Pro
```

```
                145                 150                 155                 160
Leu Gln Ala Leu Arg Ser Trp Ala Gly Glu Val Met Val Leu Gln Asp
                    165                 170                 175

Asn Phe Phe Ile Glu Lys Met Leu Pro Gly Gly Ile Leu Arg Ala Leu
                180                 185                 190

Ser Ala Gly Glu Met Ala Glu Tyr Arg Arg Pro Phe Ala Glu Pro Gly
            195                 200                 205

Glu Gly Arg Arg Pro Thr Leu Thr Trp Pro Arg Glu Leu Pro Ile Glu
        210                 215                 220

Gly Asp Pro Ala Glu Val Ala Ala Ile Val Ala Ala Tyr Ala Asp Trp
225                 230                 235                 240

Leu Ala Thr Ser Asp Val Pro Lys Leu Phe Leu Lys Ala Glu Pro Gly
                245                 250                 255

Ala Leu Ile Ala Gly Gly Ala Asn Leu Glu Thr Val Arg Lys Trp Pro
                260                 265                 270

Ala Gln Thr Glu Val Thr Val Ala Gly Ile His Phe Ile Gln Glu Asp
            275                 280                 285

Ser Pro Asp Glu Ile Gly Arg Ala Ile Ala Asp Trp Met Arg Ala Leu
        290                 295                 300

Ser
305

<210> SEQ ID NO 19
<211> LENGTH: 912
<212> TYPE: DNA
<213> ORGANISM: Artificial Sequence
<220> FEATURE:
<223> OTHER INFORMATION: Artificially modified (mutated) dehalogenase
<221> NAME/KEY: CDS
<222> LOCATION: (1)...(909)

<400> SEQUENCE: 19 atg ctc gtt gcg cag aca agg aag cat cca atg act gaa acg ccg ctg      48
Met Leu Val Ala Gln Thr Arg Lys His Pro Met Thr Glu Thr Pro Leu
1               5                   10                  15 aca aaa aac acc gtc gat gtg ctg ggc acg tcg atg gcc tat cac gcg      96
Thr Lys Asn Thr Val Asp Val Leu Gly Thr Ser Met Ala Tyr His Ala
                20                  25                  30 cgc ggc gag ggt gcg cca ata ttg ttt ctg cac ggc aac ccg acc tcg     144
Arg Gly Glu Gly Ala Pro Ile Leu Phe Leu His Gly Asn Pro Thr Ser
            35                  40                  45 tcc tat ctg tgg cgc gac gtc att ccc gaa ctg gag gga cgc ggc cgg     192
Ser Tyr Leu Trp Arg Asp Val Ile Pro Glu Leu Glu Gly Arg Gly Arg
        50                  55                  60 ctg atc gcg ccg gat ctg atc ggg atg ggc gat tcc gcc aaa ttg cca     240
Leu Ile Ala Pro Asp Leu Ile Gly Met Gly Asp Ser Ala Lys Leu Pro
65                  70                  75                  80 gat ccc ggt gcg gac acc tat cgc ttc acg act cat cgc aaa tat ctc     288
Asp Pro Gly Ala Asp Thr Tyr Arg Phe Thr Thr His Arg Lys Tyr Leu
                85                  90                  95 gat gcc ttc gtc gat gcg gtg atc ggc ccg gcg caa tcc atc gtg atg     336
Asp Ala Phe Val Asp Ala Val Ile Gly Pro Ala Gln Ser Ile Val Met
                100                 105                 110 gtg gtg cac gac tgg ggc tcg gcg ctc ggt ttc gac tgg gcc aac cgt     384
Val Val His Asp Trp Gly Ser Ala Leu Gly Phe Asp Trp Ala Asn Arg
            115                 120                 125 cac cgc aac cgt atc cgt ggt atc gcc tat atg gag ggg atc gtg cgc     432
His Arg Asn Arg Ile Arg Gly Ile Ala Tyr Met Glu Gly Ile Val Arg
        130                 135                 140
```

```
ccg atc gcc tcc tgg gat gaa tgg agc gcg tcg gcc acg ccg atc ttc      480
Pro Ile Ala Ser Trp Asp Glu Trp Ser Ala Ser Ala Thr Pro Ile Phe
145                 150                 155                 160 cag gga ttt cgc tcc gac aag ggc gag acc atg atc ctg gag cgc aac      528
Gln Gly Phe Arg Ser Asp Lys Gly Glu Thr Met Ile Leu Glu Arg Asn
                165                 170                 175 atg ttc gtc gag cgg gtg ctg ccg ggg tcg gtg ttg cgg aaa ctg acc      576
Met Phe Val Glu Arg Val Leu Pro Gly Ser Val Leu Arg Lys Leu Thr
            180                 185                 190 gag gcc gag atg gcg gaa tac cgc cgg ccc tat ccg aaa gcc gag gac      624
Glu Ala Glu Met Ala Glu Tyr Arg Arg Pro Tyr Pro Lys Ala Glu Asp
        195                 200                 205 cgc tgg ccg acg ctg acc tgg ccg cgc cag atc ccg atc gcc ggc gaa      672
Arg Trp Pro Thr Leu Thr Trp Pro Arg Gln Ile Pro Ile Ala Gly Glu
    210                 215                 220 ccc gcc gat gtg gtg cag atc gcg gcg gag tat tca cga tgg atg gcg      720
Pro Ala Asp Val Val Gln Ile Ala Ala Glu Tyr Ser Arg Trp Met Ala
225                 230                 235                 240 gag aac gac atc cca aaa ctg ttc gtc aac gcc gag ccc ggt gcg atc      768
Glu Asn Asp Ile Pro Lys Leu Phe Val Asn Ala Glu Pro Gly Ala Ile
                245                 250                 255 ctg acc ggc gcg ccc cgg gat ttc tgc cga agc tgg aaa agc cag acc      816
Leu Thr Gly Ala Pro Arg Asp Phe Cys Arg Ser Trp Lys Ser Gln Thr
            260                 265                 270 gaa gtc acc gtc gcg ggc tcg cat ttc atc cag gaa gac tcc gga ccg      864
Glu Val Thr Val Ala Gly Ser His Phe Ile Gln Glu Asp Ser Gly Pro
        275                 280                 285 gcg atc ggc cgg gcg gta gcc gcc tgg atg acg gcg aat ggg cta          909
Ala Ile Gly Arg Ala Val Ala Ala Trp Met Thr Ala Asn Gly Leu
    290                 295                 300 tag                                                                   912
```

<210> SEQ ID NO 20
<211> LENGTH: 303
<212> TYPE: PRT
<213> ORGANISM: Artificial Sequence
<220> FEATURE:
<223> OTHER INFORMATION: Artificially modified (mutated) dehalogenase

<400> SEQUENCE: 20

```
Met Leu Val Ala Gln Thr Arg Lys His Pro Met Thr Glu Thr Pro Leu
1               5                   10                  15

Thr Lys Asn Thr Val Asp Val Leu Gly Thr Ser Met Ala Tyr His Ala
            20                  25                  30

Arg Gly Glu Gly Ala Pro Ile Leu Phe Leu His Gly Asn Pro Thr Ser
        35                  40                  45

Ser Tyr Leu Trp Arg Asp Val Ile Pro Glu Leu Glu Gly Arg Gly Arg
    50                  55                  60

Leu Ile Ala Pro Asp Leu Ile Gly Met Gly Asp Ser Ala Lys Leu Pro
65                  70                  75                  80

Asp Pro Gly Ala Asp Thr Tyr Arg Phe Thr Thr His Arg Lys Tyr Leu
                85                  90                  95

Asp Ala Phe Val Asp Ala Val Ile Gly Pro Ala Gln Ser Ile Val Met
            100                 105                 110

Val Val His Asp Trp Gly Ser Ala Leu Gly Phe Asp Trp Ala Asn Arg
        115                 120                 125

His Arg Asn Arg Ile Arg Gly Ile Ala Tyr Met Glu Gly Ile Val Arg
    130                 135                 140
```

```
Pro Ile Ala Ser Trp Asp Glu Trp Ser Ala Ser Ala Thr Pro Ile Phe
145                 150                 155                 160

Gln Gly Phe Arg Ser Asp Lys Gly Glu Thr Met Ile Leu Glu Arg Asn
                165                 170                 175

Met Phe Val Glu Arg Val Leu Pro Gly Ser Val Leu Arg Lys Leu Thr
            180                 185                 190

Glu Ala Glu Met Ala Glu Tyr Arg Arg Pro Tyr Pro Lys Ala Glu Asp
        195                 200                 205

Arg Trp Pro Thr Leu Thr Trp Pro Arg Gln Ile Pro Ile Ala Gly Glu
210                 215                 220

Pro Ala Asp Val Val Gln Ile Ala Ala Glu Tyr Ser Arg Trp Met Ala
225                 230                 235                 240

Glu Asn Asp Ile Pro Lys Leu Phe Val Asn Ala Glu Pro Gly Ala Ile
                245                 250                 255

Leu Thr Gly Ala Pro Arg Asp Phe Cys Arg Ser Trp Lys Ser Gln Thr
            260                 265                 270

Glu Val Thr Val Ala Gly Ser His Phe Ile Gln Glu Asp Ser Gly Pro
        275                 280                 285

Ala Ile Gly Arg Ala Val Ala Trp Met Thr Ala Asn Gly Leu
        290                 295                 300

<210> SEQ ID NO 21
<211> LENGTH: 894
<212> TYPE: DNA
<213> ORGANISM: Artificial Sequence
<220> FEATURE:
<223> OTHER INFORMATION: Artificially modified (mutated) dehalogenase
<221> NAME/KEY: CDS
<222> LOCATION: (1)...(891)

<400> SEQUENCE: 21 atg gct agc atg acc cag gtt tcc atc tcg acc gag gac gct tcc tac     48
Met Ala Ser Met Thr Gln Val Ser Ile Ser Thr Glu Asp Ala Ser Tyr
1               5                   10                  15 cgg aag cgg gtc cgc gtg ctc gat acc gac atg gcc tat gtc gac gtg     96
Arg Lys Arg Val Arg Val Leu Asp Thr Asp Met Ala Tyr Val Asp Val
            20                  25                  30 ggc gaa ggc gat ccg atc gtg ttc ctg cac ggc aac ccg acg ccg tcg    144
Gly Glu Gly Asp Pro Ile Val Phe Leu His Gly Asn Pro Thr Pro Ser
        35                  40                  45 ttc ctg tgg cgc aac atc atc ccc tac gcc ctg ccc ttc ggc cgc tgc    192
Phe Leu Trp Arg Asn Ile Ile Pro Tyr Ala Leu Pro Phe Gly Arg Cys
50                  55                  60 ctc gcg ccc gac tac gtg ggg atg ggc aat tcc ggg ccg gcg ccg ggc    240
Leu Ala Pro Asp Tyr Val Gly Met Gly Asn Ser Gly Pro Ala Pro Gly
65                  70                  75                  80 ggg tcg tat cga ttc gtc gat cac cgg cgc tat ctc gac gcc tgg ttc    288
Gly Ser Tyr Arg Phe Val Asp His Arg Arg Tyr Leu Asp Ala Trp Phe
                85                  90                  95 gag gcc atg ggc ctg acg gag aac gtc atc ctc gtg gtg cac gac tgg    336
Glu Ala Met Gly Leu Thr Glu Asn Val Ile Leu Val Val His Asp Trp
            100                 105                 110 ggc tcg gcg ctc ggc ttc gac tgg gcg cgg cgt cac ccc gat cgg gtc    384
Gly Ser Ala Leu Gly Phe Asp Trp Ala Arg Arg His Pro Asp Arg Val
        115                 120                 125 aag gcc atc gtc tat atg gaa ggg atc gtc cgg ccg ttc ctg tcc tgg    432
Lys Ala Ile Val Tyr Met Glu Gly Ile Val Arg Pro Phe Leu Ser Trp
    130                 135                 140
```

```
gac gaa tgg ccg gcc gtc acg cgc gcc ttc ttc cag ggc cag cgc acg    480
Asp Glu Trp Pro Ala Val Thr Arg Ala Phe Phe Gln Gly Gln Arg Thr
145                 150                 155                 160 gcg gcg ggc gag gac ctg att ctc cag aag aac ctg ttc atc gag tat    528
Ala Ala Gly Glu Asp Leu Ile Leu Gln Lys Asn Leu Phe Ile Glu Tyr
                165                 170                 175 ctc ctg ccg ctg cgc ggc atc ccc aag gag gcg atc gag gtc tac cgc    576
Leu Leu Pro Leu Arg Gly Ile Pro Lys Glu Ala Ile Glu Val Tyr Arg
            180                 185                 190 cgt ccc ttc cgg aac ccc ggt gcc tcg cgc cag ccg atg ctg acc tgg    624
Arg Pro Phe Arg Asn Pro Gly Ala Ser Arg Gln Pro Met Leu Thr Trp
        195                 200                 205 acc cgc gaa ctg ccg atc gcc ggc gag ccc gcc gac gtc gtg gcc atc    672
Thr Arg Glu Leu Pro Ile Ala Gly Glu Pro Ala Asp Val Val Ala Ile
    210                 215                 220 gtc gag gac tac gcc cgc ttc ctc tcc acc agc ccg atc ccc aag ctg    720
Val Glu Asp Tyr Ala Arg Phe Leu Ser Thr Ser Pro Ile Pro Lys Leu
225                 230                 235                 240 ttc atc gac gcc gag ccc ggc ggc ttc ctg atc ggc gcc cag cgc gaa    768
Phe Ile Asp Ala Glu Pro Gly Gly Phe Leu Ile Gly Ala Gln Arg Glu
                245                 250                 255 ttc tgc cgc gcc tgg ccc aac cag acc gag gtg acg gtc cca ggc gtc    816
Phe Cys Arg Ala Trp Pro Asn Gln Thr Glu Val Thr Val Pro Gly Val
            260                 265                 270 cat ttc gtc cag gag gac agt ccg agg gcg atc ggc gag gca gtg tcc    864
His Phe Val Gln Glu Asp Ser Pro Arg Ala Ile Gly Glu Ala Val Ser
        275                 280                 285 gcc ttc gtt gtt tcg ttg cgg ggc gcg tag                            894
Ala Phe Val Val Ser Leu Arg Gly Ala
    290                 295

<210> SEQ ID NO 22
<211> LENGTH: 297
<212> TYPE: PRT
<213> ORGANISM: Artificial Sequence
<220> FEATURE:
<223> OTHER INFORMATION: Artificially modified (mutated) dehalogenase

<400> SEQUENCE: 22

Met Ala Ser Met Thr Gln Val Ser Ile Ser Thr Glu Asp Ala Ser Tyr
1               5                   10                  15

Arg Lys Arg Val Arg Val Leu Asp Thr Asp Met Ala Tyr Val Asp Val
                20                  25                  30

Gly Glu Gly Asp Pro Ile Val Phe Leu His Gly Asn Pro Thr Pro Ser
            35                  40                  45

Phe Leu Trp Arg Asn Ile Ile Pro Tyr Ala Leu Pro Phe Gly Arg Cys
        50                  55                  60

Leu Ala Pro Asp Tyr Val Gly Met Gly Asn Ser Gly Pro Ala Pro Gly
65                  70                  75                  80

Gly Ser Tyr Arg Phe Val Asp His Arg Tyr Leu Asp Ala Trp Phe
                85                  90                  95

Glu Ala Met Gly Leu Thr Glu Asn Val Ile Leu Val Val His Asp Trp
                100                 105                 110

Gly Ser Ala Leu Gly Phe Asp Trp Ala Arg Arg His Pro Asp Arg Val
            115                 120                 125

Lys Ala Ile Val Tyr Met Glu Gly Ile Val Arg Pro Phe Leu Ser Trp
        130                 135                 140

Asp Glu Trp Pro Ala Val Thr Arg Ala Phe Phe Gln Gly Gln Arg Thr
145                 150                 155                 160
```

```
Ala Ala Gly Glu Asp Leu Ile Leu Gln Lys Asn Leu Phe Ile Glu Tyr
            165                 170                 175

Leu Leu Pro Leu Arg Gly Ile Pro Lys Glu Ala Ile Glu Val Tyr Arg
            180                 185                 190

Arg Pro Phe Arg Asn Pro Gly Ala Ser Arg Gln Pro Met Leu Thr Trp
            195                 200                 205

Thr Arg Glu Leu Pro Ile Ala Gly Glu Pro Ala Asp Val Val Ala Ile
    210                 215                 220

Val Glu Asp Tyr Ala Arg Phe Leu Ser Thr Ser Pro Ile Pro Lys Leu
225                 230                 235                 240

Phe Ile Asp Ala Glu Pro Gly Gly Phe Leu Ile Gly Ala Gln Arg Glu
            245                 250                 255

Phe Cys Arg Ala Trp Pro Asn Gln Thr Glu Val Thr Val Pro Gly Val
            260                 265                 270

His Phe Val Gln Glu Asp Ser Pro Arg Ala Ile Gly Glu Ala Val Ser
            275                 280                 285

Ala Phe Val Val Ser Leu Arg Gly Ala
            290                 295

<210> SEQ ID NO 23
<211> LENGTH: 915
<212> TYPE: DNA
<213> ORGANISM: Artificial Sequence
<220> FEATURE:
<223> OTHER INFORMATION: Artificially modified (mutated) dehalogenase
<221> NAME/KEY: CDS
<222> LOCATION: (1)...(912)

<400> SEQUENCE: 23 atg aat gtg gcg cga ggc gac acg gtc gtc acc gcc gcg gag cct gat     48
Met Asn Val Ala Arg Gly Asp Thr Val Val Thr Ala Ala Glu Pro Asp
1               5                   10                  15 ggc ccg gac cac ctg cct cgg cgt cgc gtg aag gtg atg gat acc gaa     96
Gly Pro Asp His Leu Pro Arg Arg Arg Val Lys Val Met Asp Thr Glu
            20                  25                  30 atc agc tat gtc gat gtc ggt gaa ggt gag ccc gtc gtc ttt ctg cac    144
Ile Ser Tyr Val Asp Val Gly Glu Gly Glu Pro Val Val Phe Leu His
        35                  40                  45 ggc aat ccc acg tgg tcc tat caa tgg cgc aat atc att cct tac atc    192
Gly Asn Pro Thr Trp Ser Tyr Gln Trp Arg Asn Ile Ile Pro Tyr Ile
    50                  55                  60 agc ccc gtt cgc cgc tgt ctc gcg ccc gat ctt gtc ggc atg ggt tgg    240
Ser Pro Val Arg Arg Cys Leu Ala Pro Asp Leu Val Gly Met Gly Trp
65                  70                  75                  80 tcc ggc aag tcg ccg ggc aaa gcc tat cgt ttc gtc gat cag gcc cgc    288
Ser Gly Lys Ser Pro Gly Lys Ala Tyr Arg Phe Val Asp Gln Ala Arg
                85                  90                  95 tac atg gat gcc tgg ttc gag gcg ttg cag ctg acc cgg aac gtt acg    336
Tyr Met Asp Ala Trp Phe Glu Ala Leu Gln Leu Thr Arg Asn Val Thr
            100                 105                 110 ttg gtg ttg cac gac tgg ggc gcg gcc atc ggc ttc tat cgc gcc cgg    384
Leu Val Leu His Asp Trp Gly Ala Ala Ile Gly Phe Tyr Arg Ala Arg
        115                 120                 125 cgc cat cct gag cag ata aag gcg att gcc tat tat gaa gct gtc gct    432
Arg His Pro Glu Gln Ile Lys Ala Ile Ala Tyr Tyr Glu Ala Val Ala
    130                 135                 140 cac tcg cgc cga tgg gac gac ttc tct ggc ggc cgc gac cgc caa ttc    480
His Ser Arg Arg Trp Asp Asp Phe Ser Gly Gly Arg Asp Arg Gln Phe
145                 150                 155                 160
```

```
cgc cta tta cgc tcg ccc gac gga gaa cgc ctc gtc ctc gac gag aac     528
Arg Leu Leu Arg Ser Pro Asp Gly Glu Arg Leu Val Leu Asp Glu Asn
            165                 170                 175 atg ttc gtg gaa gtc gtc ctg ccg cgc ggc att ttg cgc aag cta acc     576
Met Phe Val Glu Val Val Leu Pro Arg Gly Ile Leu Arg Lys Leu Thr
        180                 185                 190 gat gac gag atg gaa gcc tac cga gct cct tat cgc gat cgc gag cgg     624
Asp Asp Glu Met Glu Ala Tyr Arg Ala Pro Tyr Arg Asp Arg Glu Arg
    195                 200                 205 cgc ctg ccg acc ctg att tgg ccg cgc gag gtg ccg atc gaa gga gag     672
Arg Leu Pro Thr Leu Ile Trp Pro Arg Glu Val Pro Ile Glu Gly Glu
210                 215                 220 ccc gcg gac gtc gtg gcc att gtc gat gag aat gcg cga tgg ctt gcg     720
Pro Ala Asp Val Val Ala Ile Val Asp Glu Asn Ala Arg Trp Leu Ala
225                 230                 235                 240 gcc agc gat cgg ctg ccg aag ctg ttc atc aag ggc gat ccc gga gca     768
Ala Ser Asp Arg Leu Pro Lys Leu Phe Ile Lys Gly Asp Pro Gly Ala
                245                 250                 255 atc cat acc gga cgc ttg ctc gat ctg gtt cgc gcg ttt ccc aat cag     816
Ile His Thr Gly Arg Leu Leu Asp Leu Val Arg Ala Phe Pro Asn Gln
            260                 265                 270 cgc gag gtg acc gtc aag ggg ctg cac cac ctg cag gac gat tcg cca     864
Arg Glu Val Thr Val Lys Gly Leu His His Leu Gln Asp Asp Ser Pro
        275                 280                 285 gac gaa atc ggc gct gcg ctg cgg gca ttc gtg ctc cgc aaa ggg att     912
Asp Glu Ile Gly Ala Ala Leu Arg Ala Phe Val Leu Arg Lys Gly Ile
    290                 295                 300 tga                                                                 915
```

<210> SEQ ID NO 24
<211> LENGTH: 304
<212> TYPE: PRT
<213> ORGANISM: Artificial Sequence
<220> FEATURE:
<223> OTHER INFORMATION: Artificially modified (mutated) dehalogenase

<400> SEQUENCE: 24

```
Met Asn Val Ala Arg Gly Asp Thr Val Val Thr Ala Ala Glu Pro Asp
1               5                   10                  15

Gly Pro Asp His Leu Pro Arg Arg Val Lys Val Met Asp Thr Glu
            20                  25                  30

Ile Ser Tyr Val Asp Val Gly Glu Gly Glu Pro Val Val Phe Leu His
        35                  40                  45

Gly Asn Pro Thr Trp Ser Tyr Gln Trp Arg Asn Ile Ile Pro Tyr Ile
    50                  55                  60

Ser Pro Val Arg Arg Cys Leu Ala Pro Asp Leu Val Gly Met Gly Trp
65                  70                  75                  80

Ser Gly Lys Ser Pro Gly Lys Ala Tyr Arg Phe Val Asp Gln Ala Arg
                85                  90                  95

Tyr Met Asp Ala Trp Phe Glu Ala Leu Gln Leu Thr Arg Asn Val Thr
            100                 105                 110

Leu Val Leu His Asp Trp Gly Ala Ala Ile Gly Phe Tyr Arg Ala Arg
        115                 120                 125

Arg His Pro Glu Gln Ile Lys Ala Ile Ala Tyr Tyr Glu Ala Val Ala
    130                 135                 140

His Ser Arg Arg Trp Asp Asp Phe Ser Gly Gly Arg Ser Arg Gln Phe
145                 150                 155                 160
```

```
Arg Leu Leu Arg Ser Pro Asp Gly Glu Arg Leu Val Leu Asp Glu Asn
            165                 170                 175

Met Phe Val Glu Val Val Leu Pro Arg Gly Ile Leu Arg Lys Leu Thr
        180                 185                 190

Asp Asp Glu Met Glu Ala Tyr Arg Ala Pro Tyr Arg Asp Arg Glu Arg
            195                 200                 205

Arg Leu Pro Thr Leu Ile Trp Pro Arg Glu Val Pro Ile Glu Gly Glu
        210                 215                 220

Pro Ala Asp Val Val Ala Ile Val Asp Glu Asn Ala Arg Trp Leu Ala
225                 230                 235                 240

Ala Ser Asp Arg Leu Pro Lys Leu Phe Ile Lys Gly Asp Pro Gly Ala
            245                 250                 255

Ile His Thr Gly Arg Leu Leu Asp Leu Val Arg Ala Phe Pro Asn Gln
        260                 265                 270

Arg Glu Val Thr Val Lys Gly Leu His His Leu Gln Asp Asp Ser Pro
            275                 280                 285

Asp Glu Ile Gly Ala Ala Leu Arg Ala Phe Val Leu Arg Lys Gly Ile
        290                 295                 300

<210> SEQ ID NO 25
<211> LENGTH: 900
<212> TYPE: DNA
<213> ORGANISM: Artificial Sequence
<220> FEATURE:
<223> OTHER INFORMATION: Artificially modified (mutated) dehalogenase
<221> NAME/KEY: CDS
<222> LOCATION: (1)...(897)

<400> SEQUENCE: 25 atg ctg gac agg att tct gcc aaa ggc aat ctt act cgt agc tgc gta     48
Met Leu Asp Arg Ile Ser Ala Lys Gly Asn Leu Thr Arg Ser Cys Val
1               5                   10                  15 agc gtc ctt gac agc gag atg agt tac gtc gcg act ggt cgg ggg cac     96
Ser Val Leu Asp Ser Glu Met Ser Tyr Val Ala Thr Gly Arg Gly His
            20                  25                  30 cca atc gtt ttc ctg cac ggg aac ccg acc tca tct tat ctt tgg cgt    144
Pro Ile Val Phe Leu His Gly Asn Pro Thr Ser Ser Tyr Leu Trp Arg
        35                  40                  45 aac gtc atc ccc cac gtc agc aac ctt ggc cgg tgc ctc gcg ccg gac    192
Asn Val Ile Pro His Val Ser Asn Leu Gly Arg Cys Leu Ala Pro Asp
    50                  55                  60 ctc gtt ggt atg ggc cag ccg gcc gcc tct cca cgg ggc gcc tat cgc    240
Leu Val Gly Met Gly Gln Pro Ala Ala Ser Pro Arg Gly Ala Tyr Arg
65                  70                  75                  80 ttt gtg gac cat tca cgt tat ctc gac gca tgg ttt gag gcc ctg gac    288
Phe Val Asp His Ser Arg Tyr Leu Asp Ala Trp Phe Glu Ala Leu Asp
                85                  90                  95 ttg cgt aga aac gtt acc ctg gtg gtg cac gat tgg gga tcg gcg ctc    336
Leu Arg Arg Asn Val Thr Leu Val Val His Asp Trp Gly Ser Ala Leu
            100                 105                 110 ggc ttt cat tgg gct tcc agg cat ccc gag cgg gtg cgg gcc atc gct    384
Gly Phe His Trp Ala Ser Arg His Pro Glu Arg Val Arg Ala Ile Ala
        115                 120                 125 tac atg gag tcg atc gtt cag ccg cgc gac tgg gaa gac ctc ccc cca    432
Tyr Met Glu Ser Ile Val Gln Pro Arg Asp Trp Glu Asp Leu Pro Pro
    130                 135                 140 agt cgg gcg ccg atc ttt cgc gac ctg cgg tcc aat aaa ggt gag cgc    480
Ser Arg Ala Pro Ile Phe Arg Asp Leu Arg Ser Asn Lys Gly Glu Arg
145                 150                 155                 160
```

```
atg atc ctc gac gaa aat gcc ttc att gag att ctc ttg ccg aag ctc    528
Met Ile Leu Asp Glu Asn Ala Phe Ile Glu Ile Leu Leu Pro Lys Leu
            165                 170                 175 gtc atc cgg act ctg acc agc gct gag atg gat gca tat cgt cgt cca    576
Val Ile Arg Thr Leu Thr Ser Ala Glu Met Asp Ala Tyr Arg Arg Pro
                180                 185                 190 ttt att gaa ccg aac tcg cgc tgg cct aca ctt atc tgg ccg cgc gag    624
Phe Ile Glu Pro Asn Ser Arg Trp Pro Thr Leu Ile Trp Pro Arg Glu
            195                 200                 205 cta ccg atc ggt ggc gaa cct gcc gac gtg gtg aaa att gtc gaa gat    672
Leu Pro Ile Gly Gly Glu Pro Ala Asp Val Val Lys Ile Val Glu Asp
        210                 215                 220 tac ggg caa tgg ctt ctc aag acc ccg ttg ccg aag ttg ttt atc aac    720
Tyr Gly Gln Trp Leu Leu Lys Thr Pro Leu Pro Lys Leu Phe Ile Asn
225                 230                 235                 240 gcc gag cca ggg tcg ctg ttg atc gga cgg gca cgt gaa ttc tgc cgc    768
Ala Glu Pro Gly Ser Leu Leu Ile Gly Arg Ala Arg Glu Phe Cys Arg
                245                 250                 255 tcc tgg cca aat caa gag gaa gtg acg gtt cgg ggt atc cat ttt att    816
Ser Trp Pro Asn Gln Glu Glu Val Thr Val Arg Gly Ile His Phe Ile
            260                 265                 270 cag gaa gac agt ccc gat gag att ggc gct gcg ctt acg cgc ttc atg    864
Gln Glu Asp Ser Pro Asp Glu Ile Gly Ala Ala Leu Thr Arg Phe Met
        275                 280                 285 agg caa ata agt cca gat tcc gtg atc cga aac taa                    900
Arg Gln Ile Ser Pro Asp Ser Val Ile Arg Asn
290                 295

<210> SEQ ID NO 26
<211> LENGTH: 299
<212> TYPE: PRT
<213> ORGANISM: Artificial Sequence
<220> FEATURE:
<223> OTHER INFORMATION: Artificially modified (mutated) dehalogenase

<400> SEQUENCE: 26

Met Leu Asp Arg Ile Ser Ala Lys Gly Asn Leu Thr Arg Ser Cys Val
1               5                   10                  15

Ser Val Leu Asp Ser Glu Met Ser Tyr Val Ala Thr Gly Arg Gly His
            20                  25                  30

Pro Ile Val Phe Leu His Gly Asn Pro Thr Ser Ser Tyr Leu Trp Arg
        35                  40                  45

Asn Val Ile Pro His Val Ser Asn Leu Gly Arg Cys Leu Ala Pro Asp
    50                  55                  60

Leu Val Gly Met Gly Gln Pro Ala Ala Ser Pro Arg Gly Ala Tyr Arg
65                  70                  75                  80

Phe Val Asp His Ser Arg Tyr Leu Asp Ala Trp Phe Glu Ala Leu Asp
                85                  90                  95

Leu Arg Arg Asn Val Thr Leu Val Val His Asp Trp Gly Ser Ala Leu
            100                 105                 110

Gly Phe His Trp Ala Ser Arg His Pro Glu Arg Val Arg Ala Ile Ala
        115                 120                 125

Tyr Met Glu Ser Ile Val Gln Pro Arg Asp Trp Glu Asp Leu Pro Pro
    130                 135                 140

Ser Arg Ala Pro Ile Phe Arg Asp Leu Arg Ser Asn Lys Gly Glu Arg
145                 150                 155                 160

Met Ile Leu Asp Glu Asn Ala Phe Ile Glu Ile Leu Leu Pro Lys Leu
                165                 170                 175
```

```
Val Ile Arg Thr Leu Thr Ser Ala Glu Met Asp Ala Tyr Arg Arg Pro
            180                 185                 190

Phe Ile Glu Pro Asn Ser Arg Trp Pro Thr Leu Ile Trp Pro Arg Glu
            195                 200                 205

Leu Pro Ile Gly Gly Glu Pro Ala Asp Val Val Lys Ile Val Glu Asp
            210                 215                 220

Tyr Gly Gln Trp Leu Leu Lys Thr Pro Leu Pro Lys Leu Phe Ile Asn
225                 230                 235                 240

Ala Glu Pro Gly Ser Leu Leu Ile Gly Arg Ala Arg Glu Phe Cys Arg
                245                 250                 255

Ser Trp Pro Asn Gln Glu Glu Val Thr Val Arg Gly Ile His Phe Ile
            260                 265                 270

Gln Glu Asp Ser Pro Asp Glu Ile Gly Ala Ala Leu Thr Arg Phe Met
            275                 280                 285

Arg Gln Ile Ser Pro Asp Ser Val Ile Arg Asn
            290                 295

<210> SEQ ID NO 27
<211> LENGTH: 888
<212> TYPE: DNA
<213> ORGANISM: Artificial Sequence
<220> FEATURE:
<223> OTHER INFORMATION: Artificially modified (mutated) dehalogenase
<221> NAME/KEY: CDS
<222> LOCATION: (1)...(885)

<400> SEQUENCE: 27 atg atc tct gca gca ttt ccg tac caa aag aag cgg cgg cag gtc ctc       48
Met Ile Ser Ala Ala Phe Pro Tyr Gln Lys Lys Arg Arg Gln Val Leu
1               5                   10                  15 ggc agc gag atg gca tac gtc gag gta gga gag ggc gac ccc atc gtg       96
Gly Ser Glu Met Ala Tyr Val Glu Val Gly Glu Gly Asp Pro Ile Val
                20                  25                  30 tcg ctg cac ggt aat ccc acc tcg tcc tac ctc tgg cgc aac aca ttg       144
Ser Leu His Gly Asn Pro Thr Ser Ser Tyr Leu Trp Arg Asn Thr Leu
            35                  40                  45 ccc tac ctg cag cca cta ggc cgc tgc atc gcc ccc gac ctg atc ggc       192
Pro Tyr Leu Gln Pro Leu Gly Arg Cys Ile Ala Pro Asp Leu Ile Gly
        50                  55                  60 atg ggc gac tcc gcc aag ctg cct aac agt ggc ccc ggc tcg tat cga       240
Met Gly Asp Ser Ala Lys Leu Pro Asn Ser Gly Pro Gly Ser Tyr Arg
65                  70                  75                  80 ttc gtc gag cac cgc cgc tac ctc gac acc ctg ctc gag gcc tta aat       288
Phe Val Glu His Arg Arg Tyr Leu Asp Thr Leu Leu Glu Ala Leu Asn
                85                  90                  95 atg cgc gag cgg gtc acc ttc gtc gcc cat gac tgg ggc tcg gcc ctc       336
Met Arg Glu Arg Val Thr Phe Val Ala His Asp Trp Gly Ser Ala Leu
            100                 105                 110 gcc ttc gat tgg gcc aat cgc cac cgc gag gca gtg aag ggt atc gcg       384
Ala Phe Asp Trp Ala Asn Arg His Arg Glu Ala Val Lys Gly Ile Ala
        115                 120                 125 cac atg gag gcg atc gtg cgg ccg cag gac tgg acc cac tgg gac acg       432
His Met Glu Ala Ile Val Arg Pro Gln Asp Trp Thr His Trp Asp Thr
    130                 135                 140 atg ggg gcg cgt cca atc ttg cag cag ttg cgt tcc gag gct ggc gag       480
Met Gly Ala Arg Pro Ile Leu Gln Gln Leu Arg Ser Glu Ala Gly Glu
145                 150                 155                 160 aag ttg atg ctg caa gaa aac ctc ttc atc gag acg ttc ctg cct aag       528
Lys Leu Met Leu Gln Glu Asn Leu Phe Ile Glu Thr Phe Leu Pro Lys
                165                 170                 175
```

```
gcc atc aag cga acc ctc tcc gcc gag gag aag gcg gag tat aga cgg      576
Ala Ile Lys Arg Thr Leu Ser Ala Glu Glu Lys Ala Glu Tyr Arg Arg
        180                 185                 190 ccg ttc gcc gag ccg ggc gag ggg cga cgg ccg acg ctg acg tgg gtc      624
Pro Phe Ala Glu Pro Gly Glu Gly Arg Arg Pro Thr Leu Thr Trp Val
    195                 200                 205 cgg cag atc ccc atc gac ggc gag ccc gcc gac gtg act tcg atc gta      672
Arg Gln Ile Pro Ile Asp Gly Glu Pro Ala Asp Val Thr Ser Ile Val
210                 215                 220 tcc gcc tat ggg gag tgg ctg gcg aaa agc aat gtg ccc aag ctg ttc      720
Ser Ala Tyr Gly Glu Trp Leu Ala Lys Ser Asn Val Pro Lys Leu Phe
225                 230                 235                 240 gtg aag gct gag ccg ggc gtc ctc gtt gct ggt ggc gcg aac ctt gac      768
Val Lys Ala Glu Pro Gly Val Leu Val Ala Gly Gly Ala Asn Leu Asp
            245                 250                 255 gcc gtc cgc tca tgg cca gca cag acc gag gtg acg gtc ccg gga atc      816
Ala Val Arg Ser Trp Pro Ala Gln Thr Glu Val Thr Val Pro Gly Ile
        260                 265                 270 cat ttc atc cag gaa gat tcg ccg gac gag att ggg cgg gcc atc gcc      864
His Phe Ile Gln Glu Asp Ser Pro Asp Glu Ile Gly Arg Ala Ile Ala
    275                 280                 285 ggc tgg att aag acg ttg ggc taa                                      888
Gly Trp Ile Lys Thr Leu Gly
290                 295
```

<210> SEQ ID NO 28
<211> LENGTH: 295
<212> TYPE: PRT
<213> ORGANISM: Artificial Sequence
<220> FEATURE:
<223> OTHER INFORMATION: Artificially modified (mutated) dehalogenase

<400> SEQUENCE: 28

```
Met Ile Ser Ala Ala Phe Pro Tyr Gln Lys Lys Arg Arg Gln Val Leu
1               5                   10                  15

Gly Ser Glu Met Ala Tyr Val Glu Val Gly Glu Gly Asp Pro Ile Val
            20                  25                  30

Ser Leu His Gly Asn Pro Thr Ser Tyr Leu Trp Arg Asn Thr Leu
        35                  40                  45

Pro Tyr Leu Gln Pro Leu Gly Arg Cys Ile Ala Pro Asp Leu Ile Gly
    50                  55                  60

Met Gly Asp Ser Ala Lys Leu Pro Asn Ser Gly Pro Gly Ser Tyr Arg
65                  70                  75                  80

Phe Val Glu His Arg Arg Tyr Leu Asp Thr Leu Leu Glu Ala Leu Asn
                85                  90                  95

Met Arg Glu Arg Val Thr Phe Val Ala His Asp Trp Gly Ser Ala Leu
            100                 105                 110

Ala Phe Asp Trp Ala Asn Arg His Arg Glu Ala Val Lys Gly Ile Ala
        115                 120                 125

His Met Glu Ala Ile Val Arg Pro Gln Asp Trp Thr His Trp Asp Thr
    130                 135                 140

Met Gly Ala Arg Pro Ile Leu Gln Gln Leu Arg Ser Glu Ala Gly Glu
145                 150                 155                 160

Lys Leu Met Leu Gln Glu Asn Leu Phe Ile Glu Thr Phe Leu Pro Lys
                165                 170                 175

Ala Ile Lys Arg Thr Leu Ser Ala Glu Glu Lys Ala Glu Tyr Arg Arg
            180                 185                 190
```

```
Pro Phe Ala Glu Pro Gly Glu Gly Arg Arg Pro Thr Leu Thr Trp Val
            195                 200                 205

Arg Gln Ile Pro Ile Asp Gly Glu Pro Ala Asp Val Thr Ser Ile Val
        210                 215                 220

Ser Ala Tyr Gly Glu Trp Leu Ala Lys Ser Asn Val Pro Lys Leu Phe
225                 230                 235                 240

Val Lys Ala Glu Pro Gly Val Leu Val Ala Gly Ala Asn Leu Asp
                245                 250                 255

Ala Val Arg Ser Trp Pro Ala Gln Thr Glu Val Thr Val Pro Gly Ile
            260                 265                 270

His Phe Ile Gln Glu Asp Ser Pro Asp Glu Ile Gly Arg Ala Ile Ala
        275                 280                 285

Gly Trp Ile Lys Thr Leu Gly
    290                 295

<210> SEQ ID NO 29
<211> LENGTH: 882
<212> TYPE: DNA
<213> ORGANISM: Artificial Sequence
<220> FEATURE:
<223> OTHER INFORMATION: Artificially modified (mutated) dehalogenase
<221> NAME/KEY: CDS
<222> LOCATION: (1)...(879)

<400> SEQUENCE: 29 atg acg gag cag gag ata tca gcg gcg ttt ccc ttc gag tcg aag ttc        48
Met Thr Glu Gln Glu Ile Ser Ala Ala Phe Pro Phe Glu Ser Lys Phe
1               5                   10                  15 gtg gat gtg caa ggc tcc cgc atg cac tac gtg gag gag ggc tcg ggc        96
Val Asp Val Gln Gly Ser Arg Met His Tyr Val Glu Glu Gly Ser Gly
            20                  25                  30 gac ccg gtg gtg ttc ctc cac ggc aac ccg acc tcg tcc tac ctg tgg       144
Asp Pro Val Val Phe Leu His Gly Asn Pro Thr Ser Ser Tyr Leu Trp
        35                  40                  45 cgg aac gtc atc cct cac gtg tcc ccg ctt gcg agg tgc atc gcg ccg       192
Arg Asn Val Ile Pro His Val Ser Pro Leu Ala Arg Cys Ile Ala Pro
    50                  55                  60 gac ctc atc ggc atg ggg aag tcg gac aaa ccg gat atc gag tac cgc       240
Asp Leu Ile Gly Met Gly Lys Ser Asp Lys Pro Asp Ile Glu Tyr Arg
65                  70                  75                  80 ttc ttc gac cac gcc ggg tac gtt gac ggg ttc atc gag gca ctg gga       288
Phe Phe Asp His Ala Gly Tyr Val Asp Gly Phe Ile Glu Ala Leu Gly
                85                  90                  95 ctg cgg aac atc acc ttc gtc gcc tac gac tgg ggc tcc gcg ctg gcg       336
Leu Arg Asn Ile Thr Phe Val Ala Tyr Asp Trp Gly Ser Ala Leu Ala
            100                 105                 110 ttc cac tac gcg cga cgg cac gag gat aac gta aag ggg ttg gcg ttc       384
Phe His Tyr Ala Arg Arg His Glu Asp Asn Val Lys Gly Leu Ala Phe
        115                 120                 125 atg gag gcc atc gtg cga ccg ctc acc tgg gac gag tgg ccg gag cag       432
Met Glu Ala Ile Val Arg Pro Leu Thr Trp Asp Glu Trp Pro Glu Gln
    130                 135                 140 gca agg cag atg ttc cag gcg ttc cgg acg ccg ggc gtc ggg gag aag       480
Ala Arg Gln Met Phe Gln Ala Phe Arg Thr Pro Gly Val Gly Glu Lys
145                 150                 155                 160 atg atc ctg gag gaa aac gcc ttc gtg gag cag gtg ttg ccg gga gcg       528
Met Ile Leu Glu Glu Asn Ala Phe Val Glu Gln Val Leu Pro Gly Ala
                165                 170                 175 atc ctc cgc aag ctg tcc gac gag gag atg gac cgc tac cgg gag ccg       576
Ile Leu Arg Lys Leu Ser Asp Glu Glu Met Asp Arg Tyr Arg Glu Pro
```

```
                    180                 185                 190
ttc ccc gac ccc acc agc cgg agg ccg acg tgg cgc tgg ccc aac gag    624
Phe Pro Asp Pro Thr Ser Arg Arg Pro Thr Trp Arg Trp Pro Asn Glu
        195                 200                 205 ata cct gtc gag ggg aag ccg ccg gac gtg gtt gag gca gtg cag gcc    672
Ile Pro Val Glu Gly Lys Pro Pro Asp Val Val Glu Ala Val Gln Ala
    210                 215                 220 tac gcc gat tgg atg ggc gag tcg gat gtg ccc aag ctc ctc ctg tac    720
Tyr Ala Asp Trp Met Gly Glu Ser Asp Val Pro Lys Leu Leu Leu Tyr
225                 230                 235                 240 gct cac cca ggc gcg atc ctc cga gag ccg ctg ctg gag tgg tgc cgc    768
Ala His Pro Gly Ala Ile Leu Arg Glu Pro Leu Leu Glu Trp Cys Arg
                245                 250                 255 aac aac atg cgc aac ctg aag acg gtc gac atc ggg ccc ggg gtg cac    816
Asn Asn Met Arg Asn Leu Lys Thr Val Asp Ile Gly Pro Gly Val His
            260                 265                 270 ttc gtg ccg gag gac cgc ccc cac gag atc ggg gag gcc atc gcg gag    864
Phe Val Pro Glu Asp Arg Pro His Glu Ile Gly Glu Ala Ile Ala Glu
        275                 280                 285 tgg tac cag cgg ctg tag                                            882
Trp Tyr Gln Arg Leu
    290

<210> SEQ ID NO 30
<211> LENGTH: 293
<212> TYPE: PRT
<213> ORGANISM: Artificial Sequence
<220> FEATURE:
<223> OTHER INFORMATION: Artificially modified (mutated) dehalogenase

<400> SEQUENCE: 30

Met Thr Glu Gln Glu Ile Ser Ala Ala Phe Pro Phe Glu Ser Lys Phe
1               5                   10                  15

Val Asp Val Gln Gly Ser Arg Met His Tyr Val Glu Glu Gly Ser Gly
                20                  25                  30

Asp Pro Val Val Phe Leu His Gly Asn Pro Thr Ser Ser Tyr Leu Trp
            35                  40                  45

Arg Asn Val Ile Pro His Val Ser Pro Leu Ala Arg Cys Ile Ala Pro
    50                  55                  60

Asp Leu Ile Gly Met Gly Lys Ser Asp Lys Pro Asp Ile Glu Tyr Arg
65                  70                  75                  80

Phe Phe Asp His Ala Gly Tyr Val Asp Gly Phe Ile Glu Ala Leu Gly
                85                  90                  95

Leu Arg Asn Ile Thr Phe Val Ala Tyr Asp Trp Gly Ser Ala Leu Ala
                100                 105                 110

Phe His Tyr Ala Arg Arg His Glu Asp Asn Val Lys Gly Leu Ala Phe
            115                 120                 125

Met Glu Ala Ile Val Arg Pro Leu Thr Trp Asp Glu Trp Pro Glu Gln
130                 135                 140

Ala Arg Gln Met Phe Gln Ala Phe Arg Thr Pro Gly Val Gly Glu Lys
145                 150                 155                 160

Met Ile Leu Glu Glu Asn Ala Phe Val Glu Gln Val Leu Pro Gly Ala
                165                 170                 175

Ile Leu Arg Lys Leu Ser Asp Glu Glu Met Asp Arg Tyr Arg Glu Pro
            180                 185                 190

Phe Pro Asp Pro Thr Ser Arg Arg Pro Thr Trp Arg Trp Pro Asn Glu
        195                 200                 205
```

```
Ile Pro Val Glu Gly Lys Pro Pro Asp Val Val Ala Val Gln Ala
    210                 215                 220

Tyr Ala Asp Trp Met Gly Glu Ser Asp Val Pro Lys Leu Leu Leu Tyr
225                 230                 235                 240

Ala His Pro Gly Ala Ile Leu Arg Glu Pro Leu Leu Glu Trp Cys Arg
                245                 250                 255

Asn Asn Met Arg Asn Leu Lys Thr Val Asp Ile Gly Pro Gly Val His
                260                 265                 270

Phe Val Pro Glu Asp Arg Pro His Glu Ile Gly Glu Ala Ile Ala Glu
            275                 280                 285

Trp Tyr Gln Arg Leu
    290

<210> SEQ ID NO 31
<211> LENGTH: 885
<212> TYPE: DNA
<213> ORGANISM: Artificial Sequence
<220> FEATURE:
<223> OTHER INFORMATION: Artificially modified (mutated) dehalogenase
<221> NAME/KEY: CDS
<222> LOCATION: (1)...(882)

<400> SEQUENCE: 31 gtg agc gag atc tcc ccg aaa gag ccc atg gac aag aag cac atc ccc        48
Val Ser Glu Ile Ser Pro Lys Glu Pro Met Asp Lys Lys His Ile Pro
1               5                   10                  15 gta ctc gga aaa tcg atg gcg tac cgg gac gta ggt gag gga gac ccg        96
Val Leu Gly Lys Ser Met Ala Tyr Arg Asp Val Gly Glu Gly Asp Pro
                20                  25                  30 atc gtc ttc ctg cac ggc aac ccc acc tcg tcg tat ctc tgg cgc aac       144
Ile Val Phe Leu His Gly Asn Pro Thr Ser Ser Tyr Leu Trp Arg Asn
            35                  40                  45 atc atc ccc cac ctc gag ccg cat gca cgc tgc atc gcg ccg gat ctc       192
Ile Ile Pro His Leu Glu Pro His Ala Arg Cys Ile Ala Pro Asp Leu
        50                  55                  60 atc gga atg gga gat tcg gag aag ctc gag ccg agc gga ccg gac cgc       240
Ile Gly Met Gly Asp Ser Glu Lys Leu Glu Pro Ser Gly Pro Asp Arg
65                  70                  75                  80 tat cgc ttc atc gaa cat cgc gaa tat ctc gat ggt ttc ttc gag gct       288
Tyr Arg Phe Ile Glu His Arg Glu Tyr Leu Asp Gly Phe Phe Glu Ala
                85                  90                  95 ctg gcc ctg caa cag aac gtc acc ctc gtc gtc cac gac tgg ggc tcc       336
Leu Ala Leu Gln Gln Asn Val Thr Leu Val Val His Asp Trp Gly Ser
            100                 105                 110 ggg ctg ggc ttc gat tgg gcc aac cgg aat cgg gag cgc atc aag ggg       384
Gly Leu Gly Phe Asp Trp Ala Asn Arg Asn Arg Glu Arg Ile Lys Gly
        115                 120                 125 atc gct tat atg gag gcc atc gtt cgc ccg ctc agc tgg caa gac tgg       432
Ile Ala Tyr Met Glu Ala Ile Val Arg Pro Leu Ser Trp Gln Asp Trp
    130                 135                 140 ccc gac gac gcc cgc gcg gtc ttt cag ggt ttt cgc tcc gaa gca gga       480
Pro Asp Asp Ala Arg Ala Val Phe Gln Gly Phe Arg Ser Glu Ala Gly
145                 150                 155                 160 gag tcg atg gtg atc gag aag aac gtc ttc gtc gaa cgg gtc ctg ccc       528
Glu Ser Met Val Ile Glu Lys Asn Val Phe Val Glu Arg Val Leu Pro
                165                 170                 175 agc tcg gtc ctg cgg acg ctc cgt gac gag gag atg gag gtc tat cgc       576
Ser Ser Val Leu Arg Thr Leu Arg Asp Glu Glu Met Glu Val Tyr Arg
            180                 185                 190 aga ccg ttt caa gac gcc gga gaa tca agg cgc ccg acc ctc acc tgg       624
Arg Pro Phe Gln Asp Ala Gly Glu Ser Arg Arg Pro Thr Leu Thr Trp
```

```
Arg Pro Phe Gln Asp Ala Gly Glu Ser Arg Arg Pro Thr Leu Thr Trp
            195                 200                 205 ccc cgc cag atc ccg atc gag ggg gag ccg gag gat gtg acc gag atc       672
Pro Arg Gln Ile Pro Ile Glu Gly Glu Pro Glu Asp Val Thr Glu Ile
210                 215                 220 gcg agc gcg tac agc gcg tgg atg gcc gag aac gat ctc ccc aag ctc       720
Ala Ser Ala Tyr Ser Ala Trp Met Ala Glu Asn Asp Leu Pro Lys Leu
225                 230                 235                 240 ttc gtt aac gcc gag ccg ggc gcg atc ctg atc ggt ccg cag cgc gag       768
Phe Val Asn Ala Glu Pro Gly Ala Ile Leu Ile Gly Pro Gln Arg Glu
                245                 250                 255 ttc tgc cgc acg tgg aag aat caa cgc gaa gtc acg gta agc ggt agc       816
Phe Cys Arg Thr Trp Lys Asn Gln Arg Glu Val Thr Val Ser Gly Ser
            260                 265                 270 cac ttc atc cag gag gac tct ccg cac gaa atc ggc gac gcg att gca       864
His Phe Ile Gln Glu Asp Ser Pro His Glu Ile Gly Asp Ala Ile Ala
                275                 280                 285 ggc tgg tac gcg gat ctc tag                                           885
Gly Trp Tyr Ala Asp Leu
        290

<210> SEQ ID NO 32
<211> LENGTH: 294
<212> TYPE: PRT
<213> ORGANISM: Artificial Sequence
<220> FEATURE:
<223> OTHER INFORMATION: Artificially modified (mutated) dehalogenase

<400> SEQUENCE: 32

Val Ser Glu Ile Ser Pro Lys Glu Pro Met Asp Lys Lys His Ile Pro
1               5                   10                  15

Val Leu Gly Lys Ser Met Ala Tyr Arg Asp Val Gly Glu Gly Asp Pro
            20                  25                  30

Ile Val Phe Leu His Gly Asn Pro Thr Ser Ser Tyr Leu Trp Arg Asn
        35                  40                  45

Ile Ile Pro His Leu Glu Pro His Ala Arg Cys Ile Ala Pro Asp Leu
    50                  55                  60

Ile Gly Met Gly Asp Ser Glu Lys Leu Glu Pro Ser Gly Pro Asp Arg
65                  70                  75                  80

Tyr Arg Phe Ile Glu His Arg Glu Tyr Leu Asp Gly Phe Phe Glu Ala
                85                  90                  95

Leu Ala Leu Gln Gln Asn Val Thr Leu Val Val His Asp Trp Gly Ser
            100                 105                 110

Gly Leu Gly Phe Asp Trp Ala Asn Arg Asn Arg Glu Arg Ile Lys Gly
        115                 120                 125

Ile Ala Tyr Met Glu Ala Ile Val Arg Pro Leu Ser Trp Gln Asp Trp
    130                 135                 140

Pro Asp Asp Ala Arg Ala Val Phe Gln Gly Phe Arg Ser Glu Ala Gly
145                 150                 155                 160

Glu Ser Met Val Ile Glu Lys Asn Val Phe Val Glu Arg Val Leu Pro
                165                 170                 175

Ser Ser Val Leu Arg Thr Leu Arg Asp Glu Glu Met Glu Val Tyr Arg
            180                 185                 190

Arg Pro Phe Gln Asp Ala Gly Glu Ser Arg Arg Pro Thr Leu Thr Trp
        195                 200                 205

Pro Arg Gln Ile Pro Ile Glu Gly Glu Pro Glu Asp Val Thr Glu Ile
    210                 215                 220
```

```
Ala Ser Ala Tyr Ser Ala Trp Met Ala Glu Asn Asp Leu Pro Lys Leu
225                 230                 235                 240

Phe Val Asn Ala Glu Pro Gly Ala Ile Leu Ile Gly Pro Gln Arg Glu
            245                 250                 255

Phe Cys Arg Thr Trp Lys Asn Gln Arg Glu Val Thr Val Ser Gly Ser
            260                 265                 270

His Phe Ile Gln Glu Asp Ser Pro His Glu Ile Gly Asp Ala Ile Ala
            275                 280                 285

Gly Trp Tyr Ala Asp Leu
        290

<210> SEQ ID NO 33
<211> LENGTH: 888
<212> TYPE: DNA
<213> ORGANISM: Artificial Sequence
<220> FEATURE:
<223> OTHER INFORMATION: Artificially modified (mutated) dehalogenase
<221> NAME/KEY: CDS
<222> LOCATION: (1)...(885)

<400> SEQUENCE: 33 atg acc acc gaa atc tcg gca gcc gac ccc ttc gag cgg cac cgg gtc       48
Met Thr Thr Glu Ile Ser Ala Ala Asp Pro Phe Glu Arg His Arg Val
1               5                   10                  15 acc gtg ctc gac tca gag atg tcg tac atc gac acc ggc ccc ggc gcc       96
Thr Val Leu Asp Ser Glu Met Ser Tyr Ile Asp Thr Gly Pro Gly Ala
            20                  25                  30 gca ggc agt gag ccg atc gtg ttt ctc cac ggg aac cca acc tcg tcc      144
Ala Gly Ser Glu Pro Ile Val Phe Leu His Gly Asn Pro Thr Ser Ser
        35                  40                  45 tac ctc tgg cgc aac atc att ccc cac gtc cag cac ctc ggg cgc tgc      192
Tyr Leu Trp Arg Asn Ile Ile Pro His Val Gln His Leu Gly Arg Cys
    50                  55                  60 ctc gca ccg gat ctg atc ggg atg ggc aac tcg gac cct tcc cct aac      240
Leu Ala Pro Asp Leu Ile Gly Met Gly Asn Ser Asp Pro Ser Pro Asn
65                  70                  75                  80 ggc agc tac cgc ttc gtc gac cac gtg aag tac ctc gac gcc tgg ttg      288
Gly Ser Tyr Arg Phe Val Asp His Val Lys Tyr Leu Asp Ala Trp Leu
                85                  90                  95 gac gcc gtc ggc gtg acc gac cag gtg acg ttc gtg gtg cat gac tgg      336
Asp Ala Val Gly Val Thr Asp Gln Val Thr Phe Val Val His Asp Trp
            100                 105                 110 gga tcg gcg ctc ggc ttc cac tgg gca gac cgc cat cgc gac gcc atc      384
Gly Ser Ala Leu Gly Phe His Trp Ala Asp Arg His Arg Asp Ala Ile
        115                 120                 125 cga ggc ttc gcc tac atg gag gcg atc gtg cgc ccc gtc gag tgg gag      432
Arg Gly Phe Ala Tyr Met Glu Ala Ile Val Arg Pro Val Glu Trp Glu
    130                 135                 140 gac tgg ccg cct gcg gac gtc ttc cga cgg atg cga tcc gag gag ggc      480
Asp Trp Pro Pro Ala Asp Val Phe Arg Arg Met Arg Ser Glu Glu Gly
145                 150                 155                 160 gac gag atg atg ctc gag ggc aac ttc ttc gtc gag gtg atc ctg ccc      528
Asp Glu Met Met Leu Glu Gly Asn Phe Phe Val Glu Val Ile Leu Pro
                165                 170                 175 cgc agc gtc ctc cgc ggg ctc act gac gaa gag atg gag gta tac cgg      576
Arg Ser Val Leu Arg Gly Leu Thr Asp Glu Glu Met Glu Val Tyr Arg
            180                 185                 190 cga ccc tac ctc gag cgc ggc gag tcg cgg cgt ccg acg ctg acc tgg      624
Arg Pro Tyr Leu Glu Arg Gly Glu Ser Arg Arg Pro Thr Leu Thr Trp
        195                 200                 205
```

| | | | | | | | | | | | | | | | | |
|---|---|---|---|---|---|---|---|---|---|---|---|---|---|---|---|---|
| ccg | cgg | gag | atc | ccg | ctg | tca | ggc | gag | ccg | gcg | gat | gtc | gtc | gag | atc | 672 |
| Pro | Arg | Glu | Ile | Pro | Leu | Ser | Gly | Glu | Pro | Ala | Asp | Val | Val | Glu | Ile | |
| | 210 | | | | 215 | | | | | 220 | | | | | | |
| gtc | agc | gcc | tac | agc | aaa | tgg | ctg | tcc | gag | acg | acc | gtg | ccg | aag | ctc | 720 |
| Val | Ser | Ala | Tyr | Ser | Lys | Trp | Leu | Ser | Glu | Thr | Thr | Val | Pro | Lys | Leu | |
| 225 | | | | | 230 | | | | | 235 | | | | | 240 | |
| ctc | gtc | act | gcc | gag | ccg | ggt | gcg | atc | ctg | aac | ggg | ccg | cag | ctg | gag | 768 |
| Leu | Val | Thr | Ala | Glu | Pro | Gly | Ala | Ile | Leu | Asn | Gly | Pro | Gln | Leu | Glu | |
| | | | | 245 | | | | | 250 | | | | | 255 | | |
| ttc | gct | cgc | ggg | ttt | gcc | aac | cag | acc | gag | gtc | cga | gtc | gcc | ggc | tcg | 816 |
| Phe | Ala | Arg | Gly | Phe | Ala | Asn | Gln | Thr | Glu | Val | Arg | Val | Ala | Gly | Ser | |
| | | | 260 | | | | | 265 | | | | | 270 | | | |
| cac | ttc | atc | cag | gag | gac | tcg | cca | cac | gag | atc | ggc | gcc | gcc | ctc | gcc | 864 |
| His | Phe | Ile | Gln | Glu | Asp | Ser | Pro | His | Glu | Ile | Gly | Ala | Ala | Leu | Ala | |
| | | 275 | | | | | 280 | | | | | 285 | | | | |
| gag | tgg | tac | ccg | acg | acg | acc | tga | | | | | | | | | 888 |
| Glu | Trp | Tyr | Pro | Thr | Thr | Thr | | | | | | | | | | |
| | 290 | | | | | 295 | | | | | | | | | | |

<210> SEQ ID NO 34
<211> LENGTH: 295
<212> TYPE: PRT
<213> ORGANISM: Artificial Sequence
<220> FEATURE:
<223> OTHER INFORMATION: Artificially modified (mutated) dehalogenase

<400> SEQUENCE: 34

Met Thr Thr Glu Ile Ser Ala Ala Asp Pro Phe Glu Arg His Arg Val
1               5                   10                  15

Thr Val Leu Asp Ser Glu Met Ser Tyr Ile Asp Thr Gly Pro Gly Ala
            20                  25                  30

Ala Gly Ser Glu Pro Ile Val Phe Leu His Gly Asn Pro Thr Ser Ser
        35                  40                  45

Tyr Leu Trp Arg Asn Ile Ile Pro His Val Gln His Leu Gly Arg Cys
    50                  55                  60

Leu Ala Pro Asp Leu Ile Gly Met Gly Asn Ser Asp Pro Ser Pro Asn
65                  70                  75                  80

Gly Ser Tyr Arg Phe Val Asp His Val Lys Tyr Leu Asp Ala Trp Leu
                85                  90                  95

Asp Ala Val Gly Val Thr Asp Gln Val Thr Phe Val Val His Asp Trp
            100                 105                 110

Gly Ser Ala Leu Gly Phe His Trp Ala Asp Arg His Arg Asp Ala Ile
        115                 120                 125

Arg Gly Phe Ala Tyr Met Glu Ala Ile Val Arg Pro Val Glu Trp Glu
    130                 135                 140

Asp Trp Pro Pro Ala Asp Val Phe Arg Arg Met Arg Ser Glu Glu Gly
145                 150                 155                 160

Asp Glu Met Met Leu Glu Gly Asn Phe Phe Val Glu Val Ile Leu Pro
                165                 170                 175

Arg Ser Val Leu Arg Gly Leu Thr Asp Glu Glu Met Glu Val Tyr Arg
            180                 185                 190

Arg Pro Tyr Leu Glu Arg Gly Glu Ser Arg Arg Pro Thr Leu Thr Trp
        195                 200                 205

Pro Arg Glu Ile Pro Leu Ser Gly Glu Pro Ala Asp Val Val Glu Ile
    210                 215                 220

Val Ser Ala Tyr Ser Lys Trp Leu Ser Glu Thr Thr Val Pro Lys Leu
225                 230                 235                 240

-continued

```
Leu Val Thr Ala Glu Pro Gly Ala Ile Leu Asn Gly Pro Gln Leu Glu
            245                 250                 255

Phe Ala Arg Gly Phe Ala Asn Gln Thr Glu Val Arg Val Ala Gly Ser
        260                 265                 270

His Phe Ile Gln Glu Asp Ser Pro His Glu Ile Gly Ala Ala Leu Ala
        275                 280                 285

Glu Trp Tyr Pro Thr Thr Thr
290                 295

<210> SEQ ID NO 35
<211> LENGTH: 861
<212> TYPE: DNA
<213> ORGANISM: Artificial Sequence
<220> FEATURE:
<223> OTHER INFORMATION: Artificially modified (mutated) dehalogenase
<221> NAME/KEY: CDS
<222> LOCATION: (1)...(858)

<400> SEQUENCE: 35 atg tac gag aaa cgg ttc gta tct gtc ctc ggt cac cgg atg gca tac      48
Met Tyr Glu Lys Arg Phe Val Ser Val Leu Gly His Arg Met Ala Tyr
1               5                  10                  15 gtc gag caa gga gcc ggg gac ccg atc gtg ttc cta cat ggc aac ccc      96
Val Glu Gln Gly Ala Gly Asp Pro Ile Val Phe Leu His Gly Asn Pro
            20                  25                  30 acc tcg tcc tac ctg tgg cgg aag gtc atc ccc gcg cta acg gag cag     144
Thr Ser Ser Tyr Leu Trp Arg Lys Val Ile Pro Ala Leu Thr Glu Gln
        35                  40                  45 gga cga tgc atc gct ccc gac ttg atc ggc atg ggc gac tcc gag aag     192
Gly Arg Cys Ile Ala Pro Asp Leu Ile Gly Met Gly Asp Ser Glu Lys
    50                  55                  60 ctg gct gac agc ggc ccc ggt agc tac cgc ttc gtg gaa cat cgg cgt     240
Leu Ala Asp Ser Gly Pro Gly Ser Tyr Arg Phe Val Glu His Arg Arg
65                  70                  75                  80 ttc ctc gat gcc ttc ctc gaa agg gtt ggg atc agc gag tcg gtg gtc     288
Phe Leu Asp Ala Phe Leu Glu Arg Val Gly Ile Ser Glu Ser Val Val
                85                  90                  95 ctg gtg atc cac gac tgg ggt tcg gcc ctc ggc ttc gac tgg gcc tac     336
Leu Val Ile His Asp Trp Gly Ser Ala Leu Gly Phe Asp Trp Ala Tyr
            100                 105                 110 cgc cac caa aac gcc gtc aag ggg atc gca tat atg gaa gcg ctg gtc     384
Arg His Gln Asn Ala Val Lys Gly Ile Ala Tyr Met Glu Ala Leu Val
        115                 120                 125 ggg cct gta ggt tgg agc gac tgg ccg gag tcg gcc cgg tcc atc ttc     432
Gly Pro Val Gly Trp Ser Asp Trp Pro Glu Ser Ala Arg Ser Ile Phe
    130                 135                 140 cag gct ttc cgc tcc gaa gcc ggg gac agc ctc atc ctc gag aag aac     480
Gln Ala Phe Arg Ser Glu Ala Gly Asp Ser Leu Ile Leu Glu Lys Asn
145                 150                 155                 160 ttc ttc gtc gag cgg gtg ctg ccc gca tcg gtg ctc gat ccc ctg cca     528
Phe Phe Val Glu Arg Val Leu Pro Ala Ser Val Leu Asp Pro Leu Pro
                165                 170                 175 gaa gaa gtg ctc gac gag tat cga cag ccg ttt ctc gaa ccg ggc gag     576
Glu Glu Val Leu Asp Glu Tyr Arg Gln Pro Phe Leu Glu Pro Gly Glu
            180                 185                 190 tct cgc cga ccc acc ctc acc tgg cct agg gag atc ccc atc gac ggt     624
Ser Arg Arg Pro Thr Leu Thr Trp Pro Arg Glu Ile Pro Ile Asp Gly
        195                 200                 205 gag ccg gcc gac gtc cac gag atc gtg tcc gcg tac aac cgc tgg att     672
Glu Pro Ala Asp Val His Glu Ile Val Ser Ala Tyr Asn Arg Trp Ile
    210                 215                 220
```

```
gga tcc tct ccg gtg ccc aag ctg tac gtc aac gcc gat ccc ggc ttc    720
Gly Ser Ser Pro Val Pro Lys Leu Tyr Val Asn Ala Asp Pro Gly Phe
225                 230                 235                 240 ttc agc cct ggc atc gtc gag gcc acg gcc gcc tgg ccc aac cag gaa    768
Phe Ser Pro Gly Ile Val Glu Ala Thr Ala Ala Trp Pro Asn Gln Glu
                245                 250                 255 aca gtc acg gtc cgt ggc cac cat ttc ttg cag gaa gac tct ggt gaa    816
Thr Val Thr Val Arg Gly His His Phe Leu Gln Glu Asp Ser Gly Glu
        260                 265                 270 gcg atc ggt gat gcc atc gcc gac tgg tac cgg cgt gtc tcg            858
Ala Ile Gly Asp Ala Ile Ala Asp Trp Tyr Arg Arg Val Ser
            275                 280                 285 tga                                                                861
```

<210> SEQ ID NO 36
<211> LENGTH: 286
<212> TYPE: PRT
<213> ORGANISM: Artificial Sequence
<220> FEATURE:
<223> OTHER INFORMATION: Artificially modified (mutated) dehalogenase

<400> SEQUENCE: 36

```
Met Tyr Glu Lys Arg Phe Val Ser Val Leu Gly His Arg Met Ala Tyr
1               5                   10                  15

Val Glu Gln Gly Ala Gly Asp Pro Ile Val Phe Leu His Gly Asn Pro
            20                  25                  30

Thr Ser Ser Tyr Leu Trp Arg Lys Val Ile Pro Ala Leu Thr Glu Gln
        35                  40                  45

Gly Arg Cys Ile Ala Pro Asp Leu Ile Gly Met Gly Asp Ser Glu Lys
    50                  55                  60

Leu Ala Asp Ser Gly Pro Gly Ser Tyr Arg Phe Val Glu His Arg Arg
65                  70                  75                  80

Phe Leu Asp Ala Phe Leu Glu Arg Val Gly Ile Ser Glu Ser Val Val
                85                  90                  95

Leu Val Ile His Asp Trp Gly Ser Ala Leu Gly Phe Asp Trp Ala Tyr
            100                 105                 110

Arg His Gln Asn Ala Val Lys Gly Ile Ala Tyr Met Glu Ala Leu Val
        115                 120                 125

Gly Pro Val Gly Trp Ser Asp Trp Pro Glu Ser Ala Arg Ser Ile Phe
    130                 135                 140

Gln Ala Phe Arg Ser Glu Ala Gly Asp Ser Leu Ile Leu Glu Lys Asn
145                 150                 155                 160

Phe Phe Val Glu Arg Val Leu Pro Ala Ser Val Leu Asp Pro Leu Pro
                165                 170                 175

Glu Glu Val Leu Asp Glu Tyr Arg Gln Pro Phe Leu Glu Pro Gly Glu
            180                 185                 190

Ser Arg Arg Pro Thr Leu Thr Trp Pro Arg Glu Ile Pro Ile Asp Gly
        195                 200                 205

Glu Pro Ala Asp Val His Glu Ile Val Ser Ala Tyr Asn Arg Trp Ile
    210                 215                 220

Gly Ser Ser Pro Val Pro Lys Leu Tyr Val Asn Ala Asp Pro Gly Phe
225                 230                 235                 240

Phe Ser Pro Gly Ile Val Glu Ala Thr Ala Ala Trp Pro Asn Gln Glu
                245                 250                 255

Thr Val Thr Val Arg Gly His His Phe Leu Gln Glu Asp Ser Gly Glu
            260                 265                 270
```

```
Ala Ile Gly Asp Ala Ile Ala Asp Trp Tyr Arg Arg Val Ser
        275                 280                 285

<210> SEQ ID NO 37
<211> LENGTH: 891
<212> TYPE: DNA
<213> ORGANISM: Artificial Sequence
<220> FEATURE:
<223> OTHER INFORMATION: Artificially modified (mutated) dehalogenase
<221> NAME/KEY: CDS
<222> LOCATION: (1)...(888)

<400> SEQUENCE: 37 atg aat gca atc gcc agt gag ccc tat ggg caa ctg agg ttc caa gag         48
Met Asn Ala Ile Ala Ser Glu Pro Tyr Gly Gln Leu Arg Phe Gln Glu
1               5                   10                  15 atc gcc ggc aag caa atg gcg tac atc gac gag ggc gtc ggt gat gcc        96
Ile Ala Gly Lys Gln Met Ala Tyr Ile Asp Glu Gly Val Gly Asp Ala
            20                  25                  30 atc gtt ttc cag cac ggc aac ccc acg tcg tcc tac ctg tgg cgc aac       144
Ile Val Phe Gln His Gly Asn Pro Thr Ser Ser Tyr Leu Trp Arg Asn
        35                  40                  45 gtt atg ccg cac ctg gaa ggg ctg ggc cgg ctg gtg gcg tgc gat ctg       192
Val Met Pro His Leu Glu Gly Leu Gly Arg Leu Val Ala Cys Asp Leu
    50                  55                  60 atc ggg atg ggg gcg tcg gag aag ctc agc cca tcg ggc ccc gac cgc       240
Ile Gly Met Gly Ala Ser Glu Lys Leu Ser Pro Ser Gly Pro Asp Arg
65                  70                  75                  80 tat aac tat gcc gag cag cgc gac tat ctg ttc gcg ctc tgg gat gcg       288
Tyr Asn Tyr Ala Glu Gln Arg Asp Tyr Leu Phe Ala Leu Trp Asp Ala
                85                  90                  95 ctc gac ctt ggc gat cac gtg gtg ctg gtg ctg cat gac tgg ggc tca       336
Leu Asp Leu Gly Asp His Val Val Leu Val Leu His Asp Trp Gly Ser
            100                 105                 110 gca ttg ggc ttc gac tgg gcc aac cag cat cgc gac cga gtg cag ggc       384
Ala Leu Gly Phe Asp Trp Ala Asn Gln His Arg Asp Arg Val Gln Gly
        115                 120                 125 atc gca ttc atg gag gcg atc gtc agc ccg atc aca tgg gcc gac ttc       432
Ile Ala Phe Met Glu Ala Ile Val Ser Pro Ile Thr Trp Ala Asp Phe
    130                 135                 140 cat ccc agc gtg cga ggc gtg ttc cag ggg ttc cgg tcg ccc gag ggt       480
His Pro Ser Val Arg Gly Val Phe Gln Gly Phe Arg Ser Pro Glu Gly
145                 150                 155                 160 gag cgg atg gtg ttg gag cag aac atc ttt gtc gaa ggg gta ctg ccc       528
Glu Arg Met Val Leu Glu Gln Asn Ile Phe Val Glu Gly Val Leu Pro
                165                 170                 175 ggg gcg atc cag cgc cga ctg tct gac gag gag atg ggc cat tac cgg       576
Gly Ala Ile Gln Arg Arg Leu Ser Asp Glu Glu Met Gly His Tyr Arg
            180                 185                 190 cag cca ttc gtc gaa ccc ggc gag gac cgg cga ccg acc ttg tcg tgg       624
Gln Pro Phe Val Glu Pro Gly Glu Asp Arg Arg Pro Thr Leu Ser Trp
        195                 200                 205 cca cgg aac atc ccc atc gac ggc gag ccg gcc gag gtc gtc gcg gtc       672
Pro Arg Asn Ile Pro Ile Asp Gly Glu Pro Ala Glu Val Val Ala Val
    210                 215                 220 gtc gac gag tac cgt agc tgg ctc gag aag agc gac att cca aag ctg       720
Val Asp Glu Tyr Arg Ser Trp Leu Glu Lys Ser Asp Ile Pro Lys Leu
225                 230                 235                 240 ttc gtg aac gcc gag ccg ggc gcg atc gtc acc ggc cgc atc cgc gac       768
Phe Val Asn Ala Glu Pro Gly Ala Ile Val Thr Gly Arg Ile Arg Asp
                245                 250                 255
```

```
tat atc cgg acg tgg gcg aac ctc agc gaa atc acg gtt ccc gga gtg      816
Tyr Ile Arg Thr Trp Ala Asn Leu Ser Glu Ile Thr Val Pro Gly Val
        260                 265                 270 cat ttc atc caa gaa gac agc cca gac gga atc ggc tcg gcc gtg gca      864
His Phe Ile Gln Glu Asp Ser Pro Asp Gly Ile Gly Ser Ala Val Ala
        275                 280                 285 cag ttc ctg cag cag cta cgc gcc taa                                  891
Gln Phe Leu Gln Gln Leu Arg Ala
        290                 295

<210> SEQ ID NO 38
<211> LENGTH: 296
<212> TYPE: PRT
<213> ORGANISM: Artificial Sequence
<220> FEATURE:
<223> OTHER INFORMATION: Artificially modified (mutated) dehalogenase

<400> SEQUENCE: 38
```

Met Asn Ala Ile Ala Ser Glu Pro Tyr Gly Gln Leu Arg Phe Gln Glu
1               5                   10                  15

Ile Ala Gly Lys Gln Met Ala Tyr Ile Asp Glu Gly Val Gly Asp Ala
            20                  25                  30

Ile Val Phe Gln His Gly Asn Pro Thr Ser Ser Tyr Leu Trp Arg Asn
        35                  40                  45

Val Met Pro His Leu Glu Gly Leu Gly Arg Leu Val Ala Cys Asp Leu
    50                  55                  60

Ile Gly Met Gly Ala Ser Glu Lys Leu Ser Pro Ser Gly Pro Asp Arg
65                  70                  75                  80

Tyr Asn Tyr Ala Glu Gln Arg Asp Tyr Leu Phe Ala Leu Trp Asp Ala
                85                  90                  95

Leu Asp Leu Gly Asp His Val Val Leu Val Leu His Asp Trp Gly Ser
            100                 105                 110

Ala Leu Gly Phe Asp Trp Ala Asn Gln His Arg Asp Arg Val Gln Gly
        115                 120                 125

Ile Ala Phe Met Glu Ala Ile Val Ser Pro Ile Thr Trp Ala Asp Phe
    130                 135                 140

His Pro Ser Val Arg Gly Val Phe Gln Gly Phe Arg Ser Pro Glu Gly
145                 150                 155                 160

Glu Arg Met Val Leu Glu Gln Asn Ile Phe Val Glu Gly Val Leu Pro
                165                 170                 175

Gly Ala Ile Gln Arg Arg Leu Ser Asp Glu Glu Met Gly His Tyr Arg
            180                 185                 190

Gln Pro Phe Val Glu Pro Gly Glu Asp Arg Arg Pro Thr Leu Ser Trp
        195                 200                 205

Pro Arg Asn Ile Pro Ile Asp Gly Glu Pro Ala Glu Val Val Ala Val
    210                 215                 220

Val Asp Glu Tyr Arg Ser Trp Leu Glu Lys Ser Asp Ile Pro Lys Leu
225                 230                 235                 240

Phe Val Asn Ala Glu Pro Gly Ala Ile Val Thr Gly Arg Ile Arg Asp
                245                 250                 255

Tyr Ile Arg Thr Trp Ala Asn Leu Ser Glu Ile Thr Val Pro Gly Val
            260                 265                 270

His Phe Ile Gln Glu Asp Ser Pro Asp Gly Ile Gly Ser Ala Val Ala
        275                 280                 285

Gln Phe Leu Gln Gln Leu Arg Ala
    290                 295

<210> SEQ ID NO 39
<211> LENGTH: 882
<212> TYPE: DNA
<213> ORGANISM: Rhodococcus rhodochrous
<220> FEATURE:
<221> NAME/KEY: CDS
<222> LOCATION: (1)...(879)

<400> SEQUENCE: 39

| | | | | | | | | | | | | | | | | |
|---|---|---|---|---|---|---|---|---|---|---|---|---|---|---|---|---|
| atg | tca | gaa | atc | ggt | aca | ggc | ttc | ccc | ttc | gac | ccc | cat | tat | gtg | gaa | 48 |
| Met | Ser | Glu | Ile | Gly | Thr | Gly | Phe | Pro | Phe | Asp | Pro | His | Tyr | Val | Glu | |
| 1 | | | | 5 | | | | | 10 | | | | | 15 | | |
| gtc | ctg | ggc | gag | cgt | atg | cac | tac | gtc | gat | gtt | gga | ccg | cgg | gat | ggc | 96 |
| Val | Leu | Gly | Glu | Arg | Met | His | Tyr | Val | Asp | Val | Gly | Pro | Arg | Asp | Gly | |
| | | | 20 | | | | | 25 | | | | | 30 | | | |
| acg | cct | gtg | ctg | ttc | ctg | cac | ggt | aac | ccg | acc | tcg | tcc | tac | ctg | tgg | 144 |
| Thr | Pro | Val | Leu | Phe | Leu | His | Gly | Asn | Pro | Thr | Ser | Ser | Tyr | Leu | Trp | |
| | | 35 | | | | | 40 | | | | | 45 | | | | |
| cgc | aac | atc | atc | ccg | cat | gta | gca | cca | agt | cat | cgg | tgc | att | gct | cca | 192 |
| Arg | Asn | Ile | Ile | Pro | His | Val | Ala | Pro | Ser | His | Arg | Cys | Ile | Ala | Pro | |
| | 50 | | | | | 55 | | | | | 60 | | | | | |
| gac | ctg | atc | ggg | atg | gga | aaa | tcg | gac | aaa | cca | gac | ctc | gat | tat | ttc | 240 |
| Asp | Leu | Ile | Gly | Met | Gly | Lys | Ser | Asp | Lys | Pro | Asp | Leu | Asp | Tyr | Phe | |
| 65 | | | | | 70 | | | | | 75 | | | | | 80 | |
| ttc | gac | gac | cac | gtc | cgc | tac | ctc | gat | gcc | ttc | atc | gaa | gcc | ttg | ggt | 288 |
| Phe | Asp | Asp | His | Val | Arg | Tyr | Leu | Asp | Ala | Phe | Ile | Glu | Ala | Leu | Gly | |
| | | | | 85 | | | | | 90 | | | | | 95 | | |
| ttg | gaa | gag | gtc | gtc | ctg | gtc | atc | cac | gac | tgg | ggc | tca | gct | ctc | gga | 336 |
| Leu | Glu | Glu | Val | Val | Leu | Val | Ile | His | Asp | Trp | Gly | Ser | Ala | Leu | Gly | |
| | | | 100 | | | | | 105 | | | | | 110 | | | |
| ttc | cac | tgg | gcc | aag | cgc | aat | ccg | gaa | cgg | gtc | aaa | ggt | att | gca | tgt | 384 |
| Phe | His | Trp | Ala | Lys | Arg | Asn | Pro | Glu | Arg | Val | Lys | Gly | Ile | Ala | Cys | |
| | | 115 | | | | | 120 | | | | | 125 | | | | |
| atg | gaa | ttc | atc | cgg | cct | atc | ccg | acg | tgg | gac | gaa | tgg | ccg | gaa | ttc | 432 |
| Met | Glu | Phe | Ile | Arg | Pro | Ile | Pro | Thr | Trp | Asp | Glu | Trp | Pro | Glu | Phe | |
| | 130 | | | | | 135 | | | | | 140 | | | | | |
| gcc | cgt | gag | acc | ttc | cag | gcc | ttc | cgg | acc | gcc | gac | gtc | ggc | cga | gag | 480 |
| Ala | Arg | Glu | Thr | Phe | Gln | Ala | Phe | Arg | Thr | Ala | Asp | Val | Gly | Arg | Glu | |
| 145 | | | | | 150 | | | | | 155 | | | | | 160 | |
| ttg | atc | atc | gat | cag | aac | gct | ttc | atc | gag | ggt | gcg | ctc | ccg | aaa | tgc | 528 |
| Leu | Ile | Ile | Asp | Gln | Asn | Ala | Phe | Ile | Glu | Gly | Ala | Leu | Pro | Lys | Cys | |
| | | | | 165 | | | | | 170 | | | | | 175 | | |
| gtc | gtc | cgt | ccg | ctt | acg | gag | gtc | gag | atg | gac | cac | tat | cgc | gag | ccc | 576 |
| Val | Val | Arg | Pro | Leu | Thr | Glu | Val | Glu | Met | Asp | His | Tyr | Arg | Glu | Pro | |
| | | | 180 | | | | | 185 | | | | | 190 | | | |
| ttc | ctc | aag | cct | gtt | gac | cga | gag | cca | ctg | tgg | cga | ttc | ccc | aac | gag | 624 |
| Phe | Leu | Lys | Pro | Val | Asp | Arg | Glu | Pro | Leu | Trp | Arg | Phe | Pro | Asn | Glu | |
| | | 195 | | | | | 200 | | | | | 205 | | | | |
| ctg | ccc | atc | gcc | ggt | gag | ccc | gcg | aac | atc | gtc | gcg | ctc | gtc | gag | gca | 672 |
| Leu | Pro | Ile | Ala | Gly | Glu | Pro | Ala | Asn | Ile | Val | Ala | Leu | Val | Glu | Ala | |
| | 210 | | | | | 215 | | | | | 220 | | | | | |
| tac | atg | aac | tgg | ctg | cac | cag | tca | cct | gtc | ccg | aag | ttg | ttg | ttc | tgg | 720 |
| Tyr | Met | Asn | Trp | Leu | His | Gln | Ser | Pro | Val | Pro | Lys | Leu | Leu | Phe | Trp | |
| 225 | | | | | 230 | | | | | 235 | | | | | 240 | |
| ggc | aca | ccc | ggc | gta | ctg | atc | ccc | ccg | gcc | gaa | gcc | gcg | aga | ctt | gcc | 768 |
| Gly | Thr | Pro | Gly | Val | Leu | Ile | Pro | Pro | Ala | Glu | Ala | Ala | Arg | Leu | Ala | |
| | | | | 245 | | | | | 250 | | | | | 255 | | |
| gaa | agc | ctc | ccc | aac | tgc | aag | aca | gtg | gac | atc | ggc | ccg | gga | ttg | cac | 816 |
| Glu | Ser | Leu | Pro | Asn | Cys | Lys | Thr | Val | Asp | Ile | Gly | Pro | Gly | Leu | His | |
| | | | 260 | | | | | 265 | | | | | 270 | | | |

```
tac ctc cag gaa gac aac ccg gac ctt atc ggc agt gag atc gcg cgc    864
Tyr Leu Gln Glu Asp Asn Pro Asp Leu Ile Gly Ser Glu Ile Ala Arg
            275                 280                 285 tgg ctc ccc gca ctc tag                                            882
Trp Leu Pro Ala Leu
    290

<210> SEQ ID NO 40
<211> LENGTH: 293
<212> TYPE: PRT
<213> ORGANISM: Rhodococcus rhodochrous

<400> SEQUENCE: 40

Met Ser Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
            20                  25                  30

Thr Pro Val Leu Phe Leu His Gly Asn Pro Thr Ser Ser Tyr Leu Trp
        35                  40                  45

Arg Asn Ile Ile Pro His Val Ala Pro Ser His Arg Cys Ile Ala Pro
    50                  55                  60

Asp Leu Ile Gly Met Gly Lys Ser Asp Lys Pro Asp Leu Asp Tyr Phe
65                  70                  75                  80

Phe Asp Asp His Val Arg Tyr Leu Asp Ala Phe Ile Glu Ala Leu Gly
                85                  90                  95

Leu Glu Glu Val Val Leu Val Ile His Asp Trp Gly Ser Ala Leu Gly
            100                 105                 110

Phe His Trp Ala Lys Arg Asn Pro Glu Arg Val Lys Gly Ile Ala Cys
        115                 120                 125

Met Glu Phe Ile Arg Pro Ile Pro Thr Trp Asp Glu Trp Pro Glu Phe
    130                 135                 140

Ala Arg Glu Thr Phe Gln Ala Phe Arg Thr Ala Asp Val Gly Arg Glu
145                 150                 155                 160

Leu Ile Ile Asp Gln Asn Ala Phe Ile Glu Gly Ala Leu Pro Lys Cys
                165                 170                 175

Val Val Arg Pro Leu Thr Glu Val Glu Met Asp His Tyr Arg Glu Pro
            180                 185                 190

Phe Leu Lys Pro Val Asp Arg Glu Pro Leu Trp Arg Phe Pro Asn Glu
        195                 200                 205

Leu Pro Ile Ala Gly Glu Pro Ala Asn Ile Val Ala Leu Val Glu Ala
    210                 215                 220

Tyr Met Asn Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
                245                 250                 255

Glu Ser Leu Pro Asn Cys Lys Thr Val Asp Ile Gly Pro Gly Leu His
            260                 265                 270

Tyr Leu Gln Glu Asp Asn Pro Asp Leu Ile Gly Ser Glu Ile Ala Arg
        275                 280                 285

Trp Leu Pro Ala Leu
    290

<210> SEQ ID NO 41
<211> LENGTH: 924
<212> TYPE: DNA
<213> ORGANISM: Mycobacterium sp.
```

```
<220> FEATURE:
<221> NAME/KEY: CDS
<222> LOCATION: (1)...(921)

<400> SEQUENCE: 41 atg tca gaa atc ggt aca ggc ttc ccc ttc gac ccc cat tat gtg gaa      48
Met Ser Glu Ile Gly Thr Gly Phe Pro Phe Asp Pro His Tyr Val Glu
1               5                  10                  15 gtc ctg ggc gag cgt atg cac tac gtc gat gtt gga ccg cgg gat ggc      96
Val Leu Gly Glu Arg Met His Tyr Val Asp Val Gly Pro Arg Asp Gly
            20                  25                  30 acg cct gtg ctg ttc ctg cac ggt aac ccg acc tcg tcc tac ctg tgg     144
Thr Pro Val Leu Phe Leu His Gly Asn Pro Thr Ser Ser Tyr Leu Trp
        35                  40                  45 cgc aac atc atc ccg cat gta gca ccg agt cat cgg tgc att gct cca     192
Arg Asn Ile Ile Pro His Val Ala Pro Ser His Arg Cys Ile Ala Pro
    50                  55                  60 gac ctg atc ggg atg gga aaa tcg gac aaa cca gac ctc gat tat ttc     240
Asp Leu Ile Gly Met Gly Lys Ser Asp Lys Pro Asp Leu Asp Tyr Phe
65                  70                  75                  80 ttc gac gac cac gtc cgc tac ctc gat gcc ttc atc gaa gcc ttg ggt     288
Phe Asp Asp His Val Arg Tyr Leu Asp Ala Phe Ile Glu Ala Leu Gly
                85                  90                  95 ttg gaa gag gtc gtc ctg gtc atc cac gac tgg ggc tca gct ctc gga     336
Leu Glu Glu Val Val Leu Val Ile His Asp Trp Gly Ser Ala Leu Gly
            100                 105                 110 ttc cac tgg gcc aag cgc aat ccg gaa cgg gtc aaa ggt att gca tgt     384
Phe His Trp Ala Lys Arg Asn Pro Glu Arg Val Lys Gly Ile Ala Cys
        115                 120                 125 atg gaa ttc atc cgg cct atc ccg acg tgg gac gaa tgg ccg gaa ttc     432
Met Glu Phe Ile Arg Pro Ile Pro Thr Trp Asp Glu Trp Pro Glu Phe
    130                 135                 140 gcc cgt gag acc ttc cag gcc ttc cgg acc gcc gac gtc ggc cga gag     480
Ala Arg Glu Thr Phe Gln Ala Phe Arg Thr Ala Asp Val Gly Arg Glu
145                 150                 155                 160 ttg atc atc gat cag aac gct ttc atc gag ggt gcg ctc ccg aaa ttc     528
Leu Ile Ile Asp Gln Asn Ala Phe Ile Glu Gly Ala Leu Pro Lys Phe
                165                 170                 175 gtc gtc cgt ccg ctt acg gag gtc gag atg gac cac tat cgc gag ccc     576
Val Val Arg Pro Leu Thr Glu Val Glu Met Asp His Tyr Arg Glu Pro
            180                 185                 190 ttc ctc aag cct gtt gac cga gag cca ctg tgg cga ttc ccc aac gag     624
Phe Leu Lys Pro Val Asp Arg Glu Pro Leu Trp Arg Phe Pro Asn Glu
        195                 200                 205 ctg ccc atc gcc ggt gag ccc gcg aac atc gtc gcg ctc gtc gag gca     672
Leu Pro Ile Ala Gly Glu Pro Ala Asn Ile Val Ala Leu Val Glu Ala
    210                 215                 220 tac atg aac tgg ctg cac cag tca cct gtc ccg aag ttg ttg ttc tgg     720
Tyr Met Asn Trp Leu His Gln Ser Pro Val Pro Lys Leu Leu Phe Trp
225                 230                 235                 240 ggc aca ccc ggt gta ctg atc tcc ccg gcc gaa gcc gcg aga ctt gcc     768
Gly Thr Pro Gly Val Leu Ile Ser Pro Ala Glu Ala Ala Arg Leu Ala
                245                 250                 255 gaa agc ctc ccc aac tgc aag aca gtg gac atc ggc ccg gga ttg cac     816
Glu Ser Leu Pro Asn Cys Lys Thr Val Asp Ile Gly Pro Gly Leu His
            260                 265                 270 ttc ctc cag gaa gac aac ccg gac ctt atc ggc agt gag atc gcg cgc     864
Phe Leu Gln Glu Asp Asn Pro Asp Leu Ile Gly Ser Glu Ile Ala Arg
        275                 280                 285 tgg ctc ccc gca ctc atc gtc ggc aag tcg atc gag ttc gac ggc ggc     912
Trp Leu Pro Ala Leu Ile Val Gly Lys Ser Ile Glu Phe Asp Gly Gly
```

```
Trp Leu Pro Ala Leu Ile Val Gly Lys Ser Ile Glu Phe Asp Gly Gly
    290                 295                 300 tgg gcc acc tga                                                      924
Trp Ala Thr
305

<210> SEQ ID NO 42
<211> LENGTH: 307
<212> TYPE: PRT
<213> ORGANISM: Mycobacterium sp.

<400> SEQUENCE: 42

Met Ser Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
                20                  25                  30

Thr Pro Val Leu Phe Leu His Gly Asn Pro Thr Ser Ser Tyr Leu Trp
            35                  40                  45

Arg Asn Ile Ile Pro His Val Ala Pro Ser His Arg Cys Ile Ala Pro
50                  55                  60

Asp Leu Ile Gly Met Gly Lys Ser Asp Lys Pro Asp Leu Asp Tyr Phe
65                  70                  75                  80

Phe Asp Asp His Val Arg Tyr Leu Asp Ala Phe Ile Glu Ala Leu Gly
                85                  90                  95

Leu Glu Glu Val Val Leu Val Ile His Asp Trp Gly Ser Ala Leu Gly
                100                 105                 110

Phe His Trp Ala Lys Arg Asn Pro Glu Arg Val Lys Gly Ile Ala Cys
            115                 120                 125

Met Glu Phe Ile Arg Pro Ile Pro Thr Trp Asp Glu Trp Pro Glu Phe
130                 135                 140

Ala Arg Glu Thr Phe Gln Ala Phe Arg Thr Ala Asp Val Gly Arg Glu
145                 150                 155                 160

Leu Ile Ile Asp Gln Asn Ala Phe Ile Glu Gly Ala Leu Pro Lys Phe
                165                 170                 175

Val Val Arg Pro Leu Thr Glu Val Glu Met Asp His Tyr Arg Glu Pro
            180                 185                 190

Phe Leu Lys Pro Val Asp Arg Glu Pro Leu Trp Arg Phe Pro Asn Glu
        195                 200                 205

Leu Pro Ile Ala Gly Glu Pro Ala Asn Ile Val Ala Leu Val Glu Ala
210                 215                 220

Tyr Met Asn Trp Leu His Gln Ser Pro Val Pro Lys Leu Leu Phe Trp
225                 230                 235                 240

Gly Thr Pro Gly Val Leu Ile Ser Pro Ala Glu Ala Ala Arg Leu Ala
                245                 250                 255

Glu Ser Leu Pro Asn Cys Lys Thr Val Asp Ile Gly Pro Gly Leu His
            260                 265                 270

Phe Leu Gln Glu Asp Asn Pro Asp Leu Ile Gly Ser Glu Ile Ala Arg
        275                 280                 285

Trp Leu Pro Ala Leu Ile Val Gly Lys Ser Ile Glu Phe Asp Gly Gly
    290                 295                 300

Trp Ala Thr
305

<210> SEQ ID NO 43
<211> LENGTH: 921
<212> TYPE: DNA
```

<213> ORGANISM: Artificial Sequence
<220> FEATURE:
<223> OTHER INFORMATION: Artificially modified (mutated) dehalogenase
<221> NAME/KEY: CDS
<222> LOCATION: (1)...(918)

<400> SEQUENCE: 43

```
atg tca gaa atc ggt aca ggc ttc ccc ttc gac ccc cat tat gtg gaa      48
Met Ser Glu Ile Gly Thr Gly Phe Pro Phe Asp Pro His Tyr Val Glu
1               5                   10                  15 gtc ctg ggc gag cgt atg cac tac gtc gat gtt gga ccg cgg gat ggc      96
Val Leu Gly Glu Arg Met His Tyr Val Asp Val Gly Pro Arg Asp Gly
            20                  25                  30 acg cct gtg ctg ttc ctg cac ggt aac ccg acc tcg tcc tac ctg tgg      144
Thr Pro Val Leu Phe Leu His Gly Asn Pro Thr Ser Ser Tyr Leu Trp
        35                  40                  45 cgc aac atc atc ccg cat gta gca ccg agt cat cgg tgc att gct cca      192
Arg Asn Ile Ile Pro His Val Ala Pro Ser His Arg Cys Ile Ala Pro
    50                  55                  60 gac ctg atc ggg atg gga aaa tcg gac aaa cca gac ctc ggt tat ttc      240
Asp Leu Ile Gly Met Gly Lys Ser Asp Lys Pro Asp Leu Gly Tyr Phe
65                  70                  75                  80 ttc gac gac cac gtc cgc tac ctc gat gcc ttc atc gaa gcc ttg ggt      288
Phe Asp Asp His Val Arg Tyr Leu Asp Ala Phe Ile Glu Ala Leu Gly
                85                  90                  95 ttg gaa gag gtc gtc ttg gtc atc cac gac tgg ggc tca gct ctc gga      336
Leu Glu Glu Val Val Leu Val Ile His Asp Trp Gly Ser Ala Leu Gly
            100                 105                 110 ttc cac tgg gcc aag cgc aat ccg gaa cgg gtc aaa ggt att gca tgt      384
Phe His Trp Ala Lys Arg Asn Pro Glu Arg Val Lys Gly Ile Ala Cys
        115                 120                 125 atg gaa ttc atc cgg tct atc ccg acg tgg gac gaa tgg ccg gaa ttc      432
Met Glu Phe Ile Arg Ser Ile Pro Thr Trp Asp Glu Trp Pro Glu Phe
    130                 135                 140 gcc cgt gag acc ttc cag gcc ttc cgg acc gcc gac gtc ggc cga gag      480
Ala Arg Glu Thr Phe Gln Ala Phe Arg Thr Ala Asp Val Gly Arg Glu
145                 150                 155                 160 ttg atc atc gat cag aac gct ttc atc gag cat gtg ctc ccg aaa tac      528
Leu Ile Ile Asp Gln Asn Ala Phe Ile Glu His Val Leu Pro Lys Tyr
                165                 170                 175 gtc gtc cgt ccg ctt acg gag gtc gag atg gac cac tat cgc gag ccc      576
Val Val Arg Pro Leu Thr Glu Val Glu Met Asp His Tyr Arg Glu Pro
            180                 185                 190 ttc ctc aag cct gct gac cga gag cca ctg tgg cga ttc ccc aac gag      624
Phe Leu Lys Pro Ala Asp Arg Glu Pro Leu Trp Arg Phe Pro Asn Glu
        195                 200                 205 ctc ccc atc gcc ggt gag ccc gcg aac atc gtc gcg ctc gtc gag gca      672
Leu Pro Ile Ala Gly Glu Pro Ala Asn Ile Val Ala Leu Val Glu Ala
    210                 215                 220 tac atg aac tgg ctg cac cag tca cct gtc ccg aag ttg ttg ttc tgg      720
Tyr Met Asn Trp Leu His Gln Ser Pro Val Pro Lys Leu Leu Phe Trp
225                 230                 235                 240 ggc aca ccc ggc cta ctg atc ccc ccg gcc gaa gcc tcg aga ctt gcc      768
Gly Thr Pro Gly Leu Leu Ile Pro Pro Ala Glu Ala Ser Arg Leu Ala
                245                 250                 255 gaa agc ctc ccc aac tgc aag aca gtg gac atc ggc ccg gga ctg cac      816
Glu Ser Leu Pro Asn Cys Lys Thr Val Asp Ile Gly Pro Gly Leu His
            260                 265                 270 ttc ctc cag gaa gac aac ccg gac ctt atc ggc agt gag atc gcg cgc      864
Phe Leu Gln Glu Asp Asn Pro Asp Leu Ile Gly Ser Glu Ile Ala Arg
        275                 280                 285
```

```
tgg ctc gcc gga ctc gcg agc ggc ctc ggc gac tac cat cat cat cat        912
Trp Leu Ala Gly Leu Ala Ser Gly Leu Gly Asp Tyr His His His His
    290                 295                 300 cat cat taa                                                            921
His His
305

<210> SEQ ID NO 44
<211> LENGTH: 306
<212> TYPE: PRT
<213> ORGANISM: Artificial Sequence
<220> FEATURE:
<223> OTHER INFORMATION: Artificially modified (mutated) dehalogenase

<400> SEQUENCE: 44

Met Ser Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
                20                  25                  30

Thr Pro Val Leu Phe Leu His Gly Asn Pro Thr Ser Ser Tyr Leu Trp
            35                  40                  45

Arg Asn Ile Ile Pro His Val Ala Pro Ser His Arg Cys Ile Ala Pro
        50                  55                  60

Asp Leu Ile Gly Met Gly Lys Ser Asp Lys Pro Asp Leu Gly Tyr Phe
65                  70                  75                  80

Phe Asp Asp His Val Arg Tyr Leu Asp Ala Phe Ile Glu Ala Leu Gly
                85                  90                  95

Leu Glu Glu Val Val Leu Val Ile His Asp Trp Gly Ser Ala Leu Gly
                100                 105                 110

Phe His Trp Ala Lys Arg Asn Pro Glu Arg Val Lys Gly Ile Ala Cys
            115                 120                 125

Met Glu Phe Ile Arg Ser Ile Pro Thr Trp Asp Glu Trp Pro Glu Phe
130                 135                 140

Ala Arg Glu Thr Phe Gln Ala Phe Arg Thr Ala Asp Val Gly Arg Glu
145                 150                 155                 160

Leu Ile Ile Asp Gln Asn Ala Phe Ile Glu His Val Leu Pro Lys Tyr
                165                 170                 175

Val Val Arg Pro Leu Thr Glu Val Glu Met Asp His Tyr Arg Glu Pro
                180                 185                 190

Phe Leu Lys Pro Ala Asp Arg Glu Pro Leu Trp Arg Phe Pro Asn Glu
            195                 200                 205

Leu Pro Ile Ala Gly Glu Pro Ala Asn Ile Val Ala Leu Val Glu Ala
210                 215                 220

Tyr Met Asn Trp Leu His Gln Ser Pro Val Pro Lys Leu Leu Phe Trp
225                 230                 235                 240

Gly Thr Pro Gly Leu Leu Ile Pro Pro Ala Glu Ala Ser Arg Leu Ala
                245                 250                 255

Glu Ser Leu Pro Asn Cys Lys Thr Val Asp Ile Gly Pro Gly Leu His
                260                 265                 270

Phe Leu Gln Glu Asp Asn Pro Asp Leu Ile Gly Ser Glu Ile Ala Arg
            275                 280                 285

Trp Leu Ala Gly Leu Ala Ser Gly Leu Gly Asp Tyr His His His His
        290                 295                 300

His His
305
```

<210> SEQ ID NO 45
<211> LENGTH: 882
<212> TYPE: DNA
<213> ORGANISM: Artificial Sequence
<220> FEATURE:
<223> OTHER INFORMATION: Artificially modified (mutated) dehalogenase
<221> NAME/KEY: CDS
<222> LOCATION: (1)...(879)

<400> SEQUENCE: 45

```
atg agc gaa gaa gcg atc tcg gcc ctc gac ccg cat cca cgc aag aaa      48
Met Ser Glu Glu Ala Ile Ser Ala Leu Asp Pro His Pro Arg Lys Lys
1               5                   10                  15 cag gaa ctg ctc ggc acc tcg atg tct tat gtc gat acc ggg act ggc      96
Gln Glu Leu Leu Gly Thr Ser Met Ser Tyr Val Asp Thr Gly Thr Gly
            20                  25                  30 gag ccg gtg gtg ttc ctg cac ggc aat cca acc tcc tcg tac ttg tgg     144
Glu Pro Val Val Phe Leu His Gly Asn Pro Thr Ser Ser Tyr Leu Trp
        35                  40                  45 cgg aac gtg att cca cat gtc gcg ccg gtc gcc agg tgc atc gct ccc     192
Arg Asn Val Ile Pro His Val Ala Pro Val Ala Arg Cys Ile Ala Pro
    50                  55                  60 gac ctg atc ggg atg gga gcg tca ggg cct tcc tct agc ggc aac tac     240
Asp Leu Ile Gly Met Gly Ala Ser Gly Pro Ser Ser Ser Gly Asn Tyr
65                  70                  75                  80 acg ttc gcc gat cat gcg cga cat ctc gat gcg ctc ctc gac gcg att     288
Thr Phe Ala Asp His Ala Arg His Leu Asp Ala Leu Leu Asp Ala Ile
                85                  90                  95 ttg cca aag ggc cag ctc agc ttg gtg gtg cac gac tgg gga tcg gcg     336
Leu Pro Lys Gly Gln Leu Ser Leu Val Val His Asp Trp Gly Ser Ala
            100                 105                 110 ctg ggc ttc cac tgg gcc aat cgc aat cgg gat cgg gta agg gga atc     384
Leu Gly Phe His Trp Ala Asn Arg Asn Arg Asp Arg Val Arg Gly Ile
        115                 120                 125 gcc tac atg gaa gcg att gtg cga ccg gtg ctg tgg tcg gag tgg ccc     432
Ala Tyr Met Glu Ala Ile Val Arg Pro Val Leu Trp Ser Glu Trp Pro
    130                 135                 140 gaa cgt gcc cga gac att ttc aag acg ctg cga act ccg gcc ggc gaa     480
Glu Arg Ala Arg Asp Ile Phe Lys Thr Leu Arg Thr Pro Ala Gly Glu
145                 150                 155                 160 gag atg att ctc aaa aac aac gta ttc gtg gag cgg atc ctg ccc ggc     528
Glu Met Ile Leu Lys Asn Asn Val Phe Val Glu Arg Ile Leu Pro Gly
                165                 170                 175 agc gtc ttg cgc aaa ttg agc tcc gaa gaa atg gac aat tat cgc cgg     576
Ser Val Leu Arg Lys Leu Ser Ser Glu Glu Met Asp Asn Tyr Arg Arg
            180                 185                 190 ccc ttt cgc gac gca gga gaa tcg cgg cgg cca aca ctc acg tgg ccg     624
Pro Phe Arg Asp Ala Gly Glu Ser Arg Arg Pro Thr Leu Thr Trp Pro
        195                 200                 205 cgt cag att ccg atc gag ggt gag ccg gcc gac gtg gtg gaa atc gtg     672
Arg Gln Ile Pro Ile Glu Gly Glu Pro Ala Asp Val Val Glu Ile Val
    210                 215                 220 cag aaa tat tcc gag tgg ctg gca cag agc gcg gtg ccc aaa ctg ctc     720
Gln Lys Tyr Ser Glu Trp Leu Ala Gln Ser Ala Val Pro Lys Leu Leu
225                 230                 235                 240 gtg aat gcg gag ccg gga gcg att ttg ata ggc gcg cag cgc gag ttt     768
Val Asn Ala Glu Pro Gly Ala Ile Leu Ile Gly Ala Gln Arg Glu Phe
                245                 250                 255 tgc cac caa tgg ccg aat cag cgc gaa gtc acg gtc aag ggc gta cac     816
Cys His Gln Trp Pro Asn Gln Arg Glu Val Thr Val Lys Gly Val His
            260                 265                 270
```

```
ttc atc cag gaa gat tcc ccg cac gag atc ggg cga gcg atc gca gac    864
Phe Ile Gln Glu Asp Ser Pro His Glu Ile Gly Arg Ala Ile Ala Asp
            275                 280                 285 tgg tac cga gga atc tga                                            882
Trp Tyr Arg Gly Ile
    290

<210> SEQ ID NO 46
<211> LENGTH: 293
<212> TYPE: PRT
<213> ORGANISM: Artificial Sequence
<220> FEATURE:
<223> OTHER INFORMATION: Artificially modified (mutated) dehalogenase

<400> SEQUENCE: 46

Met Ser Glu Glu Ala Ile Ser Ala Leu Asp Pro His Pro Arg Lys Lys
1               5                   10                  15

Gln Glu Leu Leu Gly Thr Ser Met Ser Tyr Val Asp Thr Gly Thr Gly
            20                  25                  30

Glu Pro Val Val Phe Leu His Gly Asn Pro Thr Ser Ser Tyr Leu Trp
        35                  40                  45

Arg Asn Val Ile Pro His Val Ala Pro Val Ala Arg Cys Ile Ala Pro
    50                  55                  60

Asp Leu Ile Gly Met Gly Ala Ser Gly Pro Ser Ser Gly Asn Tyr
65                  70                  75                  80

Thr Phe Ala Asp His Ala Arg His Leu Asp Ala Leu Leu Asp Ala Ile
                85                  90                  95

Leu Pro Lys Gly Gln Leu Ser Leu Val Val His Asp Trp Gly Ser Ala
            100                 105                 110

Leu Gly Phe His Trp Ala Asn Arg Asn Arg Asp Arg Val Arg Gly Ile
        115                 120                 125

Ala Tyr Met Glu Ala Ile Val Arg Pro Val Leu Trp Ser Glu Trp Pro
    130                 135                 140

Glu Arg Ala Arg Asp Ile Phe Lys Thr Leu Arg Thr Pro Ala Gly Glu
145                 150                 155                 160

Glu Met Ile Leu Lys Asn Asn Val Phe Val Glu Arg Ile Leu Pro Gly
                165                 170                 175

Ser Val Leu Arg Lys Leu Ser Ser Glu Glu Met Asp Asn Tyr Arg Arg
            180                 185                 190

Pro Phe Arg Asp Ala Gly Glu Ser Arg Arg Pro Thr Leu Thr Trp Pro
        195                 200                 205

Arg Gln Ile Pro Ile Glu Gly Glu Pro Ala Asp Val Val Glu Ile Val
    210                 215                 220

Gln Lys Tyr Ser Glu Trp Leu Ala Gln Ser Ala Val Pro Lys Leu Leu
225                 230                 235                 240

Val Asn Ala Glu Pro Gly Ala Ile Leu Ile Gly Ala Gln Arg Glu Phe
                245                 250                 255

Cys His Gln Trp Pro Asn Gln Arg Glu Val Thr Val Lys Gly Val His
            260                 265                 270

Phe Ile Gln Glu Asp Ser Pro His Glu Ile Gly Arg Ala Ile Ala Asp
        275                 280                 285

Trp Tyr Arg Gly Ile
    290

<210> SEQ ID NO 47
<211> LENGTH: 1032
```

<212> TYPE: DNA
<213> ORGANISM: Artificial Sequence
<220> FEATURE:
<223> OTHER INFORMATION: Artificially modified (mutated) dehalogenase
<221> NAME/KEY: CDS
<222> LOCATION: (1)...(1029)

<400> SEQUENCE: 47

| | | | | | | | | | | | | | | | | |
|---|---|---|---|---|---|---|---|---|---|---|---|---|---|---|---|---|
| atg | gct | act | act | gga | gaa | gcg | ata | tct | tct | gca | ttt | ccg | tac | gag | aag | 48 |
| Met | Ala | Thr | Thr | Gly | Glu | Ala | Ile | Ser | Ser | Ala | Phe | Pro | Tyr | Glu | Lys | |
| 1 | | | | 5 | | | | | 10 | | | | | 15 | | |
| cag | cgc | cgg | cgg | gtt | ctg | ggg | aga | gag | atg | gcc | tat | gtg | gaa | gtg | ggg | 96 |
| Gln | Arg | Arg | Arg | Val | Leu | Gly | Arg | Glu | Met | Ala | Tyr | Val | Glu | Val | Gly | |
| | | | 20 | | | | | 25 | | | | | 30 | | | |
| gcc | ggc | gac | ccg | atc | gtg | ctg | ctg | cac | ggc | aat | ccg | acc | tca | tcc | tac | 144 |
| Ala | Gly | Asp | Pro | Ile | Val | Leu | Leu | His | Gly | Asn | Pro | Thr | Ser | Ser | Tyr | |
| | | | | 35 | | | | | 40 | | | | | 45 | | |
| ctc | tgg | cgc | aat | gtc | ctg | ccg | cat | ctc | caa | cta | cga | ggc | cga | tgc | atc | 192 |
| Leu | Trp | Arg | Asn | Val | Leu | Pro | His | Leu | Gln | Leu | Arg | Gly | Arg | Cys | Ile | |
| | | | 50 | | | | | 55 | | | | | 60 | | | |
| gcg | ccc | gac | ctg | att | ggc | atg | ggc | gac | tcc | gat | aag | cta | cct | gac | agc | 240 |
| Ala | Pro | Asp | Leu | Ile | Gly | Met | Gly | Asp | Ser | Asp | Lys | Leu | Pro | Asp | Ser | |
| 65 | | | | | 70 | | | | | 75 | | | | | 80 | |
| ggc | ccg | agc | tcg | tat | cgc | ttc | gta | gat | cag | cgc | cgc | tac | ctc | gat | gcg | 288 |
| Gly | Pro | Ser | Ser | Tyr | Arg | Phe | Val | Asp | Gln | Arg | Arg | Tyr | Leu | Asp | Ala | |
| | | | | 85 | | | | | 90 | | | | | 95 | | |
| ctg | ctg | gag | gca | ttg | gac | gta | cgt | gag | cgt | gtg | acg | ctc | gtc | att | cat | 336 |
| Leu | Leu | Glu | Ala | Leu | Asp | Val | Arg | Glu | Arg | Val | Thr | Leu | Val | Ile | His | |
| | | | 100 | | | | | 105 | | | | | 110 | | | |
| gac | tgg | ggc | tcg | gga | ctt | ggc | ttt | gac | tgg | gcc | aac | cga | cac | cgc | gac | 384 |
| Asp | Trp | Gly | Ser | Gly | Leu | Gly | Phe | Asp | Trp | Ala | Asn | Arg | His | Arg | Asp | |
| | | | 115 | | | | | 120 | | | | | 125 | | | |
| gcc | gta | aag | ggc | atc | gca | tac | atg | gag | gcg | atc | gtg | cgc | ccg | cag | gga | 432 |
| Ala | Val | Lys | Gly | Ile | Ala | Tyr | Met | Glu | Ala | Ile | Val | Arg | Pro | Gln | Gly | |
| | | | 130 | | | | | 135 | | | | | 140 | | | |
| tgg | gac | cac | tgg | gac | gta | atg | aat | atg | cgt | cca | ttc | cta | gag | gcg | ctg | 480 |
| Trp | Asp | His | Trp | Asp | Val | Met | Asn | Met | Arg | Pro | Phe | Leu | Glu | Ala | Leu | |
| 145 | | | | | 150 | | | | | 155 | | | | | 160 | |
| cgt | tcc | gag | gcc | ggc | gag | aag | atg | gtc | ctt | gaa | gac | aac | ttt | ttc | atc | 528 |
| Arg | Ser | Glu | Ala | Gly | Glu | Lys | Met | Val | Leu | Glu | Asp | Asn | Phe | Phe | Ile | |
| | | | | 165 | | | | | 170 | | | | | 175 | | |
| gag | aag | att | tta | cca | ggc | gct | gtt | ctc | cgc | aag | ctc | acc | gcg | gat | gaa | 576 |
| Glu | Lys | Ile | Leu | Pro | Gly | Ala | Val | Leu | Arg | Lys | Leu | Thr | Ala | Asp | Glu | |
| | | | 180 | | | | | 185 | | | | | 190 | | | |
| atg | gcg | gag | tat | cgt | cgg | ccg | ttc | gct | gaa | ccc | ggc | gag | gcg | cga | cga | 624 |
| Met | Ala | Glu | Tyr | Arg | Arg | Pro | Phe | Ala | Glu | Pro | Gly | Glu | Ala | Arg | Arg | |
| | | | | 195 | | | | | 200 | | | | | 205 | | |
| ccg | act | ctg | act | tgg | cca | cgg | gag | att | cct | atc | gat | ggc | aaa | ccc | gcc | 672 |
| Pro | Thr | Leu | Thr | Trp | Pro | Arg | Glu | Ile | Pro | Ile | Asp | Gly | Lys | Pro | Ala | |
| | | | 210 | | | | | 215 | | | | | 220 | | | |
| gac | gtg | aat | acg | att | gtg | gcg | gcc | tat | tcg | gag | tgg | ctt | gcg | acg | agc | 720 |
| Asp | Val | Asn | Thr | Ile | Val | Ala | Ala | Tyr | Ser | Glu | Trp | Leu | Ala | Thr | Ser | |
| 225 | | | | | 230 | | | | | 235 | | | | | 240 | |
| gat | gtg | ccc | aag | cta | ttc | ata | aaa | gcc | gag | ccc | ggc | gca | ctc | ctt | ggc | 768 |
| Asp | Val | Pro | Lys | Leu | Phe | Ile | Lys | Ala | Glu | Pro | Gly | Ala | Leu | Leu | Gly | |
| | | | | 245 | | | | | 250 | | | | | 255 | | |
| agc | ggg | att | aac | ctt | gaa | acc | gct | cgc | tcc | tgg | cct | gcg | cag | acg | gaa | 816 |
| Ser | Gly | Ile | Asn | Leu | Glu | Thr | Ala | Arg | Ser | Trp | Pro | Ala | Gln | Thr | Glu | |
| | | | 260 | | | | | 265 | | | | | 270 | | | |
| gta | acc | gtg | gcc | gga | gtt | cat | ttt | gtg | caa | gag | gat | tcg | cca | gat | gag | 864 |
| Val | Thr | Val | Ala | Gly | Val | His | Phe | Val | Gln | Glu | Asp | Ser | Pro | Asp | Glu | |

```
                     275                 280                 285
att ggg cgc tcg gat tct ggc gac cct tgg ccc gct ggc gga cga aat      912
Ile Gly Arg Ser Asp Ser Gly Asp Pro Trp Pro Ala Gly Gly Arg Asn
    290                 295                 300 cgc cgt cta ctc gcc ccg tct ggc gca gca tct cga tca cta cag tcc      960
Arg Arg Leu Leu Ala Pro Ser Gly Ala Ala Ser Arg Ser Leu Gln Ser
305                 310                 315                 320 gtt cgc gct cag ctt cgc act gcc ctg caa tac ccc cgg cct gcg gtt     1008
Val Arg Ala Gln Leu Arg Thr Ala Leu Gln Tyr Pro Arg Pro Ala Val
                325                 330                 335 cct gtg ccg cga cag ctt cga tga                                     1032
Pro Val Pro Arg Gln Leu Arg
                340
```

<210> SEQ ID NO 48
<211> LENGTH: 343
<212> TYPE: PRT
<213> ORGANISM: Artificial Sequence
<220> FEATURE:
<223> OTHER INFORMATION: Artificially modified (mutated) dehalogenase

<400> SEQUENCE: 48

```
Met Ala Thr Thr Gly Glu Ala Ile Ser Ser Ala Phe Pro Tyr Glu Lys
1               5                   10                  15

Gln Arg Arg Arg Val Leu Gly Arg Glu Met Ala Tyr Val Glu Val Gly
            20                  25                  30

Ala Gly Asp Pro Ile Val Leu Leu His Gly Asn Pro Thr Ser Ser Tyr
        35                  40                  45

Leu Trp Arg Asn Val Leu Pro His Leu Gln Leu Arg Gly Arg Cys Ile
    50                  55                  60

Ala Pro Asp Leu Ile Gly Met Gly Asp Ser Asp Lys Leu Pro Asp Ser
65                  70                  75                  80

Gly Pro Ser Ser Tyr Arg Phe Val Asp Gln Arg Arg Tyr Leu Asp Ala
                85                  90                  95

Leu Leu Glu Ala Leu Asp Val Arg Glu Arg Val Thr Leu Val Ile His
            100                 105                 110

Asp Trp Gly Ser Gly Leu Gly Phe Asp Trp Ala Asn Arg His Arg Asp
        115                 120                 125

Ala Val Lys Gly Ile Ala Tyr Met Glu Ala Ile Val Arg Pro Gln Gly
    130                 135                 140

Trp Asp His Trp Asp Val Met Asn Met Arg Pro Phe Leu Glu Ala Leu
145                 150                 155                 160

Arg Ser Glu Ala Gly Glu Lys Met Val Leu Glu Asp Asn Phe Phe Ile
                165                 170                 175

Glu Lys Ile Leu Pro Gly Ala Val Leu Arg Lys Leu Thr Ala Asp Glu
            180                 185                 190

Met Ala Glu Tyr Arg Arg Pro Phe Ala Glu Pro Gly Glu Ala Arg Arg
        195                 200                 205

Pro Thr Leu Thr Trp Pro Arg Glu Ile Pro Ile Asp Gly Lys Pro Ala
    210                 215                 220

Asp Val Asn Thr Ile Val Ala Ala Tyr Ser Glu Trp Leu Ala Thr Ser
225                 230                 235                 240

Asp Val Pro Lys Leu Phe Ile Lys Ala Glu Pro Gly Ala Leu Leu Gly
                245                 250                 255

Ser Gly Ile Asn Leu Glu Thr Ala Arg Ser Trp Pro Ala Gln Thr Glu
            260                 265                 270
```

```
Val Thr Val Ala Gly Val His Phe Val Gln Glu Asp Ser Pro Asp Glu
            275                 280                 285

Ile Gly Arg Ser Asp Ser Gly Asp Pro Trp Pro Ala Gly Gly Arg Asn
            290                 295                 300

Arg Arg Leu Leu Ala Pro Ser Gly Ala Ala Ser Arg Ser Leu Gln Ser
305                 310                 315                 320

Val Arg Ala Gln Leu Arg Thr Ala Leu Gln Tyr Pro Arg Pro Ala Val
            325                 330                 335

Pro Val Pro Arg Gln Leu Arg
            340

<210> SEQ ID NO 49
<211> LENGTH: 280
<212> TYPE: PRT
<213> ORGANISM: Artificial Sequence
<220> FEATURE:
<223> OTHER INFORMATION: Consensus sequence

<400> SEQUENCE: 49

Met Ser Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
            20                  25                  30

Thr Pro Val Leu Phe Leu His Gly Asn Pro Thr Ser Ser Tyr Leu Trp
        35                  40                  45

Arg Asn Ile Ile Pro His Val Ala Pro Ser His Arg Cys Ile Ala Pro
    50                  55                  60

Asp Leu Ile Gly Met Gly Lys Ser Asp Lys Pro Asp Leu Tyr Phe Asp
65                  70                  75                  80

Asp His Val Arg Tyr Leu Asp Ala Phe Ile Glu Ala Leu Gly Leu Glu
                85                  90                  95

Glu Val Val Leu Val Ile His Asp Trp Gly Ser Ala Leu Gly Phe His
            100                 105                 110

Trp Ala Lys Arg Asn Pro Glu Arg Val Lys Gly Ile Ala Cys Met Glu
        115                 120                 125

Phe Ile Arg Pro Ile Pro Thr Trp Asp Glu Trp Pro Glu Phe Ala Arg
    130                 135                 140

Glu Phe Gln Ala Phe Arg Thr Ala Asp Val Gly Arg Glu Leu Ile Ile
145                 150                 155                 160

Asp Gln Asn Ala Phe Ile Glu Leu Pro Lys Val Val Arg Pro Leu Thr
                165                 170                 175

Glu Val Glu Met Asp His Tyr Arg Glu Pro Phe Leu Lys Pro Val Asp
            180                 185                 190

Arg Glu Pro Leu Trp Arg Phe Pro Asn Glu Pro Ile Ala Gly Glu Pro
        195                 200                 205

Ala Asn Ile Val Ala Leu Val Glu Ala Tyr Met Trp Leu His Gln Ser
    210                 215                 220

Pro Val Pro Lys Leu Leu Phe Gly Thr Pro Gly Val Leu Ile Pro Ala
225                 230                 235                 240

Glu Ala Ala Arg Leu Ala Glu Ser Leu Pro Asn Cys Lys Thr Val Asp
                245                 250                 255

Ile Gly Pro Gly Leu His Leu Gln Glu Asp Asn Pro Asp Leu Ile Gly
            260                 265                 270

Ser Glu Ile Ala Arg Trp Leu Leu
        275                 280
```